(12) United States Patent
Andreini et al.

(10) Patent No.: US 7,989,449 B2
(45) Date of Patent: Aug. 2, 2011

(54) 4,5-DIHYDRO-OXAZOL-2-YL AMINE DERIVATIVES

(75) Inventors: Matteo Andreini, Siena (IT); Emanuele Gabellieri, Siena (IT); Wolfgang Guba, Muellheim (DE); Guido Marconi, Siena (IT); Robert Narquizian, Saint Louis (FR); Eoin Power, Siena (IT); Massimiliano Travagli, Siena (IT); Thomas Woltering, Freiburg (DE); Wolfgang Wostl, Grenzach-Wyhlen (DE)

(73) Assignees: Hoffman-La Roche Inc., Nutley, NJ (US); Siena Biotech S.p.A., Siena (IT)

( * ) Notice: Subject to any disclaimer, the term of this patent is extended or adjusted under 35 U.S.C. 154(b) by 338 days.

(21) Appl. No.: 12/369,782

(22) Filed: Feb. 12, 2009

(65) Prior Publication Data

US 2009/0209529 A1 Aug. 20, 2009

(30) Foreign Application Priority Data

Feb. 18, 2008 (EP) ..................... 08151546

(51) Int. Cl.
| | | |
|---|---|---|
| A61K 31/421 | (2006.01) | |
| A61K 31/506 | (2006.01) | |
| A61K 31/4439 | (2006.01) | |
| A61K 31/538 | (2006.01) | |
| C07D 263/28 | (2006.01) | |
| C07D 413/10 | (2006.01) | |

(52) U.S. Cl. ..................... 514/230.5; 514/256; 514/340; 514/374; 544/105; 544/333; 546/271.4; 548/233

(58) Field of Classification Search .................. None
See application file for complete search history.

(56) References Cited

U.S. PATENT DOCUMENTS
2008/0261920 A1* 10/2008 Galley et al. .............. 514/63

FOREIGN PATENT DOCUMENTS
| | | |
|---|---|---|
| EP | 0167459 | 1/1986 |
| WO | WO 2008/092785 | 8/2008 |

OTHER PUBLICATIONS

Hardy et al., Science, vol. 297(5580) pp. 353-356 (2002).
Selkoe, Annu. Rev. Cell. Biol. vol. 10 pp. 373-403 (1994).
Vassar et al., Science, vol. 286(5440) pp. 735-741 (1999).
Luo et al., Nat. Neurosci. vol. 4(3) pp. 231-232 (2001).
Roberds et al., Hum. Mol. Genet vol. 10(12) pp. 1317-1324 (2001).
McConlogue et al., J. Biol. Chem. vol. 282(36) pp. 26326-26334 (2007).
Still, C., J. Org. Chem. vol. 43 pp. 2923-2925 (1978).
Pine et al., Synthesis pp. 165-167 (1991).

* cited by examiner

*Primary Examiner* — Kamal Saeed
(74) *Attorney, Agent, or Firm* — George W. Johnston; Patricia S. Rocha-Tramaloni; Kimberly J. Prior

(57) ABSTRACT

The present invention relates to a compounds of formula I

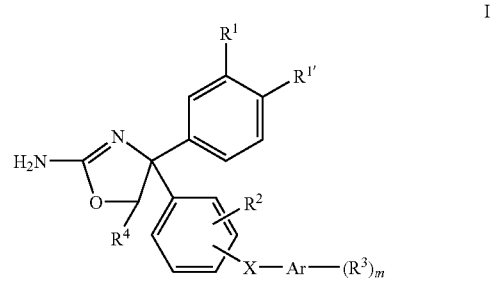

wherein $R^1$, $R^{1'}$, $R^2$, $R^3$, $R^4$, X, Ar, and m are as defined in the specification and claims and pharmaceutically active acid addition salts thereof. Compounds of the invention have Asp2 (β-secretase, BACE 1 or Memapsin-2) inhibitory activity and are useful for the treatment of diseases characterized by elevated β-amyloid levels or β-amyloid deposits, particularly Alzheimer's disease.

18 Claims, No Drawings

4,5-DIHYDRO-OXAZOL-2-YL AMINE DERIVATIVES

PRIORITY TO RELATED APPLICATION(S)

This application claims the benefit of European Patent Application No. 08151546.2, filed Feb. 18, 2008, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (1, 2) which also develop AD-like symptoms in early life. Both pathologies are also commonly observed in patients with Down's syndrome (trisomy 21). Neurofibrillar tangles are intracellular aggregates of the microtubule-associated protein tau (MAPT). Amyloid plaques occur in the extracellular space, their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes (APP, PSN1, PSN2) lead to increased level of Aβ-peptides and early brain amyloidosis; 4) transgenic mice which express such FAD genes develop a pathology which bears many resemblances to the human disease.

Aβ peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2, BACE for beta-site APP-cleaving enzyme) is an aspartyl protease which is anchored into the membrane by a transmembrane domain (3). It is expressed in many tissues of the human organism but its level is especially high in the CNS. Genetic ablation of the BACE1 gene in mice has clearly shown that its activity is essential for the processing of APP which leads to the generation of the Aβ-peptides, in the absence of BACE1 no Aβ-peptides are produced (4, 5). Mice which have been genetically engineered to express the human APP gene and which form extensive amyloid plaques and Alzheimer's disease like pathologies during aging fail to do so when β-secretase activity is reduced by genetic ablation of one of the BACE1 alleles (6). It is thus presumed that inhibitors of BACE1 activity can be useful agents for therapeutic intervention in AD.

LITERATURE

1. Hardy et al., The amyloid hypothesis of Alzheimer's disease: progress and problems on the road to therapeutics, *Science.* 2002 Jul. 19; 297(5580):353-6
2. Selkoe, Cell biology of the amyloid beta-protein precursor and the mechanism of Alzheimer's disease, *Annu Rev Cell Biol.* 1994; 10:373-403
3. Vassar et al., Beta-secretase cleavage of Alzheimer's amyloid precursor protein by the transmembrane aspartic protease BACE, *Science.* 1999 Oct. 22; 286(5440):735
4. Luo et al., Mice deficient in BACE1, the Alzheimer's beta-secretase, have normal phenotype and abolished beta-amyloid generation, *Nat. Neurosci.* 2001 March; 4(3):231-2.
5. Roberds et al., BACE knockout mice are healthy despite lacking the primary beta-secretase activity in brain: implications for Alzheimer's disease therapeutics, *Hum Mol. Genet.* 2001 Jun. 1; 10(12):1317-24
6. McConlogue et al., Partial reduction of BACE1 has dramatic effects on Alzheimer plaque and synaptic pathology in APP Transgenic Mice. *J Biol. Chem.* 2007 Sep. 7; 282 (36):26326

SUMMARY OF THE INVENTION

The present invention provides compound of formula I

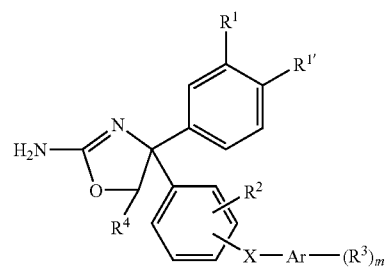

wherein
$R^1$ and $R^{1'}$ are each independently hydrogen, halogen, lower alkoxy, lower alkyl, lower alkyl substituted by halogen, lower alkoxy substituted by halogen, lower alkoxy substituted by hydroxy, —O—$(CH_2)_o$—O-lower alkyl, —$(CH_2)_p$—O-lower alkyl, —O—$S(O)_2$-lower alkyl, —$S(O)_2$-lower alkyl or cyano;
or $R^1$ and $R^{1'}$ together are —$(CH_2)_2$O—, —O—$CH_2$—O— or —N(R)—$(CH_2)_2$—O— which forms a 5- or 6-membered ring with the carbon atoms to which they are attached;
R is hydrogen or lower alkyl;
$R^2$ is hydrogen, halogen, lower alkyl, cyano, lower alkoxy, lower alkoxy substituted by halogen, —O—$(CH_2)$—$C_{3-6}$-cycloalkyl or $(CH_2)_o$—O-lower alkyl;
each $R^3$ is independently hydrogen, cyano, lower alkoxy, lower alkyl, lower alkyl substituted by halogen, lower alkoxy substituted by halogen, —$CH_2$—O-lower alkyl, —C(O)N-di-lower alkyl or halogen;

R⁴ is hydrogen or lower alkyl;

X is a bond, —NH—C(O)—, —NH— or —O—CH₂;

Ar is aryl or heteroaryl;

and wherein —X—Ar—(R³)ₘ is in the 3 or 4 position of the phenyl ring; or X—Ar—(R³)ₘ represents benzo[1,3]dioxole;

m is 0, 1 or 2;

o is 2 or 3; and p is 1, 2 or 3;

or a pharmaceutically active acid addition salt thereof.

The invention also provides pharmaceutical compositions containing compounds of formula I or a pharmaceutically active acid addition salt thereof and a pharmaceutically acceptable carrier. The invention further provides methods for the manufacture of the compounds and compositions of the invention.

Compounds of the invention have Asp2 (β-secretase, BACE 1 or Memapsin-2) inhibitory activity and are useful in the treatment of diseases characterized by elevated β-amyloid levels or β-amyloid deposits, particularly Alzheimer's disease. Therefore, the invention also provides methods of the treatment of diseases characterized by elevated β-amyloid levels or β-amyloid deposits. In particular, the invention provides methods for the treatment of Alzheimer's disease.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like. Preferred lower alkyl groups are groups with 1-4 carbon atoms.

The term "halogen" denotes chlorine, iodine, fluorine and bromine.

The term "lower alkyl substituted by halogen" denotes an alkyl group as defined above, wherein at least one hydrogen atom is replaced by halogen, for example —CF₃, —CHF₂, —CH₂CF₃, —CH₂CH₂CF₃, —CH₂CF₂CF₃ and the like. Preferred lower alkyl substituted by halogen groups are groups having 1-4 carbon atoms.

The term "lower alkoxy" denotes a group which is an alkyl group as defined above which is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes an alkoxy group as defined above wherein at least one hydrogen atom in the alkyl group is replaced by halogen. Preferred lower alkoxy substituted by halogen groups are groups having 1-4 carbon atoms.

The term "lower alkoxy substituted by hydroxy" denotes an alkoxy group as defined above wherein at least one hydrogen atom in the alkyl group is replaced by hydroxy. Preferred lower alkoxy substituted by halogen groups are groups having 1-4 carbon atoms.

The term "aryl" denotes a 6-10 membered aromatic carbon ring system, for example phenyl or naphthyl.

The term "heteroaryl" denotes a 6-10 membered ring system, wherein at least one ring atom is N, O or S with the remaining ring atoms being carbon and wherein at least one ring in the ring system is aromatic, for example pyridinyl, pyrimidinyl, quinolinyl, indolyl, benzo[1.3]dioxolyl, isoxazolyl or pyrazolyl.

The term "or R¹ and R¹' together are —(CH₂)₂O—, —O—CH₂—O— or —N(R)CH₂CH₂O— which forms a 5- or 6-membered ring with the carbon atoms to which they are attached and R is hydrogen or lower alkyl" denotes the following groups:

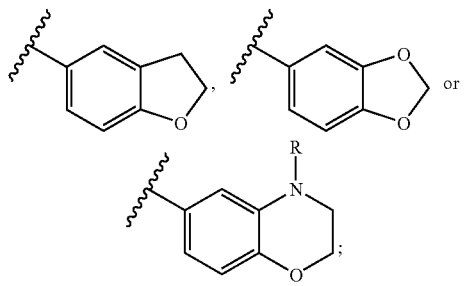

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as formic acid, hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those, wherein —X—Ar—(R³)ₘ is in the 3-position, X is a bond and Ar is phenyl, for example the following compounds (RS)-4-(3'-chloro-biphenyl-3-yl)-4-(4-methoxy-phenyl)-4,5-dihydro-oxazol-2-ylamine;

(RS)-4-(3'-methoxy-biphenyl-3-yl)-4-(4-methoxy-phenyl)-4,5-dihydro-oxazol-2-ylamine;

(RS)-4-(6-fluoro-3'-methoxy-biphenyl-3-yl)-4-(4-methoxy-3-methyl-phenyl)-4,5-dihydro-oxazol-2-ylamine;

(RS)-4-(5'-chloro-2'-fluoro-biphenyl-3-yl)-4-(4-methoxy-phenyl)-4,5-dihydro-oxazol-2-ylamine;

(RS)-4-(3'-chloro-biphenyl-3-yl)-4-(4-methoxy-phenyl)-4,5-dihydro-oxazol-2-ylamine;

(R)-4-(3'-chloro-biphenyl-3-yl)-4-(4-methoxy-phenyl)-4,5-dihydro-oxazol-2-ylamine;

(RS)-4-(3'-chloro-biphenyl-3-yl)-4-(4-methoxy-3-methyl-phenyl)-4,5-dihydro-oxazol-2-ylamine;

(RS)-4-(3'-methoxy-biphenyl-3-yl)-4-(4-methoxy-3-methyl-phenyl)-4,5-dihydro-oxazol-2-ylamine;

(RS)-4-(3'-chloro-biphenyl-3-yl)-4-(4-ethoxy-3-methyl-phenyl)-4,5-dihydro-oxazol-2-ylamine;

(RS)-4-(3'-chloro-biphenyl-3-yl)-4-(4-difluoromethoxy-3-methyl-phenyl)-4,5-dihydro-oxazol-2-ylamine;

(RS)-4-(4-difluoromethoxy-3-methyl-phenyl)-4-(2'-fluoro-5'-methoxy-biphenyl-3-yl)-4,5-dihydro-oxazol-2-ylamine;

(RS)-4-(3-chloro-4-methoxy-phenyl)-4-(6,2'-difluoro-5'-methoxy-biphenyl-3-yl)-4,5-dihydro-oxazol-2-ylamine;

(RS)-4-(6,2'-difluoro-5'-methoxy-biphenyl-3-yl)-4-(4-difluoromethoxy-3-methyl-phenyl)-4,5-dihydro-oxazol-2-ylamine;

(RS)-4-(4-difluoromethoxy-2-methyl-phenyl)-4-(2'-fluoro-5'-methoxy-biphenyl-3-yl)-4,5-dihydro-oxazol-2-ylamine; and (RS)-4-(3'-chloro-biphenyl-3-yl)-4-(4-difluoromethoxy-2-methyl-phenyl)-4,5-dihydro-oxazol-2-ylamine.

Preferred compounds of formula I are further those, wherein —X—Ar—(R³)$_m$ is in the 3-position, X is a bond and Ar is heteroaryl, for example the following compounds (RS)-4-[3-(2-Fluoro-pyridin-3-yl)-phenyl]-4-(4-methoxy-phenyl)-4,5-dihydro-oxazol-2-yl-amine;
(RS)-4-(4-fluoro-3-pyrimidin-5-yl-phenyl)-4-(4-methoxy-3-methyl-phenyl)-4,5-dihydro-oxazol-2-ylamine;
(RS)-4-(4-fluoro-3-pyridin-3-yl-phenyl)-4-(4-methoxy-3-methyl-phenyl)-4,5-dihydro-oxazol-2-ylamine;
(RS)-4-[4-fluoro-3-(6-fluoro-pyridin-3-yl)-phenyl]-4-(4-methoxy-3-methyl-phenyl)-4,5-dihydro-oxazol-2-ylamine;
(RS)-4-[3-(2-fluoro-pyridin-3-yl)-phenyl]-4-(4-methoxy-3-methyl-phenyl)-4,5-dihydro-oxazol-2-ylamine;
(RS)-4-(4-methoxy-3-methyl-phenyl)-4-[3-(5-methoxy-pyridin-3-yl)-phenyl]-4,5-dihydro-oxazol-2-ylamine;
(RS)-4-[4-fluoro-3-(5-methoxy-pyridin-3-yl)-phenyl]-4-(4-methoxy-3-methyl-phenyl)-4,5-dihydro-oxazol-2-ylamine;
(RS)-4-[4-fluoro-3-(5-fluoro-pyridin-3-yl)-phenyl]-4-(4-methoxy-3-methyl-phenyl)-4,5-dihydro-oxazol-2-ylamine;
(RS)-4-[4-fluoro-3-(2-fluoro-pyridin-3-yl)-phenyl]-4-(4-methoxy-3-methyl-phenyl)-4,5-dihydro-oxazol-2-ylamine;
(RS)-4-(4-ethoxy-3-methyl-phenyl)-4-(3-pyrimidin-5-yl-phenyl)-4,5-dihydro-oxazol-2-ylamine;
(RS)-4-(3-chloro-4-methoxy-phenyl)-4-[3-(2-fluoro-pyridin-3-yl)-phenyl]-4,5-dihydro-oxazol-2-ylamine;
(RS)-4-(3-chloro-4-methoxy-phenyl)-4-(3-pyrimidin-5-yl-phenyl)-4,5-dihydro-oxazol-2-ylamine;
(RS)-4-(3-chloro-4-methoxy-phenyl)-4-[3-(5-methoxy-pyridin-3-yl)-phenyl]-4,5-dihydro-oxazol-2-ylamine;
(RS)-4-(4-ethoxy-3-methyl-phenyl)-4-[3-(5-fluoro-pyridin-3-yl)-phenyl]-4,5-dihydro-oxazol-2-ylamine;
(RS)-4-(3-chloro-4-methoxy-phenyl)-4-[3-(5-fluoro-pyridin-3-yl)-phenyl]-4,5-dihydro-oxazol-2-ylamine;
(RS)-4-(4-ethoxy-phenyl)-4-[3-(5-methoxy-pyridin-3-yl)-phenyl]-4,5-dihydro-oxazol-2-ylamine;
(RS)-4-(4-difluoromethoxy-phenyl)-4-(3-pyrimidin-5-yl-phenyl)-4,5-dihydro-oxazol-2-ylamine;
(RS)-4-(4-difluoromethoxy-phenyl)-4-[3-(5-fluoro-pyridin-3-yl-phenyl]-4,5-dihydro-oxazol-2-ylamine;
(RS)-4-(4-difluoromethoxy-phenyl)-4-[3-(2-fluoro-pyridin-3-yl)-phenyl]-4,5-dihydro-oxazol-2-ylamine;
(RS)-4-(4-difluoromethoxy-phenyl)-4-[3-(5-methoxy-pyridin-3-yl)-phenyl]-4,5-dihydro-oxazol-2-yl amine;
(RS)-4-(3-fluoro-4-methoxy-phenyl)-4-[3-(5-methoxy-pyridin-3-yl)-phenyl]-4,5-dihydro-oxazol-2-ylamine;
(RS)-4-[3-(5-chloro-pyridin-3-yl)-phenyl]-4-(4-difluoromethoxy-3-methyl-phenyl)-4,5-dihydro-oxazol-2-ylamine;
(R)-4-[3-(5-chloro-pyridin-3-yl)-phenyl]-4-(4-difluoromethoxy-3-methyl-phenyl)-4,5-dihydro-oxazol-2-ylamine;
(RS)-4-(4-difluoromethoxy-3-methyl-phenyl)-4-(3-pyridin-3-yl-phenyl)-4,5-dihydro-oxazol-2-ylamine;
(RS)-4-(4-difluoromethoxy-3-methyl-phenyl)-4-[3-(2-fluoro-pyridin-3-yl)-phenyl]-4,5-dihydro-oxazol-2-ylamine;
(RS)-4-(4-difluoromethoxy-3-methyl-phenyl)-4-(3-pyrimidin-5-yl-phenyl)-4,5-dihydro-oxazol-2-ylamine;
(RS)-4-(4-difluoromethoxy-3-methyl-phenyl)-4-[3-(5-methoxy-pyridin-3-yl)-phenyl]-4,5-dihydro-oxazol-2-ylamine;
(RS)-4-(4-difluoromethoxy-3-methyl-phenyl)-4-[3-(5-fluoro-pyridin-3-yl)-phenyl]-4,5-dihydro-oxazol-2-ylamine;
(RS)-4-(4-difluoromethoxy-3-methyl-phenyl)-4-[3-(5-methyl-pyridin-3-yl)-phenyl]-4,5-dihydro-oxazol-2-ylamine;
(RS)-4-(4-difluoromethoxy-3-methyl-phenyl)-4-[3-(2-fluoro-5-methyl-pyridin-3-yl)-phenyl]-4,5-dihydro-oxazol-2-ylamine;
(RS)-4-(3-chloro-4-methoxy-phenyl)-4-[3-(5-chloro-pyridin-3-yl)-4-fluoro-phenyl]-4,5-dihydro-oxazol-2-ylamine;
(RS)-4-(3-chloro-4-methoxy-phenyl)-4-(4-fluoro-3-pyridin-3-yl-phenyl)-4,5-dihydro-oxazol-2-ylamine;
(RS)-4-(3-chloro-4-methoxy-phenyl)-4-[4-fluoro-3-(5-methoxy-pyridin-3-yl)-phenyl]-4,5-dihydro-oxazol-2-ylamine;
(RS)-4-(3-chloro-4-methoxy-phenyl)-4-[4-fluoro-3-(5-fluoro-pyridin-3-yl)-phenyl]-4,5-dihydro-oxazol-2-ylamine;
(RS)-4-(3-chloro-4-methoxy-phenyl)-4-[4-fluoro-3-(2-fluoro-5-methyl-pyridin-3-yl)-phenyl]-4,5-dihydro-oxazol-2-ylamine;
(RS)-4-[3-(5-chloro-pyridin-3-yl)-phenyl]-4-(4-difluoromethoxy-3-fluoro-phenyl)-4,5-dihydro-oxazol-2-ylamine;
(RS)-4-(3-chloro-4-difluoromethoxy-phenyl)-4-[3-(5-methoxy-pyridin-3-yl)-phenyl]-4,5-dihydro-oxazol-2-ylamine;
(RS)-4-(3-chloro-4-difluoromethoxy-phenyl)-4-(3-pyrimidin-5-yl-phenyl)-4,5-dihydro-oxazol-2-ylamine;
(RS)-4-(4-difluoromethoxy-3-methyl-phenyl)-4-(4-fluoro-3-pyridin-3-yl-phenyl)-4,5-dihydro-oxazol-2-ylamine;
(RS)-4-(4-difluoromethoxy-3-methyl-phenyl)-4-(4-fluoro-3-pyrimidin-5-yl-phenyl)-4,5-dihydro-oxazol-2-ylamine;
(RS)-4-(4-difluoromethoxy-3-methyl-phenyl)-4-[4-fluoro-3-(5-methoxy-pyridin-3-yl)-phenyl]-4,5-d i hydro-oxazol-2-ylamine;
(RS)-4-(4-difluoromethoxy-3-methyl-phenyl)-4-[4-fluoro-1-(5-fluoro-pyridin-3-yl)-phenyl]-4,5-dihydro-oxazol-2-ylamine;
(RS)-4-(4-difluoromethoxy-2-methyl-phenyl)-4-(3-pyrimidin-5-yl-phenyl)-4,5-dihydro-oxazol-2-ylamine;
(RS)-4-(4-difluoromethoxy-2-methyl-phenyl)-4-[3-(2-fluoro-5-methyl-pyridin-3-yl)-phenyl]-4,5-dihydro-oxazol-2-ylamine;
(RS)-4-(4-difluoromethoxy-2-fluoro-phenyl)-4-[3-(5-fluoro-pyridin-3-yl)-phenyl]-4,5-dihydro-oxazol-2-ylamine;
(RS)-4-(4-difluoromethoxy-2-methyl-phenyl)-4-[3-(5-fluoro-pyridin-3-yl)-phenyl]-4,5-dihydro-oxazol-2-ylamine;
(RS)-4-(4-difluoromethoxy-2-methyl-phenyl)-4-[3-(5-methoxy-pyridin-3-yl)-phenyl]-4,5-dihydro-oxazol-2-ylamine;
(RS)-4-[3-(5-chloro-pyridin-3-yl)-phenyl]-4-[4-(2-fluoro-ethoxy)-phenyl]-4,5-dihydro-oxazol-2-ylamine;
(RS)-5-{3-[2-amino-4-(4-difluoromethoxy-2-methyl-phenyl)-4,5-dihydro-oxazol-4-yl]-phenyl}-nicotinonitrile;
(RS)-4-[3-(5-chloro-pyridin-3-yl)-phenyl]-4-(4-difluoromethoxy-2-methyl-phenyl)-4,5-dihydro-oxazol-2-ylamine;
(RS)-4-[3-(6-chloro-pyrazin-2-yl)-phenyl]-4-(4-difluoromethoxy-3-methyl-phenyl)-4,5-dihydro-oxazol-2-ylamine;
(RS)-5-{3-[2-amino-4-(4-difluoromethoxy-3-methyl-phenyl)-4,5-dihydro-oxazol-4-yl]-phenyl}-nicotinonitrile;

(RS)-4-(4-difluoromethoxy-3-methyl-phenyl)-4-(3-pyrazin-2-yl-phenyl)-4,5-dihydro-oxazol-2-ylamine; and (RS)-4-[3-(5-chloro-pyridin-3-yl)-4-fluoro-phenyl]-4-(4-difluoromethoxy-3-methyl-phenyl)-4,5-dihydro-oxazol-2-ylamine.

Preferred compounds of formula I are further those, wherein —X—Ar—$(R^3)_m$ is in the 3-position, X is —NH— and Ar is phenyl, for example the following compounds (RS)-4-(4-difluoromethoxy-3-methyl-phenyl)-4-[3-ethoxy-5-(3-methoxy-phenylamino)-phenyl]-4,5-dihydro-oxazol-2-ylamine;

(RS)-4-(4-difluoromethoxy-3-methyl-phenyl)-4-(3-ethoxymethyl-5-phenylamino-phenyl)-4,5-dihydro-oxazol-2-ylamine;

(RS)-4-(4-difluoromethoxy-3-methyl-phenyl)-4-[3-ethoxymethyl-5-(3-methoxy-phenylamino)-phenyl]-4,5-dihydro-oxazol-2-ylamine;

(RS)-4-(3-ethoxymethyl-5-phenylamino-phenyl)-4-(4-methoxy-3-methyl-phenyl)-4,5-dihydro-oxazol-2-ylamine; and (RS)-4-[3-(2-methoxy-ethyl)-5-phenylamino-phenyl]-4-(4-methoxy-3-methyl-phenyl)-4,5-dihydro-oxazol-2-ylamine.

Preferred compounds of formula I are further those, wherein —X—Ar—$(R^3)_m$ is in the 3-position, X is —NH— and Ar is heteroaryl.

Preferred compounds of formula I are further those, wherein —X—Ar—$(R^3)$, is in the 3-position, X is —NHC(O)— and Ar is phenyl.

Preferred compounds of formula I are further those, wherein —X—Ar—$(R^3)_m$ is in the 4-position, X is a bond and Ar is phenyl.

Preferred compounds of formula I are further those, wherein —X—Ar—$(R^3)_m$ is in the 3-position, X is —O—CH$_2$— and Ar is phenyl.

One embodiment of the invention are compound of formula

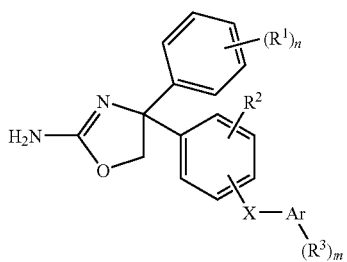

I-A wherein
each R is independently hydrogen, halogen, lower alkoxy, lower alkyl, lower alkyl substituted by halogen or lower alkoxy substituted by halogen;
$R^2$ is H or halogen;
each $R^3$ is independently hydrogen, cyano, lower alkoxy, lower alkyl, lower alkyl substituted by halogen, lower alkoxy substituted by halogen, —CH$_2$—O-lower alkyl or halogen;
X is a bond, —NHC(O)—, —NH—, NHCH$_2$—, —CH=CH— or —O—;
Ar is aryl or heteroaryl;
and wherein —X—Ar—$(R^3)_m$ is in the 3 or 4 position of the phenyl ring;
n is 1 or 2; and
m is 1 or 2;
or a pharmaceutically acceptable acid addition salt thereof.

The present compounds of formula I and their pharmaceutically acceptable salts can be prepared by methods known in the art, for example, by processes described below, which comprises
a) reacting a compound of formula

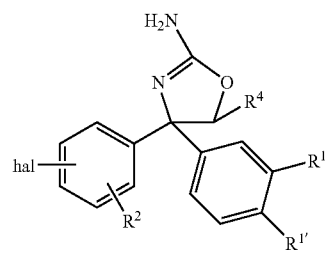

II with a boronic acid or ester of a compound of formula III

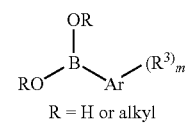

III

R = H or alkyl to obtain a compound of formula I

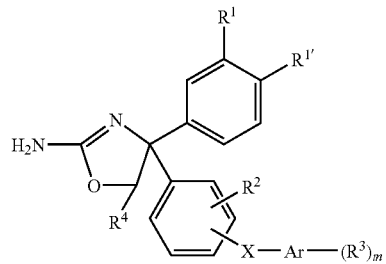

I wherein the substituents are as described above, hal is halogen such as Br or I, and the group —X—Ar—$(R^3)_m$ is in the 3 or 4-position of the phenyl group, and
b) if desired, converting the compounds obtained into pharmaceutically acceptable acid addition salts.

Compounds of the present invention possess one asymmetric carbon atom and are thus capable of existing in the form of optical isomers as well as in the form of racemic or nonracemic mixtures. The invention includes all stereoisomeric forms, including individual diastereoisomers and enantiomers of the compound of formula (I) as well as racemic and non-racemic mixtures thereof.

The optical isomers can be obtained by resolution of the racemic mixtures according to methods generally known to persons skilled in the art. A process for separation of optical isomers involves the use of column chromatography on a chiral phase optimally chosen to maximize the separation of the enantiomers.

EXPERIMENTAL PROCEDURES

General

All reagents and solvents were obtained commercially. Air and moisture sensitive liquid solutions were transferred via syringe. The course of reactions was followed by thin-layer chromatography (TLC) and/or liquid chromatography-mass spectrometry (LC-MS).

Unless otherwise specified all nuclear magnetic resonance spectra were recorded using a Varian Mercury Plus 400 MHz spectrometer equipped with a PFG ATB Broadband probe.

The 5 and 10 minute LC-MS methods were run using a waters 2795 separation module equipped with a Waters Micromass ZQ (ES ionisation) and Waters PDA 2996, using a Waters XTerra MS C18 3.5 µm 2.1×50 mm column.

Gradients were run using 0.1% formic acid/water and 0.1% formic acid/acetonitrile with gradient 5/95 to 95/5 in the run time indicated.

Preparative HLPC was run using a Waters 2767 system with a binary Gradient Module Waters 2525 pump and coupled to a Waters Micromass ZQ (ES) or Waters 2487 DAD, using a Supelco Discovery HS C18 5.0 µm 10×21.2 mm column All column chromatography was performed following the method of Still, C.; *J. Org Chem* 43, 2923 (1978). All TLC analyses were performed on silica gel (Merck 60 F254) and spots revealed by UV visualisation at 254 nm and KMnO$_4$ or ninhydrin stain.

All microwave reactions were performed in a CEM Discover instrument.

Alternatively, $^1$H NMR spectra may have been recorded on a Bruker AC-300 spectrometer at 25° C. with TMS (tetramethylsilane) or residual $^1$H of the given deuterated solvents as internal standards. Mass spectra (MS) may have been measured either with ion spray positive or negative (TSP or ISN) method on a Perkin-Elmer SCIEX API 300 or with electron impact method (EI, 70 eV) on a Finnigan MAT SSQ 7000 spectrometer. High resolution mass spectra (HRMS) may have been measured with nanospray positive (ISP) method on a Finnigan LTQ-FTMS spectrometer (7 Tesla) and the average of 7 scans is reported. Optical rotations may have been measured with a Perkin-Elmer 341 polarimeter. Melting points were taken on a Büch±510 melting point apparatus and are uncorrected. Elemental analysis was done by Solvias AG, Basel, Switzerland. Column chromatography may have been performed on Merck silica gel 60 (230-400 mesh). Analytical thin-layer chromatography may have been performed using Merck silica gel 60 F$_{254}$ precoated glass-backed plates and visualised by UV, cerium(IV) molybdophosphate, ninhydrin or iodoplatinate. Solvents and reagents may have been purchased from Fluka AG, Merck KGaA, Aldrich® or Acros Organics and used without further purification.

The compounds of Formula (I) can be prepared through a number of synthetic routes for example as illustrated in Schemes 1, 2 and 3.

The preparation of compounds of formula I of the present invention can be carried out in sequential or convergent synthetic routes. Syntheses of the compounds of the invention are shown in the following schemes 1, 2 and 3. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered.

Starting materials are either commercially available or can be prepared by methods analogous to the methods given below, by methods described in references cited in the description or in the examples, or by methods known in the art.

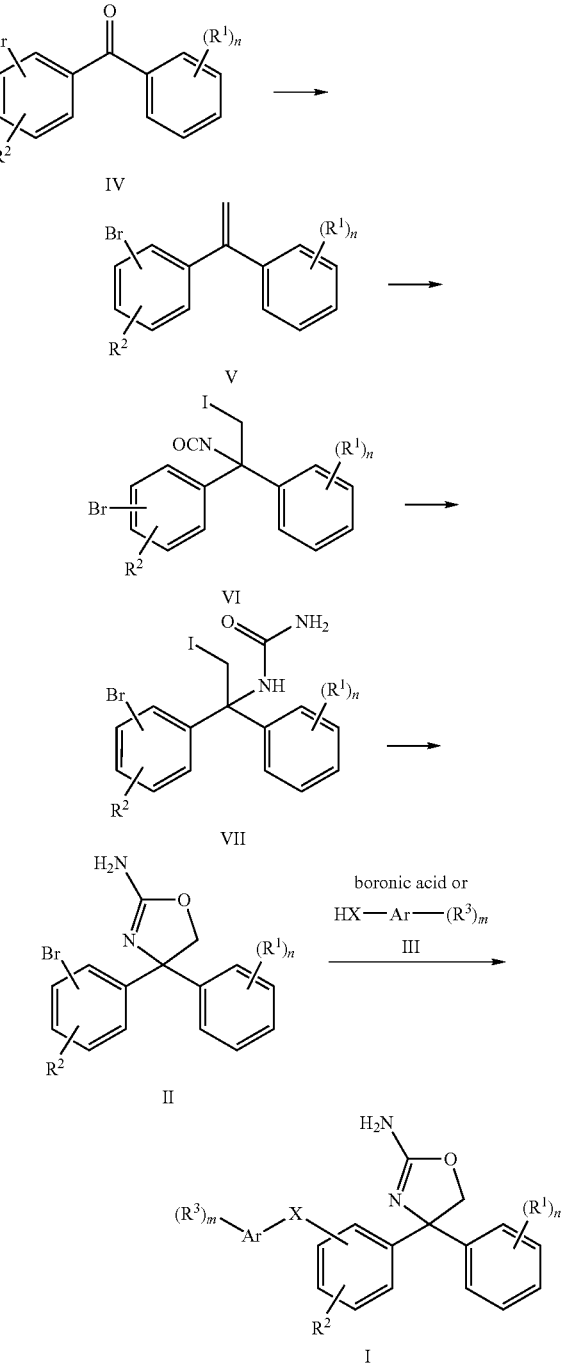

wherein the substituents are as described above, and the leaving group Br (which stands for halogen and which may also be T), and the group —X—Ar—(R$^3$)$_m$ is in the 3 or 4-position to the phenyl group. Furthermore, the group (R$^1$)$_n$ has the same meaning as R$^1$ and R$^{1'}$.

According to Scheme 1 the formation of a methyltriphenylphosphonium ylide produced by strong base such as butyllithium in solvents such as tetrahydrofuran or toluene at temperatures between −78° C. and 0° C. followed by addition of the bromobenzophenone IV yielded the desired alkenes V. The alkene can also be synthesized by Tebbe olefination. Both Tebbe's and Wittig methods used are described by Pine, H. S.; Shen, G. S. & Hoang, H. (Synthesis 1991, 165-167). The alkenes can then be reacted with a mixture of silver cyanate and iodine in solvents such as diethyl ether or mixtures of ethyl acetate and acetonitrile. The resultant iodoisocyantes VI can be reacted as crude with ammonia in methanol or by other methods such as passing ammonia gas through the reaction solution. The resultant material can then be heated in aqueous solution to yield the aminoxazolines II. More detailed description of the aminooxazoline synthesis is given in general methods 1 and 2. The resultant aryl bromides II can then be reacted with appropriate boronic acids or esters under Suzuki conditions to yield the final compounds 1. A more precise description of the conditions is given by general methods 3, 4 & 5. The compounds described in Scheme I can be isolated and purified by methods known to those skilled in the art, such as but not limited to ion exchange chromatography, solid phase extraction, liquid-liquid extraction, silica chromatography, crystallisation and preparative HPLC.

Boronic acids used include but are not limited to 2-fluoropyridine-3-boronic acid, 3-fluorophenylboronic acid, 3-chlorophenyl boronic acid, 2-fluoro-3-methoxyphenyl boronic acid, 5-fluoropyridine-3-boronic acid, 2-fluoro-5-methoxyphenylboronic acid, 3-fluoropyridine-4-boronic acid, 3-methoxyphenyl boronic acid, 3-methylphenyl boronic acid, 2-fluoropyridine-5-boronic acid, pyridine-3-boronic acid, 5-pyrimidinyl boronic acid, 5-chloro-2-fluorophenyl boronic acid, 3-cyanophenyl boronic acid or 5-cyanopyridine-3-boronic acid.

The compounds of Formula (I) can also be prepared through a number of synthetic routes including those in Schemes 2 and 2a,

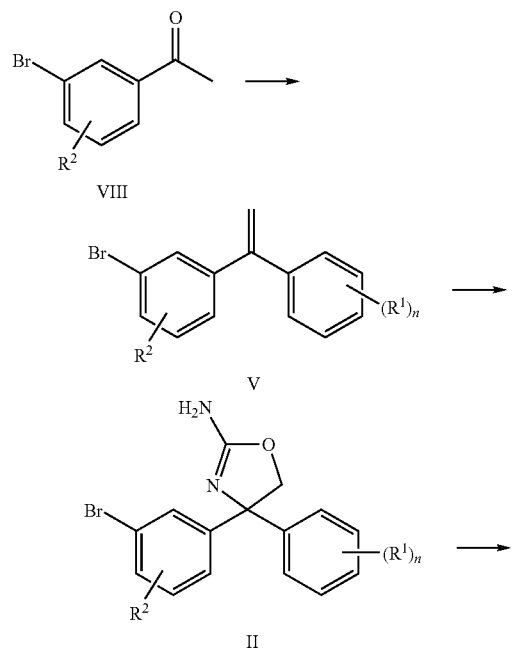

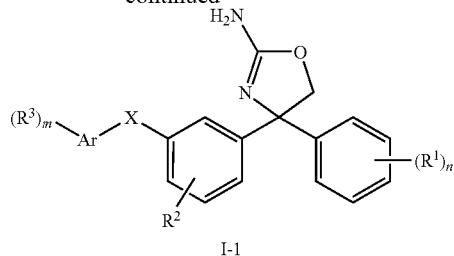

wherein the substituents are as described above, and the leaving group Br stands for halogen, which may also be I. Furthermore, the group $(R^1)_n$ has the same meaning as $R^1$ and $R^{1'}$.

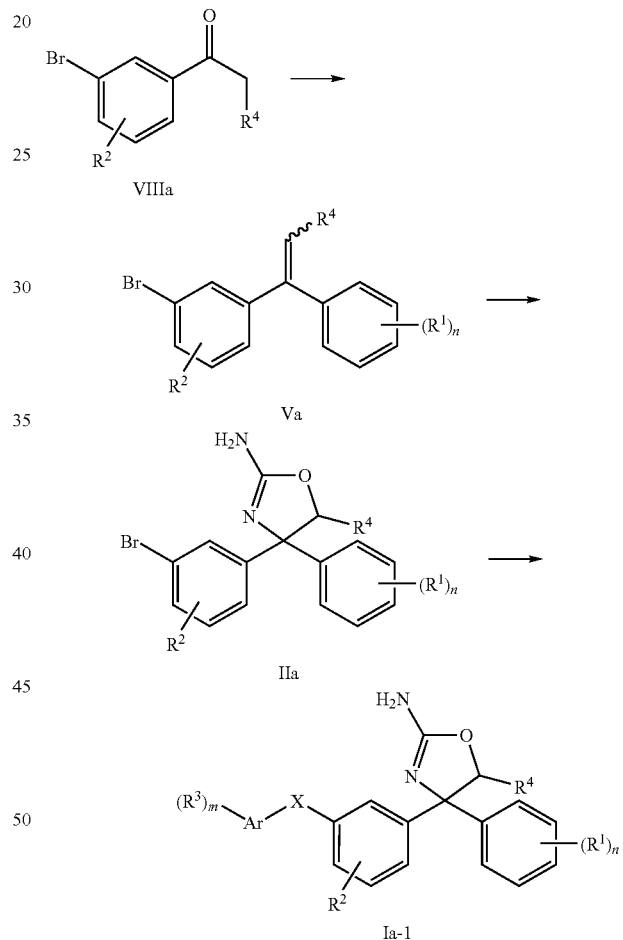

wherein the substituents are as described above and the leaving group Br stands for halogen, which may also be I. Furthermore, the group $(R^1)_n$ has the same meaning as $R^1$ and $R^{1'}$.

According to Scheme 2 and 2a, ketones of formula VIIIa can be reacted with the appropriate phenyl Grignard or phenyllithium in inert aprotic solvents such as diethyl ether or tetrahydrofuran. The crude product of this reaction can then be heated to reflux along with a catalytic amount of acid such as p-toluenesulfonic acid in an apolar solvent such as benzene or toluene using a Dean-Stark apparatus to remove the water produced. Other suitable conditions could include using a suitable dehydrating agent such as molecular sieves or magnesium sulfate. Alternatively the reaction can be effected by heating the crude in a mixture of 5:1 acetic acid:sulfuric acid. The aminoxazoline can then be synthesized according to general method 1 or 2. The Suzuki reactions can then be carried out according to the general method 3, 4 & 5 or by similar methods. Compounds described by Scheme 2 and 2a can be isolated and purified by methods known to those skilled in the art, such as but not limited to ion exchange chromatography, solid phase extraction, liquid-liquid extraction, Silica chromatography, crystallisation and preparative HPLC.

The compounds of formula (I) can also be prepared through a number of synthetic routes amongst which the ones illustrated in Scheme 3.

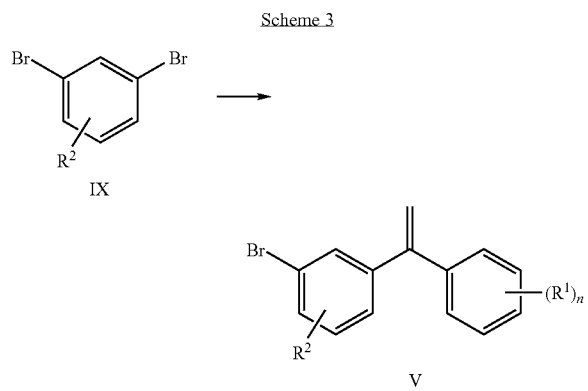

wherein the substituents are as described above and the leaving group Br stands for halogen and may also be I. Furthermore, the group $(R^1)_n$ has the same meaning as R' and $R^{1'}$.

In this scheme dibromobenzene is reacted with butyllithium in an inert aprotic solvent such as tetrahydrofuran or diethyl ether. The resulting lithium species was then reacted with a Oven acetophenone in the same vessel to yield a tertiary alcohol. The crude product of this reaction can then be heated to reflux along with a catalytic amount of acid such as p-toluenesulfonic acid in an apolar solvent such as benzene or toluene. Using these conditions a Dean-Stark apparatus was used to remove the deliberated water to yield the desired alkene. Other suitable conditions could use a suitable dehydrating agent such as molecular sieves or magnesium sulfate. Alternatively the reaction can be effected by heating the crude in a mixture of 5:1 acetic acid:sulfuric acid. The aminoxazoline can then be synthesized according to general method 1 or 2.

Non commercial acetophenones and benzophenones can be synthesized by routes such as scheme 4 or by other routes known to those skilled in the art.

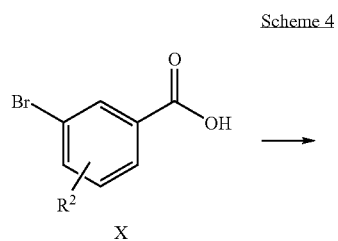

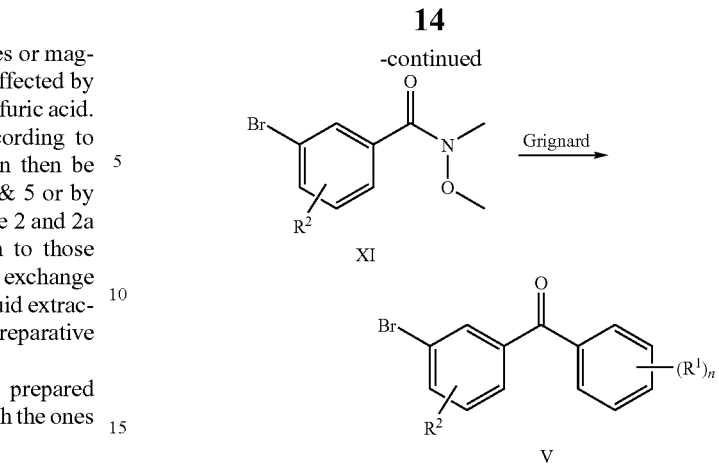

wherein the substituents are as described above and the leaving group Br stands for halogen and may also be I. Furthermore, the group $(R^1)_n$ has the same meaning as $R^1$ and $R^{1'}$.

Formation of the acyl chloride using an agent such as oxalylchloride or thionyl chloride followed by formation of the Weinreb amide using standard conditions such as triethylamine/dichloromethane. The amides can be reacted with organometallics such as methyl Grignard, phenyl Grignard or phenyllithium in inert aprotic solvents such as tetrahydrofuran or diethyl ether to yield the desired ketones. The detailed descriptions are given below.

General Method for the Synthesis of Aminoxazolines of Formula II (Building Block) from Biphenyl Alkenes General Method 1

A saturated solution of iodine (1 eq) in diethyl ether (1 g/5 mL) is added (ca 1.5 h) into a suspension of alkene (1 eq) and silver cyanate (1 eq) in diethyl ether (1 g/150 mL) at room temperature. The suspension is stirred overnight at room temperature after which point silver iodide was removed by filtration. Aqueous ammonia was then added in a large excess to the brown solution and stirred at room temperature for 4 h. The solvent was then evaporated, the crude material suspended in distilled wafer (20 mL) and refluxed for 1 h. The solution is then evaporated and the crude material solubilized in dichloromethane/methanol (1:1) and placed on an SCX-cartridge. The crude material is first washed with dichloromethane/methanol 1:1 then eluted with ammonia in methanol (2.0 M solution) to obtain the desired product. A white solid is generally recovered in yields between 30 and 40%.

General Method 2

A saturated solution of iodine (1.1 eq) in ethyl acetate (ca. 25 mL/g iodine) added dropwise (ca 25 min) into a suspension of alkene (1.0 eq) and silver cyanate (1.2 eq) in a 2:1 mixture acetonitrile/ethyl acetate (ca. 1 g/14 mL) at 0° C. The suspension is stirred for 1 h at room temperature after which solids are removed by filtration. The solvent is then evaporated. The crude material is suspended in a large excess of aqueous ammonia, stirred at room temperature for ca 4 h and then heated to reflux for ca 2 hours. The mixture is then cooled to room temperature and extracted with dichloromethane, concentrated and loaded onto an SCX-cartridge. The compound is purified by eluting first with dichloromethane/methanol 1:1 then with ammonia in methanol (2.0 M solution) to obtain the desired product. A white solid is Generally recovered in yields between 50 and 70%.

General Methods for the Suzuki Coupling from Building Block II to Desired Compounds of Formula I General Method 3

A degassed solution of aminoxazoline (1 eq) in ethanol/toluene 1:1 (2 mL for 0.30 mmol) is added to a microwave tube which has been charged with a given aryl boronic acid or ester (2 eq) and cesium carbonate (3 eq). Tetrakis(triphenylphosphine)palladium(0) (0.1 eq) is then added, the tube is sealed and placed in a microwave reactor where it is heated to 110° C. for 25 minutes (max power: 150 W). Upon completion, water (1 mL for 0.3 mmol) is added and the mixture is stirred for 5 minutes. The organic layer is then removed and loaded onto an SCX-cartridge. Dichloromethane/methanol 1:1 is passed through the column to remove impurities and the biaryl aminoxazoline is eluted with ammonia in methanol (2.0 M solution). The crude product is purified by mass triggered preparative HPLC or by silica gel chromatography (eluting with dichloromethane/methanol 0-5%).

General Method 4 (for Chloroaryl Boronic Acid or Ester)

A degassed solution of aminoxazoline (1 eq) in ethanol/toluene 1:1 (2 mL for 0.30 mmol) is added to a microwave tube which has been charged with a given aryl boronic acid or ester (1.2 eq) and cesium carbonate (3 eq). Tetrakis(triphenylphosphine)palladium(0) (0.1 eq) is then added, the tube is sealed and placed in a microwave reactor where it is heated to 110° C. for 25 minutes (max power: 150 W). Upon completion water (1 mL for 0.30 mmol) is added and the mixture is stirred for 5 minutes. The organic layer is then removed and loaded onto an SCX-cartridge. Dichloromethane/methanol 1:1 is passed through the column to remove impurities and the biaryl aminoxazoline is eluted with ammonia in methanol (2.0 M solution). The crude product is purified by mass triggered preparative HPLC or by silica gel chromatography (eluting with di chloromethane/methanol 0-5%).

General Method 5

A degassed solution of aminoxazoline (1 eq) in dimethoxyethane (2 mL for 0.30 mmol) is added into a tube which has been charged with a mixture of aryl boronic acid or ester (1.2 eq) and sodium carbonate (1 M aq soln, 2.3 eq); tetrakis(triphenylphosphine)palladium(0) (0.1 eq) is then added; the tube is sealed and heated to 85° C. overnight. Upon completion, water (~1 mL for 0.30 mmol) is added and the mixture is stirred for 5 minutes. The organic layer is then removed and loaded onto an SCX-cartridge. Dichloromethane/methanol 1:1 is passed through the column to remove impurities and the biaryl aminoxazoline is eluted with ammonia in methanol (2.0 M solution). The crude product is purified by mass triggered preparative HPLC or by silica gel chromatography (eluting with dichloromethane/methanol 0-5%).

Preparation of Building Block A (RS)-4-(3-Bromophenyl)-4-(phenyl)-4,5-dihydro-oxazol-2-ylamine 1-Bromo-3-(1-phenyl-vinyl)-benzene [29265-79-0]

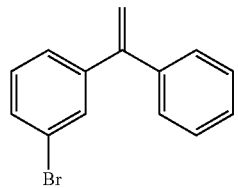

To a solution of 3-bromobenzophenone (2.2 g, 8.5 mmol, 1 eq) in 20 mL of dry tetrahydrofuran at 0° C. under $N_2$ atmosphere, was added a toluene solution of the Tebbe's reagent (17 mL of 0.5 M solution, 8.5 mmol, 1 eq.) and the mixture was allowed to warm to room temperature. The reaction mixture was examined after 20 min by TLC (cyclohexane/ethyl acetate 2%) which showed complete conversion to the desired product. Diethyl ether (50 mL) was added and some drops of NaOH 0.1 M aqueous solution was slowly added to quench the reaction. The mixture was dried over magnesium sulfate, passed through a pad of Celite and evaporated. The solid formed was triturated with cyclohexane and filtered; the solution was collected and concentrated under reduced pressure. The crude was purified by flash chromatography eluting with cyclohexane. 2.02 g of clean product was obtained as colorless liquid (yield: 91%).

Mass (calculated) $C_{14}H_{11}Br$ [259] $MH^+$ not observed

LC Rt=3.28, (5 min method) 91%

$^1$H-NMR (CDCl$_3$): 5.46 (d, 1H), 5.50 (d, 1H), 7.21 (m, 1H), 7.25 (m, 1H), 7.35 (m, 5H), 7.45 (m, 1H), 7.51 (m, 1H)

(RS)-4-(3-Bromophenyl)-4-(phenyl)-4,5-dihydro-oxazol-2-ylamine

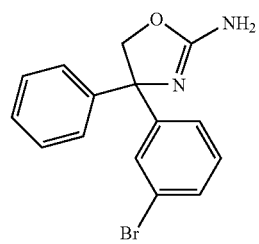

A saturated solution of iodine (2.79 g, 11 mmol, 1 eq) in 20 mL of diethyl ether was slowly dropped (ca 1.5 h) into a mixture of 1-bromo-3-(1-phenyl-vinyl)-benzene (2.8 g; 11 mmol, 1 eq) and silver cyanate (1.6 g; 11 mmol, 1 eq) in 50 mL of diethyl ether. The brown mixture was stirred overnight at room temperature. The silver iodide formed was removed by nitration. Aqueous ammonia (25% solution, 20 mL) was then added to the diethyl ether solution and the mixture was stirred vigorously at room temperature for 4 h; the reaction mixture was examined by LC-MS which showed formation of the urea intermediate. The solvent was evaporated and the crude was suspended in 20 mL of water and refluxed for 1 h. The aqueous mixture was evaporated; the crude was dissolved in dichloromethane/methanol 1:1 (10 mL) and passed through SCX (20 g) cartridge, washing with dichloromethane/methanol (100 mL) mixture and the product was recovered eluting with a solution 2.0 M of ammonia in methanol (2×50 mL). 1.39 g of product was obtained as a white solid (yield: 40%).

Mass (calculated) $C_{15}H_{13}BrN_2O$ [317]; (found) $[M+H^+]$= 318

LC Rt=2.12, (10 min method) 99%

$^1$H-NMR: (DMSO-d6): 4.64 (m, 2H), 5.39 (brs, 2H), 7.16 (t, 1H), 7.26 (m, 3H), 7.35 (m, 1H), 7.39 (m, 3H), 7.59 (t, 1H)

Preparation of Building Block B

Synthesis of 4-(4-Fluoro-3-bromophenyl)-4-(phenyl)-4,5-dihydro-oxazol-2-ylamine

2-Bromo-1-fluoro-4-(1-phenyl-vinyl)-benzene

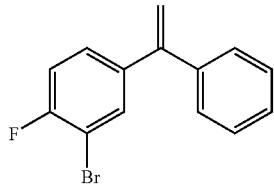

A solution of 4-fluoro-3-bromoacetophenone (3.0 g, 13.8 mmol, 1 eq) in 25 mL of dry tetrahydrofuran was added dropwise to a solution of phenyl magnesium bromide (15 mL of a 1.0 M solution in tetrahydrofuran, 15.2 mmol, 1.1 eq) in 40 mL of dry tetrahydrofuran at 0° C. and under an inert atmosphere. The reaction was stirred for 4 h while warming to room temperature. It was then was examined by TLC (cyclohexane/ethyl acetate 2%) which showed complete consumption of starting material. The solution was quenched with water, until gas evolution ceased, and 1 N hydrochloric acid was added to reach pH=5. Diethyl ether (20 mL) was added and the two phases were separated; the organic layer was dried over anhydrous magnesium sulfate, filtered and evaporated under reduced pressure. The crude (tertiary alcohol) and a catalytic amount of p-toluene sulfonic acid were dissolved in 100 mL of toluene and the mixture was heated to reflux for 3 h (using a Dean-Stark apparatus). The reaction mixture was examined by TLC (cyclohexane/ethyl acetate 3%) which showed complete consumption of starting material. The solvent was evaporated under reduced pressure and the crude was purified by flash chromatography eluting with neat cyclohexane. 2.1 g of desired product was obtained as a liquid (yield: 55%).

Mass (calculated) $C_{14}H_{10}BrF$ [277] MH⁻ not observed
LC Rt=3.03, 94% (5 min method)
$^1$H-NMR (CDCl$_3$): 5.43 (d, 1H), 5.48 (d, 1H), 7.08 (t, 1H), 7.25 (m, 1H), 7.31 (m, 5H), 7.54 (m, 1H)

(RS)-4-(4-Fluoro-3-bromophenyl)-4-(phenyl)-4,5-dihydro-oxazol-2-ylamine

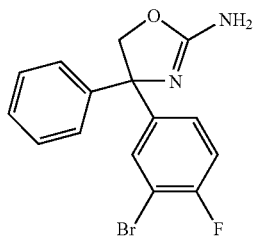

A solution of iodine (2.09 g, 8.27 mmol, 1.1 eq) in 65 mL of ethyl acetate was added dropwise (25 min) at 0° C. into a suspension of 2-bromo-1-fluoro-4-(1-phenyl-vinyl)-benzene (2.1 g, 7.52 mmol, 1.0 eq) and silver cyanate (1.35 g, 9.03 mmol, 1.2 eq) in a mixture of 19 mL of acetonitrile and 9 mL of ethyl acetate. After the addition, the reaction mixture was examined by LC-MS which showed complete consumption of the starting material. The mixture was filtered and the solution was concentrated under reduced pressure. The crude was suspended in 50 mL of ammonium hydroxide solution and stirred for 4 h at room temperature and at 60° C. overnight. The suspension was cooled and the product which precipitated was filtered, washed with water and dried under vacuum. 1.9 g of the desired product was obtained as yellow-pale solid (Yield: 75%).

Mass (calculated) $C_{15}H_{12}BrFN_2O$ [335]; (found) [M+H⁺]=336
LC Rt=1.30, (10 min method) 99%
$^1$H-NMR (CDCl$_3$): 4.04 (brs, 2H), 4.70 (d, 1H), 4.79 (d, 1H), 7.03 (t, 1H), 7.21 (m, 1H), 7.25 (m, 1H), 7.31 (m, 4H), 7.56 (dd, 1H)

Preparation of Building Block C (RS)-4-(3-Bromo-phenyl)-4-(4-methoxy-phenyl)-4,5-dihydro-oxazol-2-ylamine 1-[1-(3-Bromo-phenyl)-vinyl]-4-methoxy-benzene [34564-85-7]

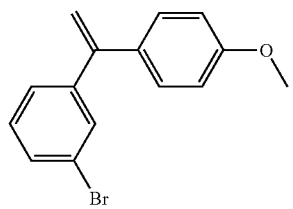

4-Bromoanisole (2.2 mL, 0.017 mol) in diethyl ether (10 mL) was added to a mixture of magnesium turnings (0.5 g, 0.02 mol) in diethyl ether (5 mL), at room temperature. The resulting mixture was heated to reflux for 1 h. The mixture was then cooled to room temperature. A solution of 3-bromoacetophenone (3.4 g, 0.017 mol) in diethyl ether was then added dropwise causing a gentle reflux. After 3 h heating to reflux the reaction mixture was examined by LC-MS which showed complete conversion to the desired product. The mixture was quenched with 1 N HCL solution (20 mL). Ethyl acetate (20 mL) was added and the aqueous phase was separated. The aqueous phase was then extracted with ethyl acetate (2×20 mL). The combined organic layers were dried over sodium sulfate, filtered and concentrated to dryness under vacuum. The crude was then dissolved in toluene (10 mL) and a catalytic amount of p-toluene sulfonic acid (30 mg) was added and refluxed for 3 h. The solvent was removed and the crude residue was purified by column chromatography (cyclohexane) to afford the title compound as a colourless oil (3.7 g, 74%).

$C_{15}H_4 3BrO$ Mass (calculated) [289]; (found) [M+H+]= 290/2
LC Rt=2.98 (5 min method, 215 nm)
$^1$H-NMR (CDCl$_3$): 3.83 (s, 3H), 5.38 (d, 2H), 6.88 (m, 2H), 7.18-7.43 (m, 4H), 7.43-751 (m, 21-1).

(RS)-4-(3-Bromo-phenyl)-4-(4-methoxy-phenyl)-4,5-dihydro-oxazol-2-ylamine

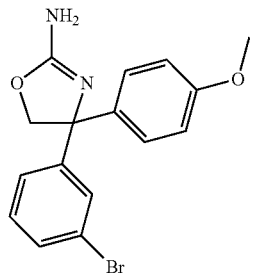

A solution of iodine (3.35 g, 13.2 mmol) in ethyl acetate (50 mL) was added dropwise to a cooled ice bath suspension of silver cyanate (2.28 g, 15 mmol), 1-[1-(3-bromo-phenyl)-vinyl]-4-methoxy-benzene (3.7 g, 12 mmol) in acetonitrile (30 mL) and ethyl acetate (15 mL). The resulting brown suspension was stirred for 1 h at room temperature at which point LC-MS indicated complete conversion of the starting material; the reaction mixture was filtered and concentrated under vacuum. Aqueous ammonia (25%, 80 mL) was added to the oil. A yellow gum formed and was stirred for 15 min at ambient temperature followed by 3 h at 105° C. The mixture was allowed to warm up to room temperature, extracted with ethyl acetate (2×50 mL), the organic layers dried and concentrated in vacuo. The residue was purified by catch-and-release SCX column; the crude was dissolved in dichloromethane/methanol 1:1 (10 mL) and passed through SCX (20 g) cartridge, washing with dichloromethane/methanol (100 mL) mixture. The product was recovered eluting with a solution 2.0 M of ammonia in methanol (2×50 mL) to afford the title compound as a yellow foam (3.17 g, 76%).

$C_{16}H_{15}BrN_2O_2$ Mass (calculated) [347]; (found) [M+H$^+$]= 349/50

LC Rt=1.38 (5 min method, 215 nm)

$^1$H-NMR (CDCl$_3$): 3.78 (s, 3H), 4.69 (d, 1H), 4.77 (d, 1H), 6.84 (m, 2H), 7.14-7.26 (m, 4H), 7.34 (m, 1H), 7.50 (m, 1H).

Preparation of Building Block D

(RS)-4-(3-Bromo-phenyl)-4-(3-methoxy-phenyl)-4,5-dihydro-oxazol-2-ylamine 1-(3-Bromo-phenyl)-1-(3-methoxy-phenyl)ethanol

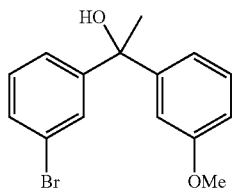

Diethyl ether (40 mL) was added to magnesium turnings (2.9 g, 120 mmol) in a dried apparatus consisting of 500 mL 3-necked flask, addition funnel and reflux condenser. Then 5 mL of a solution of 3-bromoanisole (19.6 g, 105 mmol) in diethyl ether (30 mL) was added, followed by a drop of bromine. The exothermic reaction started instantaneously, and the bromoanisole solution was added at such a rate to maintain gentle reflux of the reaction mixture (25 min). After complete addition, the light-brown hazy Grignard solution was stirred for another 20 min at room temperature. Then a solution of 3-bromoacetophenone (19.9 g, 100 mmol) in diethyl ether (30 mL) was added dropwise over 30 min, keeping the reaction mixture boiling gently. After the addition was complete, the mixture was refluxed for another 2.5 h, followed by cooling in an ice bath and careful quenching with 0.5 N cold HCl. After further dilution with ethyl acetate (100 mL) and water (100 mL), the layers were separated and the aqueous layer extracted once more with ethyl acetate (100 mL). The combined organic layers were washed with brine, dried over magnesium sulfate and concentrated under reduced pressure to give a yellow oil (31 g, quantitative yield), which was used as such in the next step.

$C_{15}H_{15}BrO_2$ Mass (calculated) [306/8]; (found) [M-water+H$^+$]=289/91

LC Rt-2.37, 59% (5 min method, 215 nm)

$^1$H-NMR (d$_6$-DMSO): 3.69 (s, 3H), 5.84 (s, OH), 6.73 (dd, 1H), 6.92-6.99 (m, 2H), 7.15-7.25 (m, 2H), 7.34-7.40 (m, 2H), 7.57 (t, 1H), ethyl acetate residues, NMR purity ca. 85%.

1-Bromo-3-(1-(3-methoxy-phenyl)-vinyl)-benzene
128358-69-21

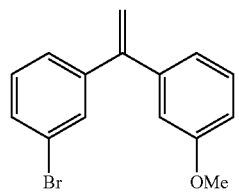

A solution of 1-(3-bromo-phenyl)-1-(3-methoxy-phenyl)-ethanol (31 g, ca. 100 mmol) in toluene (250 mL) was heated at reflux with para-toluenesulfonic acid (200 mg) in a Dean-Stark apparatus for 4 h. After TLC indicated complete conversion of starting material, the solution was left to cool, evaporated under reduced pressure and purified by flash chromatography (100 g silica gel, gradient cyclohexane 100% to 4% ethyl acetate in cyclohexane, eluant ca. 1 L, Rf 0.25 with 4% ethyl acetate in cyclohexane) to give a yellow oil (17.8 g, 62% over 2 steps).

$C_{15}H_{13}BrO$ Mass (calculated) [288/290]; (found) [M+H$^+$]= 289/91

LC Rt=3.03, 64% (5 min method, 215 nm)

¹H-NMR (d₆-DMSO): 3.73 (s, 3H), 5.54 (s, 2H), 6.78-6.81 (m, 2H), 6.93 (m, 1H), 7.25-7.35 (m, 3H), 7.43 (t, 1H), 7.54 (d, 1H). NMR purity>95%

(RS)-4-(3-Bromo-phenyl)-4-(3-methoxy-phenyl)-4,5-dihydro-oxazol-2-ylamine

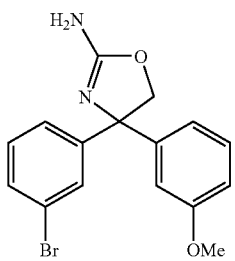

A solution of iodine (1.65 g, 6.7 mmol) in ethyl acetate (25 mL) was added dropwise over 25 min to a mixture of 1-bromo-3-(1-(3-methoxy-phenyl)-vinyl)-benzene (1.75 g, 6.1 mmol) and silver cyanate in acetonitrile (30 mL) and ethyl acetate (15 mL), cooled in an ice bath. After complete addition, the reaction suspension was stirred for another 15 min at room temperature when TLC indicated the complete conversion of starting material. The reaction mixture was filtered, and the filtrate concentrated to give a dark grey oil. 25 mL of aqueous ammonia (25%) was added to the oil, and the mixture was stirred and warmed to 70° C. for 30 min, then kept at room temperature overnight. LC-MS at this point indicated complete conversion of the intermediate urea to the desired aminoxazoline. The reaction suspension was filtered, the solid was refluxed in toluene (20 mL) for 10 min, filtered hot (to remove residual, undissolved silver iodide), and the filtrate was left to cool to room temperature, followed by 1 h at −10° C. The pale-yellow crystalline solid was filtered off and dried at the rotary evaporator to dive 4-(3-bromo-phenyl)-4-(3-methoxy-phenyl)-4,5-dihydro-oxazol-2-ylamine (1.2 g, 57%).

C₁₆H₁₅BrN₂O₂ Mass (calculated) [346/8]; (found) [M+H⁺]=347/9

LC Rt=1.33, 96% (5 min method, 215 nm)

¹H-NMR: (d₆-DMSO): 3.69 (s, 3H), 4.63 (dd, 2H), 6.30 (br, 2H), 6.74 (d, 1H), 6.94-6.98 (m, 2H), 7.17-7.25 (m, 2H), 7.34-7.42 (m, 2H), 7.58 (t, 1H).

Preparation of Building Block E (RS)-4-(4-Fluoro-3-bromophenyl)-4-(4-methoxy-3-methylphenyl)-4,5-dihydro-oxazol-2-ylamine 4-[1-(3-Bromo-4-fluoro-phenyl)-vinyl]-1-methoxy-2-methyl-benzene

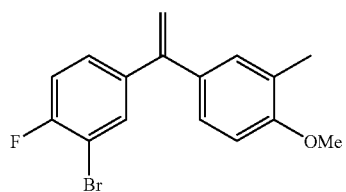

8 mL of a solution of 4-bromo-2-methylanisole (5.22 g, 26 mmol, 1.1 eq) in 40 mL of dry diethyl ether was added dropwise to a mixture of magnesium turnings (700 mg, 28.8 mmol, 1.2 eq) in 5 mL of dry diethyl ether under an inert atmosphere. A drop of bromine was added to initiate the reaction and gas evolution was observed. The remaining solution of 4-bromo-2-methylanisole (32 mL) was added and the reaction was stirred for 4 h at room temperature. The solution was then cooled to 0° C. and a solution of 4-fluoro-3-bromoacetophenone in 40 mL of dry diethyl ether was added; the mixture was stirred while warming to room temperature for 2 h. The solution was examined by TLC (cyclohexane/ethyl acetate 6%) which showed consumption of starting material. The solution was quenched with water, until gas evolution ceased, and then 1N HCl was added to reach a pH=5. The two phases formed were separated; the organic layer was dried over anhydrous magnesium sulfate, filtered and evaporated under reduced pressure. The crude (tertiary alcohol) and a catalytic amount of p-toluene sulfonic acid were dissolved in 100 mL toluene (Dean-Stark apparatus) and the mixture was heated to reflux for 3 h. The solution was examined by TLC (cyclohexane/ethyl acetate 6%) which showed consumption of starting material but many side products formed. Solvent was evaporated under reduced pressure and the crude residue was purified by flash chromatography eluting with a gradient (cyclohexane/ethyl acetate 0-4%). 1.65 g of product was obtained as liquid (20%).

Mass (calculated) C₁₆H₁₄BrFO [321] M−H⁺ not observed

LC Rt=3.15, (5 min method)

¹H-NMR (CDCl₃): 2.21 (s, 3H); 3.85 (s, 3H); 5.29 (s, 1H), 5.38 (s, 1H), 6.79 (m, 1H), 6.84 (m, 1H), 7.09 (m, 2H), 7.24 (m, 1H); 7.55 (m, 1H) 90%

(RS)-4-(4-Fluoro-3-bromophenyl)-4-(4-methoxy-3-methylphenyl)-4,5-dihydro-oxazol-2-ylamine

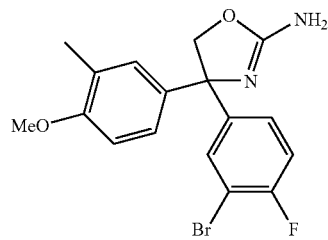

A solution of iodine (1.43 g, 5.65 mmol, 1.1 eq) in 52 mL of ethyl acetate was added dropwise (25 min) at 0° C. to a suspension of 4-[1-(3-bromo-4-fluoro-phenyl)-vinyl]-1-methoxy-2-methyl-benzene (1.65 g, 5.14 mmol, 1.0 eq) and silver cyanate (923 mg, 6.16 mmol, 1.2 eq) in acetonitrile/ethyl acetate (14 mL/7 mL). After addition was complete the reaction was examined by LC-MS which showed consumption of starting material. The mixture was filtered and the resulting solution was concentrated under reduced pressure. The crude was suspended in 50 mL of ammonium hydroxide solution and stirred for 4 h at room temperature and at 60° C. overnight. Dichloromethane was added to the suspension and the two phases were separated. The organic layer was dried over magnesium sulfate, filtered and concentrated under reduced pressure. The crude residue was purified by flash chromatography eluting with a gradient dichloromethane/methanol 0-2%. 1.1 g of the desired product was obtained as an off white solid (Yield: 57%).

Mass (calculated) C$_{17}$H$_{16}$BrFN$_2$O$_2$ [379]; (found) [M+H$^+$]= 380

LC Rt=2.17, (10 min method) purity 95% UV $^1$H-NMR (CDCl$_3$): 2.17 (s, 3H), 3.80 (s, 3H), 4.64 (d, 1H), 4.77 (d, 1H), 6.73 (m, 1H), 7.03 (m, 3H), 7.20 (m, 1H), 7.55 (dd, 1H)

Preparation of Building Block F (RS)-4-(4-Bromophenyl)-4-(phenyl)-4,5-dihydro-oxazol-2-ylamine 1-Bromo-4-(1-phenyl-vinyl)-benzene 14333-76-0]

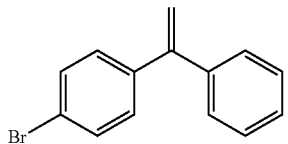

A solution of 4-bromoacetophenone (10.0 g, 50.2 mmol) in 130 mL of dry diethyl ether was added over 1.5 hours to a solution of phenyllithium (30.7 mL of 1.8 M a solution in dibutyl ether, 55.2 mmol) in 70 mL of dry diethyl ether at room temperature under an inert atmosphere. The reaction mixture was stirred while heating to reflux for 3 hours and then was examined by [C-MS which showed complete consumption of starting material. The reaction was quenched with water (500 mL), until gas evolution ceased, and 1 N HCL (31 mL). The organic layer was separated, dried over sodium sulfate and concentrated under reduced pressure. The crude product was used without any further purification. A solution of the crude (1-(4-bromo-phenyl)-1-phenyl-ethanol) and a catalytic amount of p-toluenesulfonic acid in toluene (100 mL) was heated at 120° C. for 16 h in a flask equipped with a Dean-Stark apparatus. The reaction mixture was examined by LC-MS which showed complete consumption of starting material. Solvent was evaporated under reduced pressure and the crude was purified by flash chromatography eluting with cyclohexane/ethyl acetate (100:0 to 98:2) giving 11 g of the title compound as a colorless oil (Yield: 84%)

Mass (calculated) C$_{14}$H$_{11}$Br [259] M–H+ not observed

LC Rt=3.32, (5 min method); purity 85%

$^1$H-NMR (CDCl$_3$): 7.38 (d, 2H), 7.25 (m, 5H), 7.14 (d, 2H), 5.38 (d, 2H)

(RS)-4-(4-bromophenyl)-4-(phenyl)-4,5-dihydro-oxazol-2-ylamine (Building Block F)

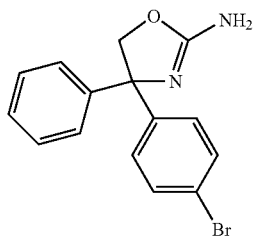

A saturated solution of iodine (4.89 g, 19.3 mmol) in 45 mL of diethyl ether was slowly added (3 h) to a suspension of 1-bromo-4-(1-phenyl-vinyl)-benzene (5.0 g; 19.3 mmol) and silver cyanate (2.89 g; 19.3 mmol) in 5 mL of diethyl ether. The brown mixture was stirred overnight at room temperature then filtered and 20 mL of a 25% aqueous ammonia solution was added to the ethereal solution. After vigorous stirring at room temperature for 4 h, the diethyl ether was evaporated under reduced pressure and the remaining aqueous suspension was stirred while heating to reflux overnight. The reaction mixture was extracted with dichloromethane, the collected organic fractions were concentrated and purified by SCX, washing the crude with a 1:1 dichloromethane/methanol mixture and recovering the product elution with a 2.0 M of ammonia/methanol solution. 2.44 g of the title product was obtained as a pale yellow solid (yield: 39%).

100 mg of product were further purified by preparative HPLC for enzymatic assay purposes.

Mass (calculated) C$_{15}$H$_{13}$BrN$_2$O [317]; (found) [M+H$^+$]= 318

LC Rt=1.87, (10 min method); purity 100%

$^1$H-NMR (d$_6$-DMSO): 8.17 (s, 1H); 7.47 (d, 2H), 7.37 (m, 2H), 7.33 (d, 2H), 7.28 (t, 2H), 7.18 (t, 1H), 4.73 (s, 2H).

Preparation of Building Block G (RS)-4-(3-bromophenyl)-4-(4-fluorophenyl)-4,5-dihydro-oxazol-2-ylamine 1-Bromo-3-[1-(4-fluorophenyl)-vinyl]-benzene

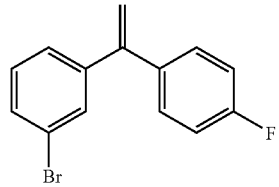

A solution of n-butyllithium (1.6 M in hexane, 21 mL, 33.5 mmol, 1.16 eq.) was added dropwise over 20 min to a solution of 1,3-dibromobenzene (3.8 mL, 31.8 mmol, 1.1 eq) in 30 mL of dry tetrahydrofuran at −78° C. and under an inert atmosphere. The white suspension formed was stirred at −78° C. for 30 min. A solution of 4'-fluoro-acetophenone (3.5 mL, 28.9 mmol, 1.0 eq.) in 20 mL of tetrahydrofuran was then added dropwise and the reaction stirred for 1 h. The reaction mixture was examined by LC-MS which showed the complete formation of tertiary alcohol. The solution was quenched with a saturated solution of ammonium chloride and water. 2 N HCl was then added to reach pH=5. The two phases were separated; the organic layer was dried over anhydrous magnesium sulfate, filtered and evaporated under reduced pressure. The residual material (tertiary alcohol) was dissolved in a mixture of acetic acid/sulfuric acid (10 mL of acetic acid, 0.3 mL of sulfuric acid) and the reaction mixture was stirred for 1 h at room temperature; then it was examined by LC-MS which showed the complete formation of desired product. The solution was quenched with ice and dichloromethane (20 mL) was added. The two phases formed and were separated. The organic layer was washed with a saturated solution of sodium bicarbonate and brine. It was then dried over anhydrous magnesium sulfate, filtered and evaporated under reduced pressure. The crude was purified by flash chromatography eluting with cyclohexane. The desired product was obtained as a liquid (5.89 g, Yield: 73%).

¹H-NMR (CDCl₃): 7.47 (m, 2H); 7.27 (m, 4H); 7.04 (m, 2H); 5.45 (m, 2H).

(RS)-4-(3-Bromophenyl)-4-(4-fluorophenyl)-4,5-dihydro-oxazol-2-ylamine (Building Block G)

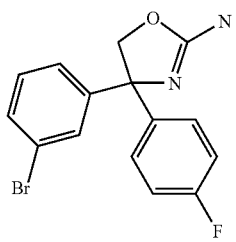

A solution of iodine (5.93 g, 23.38 mmol, 1.1 eq) in 80 mL of ethyl acetate was added dropwise (~20 min) into a suspension of 1-bromo-3-[1-(4-fluorophenyl)-vinyl]-benzene (5.89 g, 21.26 mmol, 1 eq) and silver cyanate (3.82 g, 25.51 mmol, 1.2 eq) in a mixture of 57 mL of acetonitrile and 21 mL of ethyl acetate at 0° C. Once the addition was complete the reaction was examined by TLC which showed consumption of double bond. The mixture was filtered and the solution was concentrated under reduced pressure. The crude was suspended in 170 mL of ammonium hydroxide solution, 70 mL of water were added and the mixture was then stirred for 4 h at 60° C. Dichloromethane was added to the suspension and the two phases were separated. The organic layer was dried over anhydrous magnesium sulfate, filtered and concentrated under reduced pressure. The crude was purified by flash chromatography eluting with eluting with a gradient (dichloromethane/methanol 0-2%). The solid was washed with diethyl ether to obtain 1.24 g of desired product as a white solid (Yield: 17%).

Mass (calculated) C₁₅H₁₂BrFN₂O [335]; (found) [M+H⁺]= 335-337

LC Rt=1.28 min (5 min method); Purity 89%

¹H-NMR (CDCl₃): 7.59 (t, 1H); 7.40 (m, 4H); 7.25 (m, 1H); 7.11 (m, 2H); 6.32 (bs, 2H); 4.65 (m, 2H).

Preparation of Building Block H (RS)-4-(3-Bromophenyl)-4-(4-chlorophenyl)-4,5-dihydro-oxazol-2-ylamine 1-Bromo-3-[1-(4-chlorophenyl)-vinyl)]-benzene

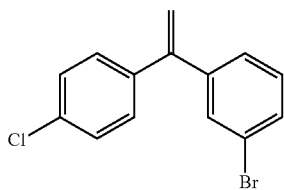

A solution of n-butyllithium (1.6 M in hexane, 18.7 mL, 29.9 mmol, 1.16 eq) was added over 20 min to a solution of 1,3-dibromobenzene (3.4 mL, 28.4 mmol, 1.1 eq) in 30 mL of dry tetrahydrofuran at −78° C. and under an inert atmosphere. The white suspension formed and was stirred at −78° C. for 30 min. A solution of 4'-chloro-acetophenone (3.4 mL, 25.8 mmol, 1.0 eq.) in 20 mL of tetrahydrofuran was then added dropwise and the reaction stirred for 1 h. The reaction mixture was examined by LC-MS which showed the complete formation of tertiary alcohol. The solution was quenched with a saturated aqueous solution of ammonium chloride and then water was added. 2 N hydrochloric acid was added to adjust the pH=5. The two phases were separated; the organic layer was dried over anhydrous magnesium sulfate, filtered and evaporated under reduced pressure. The crude was dissolved in a mixture of acetic acid/sulfuric acid (10 mL of acetic acid, 0.3 mL of sulfuric acid) and the reaction mixture was stirred for 1 h at room temperature; then it was examined by LC-MS which showed the complete formation of desired product. The solution was quenched with ice and dichloromethane (20 mL) was added. The two phases formed and were separated. The organic layer was washed with a saturated solution of sodium bicarbonate and then brine. It was then dried over anhydrous magnesium sulfate, filtered and evaporated under reduced pressure. The crude was purified by flash chromatography eluting with cyclohexane. The desired product was obtained as a pale yellow liquid (4.61 g, Yield: 61%).

¹H-NMR (CDCl₃): 7.47 (m, 2H); 7.33 (m, 2H); 7.23 (m, 4H); 5.48 (m, 2H).

(RS)-4-(3-Bromophenyl)-4-(4-chlorophenyl)-4,5-dihydro-oxazol-2-ylamine (Building Block H)

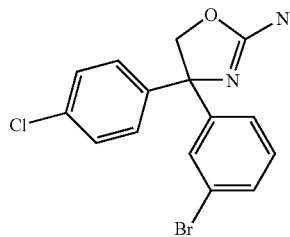

A solution of iodine (4.39 g, 17.30 mmol, 1.1 eq) in 80 mL of ethyl acetate was added dropwise (~20 min) at 0° C. into a suspension of 1-bromo-3-[1-(4-chlorophenyl)-vinyl]-benzene (4.61 g, 15.73 mmol, 1 eq) and silver cyanate (2.82 g, 18.87 mmol, 1.2 eq) in a mixture of 38 mL of acetonitrile and 18 mL of ethyl acetate. Once the addition was complete the reaction was examined by TLC which showed consumption of double bond. The mixture was filtered and the solution was concentrated under reduced pressure. The crude was suspended in 125 mL of ammonium hydroxide solution, 50 mL of water were added and the mixture was stirred for 4 h at 60° C. Dichloromethane was added to the suspension and the two phases were separated, organic layer was dried over anhydrous magnesium sulfate, filtered and concentrated under reduced pressure. The crude was purified by flash chromatography eluting with eluting with a gradient (dichloromethane/methanol 0-2%). The solid was washed with diethyl ether to obtain 1.41 g of desired product as a yellow-brown solid (Yield: 25%).

Mass (calculated) C₁₅H₁₂BrClN₂O [351]; (found) [MH+]= 352

LC Rt=1.38 min (5 min method); Purity 92%

¹H-NMR (CDCl₃): 7.59 (t, 1H); 7.38 (m, 6H); 7.24 (m, 1H); 6.33 (bs, 2H); 4.64 (m, 2H).

Preparation of Building Block I (RS)-4-(3-Bromophenyl)-4-(4-methoxy-3-methylphenyl)-4,5-dihydro-oxazol-2-ylamine 4-[1-(3-Bromo-phenyl)-vinyl]-1-methoxy-2-methyl-benzene

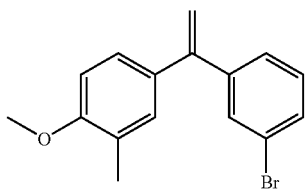

Tetrahydrofuran (5 mL) was added to magnesium turnings (330 mg, 13.56 mmol) in a dried apparatus consisting of 250 mL 3-necked flask, addition funnel and reflux condenser. Then 5 mL of a solution of 4-bromo-2-methylanisole (2.5 g, 12.43 mmol) in tetrahydrofuran (15 mL) was added, followed by a drop of bromine. The exothermic reaction started instantaneously, and the 4-bromo-2-methylanisole solution was added at such a rate to maintain gentle reflux of the reaction mixture (25 min). After complete addition, the light-brown hazy Grignard solution was stirred for another 2 h at 40° C. The mixture was then cooled to 0° C. and a solution of 3-bromoacetophenone (1.42 mL, 11.3 mmol) in tetrahydrofuran (15 mL) was added dropwise over 30 min. After the addition was complete, the mixture was stirred overnight, followed by cooling in an ice bath and careful quenching with 0.5 N cold HCl. After further dilution with ethyl acetate (100 mL) and water (100 mL), the layers were separated and the aqueous layer extracted once more with ethyl acetate (50 mL). The organic layer was dried (magnesium sulfate), filtered and evaporated under reduced pressure. The residual material (tertiary alcohol) was dissolved in a mixture of acetic acid/sulfuric acid (4 mL of acetic acid, 0.12 mL of sulfuric acid) and the reaction mixture was stirred for 3 h at room temperature; then it was examined by LC-MS which showed the complete formation of desired product. The solution was quenched with ice and dichloromethane (20 mL) was added. The two phases formed and were separated. The organic layer was washed with a saturated solution of sodium bicarbonate and brine. It was then dried over anhydrous magnesium sulfate, filtered and evaporated under reduced pressure. Crude was purified by flash chromatography eluting with cyclohexane. 1.9 g of desired product was obtained as colorless oil (Yield: 55%).

Mass (calculated) $C_{16}H_{15}BrO$ [303] M–H$^+$ not observed

LC Rt=3.05 min (5 min method)

$^1$H-NMR (CDCl$_3$): 2.23 (s, 3H); 3.86 (s, 3H); 5.35 (s, 1H); 5.43 (s, 1H); 6.80 (m, 1H); 7.13 (m, 2H): 7.21 (m, 1H); 7.28 (m, 1H); 7.46 (m, 1H); 7.53 (m, 1H)

(RS)-4-(3-Bromophenyl)-4-(4-methoxy-3-methylphenyl)-4,5-dihydro-oxazol-2-ylamine (Building Block I)

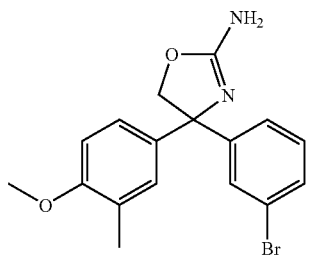

A solution of iodine (1.92 g, 7.59 mmol) in ethyl acetate (50 mL) was added dropwise over 25 min to a mixture of 4-[1-(3-bromo-phenyl)-vinyl]-1-methoxy-2-methyl-benzene (2.1 g, 6.9 mmol) and silver cyanate (1.24 g, 8.28 mmol) in acetonitrile (19 mL) and ethyl acetate (9 mL), cooled in an ice bath. After complete addition, the reaction suspension was stirred for another 15 min at room temperature when TLC indicated the complete conversion of starting material. The reaction mixture was filtered, and the filtrate concentrated to give a dark grey oil. 50 mL of aqueous ammonia (25%) was added to the oil, and the mixture was stirred and warmed to 60° C. for 4 hours. LC-MS at this point indicated complete conversion of the intermediate urea to the desired aminoxazoline, dichloromethane (40 mL) was added to the crude and the two phases were separated. The organic layer was collected, dried over anhydrous magnesium sulfate, filtered and evaporated under reduced pressure. Crude was purified by silica gel chromatography eluting with dichloromethane/methanol (gradient 0-2%) to give 1.0 g of the desired product as yellow gum (40%)

Mass (calculated) $C_{17}H_{17}BrN_2O_2$ [361]; (found) 361, 363 (M+H)$^+$.

LC Rt=1.32 min (5 min method)

$^1$H-NMR (CDCl$_3$): 2.17 (s, 3H); 3.79 (s, 3H); 4.66 (d, 1H); 4.76 (d, 1H); 6.74 (m, 1H); 7.07 (m, 2H): 7.15 (t, 1H); 7.23 (m, 1H); 7.33 (m, 1H); 7.51 (m, 1H)

Preparation of Building Block J (RS)-4-Benzo[1,3]dioxol-5-yl-4-(3-bromo-phenyl)-4,5-dihydro-oxazol-2-ylamine 5-[1-(3-Bromo-phenyl)-vinyl]-benzo[1,3]dioxole

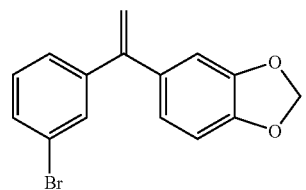

To a mixture of magnesium turnings (440 mg, 0.01 mol, 1.2 eq) in dry tetrahydrofuran (5 mL), was added 4-bromo-1,2

(methylendioxy)benzene (3.1 g, 0.01 mol, 1.1 eq) in dry tetrahydrofuran (10 mL) and bromine (0.5 mL). The resulting solution was refluxed for 2 hours. Then the mixture was cooled at room temperature and a solution of 3-bromoacetophenone (3.0 g, 0.01 mol, 1 eq) in dry tetrahydrofuran (10 mL) was added dropwise and refluxed. After 3 hours the reaction mixture was examined by LC-MS which showed complete conversion to the desired product. The mixture was quenched with 1 M HCl solution (20 mL). The aqueous phase was extracted with ethyl acetate. (3×20 mL), dried (sodium sulfate) and the solvent removed in vacuo. The crude was dissolved in toluene (30 mL) and a catalytic amount of p-toluenesulfonic acid was added. The mixture was heated to reflux for 3 h (using a Dean-Stark water trap). The solvent was removed and the residue was purified by column chromatography (cyclohexane) to afford the title compound as a colorless oil (3.7 g, 80%);

Mass (calculated) $C_{15}H_{11}BrO_2$ [303]; (found) [M+H$^+$]= 303

LC Rt=2.92 min (5 min method)

$^1$H-NMR (CDCl$_3$): 5.36 (d, 2H), 5.97 (m, 2H), 6.82 (m, 2H), 7.25 (m, 2H), 7.47 (m, 2H)

(RS)-4-Benzo[1,3]dioxol-5-yl-4-(3-bromo-phenyl)-4,5-dihydro-oxazol-2-ylamine (Building Block J)

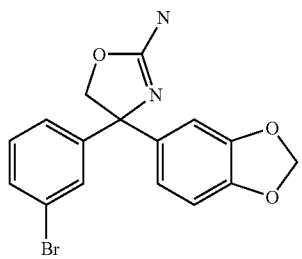

A solution of iodine (6.0 g, 23 mol, 1.1 eq) in ethyl acetate (77 mL) was added dropwise to a cooled ice bath suspension of silver cyanate (4.0 g, 26 mmol, 1.2 eq), 5-[1-(3-bromophenyl)-vinyl]-benzo[1,3]dioxole (6.7 g, 22 mmol, 1 eq) in acetonitrile (55 mL) and ethyl acetate (25 mL). The resulting brown suspension was stirred for 1 hour at room temperature by which point LC-MS which showed complete conversion of the starting material. The reaction mixture was filtered and concentrated in vacuo. Aqueous ammonia (25% soln, 50 mL) was added to the oil and the mixture was stirred for 15 min at ambient temperature followed by 3 h at 80° C. The reaction was allowed to cool to room temperature and extracted with dichloromethane (2×30 mL). The organic layers collected, dried and concentrated in vacuo. The crude was dissolved in dichloromethane/methanol 1:1 (5 mL) and passed through SCX (50 g) cartridge, the material was purified by first eluting with dichloromethane/methanol (1:1) and the product was recovered eluting with a solution 2.0 M ammonia in methanol. 5.0 g of product was obtained as a white solid (yield: 62%)

Mass (calculated) $C_{16}H_{13}BrN_2O_3$ [361]; (found) [M+H$^+$]= 363

LC Rt=1.32 min (5 min method) 99%

$^1$H-NMR (CDCl$_3$): 4.58 (m, 2H), 5.96 (s, 2H), 6.26 (bs, 2H), 6.78-6.93 (m, 3H), 7.22 (m, 1H), 7.35 (m, 2H), 7.57 (s, 1H)

Preparation of Building Block K (RS)-4-(3-Bromo-phenyl)-4-(2,3-dihydro-benzofuran-5-yl)-4,5-dihydro-oxazol-2-ylamine 5-[1-(3-Bromo-phenyl)-vinyl]-2,3-dihydro-benzofuran

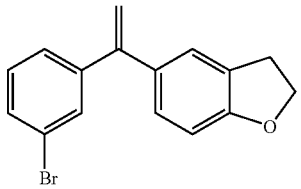

A 1.6 M solution of n-butyllithium in hexane (22.3 mL, 35.7 mmol, 1.16 eq.) was added dropwise to a solution of 1,3-dibromobenzene (8.0 g, 33.9 mmol, 1.1 eq) in 30 mL of dry tetrahydrofuran at −78° C. under nitrogen, and the mixture was stirred for 20 min. After this time, a solution of 1-(2,3-dihydro-benzofuran-5-yl)-ethanone (5.0 g, 30.8 mmol, 1.0 eq, prepared as shown in Scheme 4) in 20 mL of dry tetrahydrofuran was added over 10 minutes and the resulting solution was further stirred for 45 min. The reaction mixture was examined LCMS which showed complete conversion to the desired product. 20 mL of a saturated aqueous solution of ammonium chloride was added and the cooling bath was removed. The mixture was poured into 100 mL of a 1:1 diisopropyl ether/water mixture. The organic fraction was dried over sodium sulfate and concentrated to give a yellow oil. The oil was dissolved in 10 ml, of acetic acid. 0.3 mL of 98% sulfuric acid were added and the dark solution was stirred at room temperature. After 30 min LCMS showed complete conversion to the desired product. Crushed ice was poured in the reaction mixture which was then extracted with dichloromethane. The organic fraction was collected, washed with water, sodium bicarbonate solution and dried with over sodium sulfate. The crude product was purified by flash chromatography eluting with cyclohexane. 3.5 g of clean product was obtained as colorless liquid (yield: 38%)

Mass (calculated) $C_{16}H_{13}BrO$ [301]; (found) [M+H$^+$]= 302

LC Rt=2.97 min (5 min method) 92%

(RS)-4-(3-Bromo-phenyl)-4-(2,3-dihydro-benzofuran-5-yl)-4,5-dihydro-oxazol-2-ylamine (Building Block K)

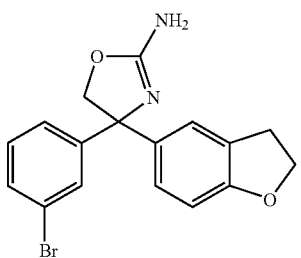

According to general method 2, a solution of iodine in ethyl acetate was added to a mixture of 5-[1-(3-bromo-phenyl)- vinyl]-2,3-dihydro-benzofuran (3.5 g, 11.6 mmol) and silver cyanate in ethyl acetate/acetonitrile. The crude product of this reaction was subsequently reacted with aqueous ammonia (30% by Vol). Purification by SCX column yielded 1.5 g of product (37%).

Mass (calculated) $C_{17}H_{15}BrN_2O_2$ [359]; (found) [M+H$^+$]= 360

LC Rt=1.33 min (5 min method) 85%

$^1$H-NMR (d$_o$-DMSO): 3.09 (t, 2H), 4.44 (t, 2H), 4.58 (m, 2H), 6.20 (brs, 2H), 6.63 (d, 1H), 7.08 (d, 1H), 7.22 (m, 2H), 7.35 (m, 2H), 7.56 (m, 1H)

Preparation of Building Block L (RS)-4-(3-Bromo-phenyl)-4-(4-isopropoxy-3-methyl-phenyl)-4,5-dihydro-oxazol-2-ylamine 4-Bromo-1-isopropoxy-2-methyl-benzene

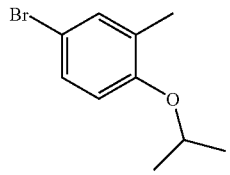

To a solution of 3-bromocresol (7.0 g, 37.4 mmol, 1.0 eq) in 20 mL of dry dimethylsulfoxide, anhydrous potassium carbonate was added (10.3 g, 74.8 mmol, 2.0 eq.) and the mixture was stirred for 20 min at room temperature. After this time, isopropyliodide (7.6 g, 44.9 mmol, 1.2 eq.) was added and the resulting mixture was further stirred for 16 hours at 60° C. The reaction mixture was examined LCMS which showed>90% conversion to the desired product. The reaction mixture was cooled to room temperature, 100 mL of water was added and the mixture was extracted with dichloromethane. The organic fraction was dried over sodium sulfate, filtered and concentrated under reduced pressure. The crude product was purified by flash chromatography eluting with cyclohexane. 7.0 g of clean product was obtained as colorless liquid (yield: 81%)

Mass (calculated) $C_{10}H_{13}BrO$ [229].

LC Rf=0.85 min (5 min method) 98%

Rf=0.85 (cyclohexane/ethyl acetate 80:20)

$^1$H-NMR (CDCl$_3$): 1.32 (d, 6H), 2.17 (s, 3H), 4.46 (sept, 1H), 6.69 (d, 1H), 7.21 (m, 1H), 7.24 (m, 1H).

4-[1-(3-Bromo-phenyl)-vinyl]-1-isopropoxy-2-methyl-benzene

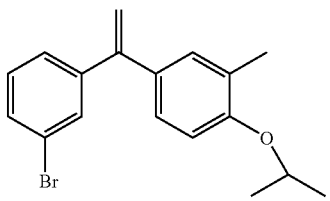

To a suspension of magnesium turnings (811 mg, 33.38 mmol, 1.2 eq) in 5 mL of dry tetrahydrofuran, 0.1 mL of 1,2-dibromoethane were added followed by 5 mL of a tetrahydrofuran solution of 4-bromo-1-isopropoxy-2-methyl-benzene (7.0 g, 30.6 mmol, 1.1 eq in 25 mL tetrahydrofuran). The resulting mixture was gently heated to initiate the reaction. The remaining solution of bromide was added dropwise at such a rate that the reaction could reflux without external heating. After the addition the reaction mixture was heated at reflux for further 2 hours. The mixture was cooled to 0° C. and a solution of 3-bromoacetophenone (5.54 g, 27.81 mmol, 1.0 eq) in tetrahydrofuran (30 mL) was added dropwise. After 2 hours LC-MS showed complete conversion to the desired product. 50 mL of water were added followed by 35 mL of 1 M aqueous HCl. The organic fraction was washed with brine, dried over sodium sulfate and concentrated to give a yellow oil. The oil was dissolved in 10 mL of acetic acid. 0.3 mL of 98% sulfuric acid were added and the dark solution was stirred at room temperature. After 30 min LCMS showed complete conversion to the desired product. Crushed ice was poured in the reaction mixture which was then extracted with dichloromethane. The organic fraction was collected, washed with water, aq. NaHCO$_3$ and dried with over sodium sulfate. The crude product was purified by flash chromatography eluting with cyclohexane. 6.8 g of clean product was obtained as colorless liquid (yield: 66%)

Mass (calculated) $C_{18}H_{19}BrO$ [321]; (found) [M+H$^+$]= 322

$^1$H-NMR (CDCl$_3$): 1.34 (d, 6H), 2.18 (s, 3H), 4.53 (sept, 1H), 5.35 (d, 2H), 6.78 (d, 1H), 6.83 (d, 1H). 7.05 (m, 1H), 7.10 (d, 1H), 7.11 (d, 1H), 7.19 (t, 1H), 7.25 (m, 1H), 7.42 (m, 1H); 7.49 (m, 1H).

(RS)-4-(3-Bromo-phenyl)-4-(4-isopropoxy-3-methyl-phenyl)-4,5-dihydro-oxazol-2-ylamine (Building Block L)

According to general method 2, a solution of iodine in ethyl acetate was added to a

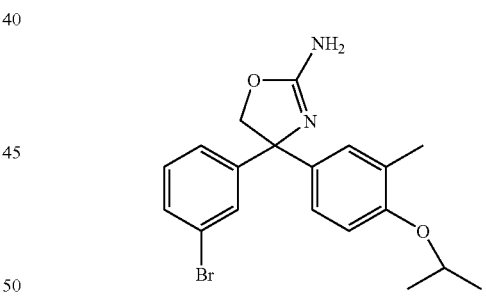

mixture of 4-[1-(3-bromo-phenyl)-vinyl]-1-isopropoxy-2-methyl-benzene (6.8, 20.5 mmol) and silver cyanate in ethyl acetate/acetonitrile. The crude product of this reaction was subsequently reacted with aqueous ammonia (30% by vol). Purification by SCX column yielded 4.3 g of product (55%).

Mass (calculated) $C_{19}H_{21}BrN_2O_2$ [389]; (found) [M+H$^+$]= 390

LC Rt=1.65 min (5 min method) 95%

$^1$H-NMR (d$_o$-DMSO): 1.21 (d, 6H), 2.18 (s, 3H), 4.49 (sept, 1H), 4.60 (m, 2H), 6.30 (brs, 2H), 6.81 (d, 1H), 7.10 (dd, 1H), 7.14 (m, 1H), 7.22 (t, 1H), 7.36 (m, 2H), 7.56 (m, 1H).

Building Block M (RS)-4-(3-Bromo-phenyl)-4-(4-ethoxy-3-methyl-phenyl)-4,5-dihydro-oxazol-2-ylamine 4-Bromo-1-ethoxy-2-methyl-benzene [871888-83-4]

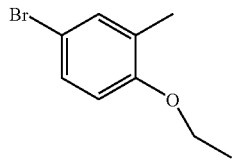

To a solution of 3-bromocresol (7.0 g, 37.4 mmol, 1.0 eq) in 20 mL of dry dimethylsulfoxide, anhydrous potassium carbonate was added (10.3 g, 74.8 mmol, 2.0 eq.) and the mixture was stirred for 20 min at room temperature. After this time, ethyliodide (8.6 g, 44.9 mmol, 1.2 eq.) was added and the resulting mixture was further stirred for 16 hours at 60° C. The reaction mixture was examined LC-MS which showed>90% conversion to the desired product. The reaction mixture was cooled to room temperature, 100 mL of water was added and the mixture was extracted with dichloromethane. The organic fraction was dried over sodium sulfate and the crude product was purified by flash chromatography eluting with cyclohexane. 7.8 g of clean product was obtained as colorless liquid (yield: 81%)

Mass (calculated) $C_9H_{11}BrO$ [215] Not observed
LC Rt=2.70 min (5 min method) 98%
$^1$H-NMR (CDCl$_3$): 1.40 (t, 3H), 2.18 (s, 3H), 4.00 (q, 2H), 6.66 (d, 1H), 7.21 (m, 1H), 7.24 (m, 1H).

4-[1-(3-Bromo-phenyl)-vinyl]-1-ethoxy-2-methyl-benzene

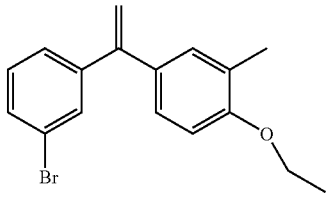

To a suspension of magnesium turnings (963 mg, 39.6 mmol, 1.2 eq) in 5 mL of dry tetrahydrofuran, 0.1 mL of 1,2-dibromoethane were added followed by 5 mL of a tetrahydrofuran solution of 4-bromo-1-ethoxy-2-methyl-benzene (7.8 g, 36.3 mmol, 1.1 eq in 25 mL tetrahydrofuran). The resulting mixture was gently heated to initiate the reaction. The remaining solution of bromide was added dropwise at such a rate that the reaction could reflux without external heating. After the addition the reaction mixture was heated at reflux for further 2 hours. The mixture was cooled to 0° C. and a solution of 3-bromoacetophenone (6.56 g, 33.0 mmol, 1.0 eq) in tetrahydrofuran (30 mL) was added dropwise. After 2 hours LCMS showed complete conversion to the desired product. 50 mL of water were added followed by 35 mL of 1M aqueous HCl. The organic fraction was washed with brine, dried over sodium sulfate and concentrated to give a yellow oil. The oil was dissolved in 10 mL of acetic acid. 0.3 mL of 98% sulfuric acid were added and the dark solution was stirred at room temperature. After 30 min LCMS showed complete conversion to the desired product. Crushed ice was added to the reaction mixture which was then extracted with dichloromethane. The organic fraction was collected, washed with water, saturated sodium bicarbonate solution and dried with over sodium sulfate. The crude product was purified by flash chromatography eluting with cyclohexane. 7.5 g of clean product was obtained as colorless liquid (yield: 63%)

Mass (calculated) $C_{17}H_{17}BrO$ [317]; (found) [M+H$^+$]=318
LC Rt=1.97 min (5 min method) 93%
TLC Rf=0.8 (cyclohexane/ethyl acetate 80:20)

(RS)-4-(3-Bromo-phenyl)-4-(4-ethoxy-3-methyl-phenyl)-4,5-dihydro-oxazol-2-ylamine (Building Block M)

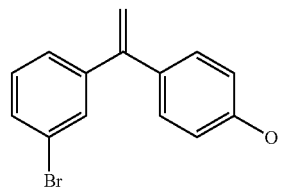

According to general method 2, a solution of iodine in ethyl acetate was added to a mixture of 4-[1-(3-bromo-phenyl)-vinyl]-1-ethyl-2-methyl-benzene (7.5 g, 23.6 mmol) and silver cyanate in ethyl acetate/acetonitrile. The crude product of this reaction was subsequently reacted with aqueous ammonia (30% by vol). Purification by SCX column yielded 5.2 g of the desired product (60%).

Mass (calculated) $C_{18}H_{19}BrN_2O_2$ [375]; (found) [M+H$^+$]=376
LC Rt=1.57 min (5 min method) 95%
$^1$H-NMR (d$_6$-DMSO): 1.30 (t, 3H), 2.07 (s, 3H), 3.95 (q, 2H), 4.58 (s, 2H), 6.22 (brs, 2H), 6.80 (d, 1H), 7.12 (m, 2H), 7.21 (t, 1H), 7.36 (m, 2H), 7.55 (m, 1H).

Preparation of Building Block N (RS)-4-(3-Bromo-phenyl)-4-[4-(2-methoxy-ethoxy)-phenyl]-4,5-dihydro-oxazol-2-ylamine 4-[1-(3-Bromo-phenyl)-vinyl]-phenol A solution of n-butyllithium (1.6 M solution in hexane, 41.6 mL, 1.1 eq) was added dropwise to a solution of 1,3-dibromobenzene (7.6 mL, 1.1 eq) in tetrahydrofuran (30 mL) at −78° C. After stirring 30 min at −78° C. 1-[4-(tetrahydro-pyran-2-yloxy)-phenyl]-ethanone (12.6 g, 57 mmol, 1 eq) in tetrahydrofuran (25 mL) was added dropwise. The mixture was allowed to warm up to room temperature and stirred for 2 h, then treated with 1 N HCl (10 mL), extracted with ethyl acetate, dried (sodium sulfate) and concentrated in vacuo. The crude was dissolved in toluene (40 mL) and p-toluenesulfonic acid (50 mg) was added. The mixture was heated at 150° C. for 3 h. The solvent was removed under reduce pressure and the residue was purified by column chromatography (cyclohexane) to afford the title compound as a colorless oil (1.2 g, 10%);

Mass (calculated) $C_{14}H_{11}BrO$ [275]; (found) [M+H+]= 277

LC Rt=2.52 min (5 min method)

$^1$H-NMR (CDCl$_3$): 5.32 (d, 2H), 6.73 (m, 2H), 7.06 (m, 2H), 7.26-7.53 (m, 4H), 9.59 (s, 1H)

1-(3-Bromophenyl)-1-(-(2-methoxy-ethoxy)-phenyl)-ethene

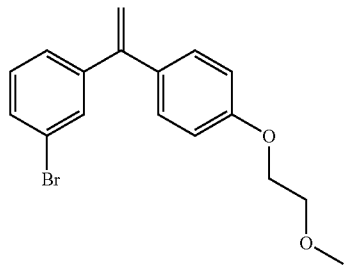

A mixture of 4-[1-(3-bromo-phenyl)-vinyl]-phenol (1.2 g, 4.0 mmol, 1 eq) N,N-dimethylformamide (10 mL), and cesium carbonate (2.8 g, 8.0 mmol, 2.0 eq) was stirred at room temperature then 1-bromo-2-methoxy-ethane (0.5 mL, 1.0 eq) was added. The mixture was heated to 50° C. overnight, cooled to room temperature and treated with water (100 mL). The reaction was extracted with dichloromethane, dried (sodium sulfate) and concentrated in vacuo. The crude was purified by flash chromatography eluting with cyclohexane to afford the title compound as a colorless oil (1.7 g, 85%);

Mass (calculated) $C_{17}H_{17}BrO_2$ [333] MH$^+$ not observed
LC Rt=2.88 min (5 min method)

$^1$H-NMR (CDCl$_3$): 3.46 (s, 3H), 3.75 (m, 2H), 4.14 (m, 2H), 5.37 (d, 2H), 6.89 (m, 2H), 7.21 (m, 3H), 7.41 (m, 1H), 7.81 (m, 1H) 8.01 (s, 1H)

(RS)-4'-(3-Bromo-phenyl)-4-[4-(2-methoxy-ethoxy)-phenyl]-4,5-dihydro-oxazol-2-ylamine (Building Block N)

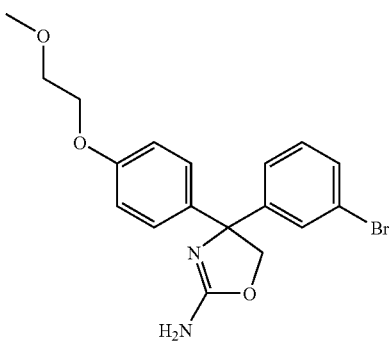

A solution of iodine (1.4 g, 5.0 mmol, 1.1 eq) in ethyl acetate (15 mL) was added dropwise to a cooled ice bath suspension of silver cyanate (0.9 g, 6.0 mmol, 1.2 eq), 1-(3-bromophenyl)-1-(-(2-methoxy-ethoxy)-phenyl)-ethene (1.7 g, 5.0 mmol, 1 eq) in acetonitrile (15 mL) and ethyl acetate (6 mL). The resulting brown suspension was stirred for 1 h at room temperature, the reaction was examined by LC-MS which showed complete conversion of the starling material, the reaction mixture was filtered and concentrated in vacuo. Aqueous ammonia (25% soln, 25 mL) was added to the oil and the mixture was stirred for 15 min at ambient temperature followed by 3 h at 80° C. The reaction was allowed to warm up to room temperature, extracted with dichloromethane (2×30 mL), the organic layers collected, dried and concentrated in vacuo. The crude was dissolved in dichloromethane/methanol 1:1 (5 mL) and passed through SCX (20 g) cartridge, washing with dichloromethane/methanol mixture and the product was recovered eluting with a solution 2.0 M of ammonia in methanol. 1.0 g of product was obtained as a yellow solid (yield: 51%)

Mass (calculated) $C_{18}H_{19}BrN_2O_3$ [391]; (found) [M+H$^+$]= 393

LC Rt=1.40 min (5 min method)

$^1$H-NMR (CDCl$_3$): 3.44 (s, 3H), 3.76 (m, 2H), 4.13 (m, 2H), 5.40 (m, 2H), 6.90 (m, 2H), 7.22 (m, 3H), 7.42 (m, 2H), 8.01 (s, 1H)

Preparation of Building Block O (RS)-4-(3-Bromophenyl)-4-(3-chloro-4-methoxyphenyl)-4,5-dihydro-oxazol-2-ylamine 4-[1-(3-Bromo-phenyl)-vinyl]-2-chloro-1-methoxybenzene

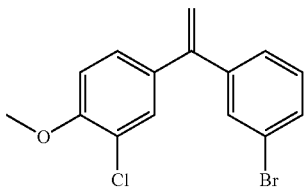

A solution of n-butyllithium (1.6 M in hexane, 19.5 mL, 31.3 mmol, 1.16 eq.) was added dropwise over 20 min to a solution of 1,3-dibromobenzene (3.59 mL, 29.7 mmol, 1.1 eq) in 30 mL of dry tetrahydrofuran at −78° C. and under an inert atmosphere. The white suspension formed was stirred at −78° C. for 30 min. A solution of 3-chloro-4-methoxyacetophenone (5 g, 27 mmol, 1.0 eq.) in 20 mL of tetrahydrofuran was then added dropwise and the reaction stirred for 1 h. The reaction mixture was examined by LC-MS which showed the complete formation of tertiary alcohol. The solution was quenched with a saturated solution of ammonium chloride and water. 2 N HCl was then added to reach pH=5. The two phases were separated; the organic layer was dried over anhydrous magnesium sulfate, filtered and evaporated under reduced pressure. The residual material (tertiary alcohol) was dissolved in a mixture of acetic acid/sulfuric acid (10 mL of acetic acid, 0.3 mL of sulfuric acid) and the reaction mixture was stirred for 3 h at room temperature; then it was examined by LC-MS which showed the complete formation of desired product. The solution was quenched with ice and dichloromethane (20 mL) was added. The two phases formed and were separated. The organic layer was washed with a saturated solution of sodium bicarbonate and brine. It was then dried over anhydrous magnesium sulfate, filtered and evaporated under reduced pressure. The crude was purified by flash chromatography eluting with cyclohexane/ethyl acetate (gradient 0-4%). The desired product was obtained as a yellow oil (4.36 g, Yield: 50%).

Mass (calculated) C$_{15}$H$_{12}$BrClO [323]; (found) [M+H$^+$]= 324

LC Rt=2.48 min (5 min method)

$^1$H-NMR (CDCl$_3$): 3.92 (s, 3H); 5.41 (d, 2H); 6.89 (m, 1H); 7.15 (m, 1H); 7.22 (m, 2H); 7.35 (m, 1H): 7.47 (m, 2H)

(RS)-4-(3-Bromophenyl)-4-(3-chloro-4-methoxyphenyl)-4,5-dihydro-oxazol-2-ylamine (Building Block O)

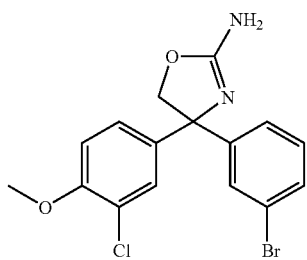

A solution of iodine (3.76 g, 14.83 mmol) in ethyl acetate (40 mL) was added dropwise over 25 min to a mixture of 4-[1-(3-bromo-phenyl)-vinyl]-2-chloro-1-methoxy-benzene (4.36 g, 13.49 mmol) and silver cyanate (2.42 g, 16.18 mmol) in acetonitrile (38 mL) and ethyl acetate (18 mL), cooled in an ice bath. After complete addition, the reaction suspension was stirred for another 15 min at room temperature when TLC indicated the complete conversion of starting material. The reaction mixture was filtered, and the filtrate concentrated to give a dark grey oil. 80 mL of aqueous ammonia (25%) was added to the oil, and the mixture was stirred and warmed to 60° C. for 4 hours. LC-MS at this point indicated complete conversion of the intermediate urea to the desired aminoxazoline. Dichloromethane (40 mL) was added to the crude and the two phases were separated; organic layer was collected, dried over magnesium sulfate anhydrous, filtered and evaporated under reduced pressure. The solid obtained was washed with cyclohexane to give 2.89 g of desired product as a pale-yellow solid (56%)

Mass (calculated) C$_{16}$H$_{14}$BrClN$_2$O$_2$ [381]; (found) [M+H$^+$]=382

LC Rt=2.07 min (5 min method)

$^1$H-NMR (d$_6$-DMSO): 3.78 (s, 3H); 4.60 (dd, 2H); 6.31 (brs, 2H); 7.05 (d, 1H); 7.24 (t, 1H); 7.31 (m, 1H); 7.37 (m, 2H); 7.42 (m, 2H); 7.58 (m, 1H)

Preparation of Building Block P (RS)-4-(3-Bromo-phenyl)-4-(3-fluoro-4-methoxyphenyl)-4,5-dihydro-oxazol-2-ylamine 4-[1-(3-Bromo-phenyl)-vinyl]-2-fluoro-1-methoxybenzene

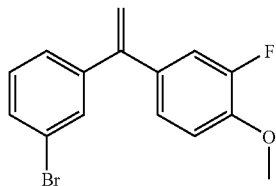

To a mixture of magnesium turnings (660 mg, 0.03 mol, 1.2 eq) in dry tetrahydrofuran (5 mL), was added a portion (⅕) of 3-bromo-4-fluoroanisole (5.0 g, 0.02 mol, 1.1 eq) in dry tetrahydrofuran (25 mL) and 1,2-dibromoethane (0.5 mL). The resulting solution was refluxed and the other (⅘) portion of the above solution was added and the resulting solution was refluxed for 2 h. After cooled at 0° C.° a solution of 3-bromoacetophenone (3 mL, 1 eq) in dry tetrahydrofuran (25 mL) was added dropwise and the reaction was stirred for 3 h at room temperature. The mixture was quenched with ammonium chloride saturated solution (20 mL). Hie aqueous phase was extracted with dichloromethane. (3×20 mL), dried (sodium sulfate) and the solvent removed in vacuo. The crude latter was dissolved in acetic acid (80 mL) and concentrated sulfuric acid (17 mL) was added The mixture was warmed to 75° C. for 30 min, cooled at room temperature and 1 N NaOH was added up to pH=7. The aqueous phase was extracted with dichloromethane (3×10 mL), dried (sodium sulfate) the solvent was removed and the residue was purified by column chromatography (cyclohexane) to afford the title compound as a colourless oil (3.3 g, 44%);

Mass (calculated) C$_{15}$H$_{12}$BrFO [307] (found) [M+H$^+$]= 309

LC Rt=2.97 min (5 min method) 95%

$^1$H-NMR (CDCl$_3$): 3.90 (s, 3H), 5.40 (d, 2H), 6.90-7.10 (m, 4H), 7.21 (m, 2H), 7.45 (m, 1H)

(RS)-4-(3-Bromo-phenyl)-4-(3-fluoro-4-methoxyphenyl)-4,5-dihydro-oxazol-2-ylamine (Building Block P)

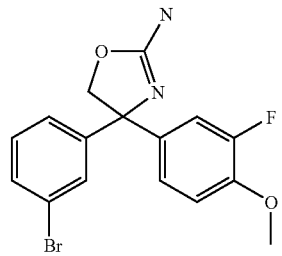

A solution of iodine (3.0 g, 0.011 mol, 1.1 eq) in ethyl acetate (36 mL) was added dropwise to a cooled ice bath suspension of silver cyanate (1.8 g, 26 mmol, 1.2 eq), 4-[1-(3-bromo-phenyl)-vinyl]-2-fluoro-1-methoxy-benzene (3.3 g, 0.012 mmol, 1 eq) in acetonitrile (25 mL) and ethyl acetate (12 mL). The resulting brown suspension was stirred for 1 h at room temperature. the reaction was examined by LC-MS which showed complete conversion of the starting material, the reaction mixture was filtered and concentrated in vacuo. Aqueous ammonia (25% soln, 50 mL) was added to the oil and the mixture was stirred for 15 min at ambient temperature followed by 3 h at 80° C. The reaction was allowed to warm up to room temperature, extracted with dichloromethane (2×30 mL), the organic layers collected, dried and concentrated in vacuo. The crude was dissolved in dichloromethane/methanol 1:1 (5 mL) and passed through SCX (50 g) cartridge, washing with dichloromethane/methanol mixture and the product was recovered eluting with a solution 2.0 M of ammonia in methanol. 2.4 g of product was obtained as a yellow solid (yield: 66%)

Mass (calculated) C$_{16}$H$_{14}$BrFN$_2$O$_2$ [365]; (found) [M+H$^+$]= 367

LC Rt=1.93 min (5 min method) 99%

$^1$H-NMR (d$_6$-DMSO): 3.77 (s, 3H), 4.61 (m, 2H), 6.32 (bs, 2H), 7.05-7.24 (m, 4H), 7.37 (m, 2H), 7.59 (s, 1H).

Preparation of Building Block Q (RS)-4-(3-Bromo-phenyl)-4-(4-isopropoxy-phenyl)-4,5-dihydro-oxazol-2-ylamine 1-Bromo-4-isopropoxy-benzene [6967-88-0]

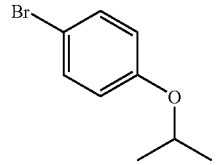

A mixture of 4-bromophenol (7.0 g, 40.0 mmol, 1 eq) dimethylsulfoxide (20 mL), and potassium carbonate (11.0 g, 80.0 mmol, 2.0 eq) was stirred at room temperature then 2-iodopropane (5.2 mL, 1.3 eq) was added. The mixture was heated to 60° C. overnight, cooled to room temperature and treated with water (200 mL). The reaction was extracted with dichloromethane, dried (sodium sulfate) and concentrated in vacuo. The crude was purified by flash chromatography eluting with cyclohexane to afford the title compound as a colorless oil (7.9 g, 92%);

Mass (calculated) C$_9$H$_{11}$BrO [215] MH$^+$ not observed

LC Rt=2.43 min (5 min method) 97%

$^1$H-NMR (CDCl$_3$): 1.34 (d, 6H), 4.97 (m, 1H), 6.77 (m, 2H), 7.34 (m, 2H)

1-Bromo-3-(1-[4-isopropoxy-phenyl]-vinyl)-benzene

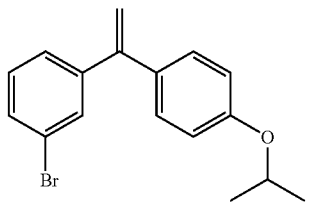

n-Butyllithium (1.6 M solution in hexane, 12.0 mL, 0.9 eq) was added dropwise to a solution of 1-bromo-4-isopropoxy-benzene (4.8 g, 22 mmol, 1.0 eq) in tetrahydrofuran (20 mL) at −78° C. After stirring 30 min 3-bromoacetophenone (3.3 mL, 1.1 eq) in tetrahydrofuran (20 mL) was added dropwise. The mixture was allowed to warm up to room temperature and stirred for 2 h, then treated with 1 N HCl (10 mL), extracted with ethyl acetate, dried (sodium sulfate) and concentrated in vacuo. The crude material was dissolved in acetic acid (50 mL) and sulfuric acid (10 mL) and the mixture was warmed to 75° C. for 30 min, cooled at room temperature and 1 N NaOH was added up to pH=7. The aqueous phase was extracted with dichloromethane (3×10 mL), dried (sodium sulfate) the solvent was removed and the residue was purified by column chromatography (cyclohexane) to afford the title compound as a colourless oil (1.8 g, 25%);

Mass (calculated) C$_{17}$H$_{17}$BrO [317]; (found) [M+H$^+$]= 318

LC Rt=2.12 min (10 min method) 99%

(RS)-4-(3-Bromo-phenyl)-4-(4-isopropoxy-phenyl)-4,5-dihydro-oxazol-2-ylamine (Building Block Q)

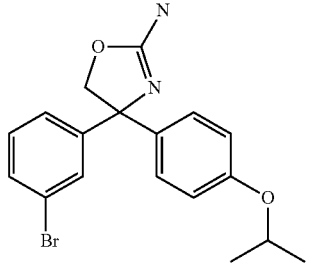

A solution of iodine (1.6 g, 6.0 mmol, 1.1 eq) in ethyl acetate (15 mL) was added dropwise to a cooled ice bath suspension of silver cyanate (1.0 g, 6.6 mmol, 1.2 eq), 1-bromo-3-(1-[4-isopropoxy-phenyl]-vinyl)-benzene (1.9 g, 6.0 mmol, 1 eq) in acetonitrile (14 mL) and ethyl acetate (7 mL). The resulting brown suspension was stirred for 1 h at room temperature. the reaction was examined by LC-MS which showed complete conversion of the starting material, the reaction mixture was filtered and concentrated in vacuo. Aqueous ammonia (25% soln, 25 mL) was added to the oil and the mixture was stirred for 15 min at ambient temperature followed by 3 h at 80° C. The reaction was allowed to warm up to room temperature, extracted with dichloromethane (2×30 mL), the organic layers collected, dried and concentrated in vacuo. The crude was dissolved in dichloromethane/methanol 1:1 (5 mL) and passed through SCX (20 g) cartridge, washing with dichloromethane/methanol mixture and the product was recovered eluting with a solution 2.0 M of ammonia in methanol. 0.7 g of product was obtained as a yellow solid (yield: 31%)

Mass (calculated) C$_{18}$H$_{19}$BrN$_2$O$_2$ [375]; (found) [M+H$^+$]= 377

LC Rt=2.28 min (5 min method)

$^1$H-NMR (CDCl$_3$): 1.20 (d, 6H), 4.53 (m, 3H), 6.81 (m, 2H), 7.24-7.36 (m, 4H), 7.58 (m, 1H), 8.15 (m, 1H)

Preparation of Building Block R (RS)-4-(3-Bromo-phenyl)-4-(4-difluoromethoxy-phenyl)-4,5-dihydro-oxazol-2-ylamine 1-Bromo-3-(1-(4-difluoromethoxy-phenyl)-vinyl)-benzene

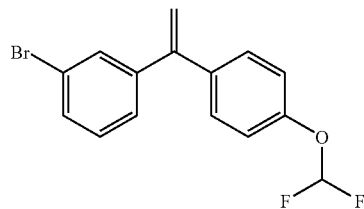

A solution of n-butyllithium (16.8 mL, 1.6 M in hexane) was added dropwise to a solution of 1,3-dibromobenzene 6.3 g in 50 mL of dry tetrahydrofuran under nitrogen at −78° C. A solution of 4-difluoromethoxyacetophenone (5 g) in dry tetrahydrofuran (50 mL) was then added to the mixture maintaining the temperature at −78° C. at which point the solution changed from a white suspension to a black solution. The mixture stirred over night while warming to room temperature it was then carefully quenched with saturated ammonium chloride solution and diluted with ethyl acetate (100 mL). The layers were separated and the organic layers were washed with brine. The solution was dried over sodium sulfate, filtered and concentrated under reduced pressure. The crude alcohol was then diluted with toluene 100 mL and p-toluenesulfonic acid (100 mg) was added. The flask was fitted with a Dean-Stark water trap and the mixture was heated to reflux for 3 hours at which point the starting material was consumed by LC. The solution was diluted with ethyl acetate and saturated sodium carbonate solution. The organic layer was then washed with brine, dried over sodium sulfate filtered and concentrated under reduced pressure. The crude was purified by flash chromatography eluting with 100% cyclohexane (Rf 0.6). 2.9 g of the product was obtained as a yellow oil (yield: 33%)

Mass (calculated) $C_{15}H_{11}BrF_2O$ [324]; (found) [M+H$^+$]= 325, 327

LC Rt=3.02 min (5 min method) 80%

$^1$H-NMR (CDCl$_3$): 5.41 (s, 2H), 6.55 (t, 1H), 7.07 (s, 2H), 7.2-7.4 (m, 5H), 7.45 (2, 1H)

(RS)-4-(3-Bromo-phenyl)-4-(4-difluoromethoxy-phenyl)-4,5-dihydro-oxazol-2-ylamine (Building Block R)

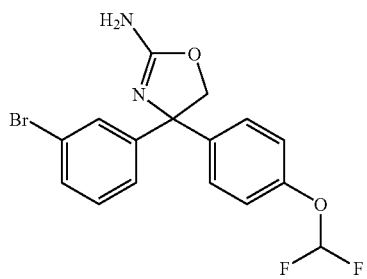

A saturated solution of iodine (2.79 g, 11 mmol, 1 eq) in 20 mL of ethyl acetate (80 mL) was slowly dropped (ca 1.5 h) into a mixture of 1-bromo-3-(1-(4-difluoromethoxy-phenyl)-vinyl)-benzene (2.9 g) and silver cyanate (1.47 g) in acetonitrile/ethyl acetate (30 mL/10 mL). The suspension was stirred at room temperature for an hour by which point the starting material was consumed and the suspension was colorless. The silver iodide formed was removed by filtration and the mixture was concentrated under reduced pressure. Aqueous ammonia (25% soln, 60 mL) was then added (40 mL) the mixture was stirred vigorously heated to 80° C. and heated for overnight at which point the reaction was complete. The aqueous mixture was extracted with ethyl acetate (2×75 mL). The organic layer was washed with brine, filtered and concentrated under reduced pressure. The crude was dissolved in dichloromethane/methanol 1:1 (10 mL) and passed through SCX (20 g) cartridge, washing with dichloromethane/methanol (100 mL) mixture and the product was recovered eluting with a solution 2.0 M of ammonia in methanol (2×50 mL). Purification by flash chromatography (dichloromethane) yielded 0.8 g of product was obtained as clear oil (23% yield).

Mass (calculated) $C_{16}H_{13}BrF_2N_2O_2$ [382]; (found) [M+H$^+$]=383, 385

LC Rt=1.48 min (5 min method) 99%

$^1$H-NMR (CDCl$_3$): 4.35 (bs, 2H), 4.65 (ABq, 2H), 6.4 (t, 1H), 7.0 (d, 2H), 7.1-7.25 (m, 5H), 7.45 (s, 1H)

Preparation of Building Block S (RS)-4-(3-Bromo-phenyl)-4-(4-difluoromethoxy-3-methyl-phenyl)-4,5-dihydro-oxazol-2-ylamine 1-(4-Difluoromethoxy-3-methyl-phenyl)-ethanone [116400-19-2]

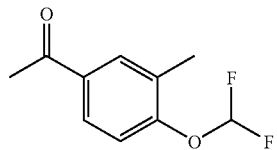

To a solution of 4-acetylcresol (5.0 g, 33 mmol, 1.0 eq) in 50 mL of a 9:1 N,N-dimethylformamide/water mixture, cesium carbonate (14.7 g, 42 mmol, 1.3 eq.) and sodium chlorodifluoroacetate (12.7 g, 83 mmol, 2.5 eq.) were added. The mixture was purged with nitrogen, then heated to 120° C. while stirring. After 24 hours the reaction mixture was cooled to mom temperature, treated with aqueous 1 M NaOH (20 mL) and extracted with ethyl acetate. The organic layer was washed with brine, dried over sodium sulfate and concentrated. The crude product was purified by flash chromatography eluting with cyclohexane/ethyl acetate (100:0 to 90:10). 3.3 g of clean product was obtained as colorless liquid (yield: 48%).

LC Rt=2.10 min (5 min method) 98%

$^1$H-NMR (CDCl$_3$): 2.33 (s, 3H); 2.57 (s, 3H); 6.58 (t, 1H), 7.11 (d, 1H), 7.79 (dd, 1H), 7.84 (d, 1H).

4-[1-(3-Bromo-phenyl)-vinyl]-1-difluoromethoxy-2-methyl-benzene

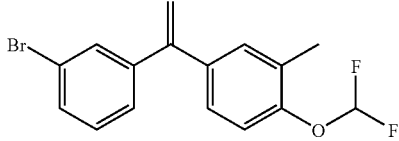

A solution of 1,3-dibromobenzene (5.2 g, 22 mmol, 1.4 eq) in 20 mL of anhydrous tetrahydrofuran was cooled to −78° C. and a n-butyllithium solution (1.6 M in hexanes, 12.3 mL, 20 mmol, 1.2 eq.) was added dropwise. After stirring for 30 minutes, the yellow suspension was transferred via cannula at −78° C. into a flask containing a tetrahydrofuran solution (10 mL) of 1-(4-difluoromethoxy-3-methyl-phenyl)-ethanone (3.3 g, 16 mmol, 1.0 eq.) at −78° C. The resulting mixture was stirred for further 1 hour, then 15 mL of a saturated aqueous ammonium chloride solution were added. The reaction mixture was extracted with diisopropyl ether. The organic layer was washed with brine, dried over sodium sulfate and concentrated. The crude product was diluted with toluene (40 mL) and a few crystals of p-toluenesulfonic acid were added. The solution was heated to reflux for 2 hours in a flask equipped with a Dean-Stark apparatus. After this time, the mixture was cooled to room temperature, concentrated and the crude purified by flash chromatography eluting with cyclohexane/ethyl acetate (100:0 to 95:5). 4.9 g of clean product was obtained as colorless liquid (yield: 87%).

Mass (calculated) $C_{16}H_{13}BrF_2O$ [339]; (found) $[M+H^+]$= 340

LC Rt=2.58 min (5 min method) 90%

$^1$H-NMR (CDCl$_3$): 2.27 (s, 3H); 5.43 (d, 2H), 6.52 (t, 1H), 7.03 (d, 1H), 7.11 (dd, 1H), 7.20 (m, 3H), 7.45 (t, 1H), 7.46 (m, 1H).

(RS)-4-(3-Bromo-phenyl)-4-(4-difluoromethoxy-3-methyl-phenyl)-4,5-dihydro-oxazol-2-ylamine (Building Block S)

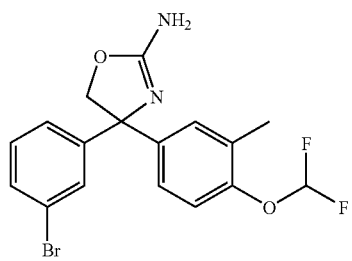

According to general method 2, a solution of iodine in ethyl acetate was added to a mixture of 4-[1-(3-bromo-phenyl)-vinyl]-1-difluoromethoxy-2-methyl-benzene (4.9 g, 14 mmol) and silver cyanate in ethyl acetate/acetonitrile. The crude product of this reaction was subsequently reacted with aqueous ammonia (30% by vol). Purification by SCX yielded 4.8 g of product (85%).

Mass (calculated) $C_{17}H_{15}BrF_2N_2O_2$ [397]; (found) $[M+H^+]$=398

LC Rt=2.25 min (5 min method) 95%

$^1$H-NMR (CDCl$_3$): 2.21 (s, 3H), 4.77 (d, 1H), 4.81 (d, 1H), 6.42 (t, 1H), 6.97 (d, 1H), 7.04 (dd, 1H), 7.11 (m, 1H), 7.16 (d, 1H), 7.18 (m, 1H), 7.35 (dt, 1H), 7.41 (t, 1H).

Preparation of Building Block T (RS)-4-(3-Bromo-phenyl)-4-(4-trifluoromethoxy-phenyl)-4,5-dihydro-oxazol-2-ylamine 4-[1-(3-Bromo-phenyl)-vinyl]-1-trifluoromethoxy-benzene

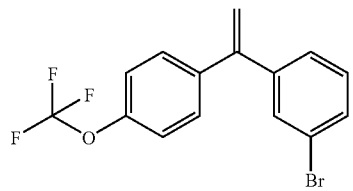

A solution of n-butyllithium (1.6 M in hexane, 17.8 mL, 28.4 mmol, 1.16 eq.) was added dropwise over 20 min to a solution of 1,3-dibromobenzene (3.26 mL, 26.95 mmol, 1.1 eq) in 25 mL of dry tetrahydrofuran at −78° C. and under an inert atmosphere. The white suspension formed was stirred at −78° C. for 30 min. A solution of 4-(trifluoromethoxy)-acetophenone (5 g, 24.5 mmol, 1.0 eq.) in 25 mL of tetrahydrofuran was then added dropwise and the reaction stirred for 1 h. The reaction mixture was examined by LC-MS which showed the complete formation of tertiary alcohol. The solution was quenched with a saturated solution of ammonium chloride and water. 2 N HCl was then added to reach pH=~5. The two phases were separated; the organic layer was dried over anhydrous magnesium sulfate, filtered and evaporated under reduced pressure. The residual material (tertiary alcohol) was dissolved in a mixture of acetic acid/sulfuric acid (10 mL of acetic acid, 0.3 mL of sulfuric acid) and the reaction mixture was stirred for 3 h at room temperature; then it was examined by LC-MS which showed the complete Formation of desired product. The solution was quenched with ice and dichloromethane (20 mL) was added. The two phases formed and were separated. The organic layer was washed with a saturated solution of sodium bicarbonate and brine. It was then dried over anhydrous magnesium sulfate, filtered and evaporated under reduced pressure. The crude was purified by flash chromatography eluting with petroleum ether to give the desired product as a colourless liquid (3.60 g, Yield: 43%).

Mass (calculated) $C_{15}H_{10}BrF_3O$ [343]; $[M+H^+]$ not observed

LC Rt=3.20 min (5 min method)

$^1$H-NMR (CDCl$_3$): 5.49 (s, 2H); 7.21 (m, 4H); 7.34 (m, 2H); 7.49 (m, 2H)

(RS)-4-(3-Bromo-phenyl)-4-(4-trifluoromethoxy-phenyl)-4,5-dihydro-oxazol-2-ylamine (Building Block T)

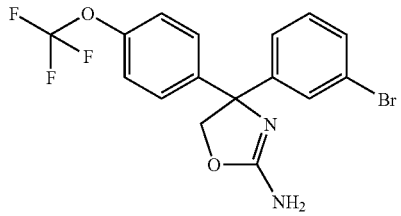

A solution of iodine (2.92 g, 11.5 mmol) in ethyl acetate (50 mL) was added dropwise over 25 min to a mixture of 4-[1-(3-bromo-phenyl)-vinyl]-1-trifluoromethoxy-benzene (3.6 g, 10.5 mmol) and silver cyanate (1.88 g, 12.6 mmol) in acetonitrile (38 mL) and ethyl acetate (18 mL), cooled in an ice bath. After complete addition, the reaction suspension was stirred for another 15 min at room temperature when TLC indicated the complete conversion of starting material. The reaction mixture was filtered, and the filtrate concentrated to give a dark grey oil. 50 mL of aqueous ammonia (25%) was added to the oil, and the mixture was stirred and warmed to 60° C. for 4 hours. LC-MS at this point indicated complete conversion of the intermediate urea to the desired aminoxazoline. dichloromethane (40 mL) was added to the crude and the two phases were separated; organic layer was collected, dried over magnesium sulfate anhydrous, filtered and evaporated under reduced pressure. Crude was purified by silica gel chromatography eluting with dichloromethane to give 1.9 g of desired product as a colorless oil (45%)

Mass (calculated) $C_{16}H_{12}BrF_3N_2O_2$ [401]; $[M+H^+]$=402

LC Rt=1.50 min (5 min method)

$^1$H-NMR (CDCl$_3$): 4.73 (s, 2H); 4.83 (brs, 2H); 7.15 (m, 2H); 7.20 (m, 2H); 7.33 (m, 2H); 7.37 (m, 1H); 7.50 (m, 1H)

Preparation of Building Block U (RS)-4-(3-Bromo-4-fluoro-phenyl)-4-(3-chloro-4-methoxy-phenyl)-4,5-dihydro-oxazol-2-ylamine 4-Bromo-2-chloro-1-methoxy-benzene [50638-47-6]

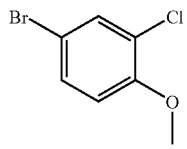

A mixture of 4-bromo-2-chlorophenol (7.0 g, 33.0 mmol, 1 eq), N,N-dimethylformamide (50 mL) and cesium carbonate (8.5 g, 42.0 mmol, 1.2 eq) was stirred at room temperature then iodomethane (2.5 mL, 1.2 eq) was added. The mixture was heated to 50° C. overnight, cooled to room temperature and treated with water (500 mL). The reaction was extracted with dichloromethane, dried (sodium sulfate) and concentrated in vacuo. The crude was purified by flash chromatography eluting with cyclohexane. 7.5 g of clean product in a quantitative yield.

Mass (calculated) $C_7H_6BrClO$ [221] $MH^+$ not observed

LC Rt=3.15 min (5 min method)

$^1$H-NMR (CDCl$_3$): 3.88 (s, 3H), 6.80 (d, 1H), 7.32 (m, 1H), 7.50 (m, 1H)

1-Bromo-3-[1-(4-methoxy-3-chlorophenyl)-vinyl]-6-fluorobenzene

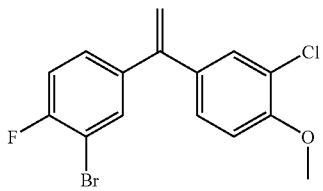

A solution of n-butyllithium (1.6 M solution in hexane, 20 mL, 1.1 eq) was added dropwise to a solution of 4-bromo-2-chloro-1-methoxy-benzene (6 g, 27 mmol, 1 eq) in tetrahydrofuran (25 mL) at −78° C. After stirring 30 min 3-bromo-4-fluoroacetophenone (5.8 g, 27 mmol, 1 eq) in tetrahydrofuran (25 mL) was added dropwise. The mixture was allowed to warm up to room temperature and stirred for 2 h, then treated with water (10 mL), extracted with ethyl acetate, dried (sodium sulfate) and concentrated in vacuo. The crude was dissolved in acetic acid (80 mL) and concentrated sulfuric acid (17 mL) was added. The mixture was warmed to 75° C. for 30 min, cooled at room temperature and neutralized with 1 N NaOH. The aqueous phase was extracted with dichloromethane (3×100 mL), dried (sodium sulfate) the solvent was removed under reduced pressure. The residue was purified by column chromatography (cyclohexane) to afford the title compound as a colourless oil (3.2 g, 36%);

Mass (calculated) $C_{15}H_{11}BrClFO$ [341]; (found) $[M+H^+]=342$

LC Rt=3.05 min (5 min method)

$^1$H-NMR (CDCl$_3$): 3.90 (s, 3H), 5.35 (d, 2H), 6.88 (m, 1H), 7.06-7.26 (m, 4H), 7.50 (m, 1H)

(RS)-4-(3-Bromo-4-fluoro-phenyl)-4-(3-chloro-4-methoxy-phenyl)-4,5-dihydro-oxazol-2-ylamine (Building Block U)

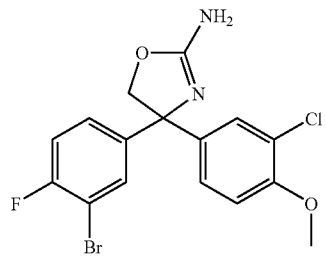

A solution of iodine (2.6 g, 10 mmol, 1.1 eq) in ethyl acetate (34 mL) was added dropwise to a cooled ice bath suspension of silver cyanate (1.7 g, 11 mmol, 1.2 eq), 1-bromo-3-[1-(4-methoxy-3-chlorophenyl)-vinyl]-6-fluorobenzene (3.2 g, 9.0 mmol, 1 eq) in acetonitrile (23 mL) and ethyl acetate (11 mL). The resulting brown suspension was stirred for 1 h at room temperature. the reaction was examined by LC-MS which showed complete conversion of the starting material, the reaction mixture was filtered and concentrated in vacuo. Aqueous ammonia (25% soln, 50 mL) was added to the oil and the mixture was stirred for 15 min at ambient temperature followed by 3 h at 80° C. The reaction was allowed to cool to room temperature and extracted with dichloromethane (2×30 mL). The organic layers were collected, dried (sodium sulfate) and concentrated in vacuo. The crude was dissolved in dichloromethane/methanol 1:1 (5 mL) and passed through SCX (50 g) cartridge, washing with dichloromethane/methanol mixture and the product was recovered eluting with a solution 2.0 M of ammonia in methanol. 1.9 g of product was obtained as a yellow solid (yield: 50%)

Mass (calculated) $C_{16}H_{13}BrClFN_2O_2$ [399]; (found) $[M+H^+]=398$

LC Rt=2.70 min (5 min method)

$^1$H-NMR (CDCl$_3$): 3.83 (s, 3H), 4.70 (m, 2H), 6.80 (m, 1H), 6.90-7.24 (m, 4H), 7.45 (m, 1H)

Preparation of Building Block V (RS)-4-(3-Bromo-phenyl)-4-(4-difluoromethoxy-3-fluoro-phenyl)-4,5-dihydro-oxazol-2-ylamine 1-(4-Difluoromethoxy-3-fluoro-phenyl)-ethanone

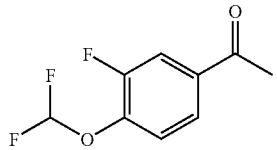

A mixture of 3-fluoro-4-hydroxy-acetophenone (5.0 g, 32.5 mmol, 1 eq) N,N-dimethylformamide (50 mL), and potassium carbonate (5.38 g, 38.93 mmol, 1.2 eq) was degassed (nitrogen) for 1 h. Sodium chlorodifluoroacetate (6 g, 38.93 mmol, 1.2 eq) was then added and the mixture was heated to 120° C. overnight. The mixture was cooled to room temperature and treated with water (10 mL). The reaction was extracted with dichloromethane, dried (sodium sulfate) and concentrated in vacuo. The crude was purified by flash chromatography eluting with cyclohexane/ethyl acetate (9:1). 3.7 g of clean product was obtained as colorless oil (yield: 56%).

Mass (calculated) $C_9H_7F_3O_2$ [204] MH$^+$ not observed.

LC Rt=3.48 min (5 min method) 90%.

$^1$H-NMR (CDCl$_3$): 2.51 (s, 1H), 6.57 (t, 1H), 7.26 (t, 1H), 7.69 (m, 2H).

4-[1-(3-phenyl)-vinyl]-1-difluoromethoxy-2-fluoro-benzene

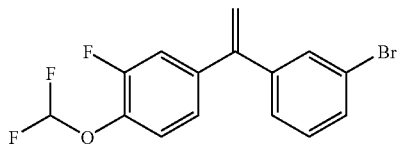

A solution of n-butyllithium (1.6 M in hexane, 13.2 mL, 21.1 mmol, 1.2 eq) was added over 20 min to a solution of 1,3-dibromobenzene (2.35 mL, 19.4 mmol, 1.1 eq) in 30 mL of dry tetrahydrofuran at −78° C. and under an inert atmosphere. The white suspension formed and was stirred at −78° C. for 30 min. A solution of 1-(4-difluoromethoxy-3-fluoro-phenyl)-ethanone (3.6 g, 17.6 mmol, 1.0 eq.) in 20 mL of tetrahydrofuran was then added dropwise and the reaction stirred for 1 h at which point LC-MS showed the complete formation of tertiary alcohol. The solution was quenched with a saturated aqueous solution of ammonium chloride and then water was added. 2 N hydrochloric acid was added to adjust the pH=5. The two phases were separated; the organic layer was dried over anhydrous magnesium sulfate, filtered and evaporated under reduced pressure. The crude was dissolved in a mixture of acetic acid/sulfuric acid (10 mL of acetic acid, 0.3 mL of sulfuric acid) and the reaction mixture was stirred for 1 h at room temperature. Examination by LC-MS which showed the complete formation of desired product. The solution was quenched with ice and dichloromethane (20 mL) was added. The two phases formed and were separated. The organic layer was washed with a saturated solution of sodium bicarbonate and then brine. It was then dried over anhydrous magnesium sulfate, filtered and evaporated under reduced pressure. The crude was purified by flash chromatography eluting with cyclohexane. The desired product was obtained as a pale yellow liquid (1.2 g, Yield: 5% over two steps).

$^1$H-NMR (CDCl$_3$): 5.43 (d, 2H), 6.51 (t, 1H), 7.02-7.42 (m, 7H).

(RS)-4'-(3-Bromo-phenyl)-4-(4-difluoromethoxy-3-fluoro-phenyl)-4,5-dihydro-oxazol-2-ylamine (Building Block V)

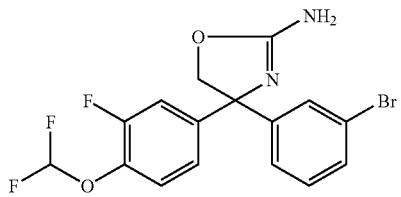

A solution of iodine (0.98 g, 3.85 mmol, 1.1 eq) in 30 mL of ethyl acetate was added dropwise (15 min) at 0° C. to a suspension of 4-[1-(3-bromo-phenyl)-vinyl]-1-difluoromethoxy-2-fluoro-benzene (1.20 g, 3.50 mmol, 1.0 eq) and silver cyanate (0.63 g, 4.21 mmol, 1.2 eq) in acetonitrile/ethyl acetate (10 mL/5 mL). After addition was complete the reaction was examined by LC-MS which showed consumption of starting material. The mixture was filtered and the resulting solution was concentrated under reduced pressure. The crude was suspended in 50 mL of ammonium hydroxide solution and stirred for 4 h at room temperature and at 60° C. overnight. Dichloromethane was added to the suspension and the two phases were separated. The organic layer was dried over magnesium sulfate, filtered and concentrated under reduced pressure. The crude residue was purified by flash chromatography eluting with a gradient dichloromethane/methanol 0-2%. 0.8 g of the desired product was obtained as a pale yellow oil (Yield: 57%). Mass (calculated) $C_{16}H_{12}BrF_3N_2O_2$ [401]; (found) [M+H$^+$]=402. LC Rt=2.24, (10 min method) purity 95% UV. $^1$H-NMR (CDCl$_3$): 4.73 (dd, 2H), 6.45 (t, 1H), 7.02-7.43 (m, 7H).

Preparation of Building Block W

(RS)-4-(3-Bromo-phenyl)-4-(3-chloro-4-difluoromethoxy-phenyl)-4,5-dihydro-oxazol-2-ylamine 1-(3-Chloro-4-difluoromethoxy-phenyl)-ethanone

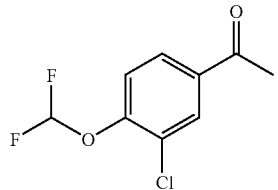

A mixture of 3-chloro-4-hydroxy acetophenone (10.0 g, 58.6 mmol, 1 eq) N,N-dimethylformamide (75 mL), water (9 mL) and cesium carbonate (24.7 g, 76.18 mmol, 1.2 eq) was degassed (nitrogen) for 1 h, then sodium chlorodifluoroacetate (22.3 g, 146.5 mmol, 2.5 eq) was added. The mixture was heated to 120° C. overnight under nitrogen atmosphere. The mixture was cooled to room temperature and treated with water (600 mL). The reaction was extracted with n-hexane (4×50 mL), organic layers were collected, dried over magnesium sulfate anhydrous, filtered and evaporated under reduced pressure. Crude was purified by flash chromatography eluting with cyclohexane/ethyl acetate (gradient 0-20%) to give 12 g as yellow liquid (yield: 92%)

Mass (calculated) $C_9H_7ClF_2O_2$ [220]; [M+H$^+$] not observed

LC Rt=2.12 min (5 min method)

$^1$H-NMR (CDCl$_3$): 2.57 (s, 3H); 6.62 (m, 1H); 7.29 (m, 1H); 7.85 (m, 1H); 8.02 (m, 1H)

4-[1-(3-Bromo-phenyl)-vinyl]-2-chloro-1-difluoromethoxy-benzene

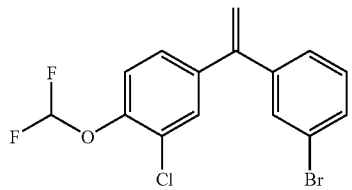

A solution of n-butyllithium (1.6 M in hexane, 16.4 mL, 26.2 mmol, 1.16 eq.) was added dropwise over 20 min to a solution of 1,3-dibromobenzene (3.00 mL, 24.8 mmol, 1.1 eq) in 25 mL of dry tetrahydrofuran at −78° C. and under an inert atmosphere. The white suspension formed was stirred at −78° C. for 30 min. A solution of 1-(3-chloro-4-difluoromethoxy-phenyl)-ethanone (7 g, 31.7 mmol, 1.0 eq.) in 25 mL of tetrahydrofuran was then added dropwise and the reaction stirred for 1 h. The reaction mixture was examined by LC-MS which showed the complete formation of tertiary alcohol. The solution was quenched with a saturated solution of ammonium chloride and water. 2 N HCl was then added to reach pH=5. The two phases were separated; the organic layer was dried over anhydrous magnesium sulfate, filtered and evaporated under reduced pressure. The crude (tertiary alcohol) and a catalytic amount of p-toluenesulfonic acid were dissolved in 70 mL toluene (Dean-Stark apparatus) and the mixture was heated to reflux for 3 h. The solution was examined by TLC (cyclohexane) which showed consumption of starting material but many side products formed. Solvent was evaporated under reduced pressure and the crude residue was purified by flash chromatography eluting with cyclohexane. The desired product was obtained as yellow oil (2.2 g, Yield: 27%).

Mass (calculated) $C_{15}H_{10}BrClF_2O$ [359]; [M+H$^+$]=not observed

LC Rt=3.13 min (5 min method)

$^1$H-NMR (CDCl$_3$): 5.49 (d, 2H); 6.56 (t, 1H); 7.21 (m, 4H); 7.40 (m, 1H); 7.46 (m, 2H)

(RS)-4-(3-Bromo-phenyl)-4-(3-chloro-4-difluoromethoxy-phenyl)-4,5-dihydro-oxazol-2-ylamine (Building Block W)

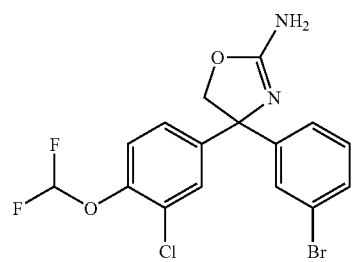

A solution of iodine (1.71 g, 6.74 mmol) in ethyl acetate (40 mL) was added dropwise over 25 min to a mixture of 4-[1-(3-bromo-phenyl)-vinyl]-2-chloro-1-difluoromethoxy-benzene (2.2 g, 6.13 mmol) and silver cyanate (1.10 g, 7.35 mmol) in acetonitrile (24 mL) and ethyl acetate (11 mL), cooled in an ice bath. After complete addition, the reaction suspension was stirred for another 15 min at room temperature when TLC indicated the complete conversion of starting material. The reaction mixture was filtered, and the filtrate concentrated to give a dark grey oil. 50 mL of aqueous ammonia (25%) was added to the oil, and the mixture was stirred and warmed to 60° C. for 4 hours. LC-MS at this point indicated complete conversion of the intermediate urea to the desired aminoxazoline. Dichloromethane (40 mL) was added to the crude and the two phases were separated; organic layer was collected, dried over magnesium sulfate anhydrous, filtered and evaporated under reduced pressure. The crude product was purified by silica gel chromatography eluting with dichloromethane/methanol (gradient: 0-6%) to give 1.02 g of desired product as a yellow oil (40%)

Mass (calculated) $C_{16}H_{12}BrClF_2N_2O_2$ [417]; [M+H$^+$]= 418

LC Rt=1.52 min (5 min method)

$^1$H-NMR: (CDCl$_3$): 4.70 (m, 2H); 6.50 (t, 1H); 7.19 (m, 4H); 7.37 (m, 1H); 7.44 (m, 1H); 7.50 (m, 1H)

Preparation of Building Block X

(RS)-4-(3-Bromo-4-fluoro-phenyl)-4-(4-difluoromethoxy-3-methyl-phenyl)-4,5-dihydro-oxazol-2-ylamine

(4-Bromo-2-methyl-phenoxy)-tert-butyl-dimethyl-silane [179636-73-8]

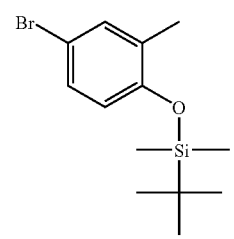

To a mixture of 2-methyl-4-bromophenol (10.0 g, 0.05 mmol, 1 eq) and dichloromethane (100 mL), were added imidazole (5.4 g, 0.08 mmol, 1.5 eq) and tert-butyldimethyl-chlorosilane (8.8 g, 0.06 mmol, 1.1 eq). After 30 min at room temperature the reaction was filtered. The filtrate was washed with 0.5 N HCl (2×30 mL) and the organic phase was dried (sodium sulfate) and concentrated in vacuo. The crude was passed through a silica pad and 8.2 g of clean product was obtained as a colorless oil (yield: 98%)

Mass (calculated) $C_{13}H_{21}BrOSi$ [301] MH$^+$ not observed

LC Rt=3.48 min (5 min method)

$^1$H-NMR (CDCl$_3$): 0.01 (s, 6H), 0.80 (s, 9H), 1.92 (s, 3H), 6.41 (m, 1H), 6.94 (m, 1H), 7.04 (m, 1H)

{4-[1-(3-Bromo-4-fluoro-phenyl)-vinyl]-phenoxy}-tert-butyl-dimethyl-silane

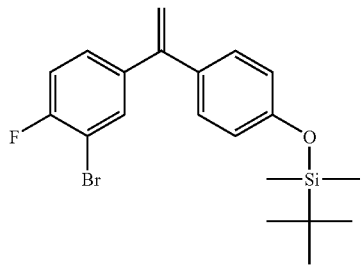

To a mixture of magnesium turnings (1.5 g, 0.06 mol, 1.2 eq) in dry tetrahydrofuran (10 mL), was added a portion (⅕) of (4-bromo-2-methyl-phenoxy)-tert-butyl-dimethyl-silane (16.0 g. 0.05 mol, 1.1 eq) in dry tetrahydrofuran (50 mL) and 1,2-dibromoethane (0.5 mL). The resulting solution was refluxed and the other (⅘) portion of the above solution was added and the resulting solution was refluxed for 2 h. After cooled at 0° C. a solution of 3-bromo-4-fluoroacetophenone (11.5 g, 0.05 mol, 1 eq) in dry tetrahydrofuran (40 mL) was added dropwise and the reaction was stirred for 3 h at room temperature. The mixture was quenched with saturated ammonium chloride solution (20 mL). The aqueous phase was extracted with dichloromethane (3×20 mL), dried (sodium sulfate) and the solvent removed in vacuo. The crude latter was dissolved in toluene (200 mL) and a catalytic amount (30 mg) of p-toluenesulfonic acid was added and refluxed for 3 h. The solvent was removed and the residue was purified by column chromatography (cyclohexane) to afford the title compound as a colourless oil (18.5 g, 39%).

Mass (calculated) C$_{20}$H$_{24}$BrFOSi [407]; (found) [M+H$^+$]= 423

LC Rt=3.44 min (5 min method)

$^1$H-NMR (CDCl$_3$): 0.0 (s, 6H), 0.80 (s, 9H), 1.99 (s, 3H), 5.05 (d, 1H), 5.16 (d, 1H), 6.50 (m, 1H), 6.76 (m, 1H), 6.86 (m, 2H), 7.01 (m, 1H), 7.32 (m, 1H)

1-[1-(3-Bromo-4-fluoro-phenyl)-vinyl]-4-difluoromethoxy-3-methylbenzene

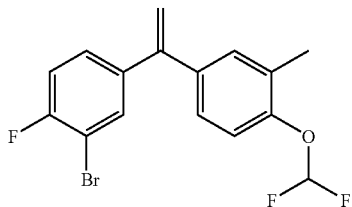

A 1 M solution of tetrabutylammonium fluoride in tetrahydrofuran (57 mL, 1.3 eq), was added to a ice bath cooled solution of {4-[1-(3-bromo-4-fluoro-phenyl)-vinyl]-phenoxy}-tert-butyl-dimethyl-silane (18.5 g, 0.04 mol, 1 eq) in dry dichloromethane (200 mL) at 0° C. After stirring for at 2 h, the solvent was removed under reduced pressure and the residue was taken up in dichloromethane. The organic phase was washed with brine, dried and concentrated in vacuo. The residue was filtered through a pad of silica gel eluting with cyclohexane/ethyl acetate (5:1). The solution was concentrated under reduced pressure and used directly for the next step without further purification. The crude (6.5 g, 0.02 mmol, 1 eq) was dissolved in N,N-dimethylformamide (28 mL), water (2.8 mL) and cesium carbonate (8.1 g, 0.02 mmol, 1.2 eq) were added and the mixture was degassed (nitrogen) for 1 h then sodium chlorodifluoroacetate (8.5 g, 55.7 mmol, 1.2 eq) was added. The mixture was heated to 120° C. overnight under nitrogen. A further equivalent of sodium chlorodifluoroacetate was added and the reaction was stirred at 120° C. for additional 3 h. The mixture was cooled to room temperature and diluted with water (300 mL). The reaction was extracted with dichloromethane, dried (sodium sulfate) and concentrated in vacuo. The crude was purified by flash chromatography eluting with cyclohexane. 2.2 g of clean product was obtained as colorless oil (yield: 30%)

Mass (calculated) C$_{16}$H$_{12}$BrF$_3$O [357]; MH$^+$ not observed

LC Rt=3.10 min (5 min method)

$^1$H-NMR (CDCl$_3$): 2.21 (s, 3H), 5.35 (m, 2H), 6.46 (t, 1H), 6.98-7.20 (m, 6H), 7.44 (m, 1H)

(RS)-4-(3-Bromo-4-fluoro-phenyl)-4-(4-difluoromethoxy-3-methyl-phenyl)-4,5-dihydro-oxazol-2-ylamine (Building Block X)

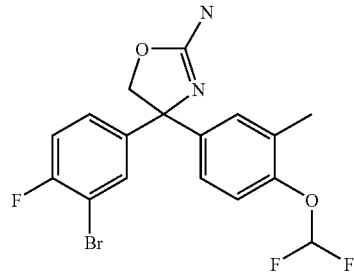

A solution of iodine (1.5 g, 0.06 mol, 1.1 eq) in ethyl acetate (20 mL) was added dropwise to a cooled ice bath suspension of silver cyanate (1.1 g, 0.07 mmol, 1.2 eq), 1-[1-(3-bromo-4-fluoro-phenyl)-vinyl]-4-difluoromethoxy-3-methylbenzene (2.2 g, 0.06 mmol, 1 eq) in acetonitrile (15 mL) and ethyl acetate (7 mL). The resulting brown suspension was stirred for 1 h at room temperature. The reaction was examined by LC-MS which showed complete conversion of the starting material, the reaction mixture was filtered and concentrated in vacuo. Aqueous ammonia (25% soln, 50 mL) was added to the oil and the mixture was stirred for 15 min at ambient temperature followed by 3 h at 80° C. The reaction was allowed to cool to room temperature, extracted with dichloromethane (2×30 mL), the organic layers collected, dried and concentrated in vacuo. The crude was dissolved in dichloromethane/methanol 1:1 (5 mL) and passed through SCX (50 g) cartridge, washing with dichloromethane/methanol mixture and the product was recovered eluting with a solution 2.0 M of ammonia in methanol. 1.7 g of product was obtained as a white solid (yield: 67%)

Mass (calculated) C$_{17}$H$_{14}$BrF$_3$N$_2$O$_2$ [415]; (found) [M+H$^+$]=417

LC Rt=1.63 min (5 min method)

$^1$H-NMR (CDCl$_3$): 2.25 (s, 3H), 4.72 (m, 2H), 6.46 (t, 1H), 6.98-7.02 (m, 6H), 7.53 (m, 1H).

Preparation of Building Block Y (RS)-4-(3-Bromo-phenyl)-4-(4-methoxy-3-trifluoromethyl-phenyl)-4,5-dihydro-oxazol-2-ylamine 4-[1-(3-Bromo-phenyl)-vinyl]-1-methoxy-2-trifluoromethyl-benzene

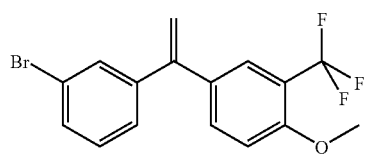

To a suspension of magnesium turnings (565 mg, 23.5 mmol, 1.2 eq) in 5 mL of dry tetrahydrofuran, 0.1 mL of 1,2-dibromoethane were added followed by 5 mL of a tetrahydrofuran solution of 5-bromo-2-methoxy-benzotrifluoride (5.0 g, 19.6 mmol, 1.0 eq in 30 mL tetrahydrofuran). The resulting mixture was gently heated to initiate the reaction. The remaining solution of bromide was added dropwise at such a rate that the reaction could reflux without external heating. After the addition the reaction mixture was heated at reflux for further 2 hours. The mixture was cooled to 0° C. and a solution of 3-bromoacetophenone (3.9 g, 19.6 mmol, 1.0 eq) in tetrahydrofuran (30 mL) was added dropwise. After 2 hours LC-MS showed complete conversion to the desired product. 50 mL of water were added followed by 25 mL of 1 M aqueous HCl. The organic fraction was washed with brine, dried over sodium sulfate and concentrated to give a yellow oil. The oil was dissolved in toluene (50 mL) and a few crystals of p-toluenesulfonic acid were added. The solution was heated to reflux for 2 hours in a flask equipped with a Dean-Stark apparatus. After this time, the mixture was cooled to room temperature, concentrated and the crude purified by flash chromatography eluting with cyclohexane/ethyl acetate (100:0 to 95:5). 5.1 g of clean product was obtained as colorless liquid (yield: 73%).

Mass (calculated) $C_{16}H_{12}BrF_3O$ [357]; (found) $[M+H^+]$=358

LC Rt=3.10 min (5 min method) 98%

$^1$H-NMR (CDCl$_3$): 3.92 (s, 3H); 5.44 (d, 2H), 6.56 (d, 1H), 7.23 (m, 2H), 7.39 (dd, 1H), 7.47 (m, 2H), 7.55 (d, 1H)

(RS)-4-(3-Bromo-phenyl)-4-(4-methoxy-3-trifluoromethyl-phenyl)-4,5-dihydro-oxazol-2-ylamine (Building Block Y)

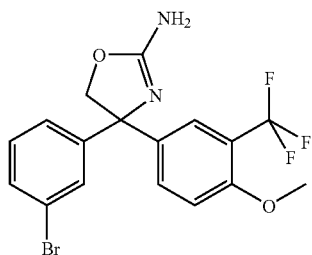

According to general method 2, a solution of iodine in ethyl acetate was added to a mixture of 4-[1-(3-bromo-phenyl)-vinyl]-1-methoxy-2-trifluoromethyl-benzene (5.1 g, 14 mmol) and silver cyanate in ethyl acetate/acetonitrile. The crude product of this reaction was subsequently reacted with aqueous ammonia (30% by vol). Purification by SCX yield 4.6 g of product (67%).

Mass (calculated) $C_{17}H_{14}BrF_3N_2O_2$ [415]; (found) $[M+H^+]$=416

LC Rt=1.52 min (5 min method) 95%

Preparation of Building Block Z (RS)-4-(3-Bromo-phenyl)-4-(4-difluoromethoxy-2-methyl-phenyl)-4,5-dihydro-oxazol-2-ylamine 1-(4-Difluoromethoxy-2-methyl-phenyl)-ethanone

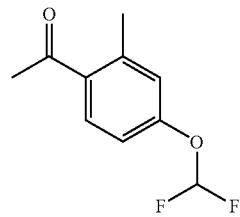

A mixture of 4-hydroxy-2-methyl-acetophenone (7.0 g, 46.0 mmol, 1 eq) N,N-dimethylformamide (25 mL), water (2.5 mL) and cesium carbonate (18.0 g, 55.2 mmol, 1.2 eq) was degassed (nitrogen) for 1 h then sodium chlorodifluoroacetate (8.5 g, 55.7 mmol, 1.2 eq) was added. The mixture was heated to 120° C. overnight under nitrogen atmosphere. The mixture was cooled to room temperature and treated with water (10 mL). The reaction was extracted with dichloromethane, dried (sodium sulfate) and concentrated in vacuo. The crude was purified by flash chromatography eluting with cyclohexane. 6.5 g of clean product was obtained as colorless oil (yield: 70%)

Mass (calculated) $C_{10}H_{10}F_2O_2$ [200] (found) $[M+H^+]$=201

LC Rt=2.12 min (5 min method)

$^1$H-NMR (CDCl$_3$): 2.52 (s, 3H), 2.55 (s, 3H), 6.55 (t, 1H), 6.96 (m, 2H), 7.74 (m, 1H).

1-[1-(3-Bromo-phenyl)-vinyl]-4-difluoromethoxy-2-methylbenzene

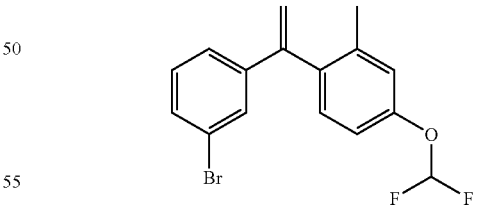

To a solution of 1,3-dibromobenzene (7.6 g, 32.2 mmol, 1 eq) in 64 mL of dry tetrahydrofuran at −78° C. under N$_2$ atmosphere, n-butyllithium (1.6 N in hexane, 20 mL, 1.1 eq) was added dropwise. The mixture was stirred at −78° C. for 1 h, then was added via cannula to a solution of 1-(4-difluoromethoxy-2-methyl-phenyl)-ethanone (6.5 g, 32.2 mmol, 1 eq) in dry tetrahydrofuran at −78° C. The mixture was allowed to warm to room temperature. The reaction mixture was examined after 1 h by TLC (cyclohexane/ethyl acetate 9:1) which showed complete conversion to the desired product. Sat. aqueous ammonium chloride (30 mL) was added, the tetrahydrofuran layer was separated aqueous phase was extracted with dichloromethane (30 mL). The organic fractions were collected, dried over sodium sulfate and evaporated. The crude was dissolved in acetic acid (65 mL) and conc. sulfuric acid (13 mL) was added and mixture was stirred at room temperature for 2 h. A solution of 15% NaOH was added to the mixture until pH 6-5, then extracted with dichloromethane (50 mL). The organic phases were collected, dried and evaporated. The crude was purified by flash chromatography eluting with cyclohexane. 6.10 g of clean product was obtained as colorless oil (yield: 55%).

Mass (calculated) $C_{16}H_{13}BrF_2O$ [307] MH+ not observed

LC Rt=3.07 min (5 min method)

$^1$H-NMR (CDCl$_3$): 2.05 (s, 3H), 5.23 (s, 1H), 5.77 (s, 1H), 6.54 (t, 1H), 6.96 (m, 2H), 7.15 (m, 4H), 7.40 (m, 1H)

(RS)-4-(3-Bromo-phenyl)-4-(4-difluoromethoxy-2-methyl-phenyl)-4,5-dihydro-oxazol-2-ylamine (Building Block Z)

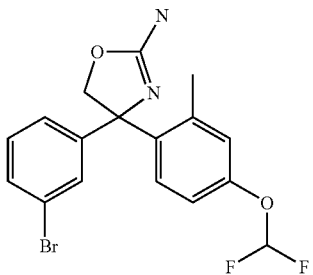

A solution of iodine (5.0 g, 19.7 mol, 1.1 eq) in ethyl acetate (56 mL) was added dropwise to a cooled ice bath suspension of silver cyanate (3.2 g, 21.3 mmol, 1.2 eq), 1-[1-(3-bromo-phenyl)-vinyl]-4-difluoromethoxy-2-methylbenzene (6.1 g, 18.0 mmol, 1 eq) in acetonitrile (42 mL) and ethyl acetate (20 mL). The resulting brown suspension was stirred for 1 h at room temperature. The reaction was examined by LC-MS which showed complete conversion of the starting material, the reaction mixture was filtered and concentrated in vacuo. Aqueous ammonia (25% soln, 50 mL) was added to the oil and the mixture was stirred for 15 min at ambient temperature followed by 3 h at 105° C. The reaction was allowed to warm up to room temperature, extracted with ethyl acetate (2×30 mL), the organic layers collected, dried and concentrated in vacuo. The crude was dissolved in dichloromethane/methanol 1:1 (10 mL) and passed through SCX (50 g) cartridge, washing with dichloromethane/methanol (100 mL) mixture and the product was recovered eluting with a solution 2.0 M of ammonia in methanol (2×50 mL). 4.0 g of product was obtained as a white solid (yield: 59%)

Mass (calculated) $C_{17}H_{15}BrF_2N_2O_2$ [397]; (found) [M+H+]=399

LC Rt=1.69 min (5 min method)

$^1$H-NMR (CDCl$_3$): 1.90 (s, 3H), 4.44 (d, 1H), 5.08 (d, 1H), 6.52 (t, 1H), 6.90-7.33 (m, 6H), 7.80 (d, 1H)

Synthesis of Building Blocks AA (RS)-4-(3-Bromo-phenyl)-4-[4-(2-fluoro-ethoxy)-phenyl]-4,5-dihydro-oxazol-2-ylamine {4-[1-(3-Bromo-phenyl)-vinyl]-phenoxy}-tert-butyl-dimethyl-silane

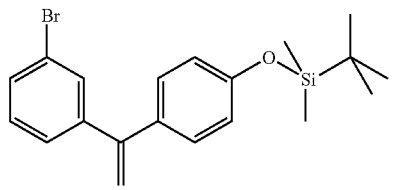

In a flask equipped with condenser and dropping funnel, magnesium turnings (1.12 g, 46.2 mmol, 1.2 eq) were suspended in dry tetrahydrofuran (40 mL) and 1,2-dibromoethane (0.1 mL, 1.16 mmol, 0.03 eq) was added. The mixture was heated to activate magnesium, then commercially available (4-bromophenoxy)-tert-butyl-dimethyl-silane [67963-68-2] (11.6 g, 40.4 mmol, 1.05 eq) in dry tetrahydrofuran (40 mL) was slowly added dropwise. The resulting mixture was stirred for 2 h at 78° C., then cooled to room temperature and 3-bromoacetophenone (7.66 g, 38.5 mmol, 1.0 eq) in dry tetrahydrofuran (20 mL) was added. The mixture was stirred at room temperature for 18 hours and then checked by TLC (cyclohexane/ethyl acetate=9/1) to show complete conversion. 0.5 M HCl (100 mL) was added and the aqueous phase extracted with dichloromethane (2×). The collected organic phases were dried over sodium sulfate. Evaporation of solvent under reduced pressure gave 16.4 g of tertiary alcohol intermediate that was dissolved in 140 mL of toluene. p-Toluensulfonic acid monohydrate (160 mg, 1.0 mmol, 0.02 eq) was added and the mixture heated to reflux in a flask fitted with a Dean-Stark apparatus. After 3 h, toluene is removed under reduced pressure and the crude olefin purified by flash chromatography (eluent: cyclohexane) to give 11.0 (yield 74%) of the desired product.

Mass (calculated) $C_{20}H_{25}BrOSi$ [389] MH+ not observed

LC Rt=3.68 min (5 min method) 91%

$^1$H-NMR (CDCl$_3$): 0.21 (s, 6H), 0.97 (s, 9H), 5.34 (s, 1H), 5.42 (s, 1H), 6.80 (d, 2H), 7.21 (m, 4H), 7.42 (m, 1H), 7.51 (m, 1H)

4-[1-(3-Bromo-phenyl)-vinyl]-phenol

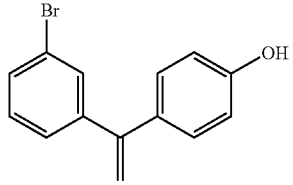

M Tetrabutylammonium fluoride in tetrahydrofuran (36.9 mL, 36.9 mmol, 1.3 eq) was added to a solution of {4-[1-(3-bromo-phenyl)-vinyl]-phenoxy}-tert-butyl-dimethyl-silane (11.0 g, 28.4 mmol, 1.0 eq) in tetrahydrofuran (140 mL). After 1 h at room temperature, the solvent was removed under reduced pressure and dichloromethane (100 mL) was added.

The organic phase was washed with sat. sodium carbonate (2×) and dried over sodium sulfate. Evaporation of solvent gave crude phenol that was purified by silica column (eluent: cyclohexane/ethyl acetate=95:5 then 1:1) to give 5.88 g (yield 75%) of desired product.

Mass (calculated) $C_{14}H_{11}BrO$ [275]; (found) [M+H$^+$]= 276

LC Rt=2.57 min (5 min method) 92%

$^1$H-NMR: (CDCl$_3$): 2.63 (brs, 1H), 5.33 (d, 1H), 5.41 (d, 1H), 6.81 (d, 2H), 7.19 (m, 3H), 7.25 (m, 1H), 7.44 (m, 1H), 7.49 (m, 1H)

1-Bromo-3-(1-[4-{2-fluoro-ethoxy}phenyl]-vinyl)-benzene

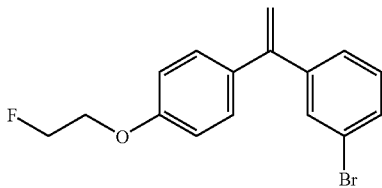

Cesium carbonate (2.18 g, 6.67 mmol, 1.2 eq) and 1-fluoro-2-iodoethane (1.1 g, 6.4 mmol, 1.2 eq) were added to a solution of 4-[1-(3-bromo-phenyl)-vinyl]-phenol (1.5 g, 5.3 mmol, 1.0 eq) in dry N,N-dimethylformamide (15 mL). The mixture was stirred overnight at 55° C.; dichloromethane (100 mL) and water (50 mL) were then added. The organic phase was washed with water (3×) and dried over sodium sulfate. Evaporation of solvent gave crude ether that was purified by flash chromatography (eluent: cyclohexane/ethyl acetate=9:1 then) to give 931 mg (yield 54%) of desired product as yellow oil.

Mass (calculated) $C_{16}H_{14}BrFO$ [321]; (found) [M+H$^+$]= 322

LC Rt=1.68 min (3 min method) 87%

$^1$H-NMR (CDCl$_3$): 4.21 (m, 1H), 4.29 (m, 1H), 4.72 (m, 1H), 4.85 (m, 1H), 5.38 (d, 1H), 5.44 (d, 1H), 6.92 (d, 2H), 7.21 (t, 1H), 7.27 (d, 2H), 7.32 (m, 1H), 7.46 (m, 1H), 7.50 (t, 1H)

(RS)-4-(3-Bromo-phenyl)-4-[4-(2-fluoro-ethoxy)-phenyl]-4,5-dihydro-oxazol-2-ylamine (Building Block AA)

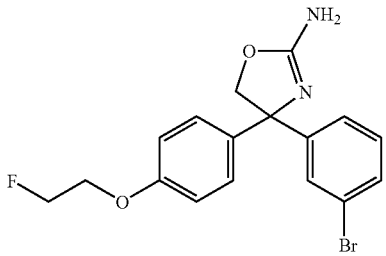

A saturated solution of iodine (810 mg, 3.2 mmol, 1.1 eq) in 15 mL of ethyl acetate was slowly dropped (ca 30 min) into a mixture of 1-bromo-3-(1-[4-{2-fluoro-ethoxy}phenyl]-vinyl)-benzene (931 mg; 2.9 mmol, 1 eq) and silver cyanate (525 mg; 3.5 mmol, 1.2 eq) in 10 mL of ethyl acetate and 10 mL of acetonitrile stirring at 0° C. The brown mixture was stirred for 3 h at room temperature. The silver iodide formed was removed by filtration and solvent evaporated at reduced pressure, giving the iodocyanate as brown viscous oil. 1,4-dioxane (5 mL) and aqueous ammonia (25% soln, 25 mL) were then added and the mixture was stirred vigorously at room temperature for 12 h and then at 105° C. for 1 h. The reaction mixture was examined by LC-MS which showed formation of the aminooxazoline. The mixture was extracted with dichloromethane (3×) and the collected organic phase dried over sodium sulfate. Evaporation of solvent and purification through SCX cartridge, washing with dichloromethane/methanol (70 mL) mixture and recovering the product eluting with a solution 2.0 M of ammonia in methanol (2×25 mL), gave 832 mg (yield 76%) of pure aminooxazoline as a yellow oil.

Mass (calculated) $C_{17}H_{16}BrFN_2O_2$ [379]; (found) [M+H$^+$]=380

LC Rt=1.02 min (3 min method) 85%

$^1$H-NMR (CDCl$_3$): 4.16 (m, 1H), 4.23 (m, 1H), 4.50 (brs, 2H), 4.73 (m, 4H), 6.87 (d, 2H), 7.16 (t, 1H), 7.23 (m, 3H), 7.35 (m, 1H), 7.51 (t, 1H)

Preparation of Building Block AB (RS)-4-(3-Bromo-phenyl)-4-(4-difluoromethoxy-2-fluoro-phenyl)-4,5-dihydro-oxazol-2-ylamine 1-(4-Difluoromethoxy-2-fluoro-phenyl)-ethanone

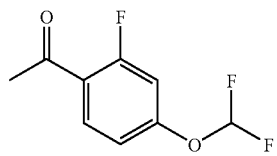

To a solution of 2-fluoro-4-hydroxyacetophenone (10.0 g, 65 mmol, 1.0 eq) in 95 mL of a 9:1 N,N-dimethylformamide/water mixture, cesium carbonate (28.6 g, 81 mmol, 1.3 eq.) and sodium chlorodifluoroacetate (24.7 g, 162 mmol, 2.5 eq.) were added. The mixture was purged with nitrogen, and then heated to 120° C. while stirring. After 2.5 hours the reaction mixture was cooled to room temperature, treated with water (100 mL) and extracted with diisopropyl ether. The organic layer was washed with brine, dried over sodium sulfate and concentrated. The crude product was purified by flash chromatography eluting with cyclohexane/ethyl acetate (100:0 to 95:5). 8.25 g of clean product was obtained as colorless liquid (yield: 65%).

Mass (calculated) $C_9H_7F_3O_2$ [204] (found) [M+H$^+$]=205

LC Rt=2.07 min (5 min method) 95%

TLC Rf=0.8 (cyclohexane/ethyl acetate 95:5)

1-[1-(3-Bromo-phenyl)-vinyl]-4-difluoromethoxy-2-fluoro-benzene

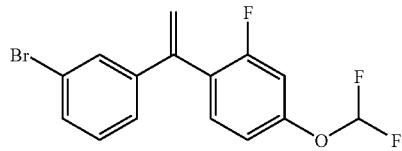

A solution of 1,3-dibromobenzene (10.5 g, 44.4 mmol, 1.1 eq) in 30 mL of anhydrous tetrahydrofuran was cooled to −78° C. and a n-butyllithium solution (1.6 M in hexanes, 27.8 mL, 44.4 mmol, 1.1 eq.) was added dropwise. After stirring for 30 minutes, the yellow suspension was transferred via cannula at −78° C. into a flask containing a tetrahydrofuran solution (38 mL) of 1-(4-difluoromethoxy-2-fluoro-phenyl)-ethanone (8.25 g, 40.4 mmol, 1.0 eq.) at −78° C. The cooling bath was removed and the mixture was allowed to warm up to room temperature. Then 30 mL of a saturated aqueous ammonium chloride solution were added. The reaction mixture was extracted with diisopropyl ether. The organic layer was washed with brine, dried over sodium sulfate and concentrated. The crude product was diluted with toluene (50 mL) and a few crystals of p-toluenesulfonic acid were added. The solution was heated to reflux for 2 hours in a flask equipped with a Dean-Stark apparatus. After this time, the mixture was cooled to room temperature, concentrated and the crude purified by flash chromatography eluting with cyclohexane/ethyl acetate (100:0 to 98:2). 10.6 g of clean product was obtained as colorless liquid (yield: 75%).

Mass (calculated) $C_{15}H_{10}BrF_3O$ [343]; (found) [M+H$^+$]=344

LC Rt=2.93 min (5 min method) 95%

$^1$H-NMR (CDCl$_3$): 5.50 (d, 2H), 6.48 (t, 1H), 6.82 (dd, 1H), 6.86 (dd, 1H), 7.14 (m, 2H), 7.18 (t, 1H), 7.37 (m, 2H).

(RS)-4-(3-Bromo-phenyl)-4-(4-difluoromethoxy-2-fluoro-phenyl)-4,5-dihydro-oxazol-2-ylamine (Building Block AB)

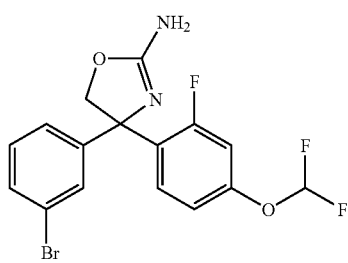

According to general method 2, a solution of iodine in ethyl acetate was added to a mixture of 4-[1-(3-bromo-phenyl)-vinyl]-1-difluoromethoxy-3-fluoro-benzene (4.9 g, 14 mmol) mid silver cyanate in ethyl acetate/acetonitrile. The crude product of this reaction was subsequently reacted with aqueous ammonia (30% by vol). Purification by SCX yield 2.0 g of product (35%).

Mass (calculated) $C_{16}H_{12}BrF_3N_2O_2$ [401]; (found) [M+H$^+$]=402

LC Rt=1.57 min (5 min method) 95%

$^1$H-NMR (CDCl$_3$): 5.00 (d, 1H), 5.02 (d, 1H), 6.50 (t, 1H), 6.83 (d, 1H), 6.93 (d, 1H), 7.16 (m, 2H), 7.33 (m, 1H), 7.43 (m, 1H), 7.76 (t, 1H).

Building Block AC

Methanesulfonic acid 4-[(RS)-2-amino-4-(3-bromo-4-fluoro-phenyl)-4,5-dihydro-oxazol-4-yl]-2-methyl-phenyl ester

Methanesulfonic acid 4-[1-(3-bromo-4-fluoro-phenyl)-vinyl]-2-methyl-phenyl ester

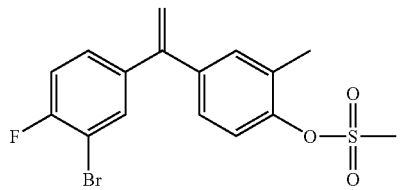

4-[1-(4-Fluoro-3-bromo-phenyl)-vinyl]-phenol was produced from {4-[1-(3-bromo-4-fluoro-phenyl)-vinyl]-phenoxy}-tert-butyl-dimethyl-silane according to Building Block X & AA. To a solution of 4-[1-(4-fluoro-3-bromo-phenyl)-vinyl]-phenol (1.5 g, 4.88 mmol, 1.0 eq) in DCM (15 mL), triethylamine (2.0 mL, 14.65 mmol, 3.0 eq) was added and the reaction mixture cooled to 0° C. Then methanesulfonyl chloride (0.416 mL, 5.37 mmol, 1.1 eq) was added dropwise and the mixture was allowed to warm to room temperature and stirred 16 h. The reaction was examined by TLC (ethyl acetate/cyclohexane 20%) which showed complete conversion to the desired product. After night time water was added and organic and water phase were separated. Organic solution was dried over magnesium sulfate filtered and evaporated. The crude was purified by flash chromatography eluting with cyclohexane, then ethyl acetate/cyclohexane 20%. 1.4 g of clean product was obtained as colorless liquid (yield: 75%)

Mass (calculated) $C_{16}H_{14}BrFO_3S$ [385] MH$^+$ not observed $^1$H-NMR (CDCl$_3$): 1.15 (s, 3H), 2.91 (s, 3H), 5.22 (d, 2H), 6.95 (s, 1H), 7.0 (d, 2H), 7.08 (d, 2H), 7.20 (m, 1H)

TLC (cyclohexane/ethyl acetate, 8:2) Rf: 0.3.

Methanesulfonic acid 4-[(RS)-2-amino-4-(3-bromo-4-fluoro-phenyl)-4,5-dihydro-oxazol-4-yl]-2-methyl-phenyl ester (Building Block AC)

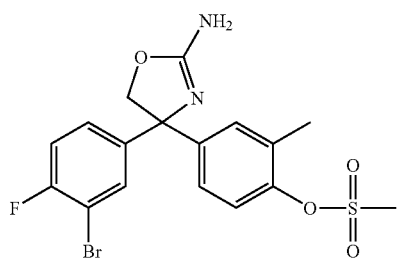

According to general method 2, a solution of iodine in ethyl acetate was added to a mixture of methanesulfonic acid 4-[1-(3-bromo-4-fluoro-phenyl)-vinyl]-2-methyl-phenyl ester (1400 mg, 3.6 mmol) and silver cyanate 1.1 eq in ethyl acetate/acetonitrile. The crude product of this reaction was subsequently reacted with aqueous ammonia (30% by vol).

Purification by SCX followed by silica column (dichloromethane/methanol, 95:5) yield 650 mg of product (40%).

Mass (calculated) $C_{17}H_{16}BrFN_2O_4S$ [443] found (444) MH$^+$, LC Rt: 2.12 (10 min method) 93%

$^1$H-NMR (d$_6$-DMSO): 2.23 (s, 3H), 3.39 (s, 3H), 4.64 (m, 2H), 6.32 (m, 2H), 7.23 (t, 1H), 7.29 (m, 2H), 7.40 (d, 1H), 7.44 (m, 1H), 7.73 (dd, 1H).

Building Block AD

Methanesulfonic acid 4-[(RS)-2-amino-4-(3-bromo-phenyl)-4,5-dihydro-oxazol-4-yl]-phenyl ester Methanesulfonic acid 4-[1-(3-bromo-phenyl)-vinyl]-phenyl ester

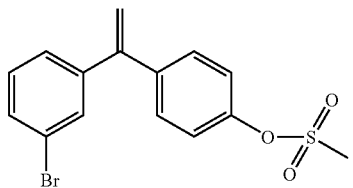

To a solution of 4-[1-(3-bromo-phenyl)-vinyl]-phenol (1.5 g, 5.45 mmol, 1.0 eq) in dichloromethane (15 mL), triethylamine (2.26 mL, 16.35 mmol, 3.0 eq) was added and the reaction mixture cooled to 0° C. Then methanesulfonyl chloride (0.465 mL, 6.0 mmol, 1.1 eq) was added dropwise and the mixture was allowed to warm to room temperature and stirred 16 h. The reaction was examined by TLC (ethyl acetate/cyclohexane 20%) which showed complete conversion to the desired product. After night time water was added and organic and water phase were separated. Organic solution was dried over magnesium sulfate filtered and evaporated. The crude was purified by flash chromatography eluting with cyclohexane, then ethyl acetate/cyclohexane 20%. 1.6 g of clean product was obtained as colorless liquid (yield: 65%).

Mass (calculated) $C_{15}H_{13}BrO_3S$ [353] MH$^+$ not observed.

$^1$H-NMR (CDCl$_3$): 3.13 (s, 3H), 5.34 (d, 2H), 6.99 (t, 1H), 7.04 (m, 1H), 7.09 (m, 2H), 7.12 (m, 1H), 7.16 (m, 2H), 7.42 (dd, 1H). TLC (cyclohexane/ethyl acetate, 8:2) Rf: 0.3.

Methanesulfonic acid 4-[(RS)-2-amino-4-(3-bromo-phenyl)-4,5-dihydro-oxazol-4-yl]-phenyl ester (Building Block AD)

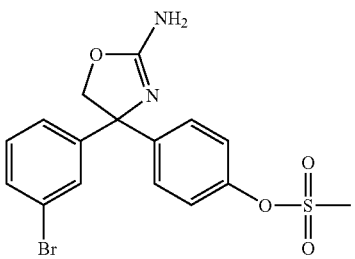

According to general method 2, a solution of iodine in ethyl acetate was added to a mixture of methanesulfonic acid 4-[1-(3-bromo-phenyl)-vinyl]-phenyl ester (1600 mg, 4.53 mmol) and silver cyanate (1.1 eq) in ethyl acetate/acetonitrile. The crude product of this reaction was subsequently reacted with aqueous ammonia (30% by vol). Purification by SCX followed by silica column (dichloromethane/methanol, 95:5) yielded 480 mg of product (35%).

Mass (calculated) $C_{16}H_{15}BrN_2O_4S$ [411] found (412) MH$^+$,

LC Rt=1.83 min (10 min method) 94%

$^1$H-NMR (d$_6$-DMSO): 3.13 (s, 3H), 4.73 (m, 2H), 7.18 (t, 1H), 7.25 (m, 3H), 7.37 (m, 3H), 7.53 (m, 1H).

Preparation of Building Block AE (RS)-2-{4-[2-Amino-4-(3-bromo-phenyl)-4,5-dihydro-oxazol-4-yl]-phenoxy}-ethanol 2-(2-{4-[1-(3-Bromo-phenyl)-vinyl]-phenoxy}-ethoxy)-tetrahydro-pyran

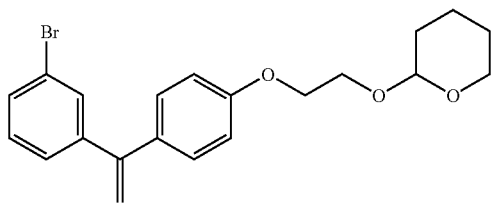

Cesium carbonate (4.36 g, 13.4 mmol, 1.2 eq) and 2-(2-bromoethoxy)-tetrahydro-2H-pyran (1.94 mL, 12.8 mmol, 1.2 eq) were added to a solution of 4-[1-(3-bromo-phenyl)-vinyl]-phenol (2.9 g, 10.7 mmol, 1.0 eq) in dry N,N-dimethylformamide (35 mL). The mixture was stirred overnight at 55° C. Dichloromethane (100 mL) and water (50 mL) were then added. The organic phase was washed with water (3×) and dried over sodium sulfate. Evaporation of solvent and purification by flash chromatography (eluent: cyclohexane/ethyl acetate=9:1 then 8:2) gave 2.0 g of desired product as yellow oil (yield 47%).

Mass (calculated) $C_{21}H_{23}BrO_3$ [403]; (found) [M+H$^+$]=404

LC Rt=3.15 min (5 min method) 80%

(RS)-2-{4-[2-Amino-4-(3-bromo-phenyl)-4,5-dihydro-oxazol-4-yl]-phenoxy}-ethanol (Building Block AE)

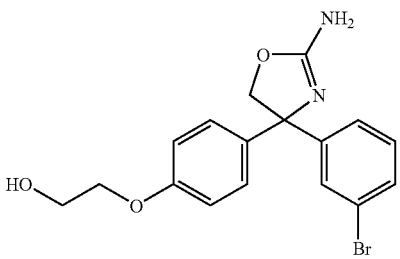

A saturated solution of iodine (1.42 g, 5.6 mmol, 1.1 eq) in 10 mL of ethyl acetate was slowly dropped (ca 30 min) into a mixture of 2-(2-{4-[1-(3-bromo-phenyl)-vinyl]-phenoxy}-ethoxy)-tetrahydro-pyran (2.0 g, 5.1 mmol, 1 eq) and silver cyanate (0.92 g, 6.1 mmol, 1.2 eq) in 25 mL of ethyl acetate and 15 mL of acetonitrile stirring at 0° C. The brown mixture was stirred for 2 h at room temperature. The silver iodide formed was removed by filtration and solvent evaporated at reduced pressure, giving the iodocyanate as brown viscous oil. 1,4-Dioxane (8 mL) and aqueous ammonia (25% soln, 40 mL) were then added and the mixture was stirred vigorously at room temperature for 1 h and then at 105° C. for 2 h. The reaction mixture was examined by LC-MS which showed formation of the tetrahydropyranyl protected aminooxazoline. The mixture was extracted with dichloromethane (3×) and the collected organic phase dried over sodium sulfate. Evaporation of solvent and purification through SCX cartridge, washing with dichloromethane/methanol (100 mL) mixture and recovering the product eluting with a solution 2.0 M of ammonia in methanol (2×50 mL), gave 1.51 g (yield 78%) of pure aminooxazoline without THP-ether protection, as a white solid.

Mass (calculated) $C_{17}H_{17}BrN_2O_3$ [377]; (found) [M+H$^+$]= 378

LC Rt=1.22 min (5 min method) 78%

$^1$H-NMR (d$_6$-DMSO): 3.68 (q, 2H), 3.93 (t, 2H), 4.61 (s, 2H), 4.84 (t, 1H), 6.26 (brs, 2H), 6.84 (d, 2H), 7.24 (t, 1H), 7.28 (d, 2H), 7.37 (m, 2H), 7.58 (t, 1H)

Preparation of Building Block AF (RS)-4-(3-Bromo-phenyl)-4-(4-ethoxy-phenyl)-4,5-dihydro-oxazol-2-ylamine 1-Bromo-3-(1-[4-{ethoxy}phenyl]-vinyl)-benzene

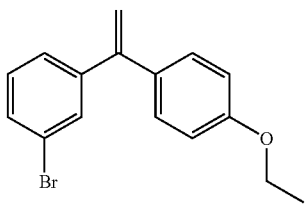

To a solution of commercially available 1-bromo-4-ethoxy-benzene [588-96-5] (0.1 g, 25 mmol, 1.0 eq) in tetrahydrofuran (20 mL) was added dropwise a solution of n-butyllithium (1.6 M solution in hexane, 14.0 mL, 0.9 eq) at −78° C. After stirring 30 min at −78° C. 3-bromoacetophenone (3.7 mL, 1.1 eq) in tetrahydrofuran (20 mL) was added dropwise. The mixture was allowed to warm up to room temperature and stirred for 2 h, then treated with 1 N HCl (10 mL), extracted with ethyl acetate, dried (sodium sulfate) and concentrated in vacuo. The crude was dissolved in acetic acid (50 mL) and sulfuric acid (10 mL) and the mixture was warmed to 75° C. for 30 min, cooled to room temperature and 1 N NaOH was added up to pH=7. The aqueous phase was extracted with dichloromethane (3×10 mL), dried (sodium sulfate) the solvent was removed and the residue was purified by column chromatography (cyclohexane) to afford the title compound as a colorless oil (2.3 g, 30%);

Mass (calculated) $C_{16}H_{15}BrO$ [303]; MH$^+$ not observed.

LC Rt=2.43 min (5 min method)

(RS)-4-(3-Bromo-phenyl)-4-(4-ethoxy-phenyl)-4,5-dihydro-oxazol-2-ylamine (Building Block AF)

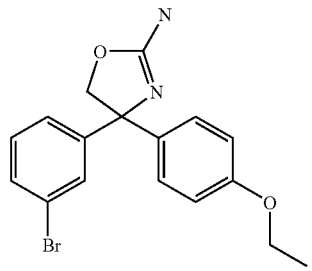

A solution of iodine (2.1 g, 8.0 mmol, 1.1 eq) in ethyl acetate (20 mL) was added dropwise to a cooled (ice bath) suspension of silver cyanate (1.4 g, 9.0 mmol, 1.2 eq), 1-bromo-3-(1-[4-ethoxy-phenyl]-vinyl)-benzene (2.3 g, 7.0 mmol, 1 eq) in acetonitrile (18 mL) and ethyl acetate (9 mL). The resulting brown suspension was stirred for 1 h at room temperature. The reaction was examined by LC-MS which showed complete conversion of the starting material, the reaction mixture was filtered and concentrated in vacuo. Aqueous ammonia (25% soln, 25 mL) was added to the oil and the mixture was stirred for 15 min at room temperature followed by 3 h at 80° C. The reaction was allowed to cool to room temperature, extracted with dichloromethane (2×30 mL), the organic layers collected, dried and concentrated in vacuo. The crude material was dissolved in dichloromethane/methanol 1:1 (5 mL) and passed through SCX (20 g) cartridge, washing with dichloromethane/methanol mixture and the product was recovered eluting with a solution 2.0 M of ammonia in methanol. 0.67 g of product was obtained as a yellow solid (yield: 26%)

Mass (calculated) $C_{17}H_{17}BrN_2O_2$ [361]; (found) [M+H$^+$]= 362

LC Rt=2.25 min (10 min method) 99%

$^1$H-NMR (CDCl$_3$): 1.39 (t, 3H), 3.99 (q, 2H), 4.70 (m, 2H), 6.84 (m, 2H), 7.26 (m, 4H), 7.36 (m, 1H), 7.48 (s, 1H)

Preparation of Building Block AG (RS)-4-(3-Bromo-2-fluoro-phenyl)-4-(4-methoxy-3-methyl-phenyl)-4,5-dihydro-oxazol-2-ylamine 3-Bromo-2-fluoro-N-methoxy-N-methylbenzamide 1680610-73-51

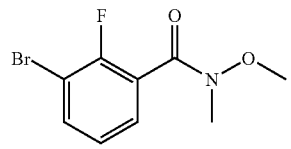

Carbonyldiimidazole (7.76 g) was added portionwise to commercially available 3-bromo-2-fluorobenzoic acid [161957-56-8] (9.53 g) in dichloromethane (100 mL) over 30 min. The mixture was then heated at reflux for 30 min (until gas evolution ceased). The reaction was then cooled to room temperature and triethylamine (6.37 mL) followed by N,O-dimethylhydroxylamine hydrochloride (4.7 g) were added.

The reaction was left to stir at room temperature for 16 h before being washed with 10% citric acid (2×100 mL) and sat. NaHCO$_3$ (2×100 mL), and then dried over sodium sulfate. The solvent was removed by evaporation to yield the product as a brown oil (10.89 g, 95%). NMR (CDCl$_3$): 3.20-3.80 (6H, m, ArCONCH$_3$OCH$_3$), 7.10 (1H, t, Ar), 7.35 (1H, td, Ar), 7.60 (1H, dt, Ar).

1-(3-Bromo-2-fluorophenyl)-ethanone
[161957-61-5]

Methylmagnesium bromide (3 M in diethyl ether, 21 mL) was added to 3-bromo-2-fluoro-N-methoxy-N-methylbenzamide (10.89 g) in tetrahydrofuran (100 mL) at −78° C. This was allowed to warm to room temperature and stir for 16 h. The reaction was then cooled to 0° C. and carefully quenched with 2 M HCl until pH=1. The solvent was removed by evaporation and the product extracted with ethyl acetate (3×100 mL). The organic layers were combined, dried over sodium sulfate and the solvent removed by evaporation to yield the product as a light brown solid. This was dissolved in dichloromethane (200 mL) and washed with sat. NaHCO$_3$ (200 mL). The dichloromethane layer was dried over sodium sulfate and the solvent removed by evaporation to yield 1-(3-bromo-2-fluorophenyl)-ethanone as a yellow oil (8.8 g, 97%). $^1$H NMR (CDCl$_3$): 2.67 (3H, d, ArCOCH$_3$), 7.11 (1H, t, Ar), 7.69-7.81 (2H, m, Ar).

(RS)-1-(3-Bromo-2-fluorophenyl)-1-(4-methoxy-3-methylphenyl)ethanol

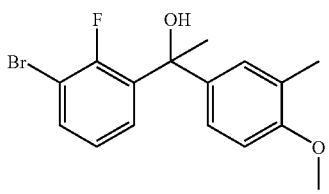

Magnesium turnings (981 mg) and a crystal of iodine were suspended in tetrahydrofuran (10 mL) at room temperature. To this was added=5 mL of a solution of 4-bromo-2-methylanisole (7.1 g) in tetrahydrofuran (100 mL). The mixture was then heated at reflux until initiation (colour change from brown to colourless ~15-30 min) after which time the heat was removed. The remaining 4-bromo-2-methylanisole solution was added dropwise to maintain a gentle reflux and the resultant mixture was then heated at reflux for 2 h. Upon cooling to room temperature, a solution of 1-(3-bromo-2-fluorophenyl)-ethanone (7.3 g) in tetrahydrofuran (100 mL) was added dropwise, again maintaining a gentle reflux and this was then heated at reflux for 2 h before being allowed to cool to room temperature. The mixture was then poured onto ice-water (400 mL) and the solvent removed by evaporation. The product was extracted with ethyl acetate (3×100 mL), dried over sodium sulfate and the solvent removed by evaporation to yield a yellow oil. Purification by flash chromatography on silica (20:1-5:1 hexanes/ethyl acetate) yielded (R,S)-1-(3-bromo-2-fluorophenyl)-1-(4-methoxy-3-methylphenyl)ethanol as a yellow oil (6.37 g, 56%). $^1$H NMR (CDCl$_3$): 1.94 (3H, s, ArCH$_3$), 2.17 (3H, s, ArCH$_3$), 3.80 (3H, s, ArOCH$_3$), 6.75 (1H, d, Ar), 7.00-7.16 (3H, m, Ar), 7.47 (1H, t, Ar), 7.63 (1H, t, Ar).

1-Bromo-2-fluoro-3-[(1-(4-methoxy-3-methylphenyl)vinyl]-benzene

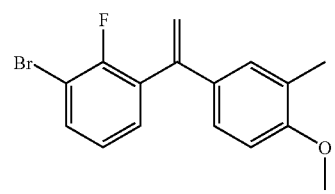

Concentrated sulfuric acid (1 mL) was added to (R,S)-1-(3-bromo-2-fluorophenyl)-1-(4-methoxy-3-methylphenyl)ethanol (6.37 g) in methanol (100 mL) and the reaction heated at reflux. After 4 h the reaction was cooled to room temperature and the solvent was removed by evaporation. The reaction was then quenched with water and the product extracted with hexane (3×100 mL). The organic layers were combined, dried over Na$_2$SO$_4$ and the solvent removed by evaporation to yield a yellow oil. Purification by dry flash chromatography on silica (hexane) yielded the title compounds as a pale yellow oil (3.73 g, 62%). $^1$H NMR (CDCl$_3$): 2.20 (3H, s, ArCH$_3$), 3.83 (3H, s, ArOCH$_3$), 5.27 and 5.67 (each 1H, s, Ar$_2$C=CH$_2$), 6.77 (1H, d, Ar), 7.01-7.10 (2H, m, Ar), 7.25 (1H, dt, Ar), 7.52 (1H, dt, Ar).

(RS)-4-(3-Bromo-2-fluoro-phenyl)-4-(4-methoxy-3-methyl-phenyl)-4,5-dihydro-oxazol-2-ylamine
(Building Block AG)

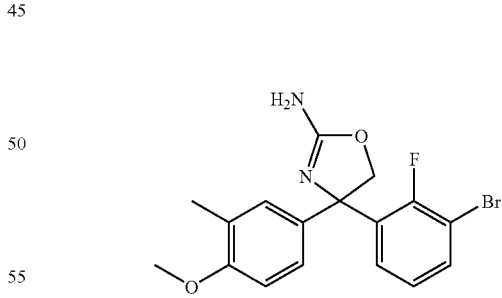

In an analogous manner to that described in the preparation of Building Block C, the 1-bromo-2-fluoro-3-[1-(4-methoxy-3-methylphenyl)-vinyl]-benzene was consecutively treated with iodine and silver cyanate, thereupon with ammonium hydroxide solution to yield the title compound (yield: 68%) as an orange gum. [M+H]$^+$=381.0.

Preparation of Building Block AH

(RS)-4-(3-Bromo-5-fluoro-phenyl)-4-(4-methoxy-3-methyl-phenyl)-4,5-dihydro-oxazol-2-ylamine

1-(3-Bromo-5-fluorophenyl)-ethanone

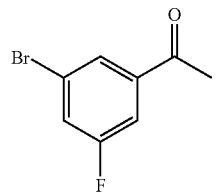

Methyllithium (1.3 M in diethyl ether, 35 mL) was added dropwise to 3-bromo-5-fluorobenzoic acid (5 g) in diethyl ether at −78° C. keeping the temperature below −60° C. The reaction was then left to warm to −10° C. and was stirred for 1 h before being carefully quenched with saturated ammonium chloride (100 mL) until pH=3. The product was extracted with diethyl ether (2×100 mL), dried over sodium sulfate and the solvent removed by evaporation to yield 1-(3-bromo-5-fluorophenyl)ethanone as an off-white solid (4.67 g, 94%). $^1$H NMR (CDCl$_3$): 2.59 (3H, s, ArCOCH$_3$), 7.44 (1H, dd, Ar), 7.59 (1H, dd, Ar), 7.87 (1H, s, Ar).

(RS)-1-(3-Bromo-5-fluorophenyl)-1-(4-methoxy-3-methylphenyl)-ethanol

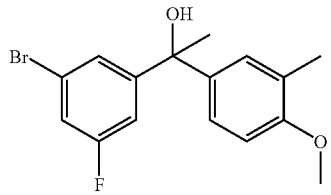

Magnesium turnings (627 mg) and a crystal of iodine were suspended in tetrahydrofuran (10 mL) at room temperature. To this was added ~5 mL of a solution of 4-bromo-2-methylanisole (4.54 g) in tetrahydrofuran (50 mL). The mixture was then heated to reflux until initiation (colour change from brown to colourless ~15-30 min) after which time the heat was removed. The remaining 4-bromo-2-methylanisole solution was added dropwise to maintain a gentle reflux and then heated at reflux for 2 h. Upon cooling to room temperature, a solution of 1-(3-bromo-5-fluorophenyl)-ethanone (4.67 g) in tetrahydrofuran (50 mL) was added dropwise, again maintaining a gentle reflux. This was then heated at reflux for 2 h before being allowed to cool to room temperature, poured onto ice-water (400 mL), and the solvent removed by evaporation. The product was extracted with ethyl acetate (3×100 mL), dried over sodium sulfate and the solvent removed by evaporation to yield a yellow oil. Purification by flash chromatography on silica (20:1-5:1 hexane/ethyl acetate) yielded the alcohol as a yellow oil (4.4 60%). $^1$H NMR (CDCl$_3$): 1.88 (3H, s, ArCH$_3$), 2.19 (3H, s, ArCH$_3$), 3.8 (3H, s, ArOCH$_3$), 6.76 (1H, d, Ar), 7.00-7.20 (4H, m, Ar), 7.34 (1H, t, Ar).

4-[1-(3-Bromo-5-fluorophenyl)vinyl]-1-methoxy-2-methyl-benzene

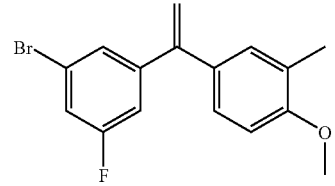

Concentrated sulfuric acid (1 mL) was added to (R,S)-1-(3-bromo-5-fluorophenyl)-1-(4-methoxy-3-methylphenyl)-ethanol (4.4 g) in methanol (100 mL) and the reaction was heated at reflux. After 4 h, the reaction was cooled to room temperature and the solvent was removed by evaporation. The reaction was quenched with water and the product was extracted with hexane (3×100 mL). The organic layers were combined, dried over sodium sulfate and the solvent was removed by evaporation to yield a yellow oil. Purification by dry flash chromatography eluting with hexane yielded the product as a pale yellow oil (3 g, 72%). $^1$H NMR (CDCl$_3$): 2.21 (3H, s, ArCH$_3$), 3.85 (3H, s, ArOCH$_3$), 5.34 and 5.42 (each 1H, s, Ar$_2$C=CH$_2$), 6.80 (1H, d, Ar), 6.97 (1H d, Ar), 7.00-7.10 (2H, m, Ar), 7.19 (1H, dt, Ar), 7.28 (1H, d, Ar).

(RS)-4-(3-Bromo-5-fluoro-phenyl)-4-(4-methoxy-3-methyl-phenyl)-4,5-dihydro-oxazol-2-ylamine (Building Block AH)

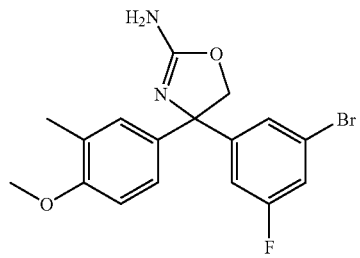

In an analogous manner to that described in the preparation of Building Block C, the 1-bromo-3-fluoro-5-[1-(4-methoxy-3-methylphenyl)-vinyl]-benzene was consecutively treated with iodine and silver cyanate, thereupon with ammonium hydroxide solution to yield the title compound (yield: 23%) as an off white solid. [M+H]$^+$=379.2.

Preparation of Building Block AM (RS)-4-(3-Bromo-4-chloro-phenyl)-4-(4-methoxy-3-methyl-phenyl)-4,5-dihydro-oxazol-2-ylamine 3-Bromo-4-chloro-N-methoxy-N-methylbenzamide [203179-00-4]

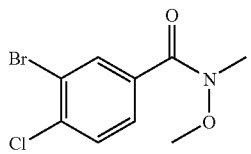

Carbonyldiimidazole (7.2 g, 0.045 mol) was added in portions to a stirred suspension of 3-bromo-4-chlorobenzoic acid (10.0 g, 0.042 mol) in dichloromethane (120 mL). The reaction mixture was stirred at room temperature for 30 minutes then at reflux for 30 minutes. Triethylamine (6.3 mL, 0.045 mol) and N,O-dimethylhydroxylamine hydrochloride (4.2 g, 0.043 mol) were added and the reaction mixture was stirred at room temperature overnight, then diluted with water (75 mL) and the layers separated. The aqueous fraction was extracted with dichloromethane (2×50 mL) and the combined organic extracts were washed with citric acid (10%; 2×50 mL), NaHCO$_3$ (50 mL) and brine (50 mL), dried (sodium sulfate) and concentrated to give 3-bromo-4-chloro-N-methoxy-N-methylbenzamide as a colourless oil (9.3 g, 79%). $^1$H NMR (300 MHz; DMSO-d$_6$) 7.98 (1H, s, Ar), 7.60 (1H, d, J 7.2, Ar), 7.48 (1H, d, J 7.2, Ar), 3.54 (3H, s, Me), 3.36 (3H, s, Me).

1-(3-Bromo-4-chlorophenyl)-ethanone [54826-14-1]

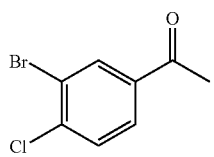

Methylmagnesium bromide (3 M in diethyl ether, 16.7 mL) was added to 3-bromo-4-chloro-N-methoxy-N-methylbenzamide (9.3 g) in tetrahydrofuran (100 mL) at −78° C. This was then allowed to warm to room temperature and was stirred for 16 hours. The reaction was then cooled to 0° C. and carefully quenched with 2 M HCl until pH=1. The solvent was removed by evaporation and the product was extracted with ethyl acetate (3×100 mL). The organic layers were combined, dried over sodium sulfate and the solvent removed by evaporation to yield the product as a light brown solid. This was dissolved in dichloromethane (200 mL) and washed with sat. NaHCO$_3$ (200 mL). The dichloromethane layer was dried over sodium sulfate and the solvent removed by evaporation to yield 1-(3-bromo-4-chlorophenyl)-ethanone as a light brown solid (7.14 g, 92%). $^1$H NMR (CDCl$_3$): 2.58 (3H, d, ArCOCH$_3$), 7.54 (1H, d, Ar), 7.80 (1H, dd Ar), 8.19 (1H, s, Ar).

(RS)-1-(3-Bromo-4-chlorophenyl)-1-(4-methoxy-3-methylphenyl)-ethanol

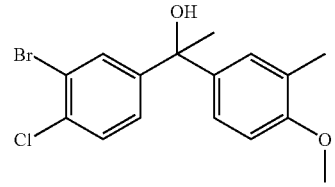

5-Bromo-2-methoxytoluene (6.4 g, 0.032 mol) was dissolved in tetrahydrofuran (100 mL) and 5 mL of the solution was added to a stirred mixture of magnesium turnings (0.90 g, 0.037 mol) and iodine (a catalytic amount) in tetrahydrofuran (10 mL). The mixture was heated to vigorous reflux until some of the iodine colour was lost. The flask was removed from the heat and the remainder of the bromide was added so as to maintain a gentle reflux. The flask was then returned to the heat and stirred at reflux for 2 hours. The flask was removed from the heat and a solution of 1-(3-bromo-4-chlorophenyl)-ethanone (7.1 g, 0.030 mol) in tetrahydrofuran (100 mL) was added so as to maintain a gentle reflux. The reaction mixture was returned to the heat and stirred at reflux for 3 hours then cooled to room temperature and poured into ice-water (300 mL). The mixture was stirred for 5 minutes then concentrated to remove tetrahydrofuran. The aqueous residue was diluted with aqueous ammonium chloride (100 mL), extracted with ethyl acetate (3 200 mL) and the combined organic extracts were washed with water (100 mL) and brine (100 mL), dried (sodium sulfate) and concentrated to give the crude product as a red oil which was purified by flash chromatography (5 to 10% ethyl acetate/hexane) to give the desired alcohol as a bright yellow oil (6.7 g, 71%). $^1$H NMR (300 MHz; CDCl$_3$) 7.72 (1H, d, J 2.1, Ar), 7.35 (1H, d, 8.5, Ar), 7.23-7.13 (3H, m, Ar), 6.76 (1H, d, J 8.5, Ar), 3.82 (3H, s, OMe), 2.19 (3H, s, Me), 2.11 (1H, s, OH), 1.88 (3H, s, Me).

2-Bromo-1-chloro-4-[1-(4-methoxy-3-methylphenyl)-vinyl]-benzene

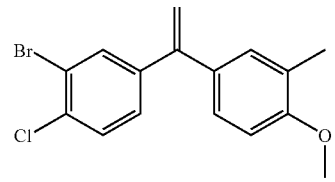

Concentrated sulfuric acid (1.5 mL) was added cautiously to a stirred solution of 1-(3-bromo-4-chlorophenyl)-1-(4-methoxy-3-methylphenyl)-ethanol (6.7 g, 0.019 mol) in methanol (200 mL). The reaction mixture was stirred at reflux for 90 minutes then concentrated to remove methanol. The residue was partitioned between hexane (100 mL) and water (150 mL) and the layers separated. The aqueous fraction was extracted with hexane (2×75 mL) and the combined organic extracts were washed with brine (75 mL), dried (sodium sulfate) and concentrated to give the crude product as a yellow oil, which was purified by dry flash chromatography (0 to 1% ethyl acetate/hexane) to give the alkene as a slowly crystallising colourless oil (4.5 g, 70%), mp 79-81° C. $^1$H NMR (300 MHz; CDCl$_3$) 7.61 (1H, d, J 2.1, Ar), 7.39 (1H, d J 8.3, Ar), 7.21 (1H, dd J 8.3 & 2.1, Ar), 7.09-7.06 (2H, m, Ar), 6.79 (1H, d, J 8.3, Ar), 5.41 (1H, s, olefinic), 5.33 (1H, s, olefinic), 3.85 (3H, s, OMe), 2.21 (3H, s, Me).

(RS)-4-(3-Bromo-4-chloro-phenyl)-4-(4-methoxy-3-methyl-phenyl)-4,5-dihydro-oxazol-2-ylamine (Building Block AM)

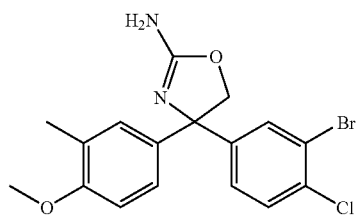

In an analogous manner to that described in the preparation of Building Block C, the 2-bromo-1-chloro-4-[1-(4-methoxy-3-methylphenyl)-vinyl]-benzene was consecutively treated with iodine and silver cyanate, thereupon with ammonium hydroxide solution to yield the title compound (yield: 36%) as an orange gum. [M+H]$^+$=397.0.

Preparation of Building Block AN (RS)-4-(3-Bromo-4-methyl-phenyl)-4-(4-methoxy-3-methyl-phenyl)-4,5-dihydro-oxazol-2-ylamine 2-Bromo-4-[1-(4'-(4-methoxy-3-methylphenyl)-vinyl]-1-methyl-benzene

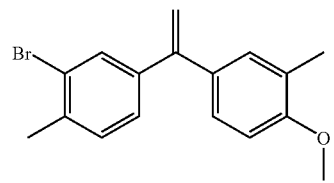

Magnesium turnings (342 mg) and a crystal of iodine were suspended in tetrahydrofuran (5 mL) at room temperature. To this was added=5 mL of a solution of 4-bromo-2-methylanisole (2.48 g) in tetrahydrofuran (25 mL). The mixture was then heated to reflux until initiation (colour change from brown to colourless ~15-30 mins) after which time the heat was removed. The remaining 4-bromo-2-methylanisole solution was added dropwise to maintain a gentle reflux and the mixture was then heated to reflux for 2 hours. On cooling to room temperature, a solution of 4-methyl-3-bromoacteophenone (2.5 g) in tetrahydrofuran (25 mL) was added dropwise, again maintaining a gentle reflux. This was then heated to reflux for 2 hours before being cooled to room temperature and the solvent removed under vacuum. The reaction was quenched with 2 M HCl (20 mL) and the product extracted with ethyl acetate (3×20 mL). The organic layers were combined, dried over sodium sulfate and the solvent removed under vacuum to yield a yellow oil. Purification by dry flash chromatography (hexane) yielded 2-bromo-4-[1-(4-methoxy-3-methylphenyl)-vinyl]-1-methyl-benzene as a colourless oil which solidified upon standing (2.19 g, 59%), mp 48-51° C. $^1$H NMR (CDCl$_3$): 2.20 (3H, s, ArCH$_3$), 2.41 (3H, s, ArCH$_3$), 3.85 (3H, s, ArOCH$_3$), 5.30 and 5.35 (each 1H, s, Ar$_2$C=CH$_2$), 6.79 (1H, d, Ar), 7.09-7.17 (4H, m, Ar), 7.53 (1H, s, Ar)

(RS)-4-(3-Bromo-4-methyl-phenyl)-4-(4-methoxy-3-methyl-phenyl)-4,5-dihydro-oxazol-2-ylamine (Building Block AN)

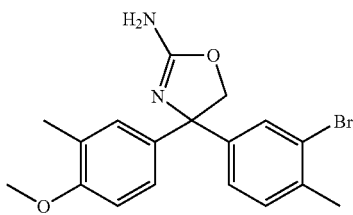

In an analogous manner to that described in the preparation of Building Block C, the 1-bromo-2-methyl-5-[1-(4-methoxy-3-methylphenyl)-vinyl]-benzene was consecutively treated with iodine and silver cyanate, thereupon with ammonium hydroxide solution to yield the title compound (yield: 29%) as an orange gum. [M+H]$^+$=375.1

Preparation of Building Block AO (R)-(+4-(3-Bromo-phenyl)-4-(4-difluoromethoxy-3-methyl-phenyl)-4,5-dihydro-oxazol-2-ylamine

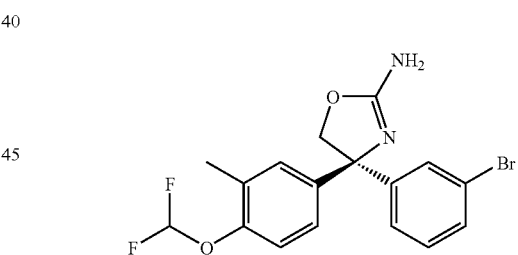

A solution of 1.95 g of (RS)-4-(3-bromo-phenyl)-4-(4-difluoromethoxy-3-methyl-phenyl)-4,5-dihydro-oxazol-2-ylamine (Building Block S) in dichloromethane was divided in 200 mg aliquots which were separated on chiral HPLC (Chiralpak AD) using a 92:8-mixture of heptane and isopropanol as the eluent. The fractions showing e.e. values in the range of 99.7% to 98.4% of the first eluting enantiomer were combined to give 994 mg of the (S)-(+)-4-(3-bromo-phenyl)-4-(4-difluoromethoxy-3-methyl-phenyl)-4,5-dihydro-oxazol-2-ylamine as a colourless oil which crystallised on standing. The later eluting enantiomer (R)-(−)-4-(3-bromophenyl)-4-(4-difluoromethoxy-3-methyl-phenyl)-4,5-dihydro-oxazol-2-ylamine was isolated to give 628 mg (96.8% e.e.) as a colourless oil which crystallised on standing. In addition, a fraction (137 mg) consisting of both isomers was also obtained.

Preparation of Building Block AP (4RS,5RS)-4-(3-Bromo-phenyl)-4-(4-methoxy-phenyl)-5-methyl-4,5-dihydro-oxazol-2-ylamine (E/Z)-1-[1-(3-Bromo-phenyl)-propenyl]-4-methoxybenzene

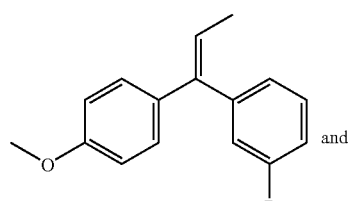
and

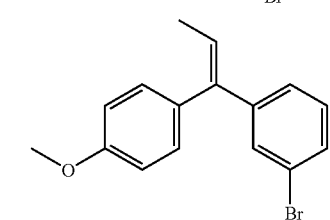

In an analogous reaction sequence to that described for Building Block C, the reaction of 3-bromopropiophenone with 4-methoxyphenylmagnesium bromide yielded the 1-(3-bromo-phenyl)-1-(4-methoxy-phenyl)-propan-1-ol which was used as crude material in the following elimination reaction with a catalytic amount of p-toluenesulfonic acid to yield the (E/Z)-mixture of 1-[1-(3-bromo-phenyl)-propenyl]-4-methoxy-benzene.

(4RS,5RS)-4-(3-Bromo-phenyl)-4-(4-methoxy-phenyl)-5-methyl-4,5-dihydro-oxazol-2-ylamine (Building Block AP)

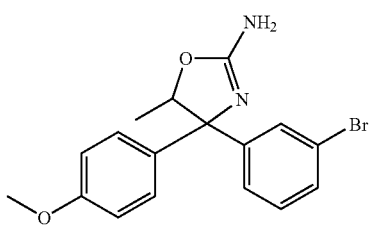

In an analogous manner to that described in the preparation of Building Block C, the (E/Z)-1-[1-(3-bromo-phenyl)-propenyl]-4-methoxy-benzene was consecutively treated with iodine and silver cyanate, thereupon with ammonium hydroxide solution. After chromatography on silica gel using a gradient of dichloromethane/methanol=100/0 to 95/5 as the eluent the (4RS,5RS)-4-(3-bromo-phenyl)-4-(4-methoxyphenyl)-5-methyl-4,5-dihydro-oxazol-2-ylamine was obtained as a light yellow solid (Yield: 13%). Mass (calculated) $C_{17}H_{17}BrN_2O_2$ [360]; (found)=[M+H]$^+$=361, 363.

Preparation of Building Block AQ (RS)-4-(3-Bromo-phenyl)-4-(3-difluoromethoxyphenyl)-4,5-dihydro-oxazol-2-ylamine 1-Bromo-3-[1-(3-difluoromethoxy-phenyl)-vinyl]-benzene

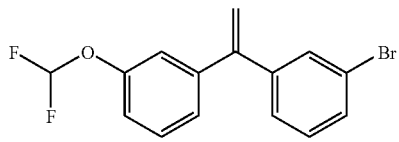

In an analogous reaction sequence to that described for Building Block C, the reaction of 1-(3-difluoromethoxy-phenyl)-ethanone with 3-bromophenyllithium yielded the (3-bromo-phenyl)-(3-difluoromethoxy-phenyl)-methanol which was used as crude material in the following elimination reaction with a catalytic amount of p-toluenesulfonic acid to yield the 1-bromo-3-[1-(3-difluoromethoxy-phenyl)-vinyl]-benzene (yield: 68% of theory) as a light yellow oil. TLC: $R_f$: 0.66 (silica gel; heptane:ethyl acetate=4:1, UV, 254 nm).

(RS)-4-(3-Bromo-phenyl)-4-(3-difluoromethoxyphenyl)-4,5-dihydro-oxazol-2-ylamine (Building Block AQ)

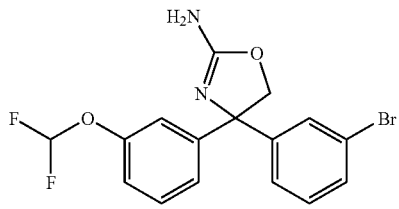

In an analogous manner to that described in the preparation of Building Block C, the 1-bromo-3-[1-(3-difluoromethoxy-phenyl)-vinyl]-benzene was consecutively treated with iodine and silver cyanate, thereupon with ammonium hydroxide solution to yield the title compound (yield: 13%) as a colourless oil. Mass (calculated) $C_{16}H_{13}BrF_2N_2O_2$ [382]; (found) [M+H]$^+$=383, 385.

Preparation of Building Block AR (RS)-4-(3-Bromo-phenyl)-4-(4-methyl-3,4-dihydro-2H-benzo oxazin-6-yl)-4,5-dihydro-oxazol-2-ylamine 6-[1-(3-Bromo-phenyl)-vinyl]-4-methyl-3,4-dihydro-2H-benzo[1,4]oxazine

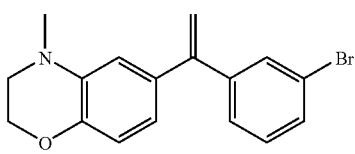

In an analogous reaction sequence to that described for Building Block C, the 6-bromo-4-methyl-3,4-dihydro-2H-benzo[1,4]oxazine [Tetrahedron Letters (2006), 47(44), 7823-7826] was transformed to the corresponding Grignard reagent and reacted with 3-bronco-acetophenone to yield the (RS)-1-(3-bromo-phenyl)-1-(4-methyl-3,4-dihydro-2H-benzo[1,4]oxazin-6-yl)-ethanol which was used as crude material in the following elimination reaction with a catalytic amount of p-toluenesulfonic acid to yield the title compound (yield: 87% of theory) as a light yellow oil. TLC: $R_f$: 0.52 (silica gel; heptane:ethyl acetate=2:1, UV, 254 nm).

(RS)-4-(3-Bromo-phenyl)-4-(4-methyl-3,4-dihydro-2H-benzo[1,4]oxazin-6-yl)-4,5-dihydro-oxazol-2-ylamine (Building Block AR)

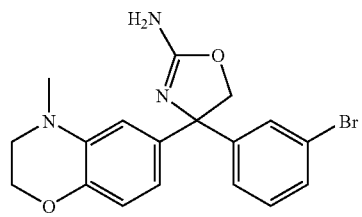

In an analogous manner to that described in the preparation of Building Block C, the 6-[1-(3-bromo-phenyl)-vinyl]-4-methyl-3,4-dihydro-2H-benzo[1,4]oxazine was consecutively treated with iodine and silver cyanate, thereupon with ammonium hydroxide solution to yield the title compound (yield: 37%) as a light brown foam. Mass (calculated) $C_{18}H_{18}BrN_3O_2$ [387]; (found) $[M+H]^+$=388, 390.

Preparation of Building Block AS (RS)-4-(3-Bromo-phenyl)-4-m-tolyl-4,5-dihydro-oxazol-2-ylamine 1-Bromo-3-[1-(3-methyl-phenyl)-vinyl]-benzene

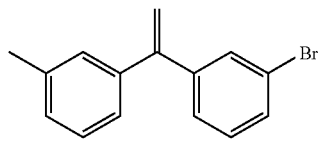

In an analogous reaction sequence to that described for Building Block C, the reaction of 3-methyl phenylmagnesium bromide with 3-bromoacetophenone yielded the 1-(3-bromo-phenyl)-1-m-tolyl-ethanol which was used as crude material in the following elimination reaction with a catalytic amount of p-toluenesulfonic acid to yield the title compound (yield: 66% of theory) as a colourless oil. TLC: $R_f$: 0.83 (silica gel; heptane:ethyl acetate=4:1, UV, 254 nm).

(RS)-4-(3-Bromo-phenyl)-4-m-tolyl-4,5-dihydro-oxazol-2-ylamine (Building Block AS)

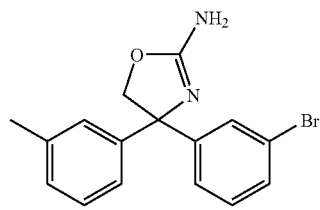

In an analogous manner to that described in the preparation of Building Block C, the 1-bromo-3-[1-(3-methyl-phenyl)-vinyl]-benzene was consecutively treated with iodine and silver cyanate, thereupon with ammonium hydroxide solution to yield the title compound (yield: 48%) as a white solid. Mass (calculated) $C_{16}H_{15}BrN_2O$ [330]; (found) $[M+H]^+$= 331, 333.

Preparation of Building Block AT (RS)-4-(3-Bromo-phenyl)-4-(4-fluoro-3-methoxy-phenyl)-4,5-dihydro-oxazol-2-ylamine 4-[1-(3-Bromo-phenyl)-vinyl]-1-fluoro-2-methoxy-benzene

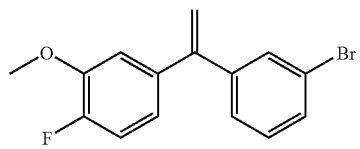

In an analogous reaction sequence to that described for Building Block C, the reaction of 4-fluoro-3-methoxyacetophenone with 3-bromophenyllithium yielded the (RS)-1-(3-bromo-phenyl)-1-(4-fluoro-3-methoxy-phenyl)-ethanol which was used as crude material in the following elimination reaction with a catalytic amount of p-toluenesulfonic acid to yield the title compound (yield: 91% of theory) as a light yellow oil. TLC: $R_f$: 0.69 (silica gel; heptane:ethyl acetate=4:1, UV, 254 nm).

(RS)-4-(3-Bromo-phenyl)-4-(4-fluoro-3-methoxy-phenyl)-4,5-dihydro-oxazol-2-ylamine (Building Block AT)

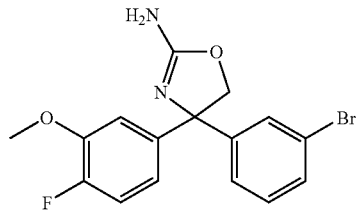

In an analogous manner to that described in the preparation of Building Block C, the 4-[1-(3-bromo-phenyl)-vinyl]-1-fluoro-2-methoxy-benzene was consecutively treated with iodine and silver cyanate, thereupon with ammonium hydroxide solution to yield the title compound (yield: 62%) as a white solid. Mass (calculated)) $C_{16}H_{14}BrFN_2O_2$ [364]; (found) [M+H]$^+$=365, 367.

Preparation of Building Block AU (RS)-4-(3-Bromo-5-ethoxy-phenyl)-4-(4-methoxy-3-methyl-phenyl)-4,5-dihydro-oxazol-2-ylamine 3-Bromo-5-ethoxy-benzonitrile

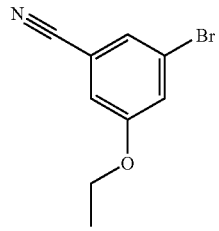

In analogy to the procedure described in WO2007060448, the reaction of 3-bromo-5-fluorobenzonitrile with ethanol using sodium bis(trimethylsilyl)amide as the base yielded the title compound as a light brown oil (yield: 44% of theory).

3-Bromo-5-ethoxy-benzoic acid [855198-27-5]

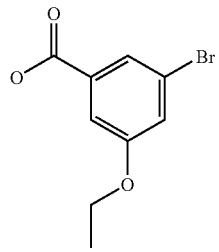

A solution of 3-bromo-5-ethoxy-benzonitrile (529 mg, 2.3 mmol) in a mixture of ethanol (8 mL) and water (1 mL) was treated with a solution of sodium hydroxide (47%, 0.66 mL) and the mixture heated under reflux for 1 hour. For the working-up, the mixture was evaporated under reduced pressure and the oily residue dissolved in tert-butylmethyl ether (60 mL) and water (30 mL). The organic layer was separated and evaporated, then treated again with tert-butylmethyl ether (120 mL) and 1 N hydrochloric acid (60 mL). The organic layer was separated and re-extracted twice with tert-butylmethyl ether (2×60 mL). The organic layers were combined, washed with brine, dried over sodium sulfate, and evaporated under reduced pressure. The title compound was obtained in quantitative yield and engaged in the next step without further purification. Mass (calculated) $C_9H_9BrO_3$ [244]; (found) [M−H]$^+$=243, 245.

3-Bromo-5-ethoxy-N-methoxy-N-methyl-benzamide

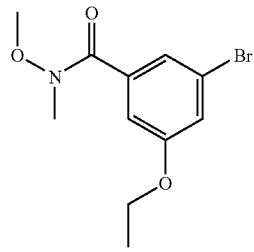

The title compound was obtained by a standard condensation of 3-bromo-5-ethoxy-benzoic acid and N,O-dimethylhydroxylamine hydrochloride as a colourless oil. Mass (calculated) $C_{11}H_{14}BrNO_3$ [287]; (found) [M+H]$^+$=288, 290.

(3-Bromo-5-ethoxy-phenyl)-(4-methoxy-3-methyl-phenyl)-methanone

A solution of 4-bromo-2-methylanisole (0.984 g, 4.9 mmol) in tetrahydrofuran (3 mL) was added dropwise to magnesium powder (0.127 g, 5.2 mmol) in tetrahydrofuran (1 mL) at room temperature. Under external heating the reaction mixture was brought up to reflux. After complete addition, reflux was maintained for 1 hour. Thereafter the mixture was cooled to 15° C., then diluted with tetrahydrofuran (1 mL) before a solution of 3-bromo-5-ethoxy-N-methoxy-N-methyl-benzamide (1.238 g, 4.3 mmol) in tetrahydrofuran (3 mL) was added dropwise. After complete addition, the mixture was heated to reflux for 1.5 hours. For the working-up, it was cooled to 5° C. and hydrolysed with a saturated solution of ammonium chloride (25 mL). The aqueous layer was extracted twice with ethyl acetate (2×50 mL), thereupon, the organic layers combined, washed with brine, dried over sodium sulfate and evaporated under reduced pressure. The crude product was chromatographed on silica gel using a gradient of heptane/ethyl acetate=100/0 to 6/1 as the eluent. There were obtained 1.16 g (77% of theory) of the title com-

1-Bromo-3-(ethoxy)-5-(1-(4-methoxy-3-methyl-phenyl)-vinyl-benzene

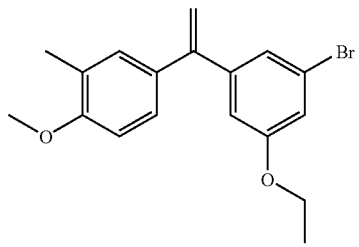

The suspension of (3-bromo-5-ethoxy-phenyl)-(4-methoxy-3-methyl-phenyl)-methanone (1.12 g, 3.2 mmol) and methyltriphenylphosphonium bromide (2.92 g, 8.2 mmol) in tetrahydrofuran (60 mL) was cooled to −15° C. and treated with potassium tert-butylate (0.916 g, 8.2 mmol). After 10 minutes at −15° C., the yellow suspension was left to warm to room temperature. After 15 hours ethyl acetate (150 mL) and water (100 mL) were added. The organic layer was separated, dried over sodium sulfate and evaporated under reduced pressure. The residue was chromatographed on silica gel using a gradient of heptane/ethyl acetate=100/0 to 6/1 as the eluent. There were obtained 1.00 g (90% of theory) of the title compound as a light yellow oil. Mass (calculated) $C_{18}H_{19}BrO_2$ [346]; (found) [M+H]$^+$=347, 349.

(RS)-4-(3-Bromo-5-ethoxy-phenyl)-4-(4-methoxy-3-methyl-phenyl)-4,5-dihydro-oxazol-2-ylamine (Building Block AU)

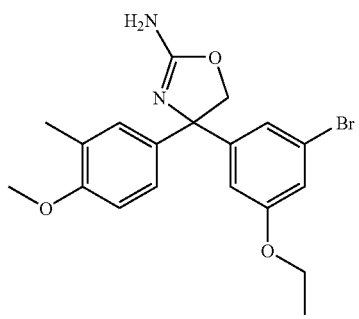

In an analogous manner to that described in the preparation of Building Block C, the 1-bromo-3-(ethoxy)-5-[1-(4-methoxy-3-methyl-phenyl)-vinyl]-benzene was consecutively treated with iodine and silver cyanate, thereupon with ammonium hydroxide solution to yield the title compound (yield: 69%) as a colourless oil. Mass (calculated) $C_{19}H_{21}BrN_2O_3$ [404]; (found) [M+H]$^+$=405, 407.

Preparation of Building Block AV (RS)-4-(3-Bromo-5-ethoxy-phenyl)-4-(4-difluoromethoxy-3-methyl-phenyl)-4,5-dihydro-oxazol-2-ylamine

1,3-Dibromo-5-ethoxy-benzene

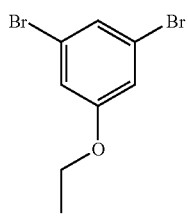

A dispersion of 3,5-dibromophenol (0.398 g, 1.6 mmol) and potassium carbonate (0.437 g, 3.2 mmol) in 2-butanone (4 mL) was treated with diethyl sulfate (0.246 g, 1.6 mmol) and the reaction mixture heated at 90° C. for 15 hours. The resulting thick suspension was cooled to room temperature, diluted with dichloromethane and extracted with water. The organic layer was separated, dried over sodium sulfate and evaporated under reduced pressure. The title compound was obtained as a light brown oil (0.38 g, 86% of theory) which was used in the next step without further purification.

1-Bromo-3-(ethoxy)-5-[1-(4-difluoromethoxy-3-methyl-phenyl)-vinyl]-benzene

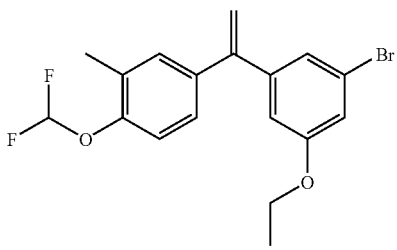

In an analogous reaction sequence to that described for Building Block C, the treatment of 1-(4-difluoromethoxy-3-methyl-phenyl)-ethanone with 1,3-dibromo-5-ethoxymethyl-benzene beforehand transformed to the corresponding Grignard reagent, yielded the (RS)-1-(3-bromo-5-ethoxy-phenyl)-1-(4-difluoromethoxy-3-methyl-phenyl)-ethanol which was used as crude material in the following elimination reaction with a catalytic amount of p-toluenesulfonic acid to yield the title compound (yield: 67% of theory) as a colourless oil. TLC: $R_f$: 0.71 (silica gel; heptane:ethyl acetate=4:1, UV, 254 nm).

(RS)-4-(3-Bromo-5-ethoxy-phenyl)-4-(4-difluoromethoxy-3-methyl-phenyl)-4,5-dihydro-oxazol-2-ylamine (Building Block AV)

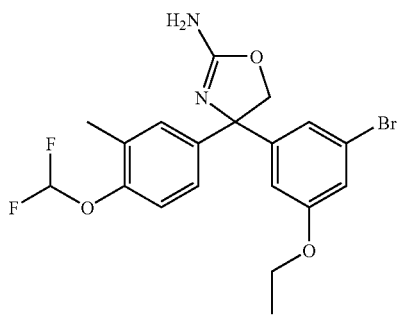

In an analogous manner to that described in the preparation of Building Block C, the 1-bromo-3-(ethoxy)-5-[1-(4-difluoromethoxy-3-methyl-phenyl)-vinyl]-benzene was consecutively treated with iodine and silver cyanate, thereupon with ammonium hydroxide solution to yield the title compound (yield: 71%) as a colourless oil. Mass (calculated) $C_{19}H_{19}BrF_2N_2O_3$ [440]; (found) $[M+H]^+=441, 443$.

Preparation of Building Block AW (RS)-4-(3-Bromo-5-ethoxymethyl-phenyl)-4-(4-difluoromethoxy-3-methyl-phenyl)-4,5-dihydro-oxazol-2-ylamine 1,3-Dibromo-5-ethoxymethyl-benzene

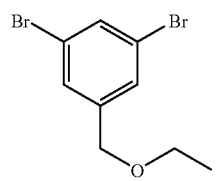

A solution of 3,5-dibromobenzyl alcohol (2.0 h, 8 mmol) in tetrahydrofuran (80 mL) was cooled to 5° C. and treated with sodium hydride (dispersion in oil 55%; 316 mg, 8 mmol). The mixture was left to warm to room temperature and stirred for 15 min. Ethyliodide (2.35 g, 15 mmol) was added and the mixture stirred for 5 h. For the working-up, the reaction mixture was evaporated, then extracted with a mixture of ethyl acetate and saturated sodium hydrogencarbonate solution. After the aqueous layer was re-extracted twice with ethyl acetate, the organic layers were combined, dried over sodium sulfate, and evaporated under reduced pressure. There were obtained 1.15 g of the title compound (yield: 52%) as a yellow oil in sufficient purity to be engaged in the next step without further purification.

1-Bromo-3-(ethoxymethyl)-5-[1-(4-difluoromethoxy-3-methyl-phenyl)-vinyl]-benzene

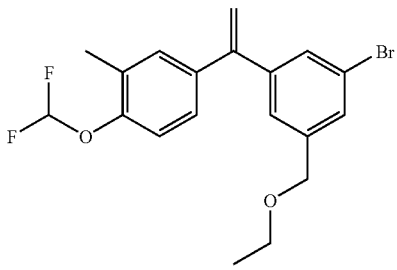

In an analogous reaction sequence to that described for Building Block C, the treatment of 1-(4-difluoromethoxy-3-methyl-phenyl)-ethanone with 1,3-dibromo-5-ethoxymethyl-benzene beforehand reacted with n-butyllithium, yielded the (RS)-1-(3-bromo-5-ethoxymethyl-phenyl)-1-(4-difluoromethoxy-3-methyl-phenyl)-ethanol which was used as crude material in the following elimination reaction with a catalytic amount of p-toluenesulfonic acid to yield the title compound (yield: 47% of theory) as a light yellow oil. Mass (calculated) $C_{19}H_{19}BrF_2O_2$ [396]; (found) $[M]^+=396, 398$.

(RS)-4-(3-Bromo-5-ethoxymethyl-phenyl)-4-(4-difluoromethoxy-3-methyl-phenyl)-4,5-dihydro-oxazol-2-ylamine (Building Block AW)

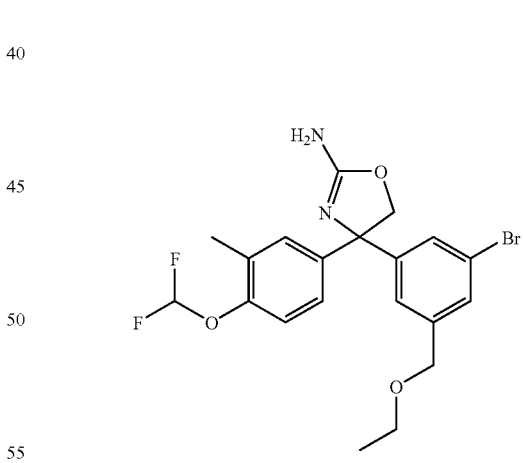

In an analogous manner to that described in the preparation of Building Block C, the 1-bromo-3-(ethoxymethyl)-5-[1-(4-difluoromethoxy-3-methyl-phenyl)-vinyl]-benzene was consecutively treated with iodine and silver cyanate, thereupon with ammonium hydroxide solution to yield the title compound (yield: 25%) as a white solid. Mass (calculated)) $C_{20}H_{21}BrF_2N_2O_3$ [454]; (found) $[M]^+=455, 457$.

83

Preparation of Building Block AX (RS)-4-(3-Bromo-5-ethoxymethyl-phenyl)-4-(4-methoxy-3-methyl-phenyl)-4,5-dihydro-oxazol-2-ylamine 1-Bromo-3-(ethoxymethyl)-5-[1-(4-methoxy-3-methyl-phenyl)-vinyl]-benzene

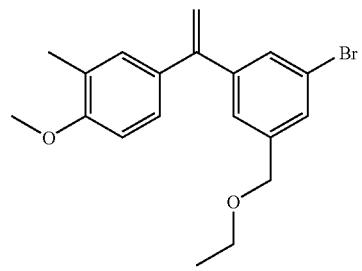

In an analogous reaction sequence to that described for Building Block C, the treatment of 1-(4-methoxy-3-methyl-phenyl)-ethanone with 1,3-dibromo-5-ethoxymethyl-benzene beforehand reacted with n-butyllithium, yielded the (RS)-1-(3-bromo-5-ethoxymethyl-phenyl)-1-(4-methoxy-3-methyl-phenyl)-ethanol which was used as crude material in the following elimination reaction with a catalytic amount of p-toluenesulfonic acid to yield the title compound (yield: 86% of theory) as a colourless oil. Mass (calculated) $C_{19}H_{21}BrO_2$ [360]; (found) $[M+H]^+=361, 363$.

(RS)-4-(3-Bromo-5-ethoxymethyl-phenyl)-4-(4-methoxy-3-methyl-phenyl)-4,5-dihydro-oxazol-2-ylamine (Building Block AX)

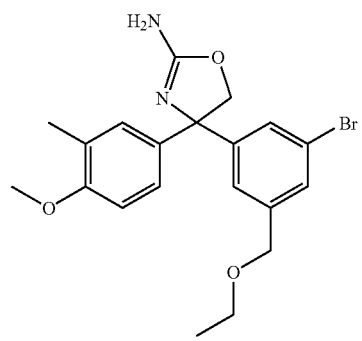

In an analogous manner to that described in the preparation of Building Block C, the 1-bromo-3-(ethoxymethyl)-5-[1-(4-methoxy-3-methyl-phenyl)-vinyl]-benzene was consecutively treated with iodine and silver cyanate, thereupon with ammonium hydroxide solution to yield the title compound (yield: 42%) as a white foam. Mass (calculated)) $C_{20}H_{23}BrN_2O_3$ [418]; (found) $[M+H]^+=419, 421$.

84

Preparation of Building Block AY (RS)-4-[3-bromo-5-(2-methoxy-ethyl)-phenyl]-4-(4-methoxy-3-methyl-phenyl)-4,5-dihydro-oxazol-2-ylamine 2-(3,5-Dibromo-phenyl)-ethanol [75894-93-8]

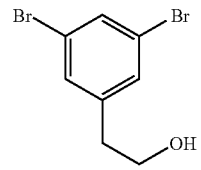

A solution of (3,5-dibromo-phenyl)acetic acid (1.543 g, 5.2 mmol) in tetrahydrofuran (40 mL) was cooled to 0° C. Within 30 minutes borane tetrahydrofuran complex (1 M, 9.19 mL) was added. After complete addition the ice bath was removed and the reaction mixture warmed to room temperature within 25 minutes. After 3 hours, the mixture was cooled to −2° C., quenched by addition of methanol (10 mL) and evaporated under reduced pressure. The residue was dissolved in dichloromethane, the resulting solution was washed with hydrochloric acid (1 N, 50 mL), a saturated solution of sodium hydrogencarbonate (50 mL), and brine. The organic layer was dried over sodium sulfate and evaporated under reduced pressure and yielded. The residue was chromatographed on silica gel using a gradient of heptane/ethyl acetate=100/0 to 2/1 as the eluent. There were obtained 1.29 g (88% of theory) of the title compound as a light yellow oil.

Mass (calculated) $C_8H_8Br_2O$ [278]; (found) $[M]^+=278, 280$.

1,3-Dibromo-5-(2-methoxy-ethyl)-benzene

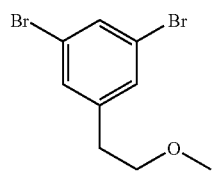

In analogy to the procedure described for Building Block AW, the alkylation of 2-(3,5-dibromo-phenyl)-ethanol with iodomethane using sodium hydride as the base yielded the title compound 86% yield as a light yellow oil.

[3-Bromo-5-(2-methoxy-ethyl)-phenyl]-(4-methoxy-3-methyl-phenyl)-methanone

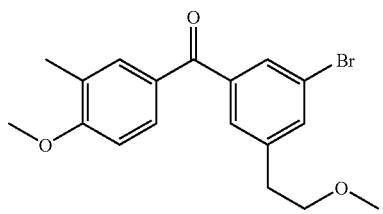

In analogy to the procedure described for the preparation of the Building Block AU, the reaction of 4,N-dimethoxy-3,N-dimethyl-benzamide, beforehand prepared by a standard condensation of 4-methoxy-3-methyl-benzoic acid and N,O-dimethylhydroxylamine hydrochloride, and 1,3-dibromo-5-(2-methoxy-ethyl)-benzene, beforehand reacted with n-butyl lithium, yielded the title compound as a colourless oil (yield: 53% of theory). Mass (calculated) $C_{18}H_{19}BrO_3$ [362]; (found) $[M+H]^+=363, 365$.

1-Bromo-3-(2-methoxyethyl)-5-[1-(4-methoxy-3-methyl-phenyl)-vinyl]-benzene

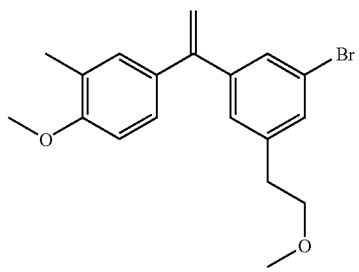

In analogy to the procedure described for the preparation of the Building Block AU, the Wittig olefination of [3-bromo-5-(2-methoxy-ethyl)-phenyl]-(4-methoxy-3-methyl-phenyl)-methanone with methyltriphenylphosphonium bromide yielded the title compound as a colourless oil (yield: 79% of theory). TLC: $R_f$: 0.59 (silica gel; heptane:ethyl acetate=4:1, UV, 254 nm).

(RS)-4-[3-Bromo-5-(2-methoxy-ethyl)-phenyl]-4-(4-methoxy-3-methyl-phenyl)-4,5-dihydro-oxazol-2-ylamine (Building Block AY)

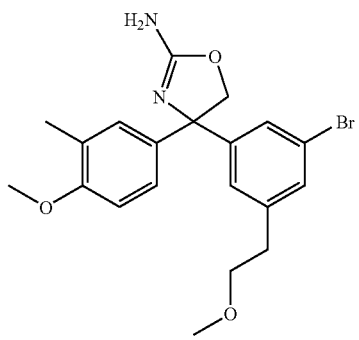

In an analogous manner to that described in the preparation of Building Block C, the 1-bromo-3-(2-methoxyethyl)-5-[1-(4-methoxy-3-methyl-phenyl)-vinyl]-benzene was consecutively treated with iodine and silver cyanate, thereupon with ammonium hydroxide solution to yield the title compound (yield: 58%) as a white foam. Mass (calculated) $C_{20}H_{23}BrN_2O_3$ [418]; (found) $[M]^+=419, 421$.

Preparation of Building Block AZ (RS)-4-[3-Bromo-5-(2,2,2-trifluoro-ethoxy)-phenyl]-4-(4-methoxy-3-methyl-phenyl)-4,5-dihydro-oxazol-2-ylamine 3-Bromo-5-(2,2,2-trifluoro-ethoxy)-benzonitrile

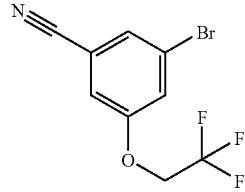

In analogy to the procedure described in WO2007060448, the reaction of 3-bromo-5-fluorobenzonitrile with 2,2,2-trifluoro-ethanol using sodium bis(trimethylsilyl)amide as the base yielded the title compound as a white solid (yield: 77% of theory).

3-Bromo-5-(2,2,2-trifluoro-ethoxy)-benzoic acid

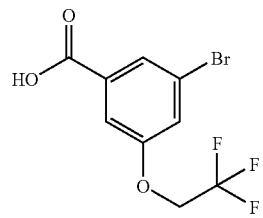

In analogy to the procedure described for the synthesis of the Building Block AU, the saponification of the 3-bromo-5-(2,2,2-trifluoro-ethoxy)-benzonitrile gave the title compound as a white solid (yield: 91% of theory). Mass (calculated) $C_9H_6BrF_3O_3$ [298]; (found) $[M-H]^+=297, 299$.

3-Bromo-N-methoxy-N-methyl-5-(2,2,2-trifluoro-ethoxy)-benzamide

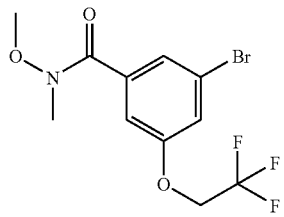

The title compound was obtained by a standard condensation of 3-bromo-5-(2,2,2-trifluoro-ethoxy)-benzoic acid and N,O-dimethylhydroxylamine hydrochloride as a white solid.

Mass (calculated) $C_{11}H_{11}BrF_3NO_3$ [341]; (found) [M+H]$^+$=342, 344.

[3-Bromo-5-(2,2,2-trifluoro-ethoxy)-phenyl]-(4-methoxy-3-methyl-phenyl)-methanone

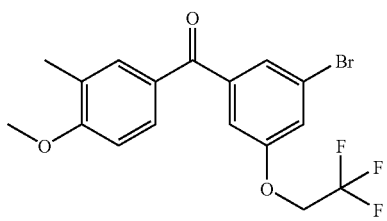

In analogy to the procedure described for the preparation of the Building Block AU, the reaction of the 3-bromo-N-methoxy-N-methyl-5-(2,2,2-trifluoro-ethoxy)-benzamide and 4-bromo-1-methoxy-2-methyl-benzene, beforehand transformed to the Grignard reagent, yielded the title compound as a white solid (yield: 75% of theory). Mass (calculated) $C_{17}H_{14}BrF_3O_3$ [402]; (found) [M]$^+$=403, 405.

1-Bromo-3-(2,2,2-trifluoro-ethoxy)-5-[1-(4-methoxy-3-methyl-phenyl)-vinyl]-benzene

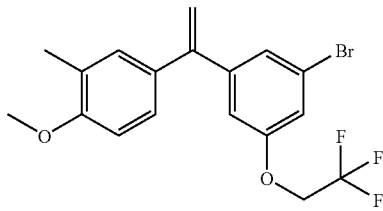

In analogy to the procedure described for the preparation of the Building Block AU, the Wittig olefination of [3-bromo-5-(2,2,2-trifluoro-ethoxy)-phenyl]-(4-methoxy-3-methyl-phenyl)-methanone with methyltriphenylphosphonium bromide yielded the title compound as a colourless oil (yield: 81% of theory). TLC: Rf: 0.62 (silica gel; heptane:ethyl acetate=4:1, UV, 254 nm).

(RS)-4-[3-Bromo-5-(2,2,2-trifluoro-ethoxy)-phenyl]-4-(4-methoxy-3-methyl-phenyl)-4,5-dihydro-oxazol-2-ylamine (Building Block AZ)

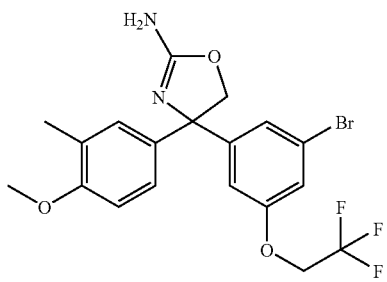

In an analogous manner to that described in the preparation of Building Block C, the 1-bromo-3-(2,2,2-trifluoro-ethoxy)-5-[1-(4-methoxy-3-methyl-phenyl)-vinyl]-benzene was consecutively treated with iodine and silver cyanate, thereupon with ammonium hydroxide solution to yield the title compound (yield: 49%) as a white foam. Mass (calculated) $C_{19}H_{18}BrF_3N_2O_3$ [458]; (found) [M+H]$^+$=459, 461.

Preparation of Building Block BA

(RS)-4-(3-Bromo-5-cyclopropylmethoxy-phenyl)-4-(4-methoxy-3-methyl-phenyl)-4,5-dihydro-oxazol-2-ylamine

3-Bromo-5-cyclopropylmethoxy-benzonitrile

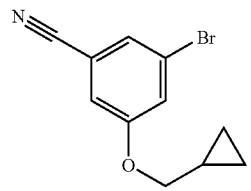

In analogy to the procedure described in WO2007060448, the reaction of 3-bromo-5-fluorobenzonitrile with hydroxymethylcyclopropane using sodium bis(trimethylsilyl)amide as the base yielded the title compound as a white solid (yield: 84% of theory). TLC: R$_f$: 0.55 (silica gel:heptane:ethyl acetate=6:1, UV, 254 nm).

3-Bromo-5-cyclopropylmethoxy-benzoic acid

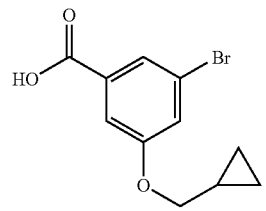

In analogy to the procedure described for the synthesis of the Building Block AU, the saponification of the 3-bromo-5-(cyclopropylmethoxy)-benzonitrile gave the title compound as a white solid (yield: 97% of theory). Mass (calculated) $C_{11}H_{11}BrO_3$ [270]; (found) [M–H]$^+$=269, 271.

3-Bromo-5-cyclopropylmethoxy-N-methoxy-N-methyl-benzamide

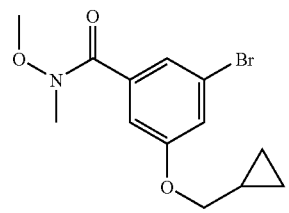

The title compound was obtained by a standard condensation of 3-bromo-5 cyclopropylmethoxy-benzoic acid and N,O-dimethylhydroxylamine hydrochloride as a colourless oil. Mass (calculated) $C_{13}H_{16}BrNO_3$ [313]; (found) [M+H]$^+$=314, 316.

(3-Bromo-5-cyclopropylmethoxy-phenyl)-(4-methoxy-3-methyl-phenyl)methanone

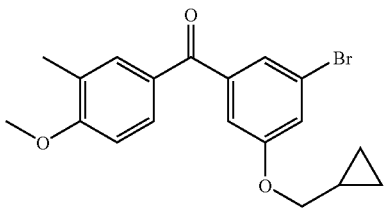

In analogy to the procedure described for the preparation of the Building Block AU, the reaction of the 3-bromo-5-cyclopropylmethoxy-N-methoxy-N-methyl-benzamide and 4-bromo-1-methoxy-2-methyl-benzene, beforehand transformed to the Grignard reagent, yielded the title compound as a colourless oil (yield: 76% of theory). Mass (calculated) $C_{19}H_{19}BrO_3$ [374]; (found) [M+H]$^+$=375, 377.

1-Bromo-3-(cyclopropylmethoxy)-5-[1-(4-methoxy-3-methyl-phenyl)-vinyl]-benzene

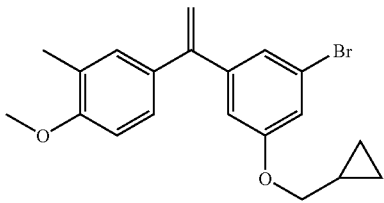

In analogy to the procedure described for the preparation of the Building Block AU, the Wittig olefination of (3-bromo-5-cyclopropylmethoxy-phenyl)-(4-methoxy-3-methyl-phenyl)methanone with methyltriphenylphosphonium bromide yielded the title compound as a colourless oil (yield: 90% of theory). TLC: Rf: 0.63 (silica gel; heptane:ethyl acetate=4:1, UV, 254 nm).

(RS)-4-(3-Bromo-5-cyclopropylmethoxy-phenyl)-4-(4-methoxy-3-methyl-phenyl)-4,5-dihydro-oxazol-2-ylamine (Building Block BA)

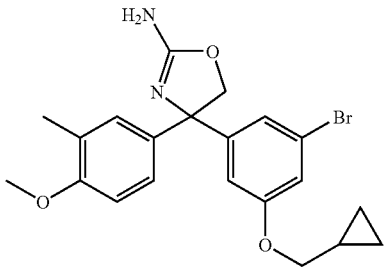

In an analogous manner to that described in the preparation of Building Block C, the 1-bromo-3-(cyclopropylmethoxy)-5-[1-(4-methoxy-3-methyl-phenyl)-vinyl]-benzene was consecutively treated with iodine and silver cyanate, thereupon with ammonium hydroxide solution to yield the title compound (yield: 49%) as a white foam. Mass (calculated) $C_{21}H_{23}BrN_2O_3$ [430]; (found) [M+H]$^+$=431, 433.

Preparation of Building Block BB (R)-4-(3-Bromo-4-fluoro-phenyl)-4-(4-methoxy-3-methyl-phenyl)-4,5-dihydro-oxazol-2-ylamine

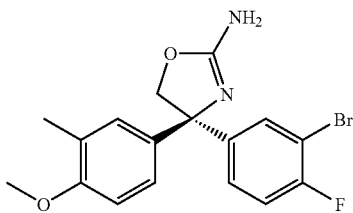

A solution of 0.90 g of (RS)-4-(3-bromo-4-fluoro-phenyl)-4-(4-methoxy-3-methyl-phenyl)-4,5-dihydro-oxazol-2-ylamine (Building Block E) in dichloromethane was divided in 200 mg aliquots which were separated on chiral HPLC (Chiralpak AD) using a 90:10-mixture of heptane and ethanol as the eluent. The fractions of the first eluting enantiomer were combined to give 406 mg of the (S)-(+)-4-(3-bromo-4-fluoro-phenyl)-4-(4-methoxy-3-methyl-phenyl)-4,5-dihydro-oxazol-2-ylamine as a white solid. The later eluting enantiomer (R)-4-(3-bromo-4-fluoro-phenyl)-4-(4-methoxy-3-methyl-phenyl)-4,5-dihydro-oxazol-2-ylamine was isolated to give 381 mg as a white solid.

Preparation of Building Block BD (RS)-4-(3-Bromo-phenyl)-4-(4-methanesulfonyl-phenyl)-4,5-dihydro-oxazol-2-ylamine 1-Bromo-3-(1-[4-methylsulfanyl-phenyl]-vinyl)-benzene

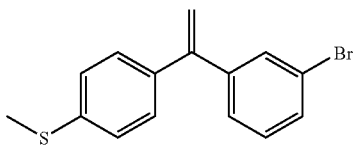

A solution of n-butyllithium (1.6 M in hexane, 4.50 mL, 7.20 mmol, 1.2 eq) was added over 20 min to a solution of 1,3-dibromobenzene (0.80 mL, 6.61 mmol, 1.1 eq) in 15 mL of dry tetrahydrofuran at −78° C. and under an inert atmosphere. The white suspension formed and was stirred at −78° C. for 30 min. A solution of 1-(4-methylsulfanyl-phenyl)-ethanone (1 g, 6.01 mmol, 1.0 eq.) in 10 mL of tetrahydrofuran was then added dropwise and the reaction stirred for 1 h. The reaction mixture was examined by LC-MS which showed the complete formation of tertiary alcohol. The solution was quenched with a saturated aqueous solution of ammonium chloride and then water was added. 2N hydrochloric acid was added to adjust the pH=5. The two phases were separated; the organic layer was dried over anhydrous magnesium sulfate, filtered and evaporated under reduced pressure. The crude was dissolved in a mixture of acetic acid/sulfuric acid (10 mL of acetic acid, 0.3 mL of sulfuric acid) and the reaction mixture was stirred for 1 h at room temperature; then it was examined by LC-MS which showed the complete formation of desired product. The solution was quenched with ice and dichloromethane (20 mL) was added. The two phases formed and were separated. The organic layer was washed with a saturated solution of sodium bicarbonate and then brine. It was then dried over anhydrous magnesium sulfate, filtered and evaporated under reduced pressure. The crude was purified by flash chromatography eluting with cyclohexane. The desired product was obtained as an orange liquid (1.61 g, Yield: 88% over two steps).

$^1$H-NMR (CDCl$_3$): 2.50 (s, 3H), 5.44 (d, 2H), 7.11 (t, 1H), 7.20-7.93 (m, 7H).

1-Bromo-3-(1-[4-methanesulfonyl-phenyl]-vinyl)-benzene

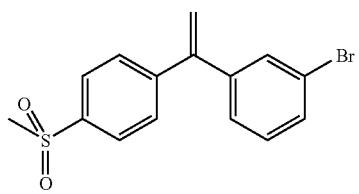

To a solution of 1-bromo-3-(1-[4-methylsulfanyl-phenyl]-vinyl)-benzene (0.5 g, 0.16 mmol, 1 eq) in methanol (15 mL) was added over 5 min Oxone® (2.0 g, 0.32 mmol, 2.0 eq) dissolved in water (15 mL). After stirring at 25° C. for 2 h, the reaction mixture was diluted with water (40 mL) and extracted with dichloromethane (3×40 mL). The organic layer was washed with brine (20 mL) and dried on magnesium sulfate. After filtration and concentration, the crude material was chromatographed (silica gel: cyclohexane/ethyl acetate, 4:1) to give an oil (0.3 g, 56% yield).

$^1$H-NMR (CDCl$_3$): 3.09 (s, 3H), 5.60 (d, 2H), 7.11 (t, 1H), 7.22-7.93 (m, 7H).

(RS)-4-(3-Bromo-phenyl)-4-(4-methanesulfonyl-phenyl)-4,5-dihydro-oxazol-2-ylamine (Building Block BD)

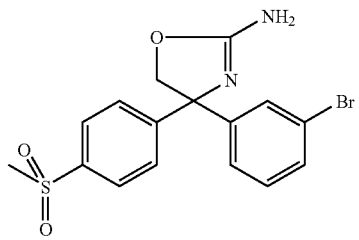

A solution of iodine (0.23 g, 0.9 mmol, 1.1 eq) in 30 mL of ethyl acetate was added dropwise (15 min) at 0° C. to a suspension of 1-bromo-3-(1-[4-methanesulfonyl-phenyl]-vinyl)-benzene (0.3 g, 0.83 mmol, 1.0 eq) and silver cyanate (0.15 g, 1.03 mmol, 1.2 eq) in acetonitrile/ethyl acetate (10 mL/5 mL). After addition was complete the reaction was examined by LC-MS which showed consumption of starting material. The mixture was filtered and the resulting solution was concentrated under reduced pressure. The crude was suspended in 50 mL of ammonium hydroxide solution and stirred for 4 h at room temperature an at 60° C. overnight. Dichloromethane was added to the suspension and the two phases were separated. The organic layer was dried over magnesium sulfate, filtered and concentrated under reduced pressure. The crude residue was purified by flash chromatography eluting with a gradient dichloromethane/methanol 0-2%. 0.15 g of the desired product was obtained as a pale yellow oil (Yield: 25%).

Mass (calculated) C$_{16}$H$_{15}$BrN$_2$O$_3$S [395]; (found) [M+2H$^+$]=397

LC Rt=1.52 min (10 min method) purity 95% UV $^1$H-NMR: (DMSO-d$_6$): 3.15 (s, 3H), 4.70 (s, 2H), 6.38 (br s, 2H), 7.25 (t, 1H), 7.36-7.44 (m, 2H), 7.65 (t, 1H), 7.68-7.84 (dd, 4H).

Preparation of Building Block BE (RS)-4-(4-Difluoromethoxy-3-methyl-phenyl)-4-[3-(4,4,5,5-tetramethyl-[1,3,2]dioxaborolan-2-yl)-phenyl]-4,5-dihydro-oxazol-2-ylamine

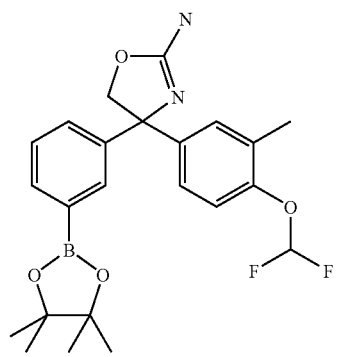

A degassed solution of 4-(3-bromo-phenyl)-4-(4-difluoromethoxy-3-methyl-phenyl)-4,5-dihydro-oxazol-2-ylamine (Building Block S, 1.0 g, 2.5 mmol, 1.0 eq) in dimethylsulfoxide (8 mL) was added into a tube which has been charged with a mixture of bis(pinacolato)diboron (0.83 g, 3.2 mmol, 1.1 eq), potassium acetate (0.73 g, 7.5 mmol, 3.0 eq) and [1,1'-bis(diphenylphosphino)ferrocene]dichloropalladium(11) dichloromethane complex (37 mg, 0.05 mmol, 0.03 eq) was then added; the tube is sealed and heated to 85° C. for 3 h. Upon completion, water (80 mL) was added extracted with ethyl acetate (3×15 mL), dried (sodium sulfate) and concentrated in vacuo. The crude product was purified by mass triggered preparative HPLC to yield a white solid (20%).

Mass (calculated) C$_{23}$H$_{27}$BF$_2$N$_2$O$_4$ [444]; (found) [M+H$^+$]=445

LC Rt=1.75 min (5 min method)

TABLE 1

List of intermediates of formula II

| Intermediate compound of formula II | Building Block |
|---|---|
| (structure) | A |
| (structure) | B |
| (structure) | C |
| (structure) | D |
| (structure) | E |
| (structure) | F |
| (structure) | G |
| (structure) | H |
| (structure) | I |
| (structure) | J |
| (structure) | K |
| (structure) | L |

TABLE 1-continued

List of intermediates of formula II

| Intermediate compound of formula II | Building Block |
|---|---|
| (4-ethoxy-3-methylphenyl)(3-bromophenyl) substituted 2-amino-4,5-dihydrooxazole | M |
| (4-(2-methoxyethoxy)phenyl)(3-bromophenyl) substituted 2-amino-4,5-dihydrooxazole | N |
| (3-chloro-4-methoxyphenyl)(3-bromophenyl) substituted 2-amino-4,5-dihydrooxazole | O |
| (3-fluoro-4-methoxyphenyl)(3-bromophenyl) substituted 2-amino-4,5-dihydrooxazole | P |
| (4-isopropoxyphenyl)(3-bromophenyl) substituted 2-amino-4,5-dihydrooxazole | Q |
| (4-(difluoromethoxy)phenyl)(3-bromophenyl) substituted 2-amino-4,5-dihydrooxazole | R |
| (4-(difluoromethoxy)-3-methylphenyl)(3-bromophenyl) substituted 2-amino-4,5-dihydrooxazole | S |
| (4-(trifluoromethoxy)phenyl)(3-bromophenyl) substituted 2-amino-4,5-dihydrooxazole | T |
| (3-chloro-4-methoxyphenyl)(3-bromo-4-fluorophenyl) substituted 2-amino-4,5-dihydrooxazole | U |

TABLE 1-continued
List of intermediates of formula II
| Intermediate compound of formula II | Building Block |
|---|---|
| 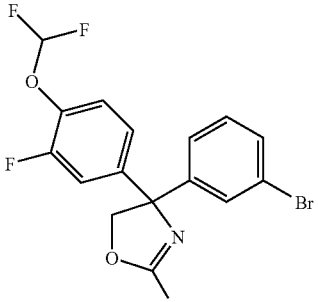 | V |
| 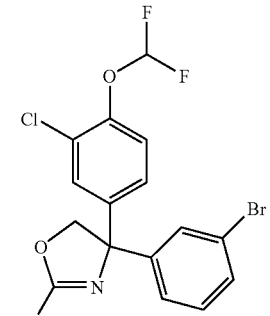 | W |
| 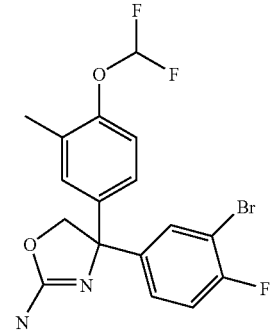 | X |
| 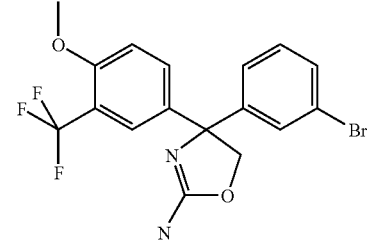 | Y |
| 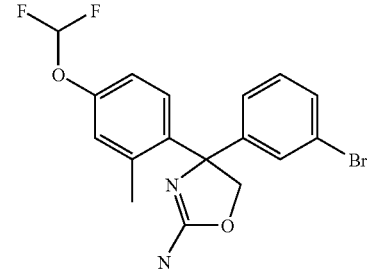 | Z |
| 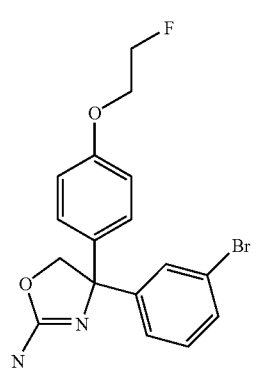 | AA |
| 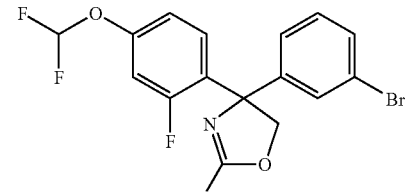 | AB |
| 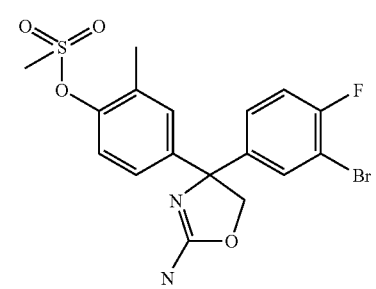 | AC |
| 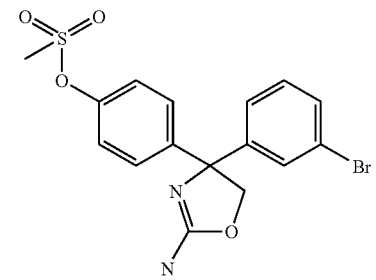 | AD |
| 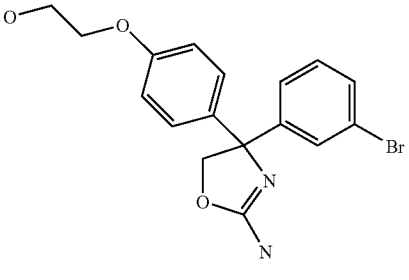 | AE |

TABLE 1-continued
List of intermediates of formula II
| Intermediate compound of formula II | Building Block |
|---|---|
| 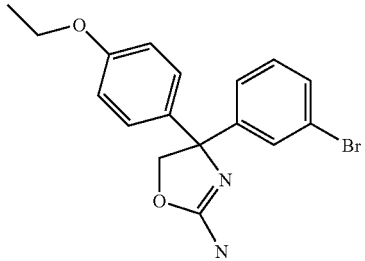 | AF |
| 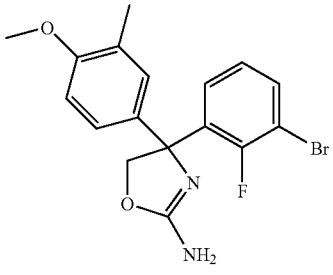 | AG |
| 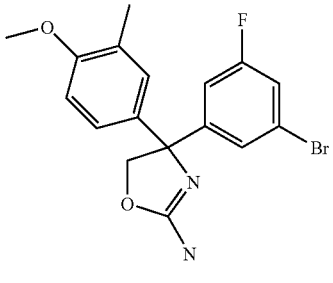 | AH |
| 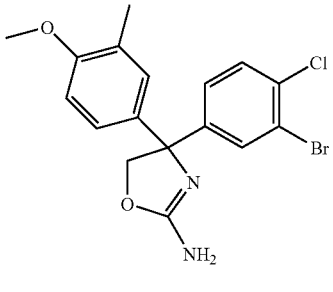 | AM |
| 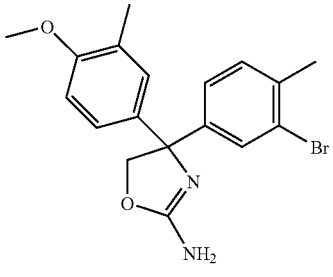 | AN |
| 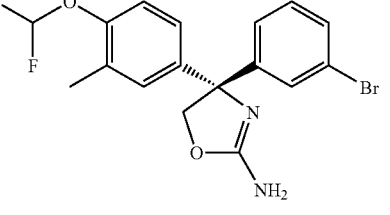 | AO |
| 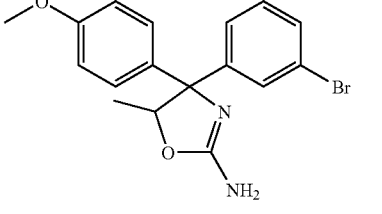 | AP |
| 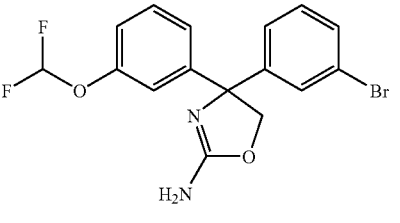 | AQ |
| 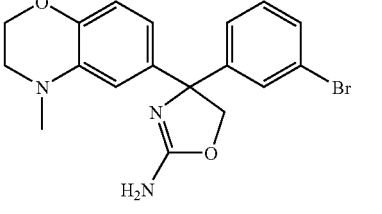 | AR |
| 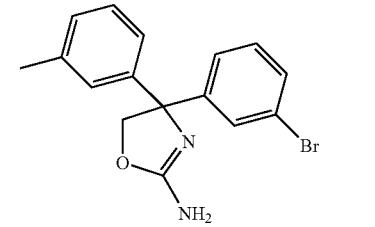 | AS |
| 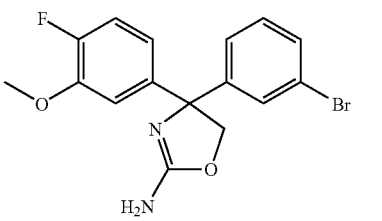 | AT |

TABLE 1-continued

List of intermediates of formula II

| Intermediate compound of formula II | Building Block |
|---|---|
| (structure) | AU |
| (structure) | AV |
| (structure) | AW |
| (structure) | AX |
| (structure) | AY |
| (structure) | AZ |
| (structure) | BA |
| (structure) | BB |

TABLE 1-continued

List of intermediates of formula II

| Intermediate compound of formula II | Building Block |
|---|---|
| [structure: 4-(4-methylsulfonylphenyl)-4-(3-bromophenyl)-4,5-dihydro-oxazol-2-ylamine] | BD |
| [structure: oxazoline with 3-methyl-4-difluoromethoxyphenyl and phenyl-boronic acid pinacol ester substituents] | BE |

TABLE 2

Experimental procedures with the synthesis of Examples 1-207.

Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 1 | [structure] | (RS)-4-[3-(2-Fluoro-pyridin-3-yl)-phenyl]-4-phenyl-4,5-dihydro-oxazol-2-ylamine | 334 | 92 | (DMSO-d$_6$) δ (ppm): 8.22 (m, 1H); 8.04 (m, 1H); 7.66 (m, 1H); 7.43 (m, 6H); 7.27 (m, 2H); 7.16 (m, 1H); 6.24 (bs, 2H); 4.71 (m, 2H). | A/3 |
| 2 | [structure] | (RS)-4-(3'-Fluoro-biphenyl-3-yl)-4-phenyl-4,5-dihydro-oxazol-2-ylamine | 333 | 96 | $^1$H-NMR (CDCl$_3$) δ (ppm): 7.59 (m, 1H); 7.44 (m, 1H); 7.38 (m, 3H); 7.33 (m, 5H); 7.25 (m, 2H); 7.01 (m, 1H); 5.01 (bs, 2H); 4.83 (m, 2H). | A/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 3 | 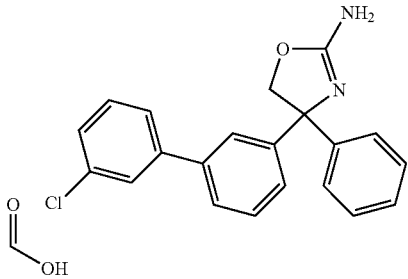 | (RS)-4-(3'-Chloro-biphenyl-3-yl)-4-phenyl-4,5-dihydro-oxazol-2-ylamine formate | 349 | 100 | $^1$H-NMR (CDCl$_3$) δ (ppm): 9.80 (bs, 3H); 8.52 (s, 1H); 7.52 (m, 2H); 7.49 (m, 1H); 7.45 (m, 1H); 7.42 (m, 1H); 7.33 (m, 8H); 5.08 (d, 1H); 5.04 (d, 1H). | A/4 |
| 3A | 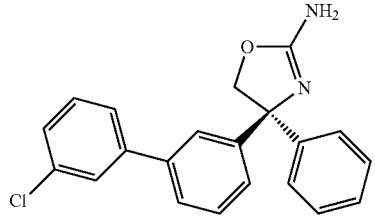 | (S)-4-(3'-Chloro-biphenyl-3-yl)-4-phenyl-4,5-dihydro-oxazol-2-ylamine | 349* | 99.8* | | Chiral |
| 3B | 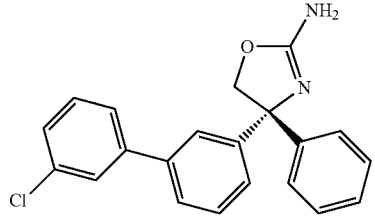 | (R)-4-(3'-Chloro-biphenyl-3-yl)-4-phenyl-4,5-dihydro-oxazol-2-ylamine | 349* | 94.4* | | Chiral |
| 4 | 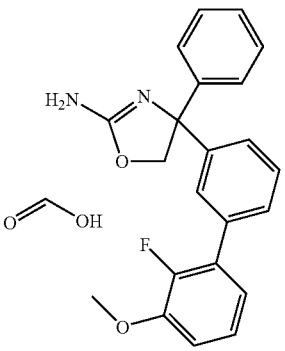 | (RS)-4-(2'-Fluoro-3'-methoxy-biphenyl-3-yl)-4-phenyl-4,5-dihydro-oxazol-2-ylamine formate | 363 | 98 | $^1$H-NMR (DMSO-d$_6$) δ (ppm): 8.13 (s, 1H); 7.56 (m, 1H); 7.42 (m, 3H); 7.31 (m, 4H); 7.16 (m, 3H); 6.94 (m, 1H); 6.31 (bs, 3H); 4.70 (m, 2H); 3.84 (s, 3H). | A/3 |

TABLE 2-continued

*Experimental procedures with the synthesis of Examples 1-207.*

*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | $^1$H-NMR | Build. Block/ Synthetic Method |
|---|---|---|---|---|---|---|
| 5 | 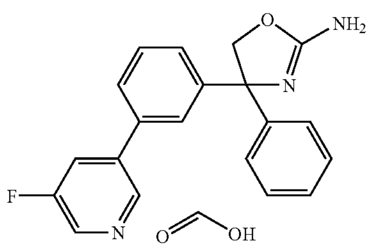 | (RS)-4-[3-(5-Fluoro-pyridin-3-yl)-phenyl]-4-phenyl-4,5-dihydro-oxazol-2-ylamine formate | 334 | 100 | $^1$H-NMR (DMSO-d$_6$) δ (ppm): 8.72 (m, 1H); 8.56 (bd, 1H); 8.14 (s, 1H); 8.00 (m, 1H); 7.79 (m, 1H); 7.57 (m, 1H); 7.51 (m, 1H); 7.46 (m, 2H); 7.40 (m, 1H); 7.27 (m, 2H); 7.15 (m, 1H); 6.31 (bs, 3H); 4.81 (d, 1H), 4.69 (d, 1H). | A/3 |
| 6 | 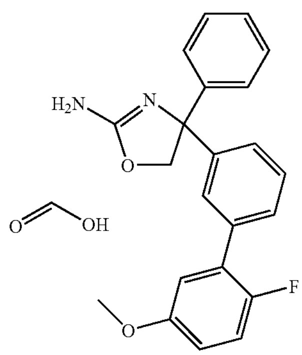 | (RS)-4-(2'-Fluoro-5'-methoxy-biphenyl-3-yl)-4-phenyl-4,5-dihydro-oxazol-2-ylamine formate | 363 | 100 | $^1$H-NMR (CD$_3$OD) δ (ppm): 8.42 (s, 1H); 7.53 (m, 3H); 7.40 (m, 6H); 7.08 (m, 1H); 6.92 (m, 2H); 5.31 (m, 2H); 3.79 (s, 3H). | A/3 |
| 7 | 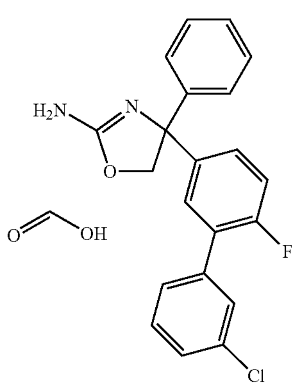 | (RS)-4-(3'-Chloro-6-fluoro-biphenyl-3-yl)-4-phenyl-4,5-dihydro-oxazol-2-ylamine formate | 367 | 100 | $^1$H-NMR (CD$_3$OD) δ (ppm): 8.40 (s, 1H); 7.52 (m, 1H); 7.42 (m, 10H); 7.27 (m, 1H); 5.29 (m, 2H). | B/4 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 8 | 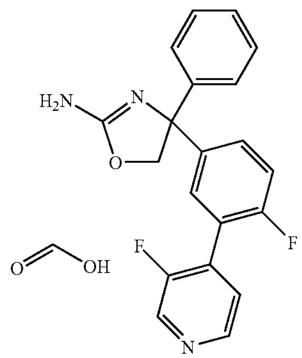 | (RS)-4-[4-Fluoro-3-(3-fluoro-pyridin-4-yl)-phenyl]-4-phenyl-4,5-dihydro-oxazol-2-ylamine formate | 352 | 100 | $^1$H-NMR (CD$_3$OD) δ (ppm): 8.57 (m, 1H); 8.49 (m, 1H); 8.35 (s, 1H); 7.85 (m, 1H); 7.59 (m, 1H); 7.41 (m, 7H); 5.33 (m, 2H). | B/3 |
| 9 | 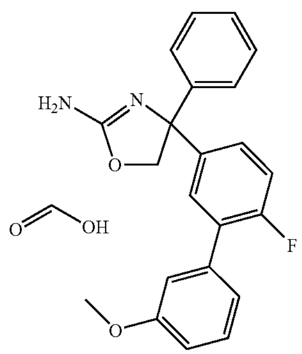 | (RS)-4-(6-Fluoro-3'-methoxy-biphenyl-3-yl)-4-phenyl-4,5-dihydro-oxazol-2-ylamine formate | 363 | 100 | $^1$H-NMR (CD$_3$OD) δ (ppm): 8.42 (s, 1H); 7.40 (m, 8H); 7.24 (m, 1H); 7.03 (m, 2H); 6.94 (m, 1H); 5.23 (m, 2H); 3.81 (s, 3H). | B/3 |
| 10 | 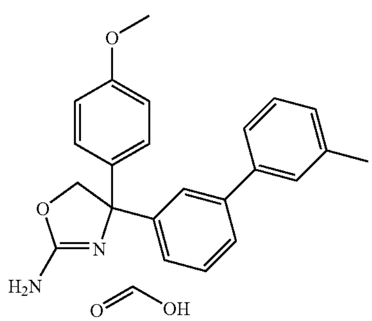 | (RS)-4-(4-Methoxy-phenyl)-4-(3'-methyl-biphenyl-3-yl)-4,5-dihydro-oxazol-2-ylamine formate | 359 | 99 | $^1$H-NMR (DMSO-d$_6$) δ (ppm): 8.15 (s, 1H); 7.65 (m, 1H); 7.37 (m, 8H); 7.15 (m, 1H); 6.82 (m, 2H); 4.70 (m, 2H); 3.68 (s, 3H); 2.35 (s, 3H). | C/3 |
| 11 | 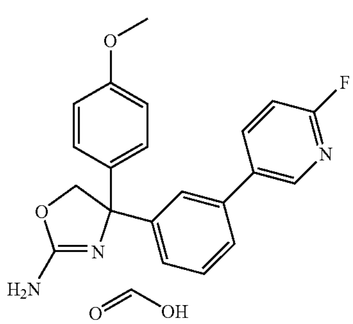 | (RS)-4-[3-(6-Fluoro-pyridin-3-yl)-phenyl]-4-(4-methoxy-phenyl)-4,5-dihydro-oxazol-2-ylamine formate | 364 | 95 | $^1$H-NMR (DMSO-d$_6$) δ (ppm): 8.46 (m, 1H); 8.20 (m, 1H); 8.14 (s, 1H); 7.69 (m, 1H); 7.38 (m, 6H); 6.82 (m, 2H); 6.40 (bs, 3H); 4.75 (d, 1H); 4.68 (d, 1H); 3.68 (s, 3H). | C/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 12 | 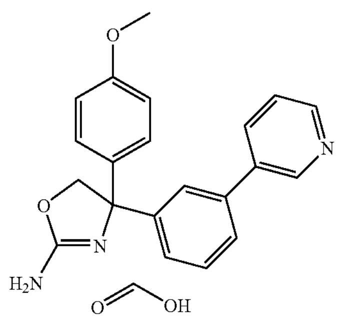 | (RS)-4-(4-Methoxy-phenyl)-4-(3-pyridin-3-yl-phenyl)-4,5-dihydro-oxazol-2-ylamine formate | 364 | 100 | $^1$H-NMR (DMSO-d$_6$) δ (ppm): 8.81 (m, 1H); 8.55 (m, 1H); 8.15 (s, 1H); 7.99 (m, 1H); 7.71 (m, 1H); 7.47 (m, 4H); 7.35 (m, 2H); 6.83 (m, 2H); 4.79 (d, 1H); 4.71 (d, 1H); 3.68 (s, 3H). | C/3 |
| 13 | 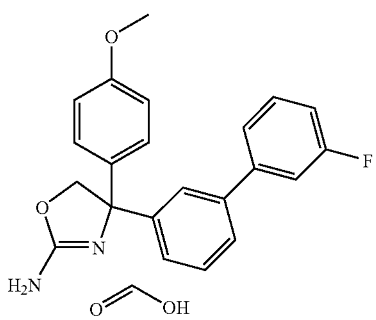 | (RS)-4-(3'-Fluoro-biphenyl-3-yl)-4-(4-methoxy-phenyl)-4,5-dihydro-oxazol-2-ylamine formate | 363 | 100 | $^1$H-NMR (DMSO-d$_6$) δ (ppm): 8.15 (s, 1H); 7.68 (m, 1H); 7.42 (m, 8H); 7.18 (m, 1H); 6.83 (m, 2H); 4.76 (d, 1H); 4.71 (d, 1H); 3.68 (s, 3H). | C/3 |
| 14 | 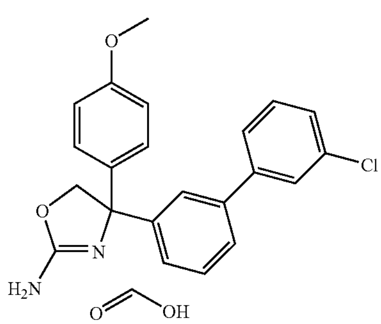 | (RS)-4-(3'-Chloro-biphenyl-3-yl)-4-(4-methoxy-phenyl)-4,5-dihydro-oxazol-2-ylamine formate | 379 | 100 | $^1$H-NMR (DMSO-d$_6$) δ (ppm): 8.15 (s, 1H); 7.66 (m, 2H); 7.55 (m, 1H); 7.41 (m, 7H); 6.82 (m, 2H); 4.72 (m, 2H); 3.68 (s, 3H). | C/4 |
| 15 | 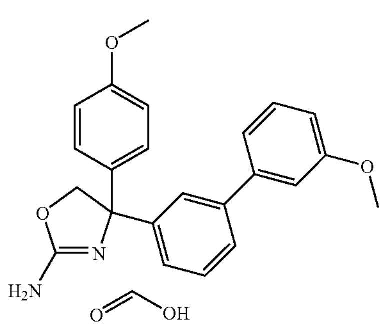 | (RS)-4-(3'-Methoxy-biphenyl-3-yl)-4-(4-methoxy-phenyl)-4,5-dihydro-oxazol-2-ylamine formate | 375 | 100 | $^1$H-NMR (DMSO-d$_6$) δ (ppm): 8.14 (s, 1H); 7.63 (m, 1H); 7.44 (m, 1H); 7.34 (m, 5H); 7.10 (m, 2H); 6.91 (m, 1H); 6.83 (m, 2H); 4.70 (m, 2H); 3.79 (s, | C/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | ¹H-NMR | Build. Block/ Synthetic Method |
|---|---|---|---|---|---|---|
| 16 | 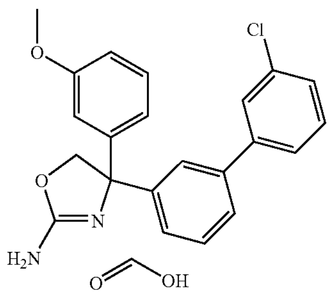 | (RS)-4-(3'-Chloro-biphenyl-3-yl)-4-(3-methoxy-phenyl)-4,5-dihydro-oxazol-2-ylamine formate | 379 | 96 | ¹H-NMR (DMSO-d$_6$) δ (ppm): 8.13 (s, 1H); 7.72 (m, 1H); 7.64 (m, 1H); 7.55 (m, 1H); 7.42 (m, 5H); 7.18 (m, 1H); 7.02 (m, 2H); 6.73 (m, 1H); 6, 37 (bs, 3H); 4.78 (d, 1H); 4.68 (d, 1H), 3.69 (s, 3H). | D/4 |
| 17 | 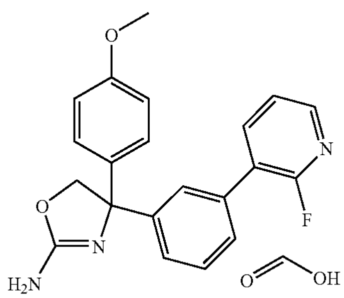 | (RS)-4-[3-(2-Fluoro-pyridin-3-yl)-phenyl]-4-(4-methoxy-phenyl)-4,5-dihydro-oxazol-2-yl-amine formate | 364 | 95 | ¹H-NMR (DMSO-d$_6$) δ (ppm): 8.22 (m, 1H); 8.14 (s, 1H); 8.03 (m, 1H); 7.63 (m, 1H); 7.43 (m, 4H); 7.33 (m, 2H); 6.83 (m, 2H); 4.69 (m, 2H); 3.69 (s, 3H). | C/5 |
| 18 | 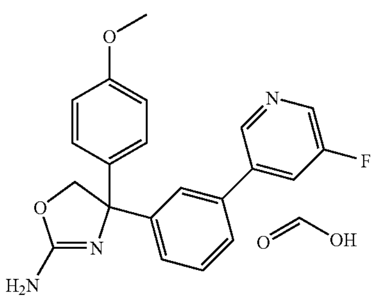 | (RS)-4-[3-(5-Fluoro-pyridin-3-yl)-phenyl]-4-(4-methoxy-phenyl)-4,5-dihydro-oxazol-2-ylamine formate | 364 | 96 | ¹H-NMR (DMSO-d$_6$) δ (ppm): 8.73 (m, 1H); 8.56 (m, 1H); 8.15 (s, 1H); 8.00 (m, 1H); 7.76 (m, 1H); 7.58 (m, 1H); 7.49 (m, 1H); 7.38 (m, 3H); 6.83 (m, 2H); 4.80 (d, 1H); 4.69 (d, 1H); 3.68 (s, 3H). | C/5 |
| 19 | 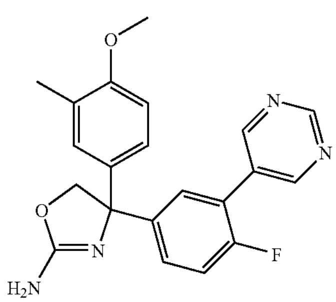 | (RS)-4-(4-Fluoro-3-pyrimidin-5-yl-phenyl)-4-(4-methoxy-3-methyl-phenyl)-4,5-dihydro-oxazol-2-ylamine | 379 | 99 | ¹H-NMR (CDCl$_3$) δ (ppm): 9.19 (s, 1H); 8.88 (m, 2H); 7.44 (m, 1H); 7.37 (m, 1H); 7.15 (m, 1H); 7.10 (m, 2H); 6.67 (m, 1H); 4.83 (d, 1H); 4.72 (d, 1H); 3.81 (s, 3H); 2.18 (s, 3H). | E/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 19A | 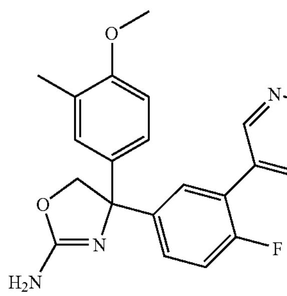 | (R)-4-(4-Fluoro-3-pyrimidin-5-yl-phenyl)-4-(4-methoxy-3-methyl-phenyl)-4,5-dihydro-oxazol-2-ylamine | 379 | 99 | $^1$H-NMR (CDCl$_3$) δ (ppm): 9.19 (s, 1H); 8.88 (m, 1H); 7.44 (m, 2H); 7.37 (m, 1H); 7.15 (m, 1H); 7.10 (m, 2H); 6.67 (m, 1H); 4.83 (d, 1H); 4.72 (d, 1H); 3.81 (s, 3H); 2.18 (s, 3H). | BB/3 |
| 20 | 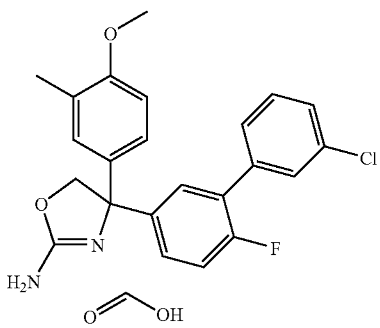 | (RS)-4-(3'-Chloro-6-fluoro-biphenyl-3-yl)-4-(4-methoxy-3-methyl-phenyl)-4,5-dihydro-oxazol-2-ylamine formate | 411 | 99 | $^1$H-NMR (CD$_3$OD) δ (ppm): 8.36 (s, 1H); 7.53 (m, 1H); 7.41 (m, 5H); 7.28 (m, 1H); 7.13 (m, 2H); 6.94 (m, 1H); 5.24 (m, 2H); 3.83 (s, 3H); 2.19 (s, 3H). | E/4 |
| 21 | 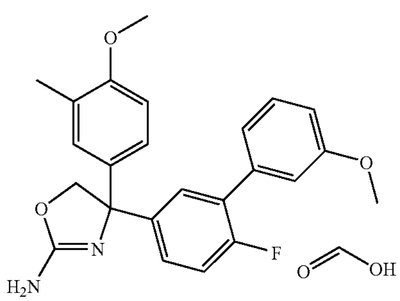 | (RS)-4-(6-Fluoro-3'-methoxy-biphenyl-3-yl)-4-(4-methoxy-3-methyl-phenyl)-4,5-dihydro-oxazol-2-ylamine formate | 407 | 99 | $^1$H-NMR (CD$_3$OD) δ (ppm): 8.46 (s, 1H); 7.41 (m, 1H); 7.33 (m, 2H); 7.23 (m, 1H); 7.13 (m, 2H); 7.04 (m, 2H); 6.94 (m, 2H); 5.16 (m, 2H); 3.83 (s, 3H); 3.81 (s, 3H); 2.18 (s, 3H). | E/3 |
| 22 | 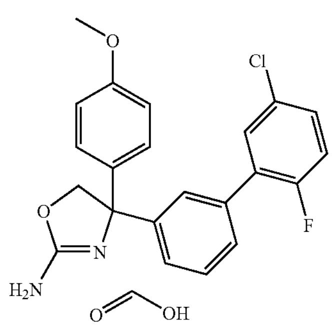 | (RS)-4-(5'-Chloro-2'-fluoro-biphenyl-3-yl)-4-(4-methoxy-phenyl)-4,5-dihydro-oxazol-2-ylamine formate | 397 | 98 | $^1$H-NMR (DMSO-d$_6$) δ (ppm): 8.15 (s, 1H); 7.59 (m, 1H); 7.52 (m, 1H); 7.40 (m, 7H); 6.83 (m, 2H); 4.69 (m, 2H); 3.68 (s, 3H). | C/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 23 | 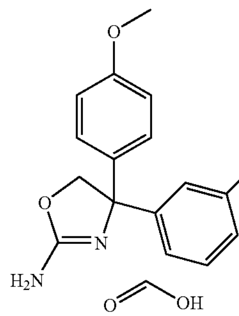 | (RS)-4-(4-Methoxy-phenyl)-4-(3-pyrimidin-5-yl-phenyl)-4,5-dihydro-oxazol-2-ylamine formate | 347 | 98 | $^1$H-NMR (DMSO-d$_6$) δ (ppm): 9.17 (s, 1H); 9.07 (s, 2H); 8.13 (s, 1H); 7.78 (m, 1H); 7.59 (m, 1H); 7.51 (m, 1H); 7.42 (m, 1H); 7.36 (m, 2H); 6.82 (m, 2H); 4.77 (d, 1H); 4.66 (d, 1H); 3.68 (s, 3H). | C/3 |
| 24 | 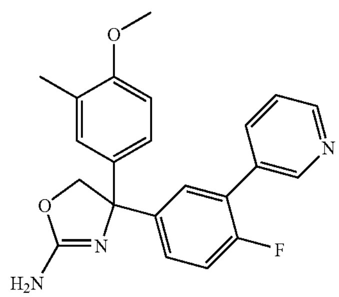 | (RS)-4-(4-Fluoro-3-pyridin-3-yl-phenyl)-4-(4-methoxy-3-methyl-phenyl)-4,5-dihydro-oxazol-2-ylamine | 378 | 99 | $^1$H-NMR (CDCl$_3$) δ (ppm): 8.74 (m, 1H); 8.58 (m, 1H); 7.83 (m, 1H); 7.43 (m, 1H); 7.33 (m, 2H); 7.11 (m, 3H); 6.76 (m, 1H); 4.82 (d, 1H); 4.74 (d, 1H), 3.80 (s, 3H); 2.19 (s, 3H). | E/3 |
| 25 | 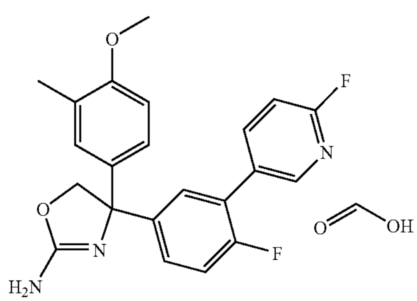 | (RS)-4-[4-Fluoro-3-(6-fluoro-pyridin-3-yl)-phenyl]-4-(4-methoxy-3-methyl-phenyl)-4,5-dihydro-oxazol-2-ylamine formate | 396 | 90 | $^1$H-NMR (CD$_3$OD) δ (ppm): 8.44 (m, 1H); 8.34 (s, 1H); 8.11 (m, 1H); 7.49 (m, 1H); 7.39 (m, 1H); 7.28 (m, 1H); 7.13 (m, 3H); 6.91 (m, 1H); 5.13 (m, 2H); 3.82 (s, 3H); 2.18 (s, 3H) | E/3 |
| 26 | 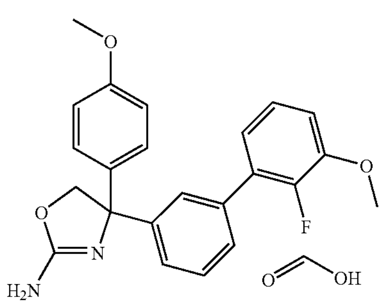 | (RS)-4-(2'-Fluoro-3'-methoxy-biphenyl-3-yl)-4-(4-methoxy-phenyl)-4,5-dihydro-oxazol-2-yl-amine formate | 393 | 100 | $^1$H-NMR (DMSO-d$_6$) δ (ppm): 8.17 (s, 1H); 7.54 (m, 1H); 7.37 (m, 1H); 7.17 (m, 5H); 6.95 (m, 1H); 6.85 (m, 2H); 4.73 (s, 2H); 3.85 (s, 3H); 3.69 (s, 3H). | C/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 27 | 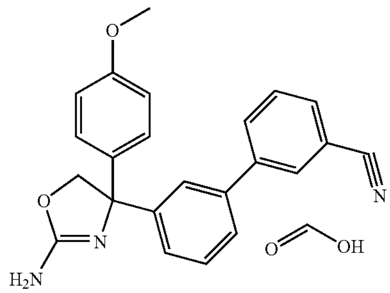 | (RS)-3'-[2-Amino-4-(4-methoxy-phenyl)-4,5-dihydro-oxazol-4-yl]-biphenyl-3-carbonitrile formate | 370 | 95 | $^1$H-NMR (DMSO-d$_6$) δ (ppm): 8.16 (s, 1H); 8.10 (m, 1H); 7.94 (m, 1H); 7.81 (m, 1H); 7.74 (m, 1H); 7.65 (m, 1H); 7.54 (m, 1H); 7.40 (m, 4H); 6.82 (m, 2H); 4.79 (d, 1H); 4.70 (d, 1H); 3.68 (s, 3H). | C/3 |
| 28 | 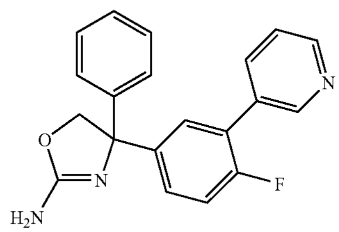 | (RS)-4-(4-Fluoro-3-pyridin-3-yl-phenyl)-4-phenyl-4,5-dihydro-oxazol-2-ylamine | 334 | 95 | $^1$H-NMR (CDCl$_3$) δ (ppm): 8.73 (m, 1H); 8.57 (m, 1H); 7.82 (m, 1H); 7.42 (m, 1H); 7.32 (m, 6H); 7.24 (m, 1H); 7.11 (m, 1H); 4.79 (m, 2H). | B/3 |
| 29 | 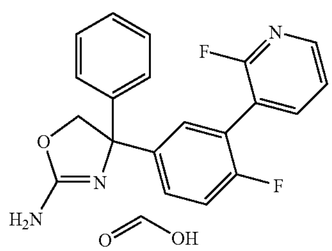 | (RS)-4-[4-Fluoro-3-(2-fluoro-pyridin-3-yl)-phenyl]-4-phenyl-4,5-dihydro-oxazol-2-ylamine formate | 352 | 95 | $^1$H-NMR (CD$_3$OD) δ (ppm): 8.38 (s, 1H); 8.25 (m, 1H); 7.97 (m, 1H); 7.38 (m, 9H); 5.18 (m, 2H). | B/3 |
| 30 | 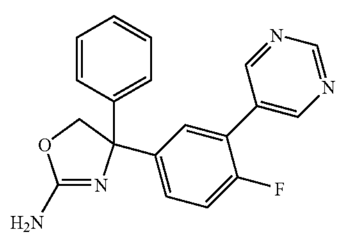 | (RS)-4-(4-Fluoro-3-pyrimidin-5-yl-phenyl)-4-phenyl-4,5-dihydro-oxazol-2-ylamine | 335 | 95 | $^1$H-NMR (CDCl$_3$) δ (ppm): 9.19 (s, 1H); 8.89 (m, 2H); 7.45 (m, 1H); 7.37 (m, 5H); 7.28 (m, 1H); 7.17 (m, 1H); 4.84 (m, 2H). | B/3 |
| 31 | 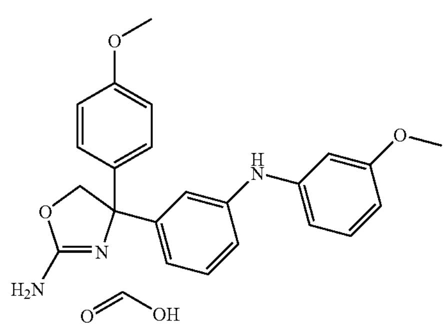 | (RS)-4-(4-Methoxy-phenyl)-4-[3-(3-methoxy-phenylamino)-phenyl]-4,5-dihydro-oxazol-2-ylamine formate | 390 | 95 | $^1$H-NMR (DMSO-d$_6$) δ (ppm): 8.16 (s, 1H); 8.15 (bs, 1H); 7.28 (m, 2H); 7.10 (m, 3H); 6.84 (m, 4H); 6.54 (m, 2H); 6.34 (m, 1H); 4.69 (d, 1H); 4.60 (d, 1H); 3.70 (s, 3H); 3.68 (s, 3H). | C/ (see below) |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 32 | 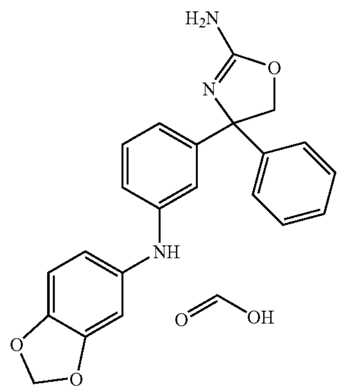 | (RS)-4-[3-(1,3-Benzodioxol-5-ylamino)-phenyl]-4-phenyl-4,5-dihydro-oxazol-2-ylamine formate | 374 | 95 | $^1$H-NMR (DMSO-d$_6$) δ (ppm): 8.14 (s, 1H); 7.89 (bs, 1H); 7.37 (m, 1H); 7.26 (m, 2H); 7.16 (m, 1H); 7.06 (m, 1H); 7.01 (m, 1H); 6.73 (m, 3H); 6.58 (m, 1H); 6.45 (m, 1H); 5.92 (s, 2H); 4.68 (d, 1H); 4.59 (d, 1H). | A/ (see below) |
| 33 | 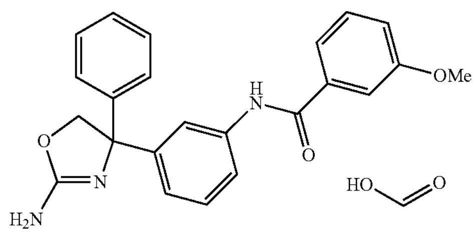 | (RS)-N-[3-(2-Amino-4-phenyl-4,5-dihydro-oxazol-4-yl)-phenyl]-3-methoxy-benzamide formate | 388 | 100 | $^1$H-NMR (DMSO-d$_6$) δ (ppm): 10.18 (s, 1H); 8.14 (s, 1H); 7.81 (m, 1H); 7.61 (m, 1H); 7.47 (m, 1H); 7.45 (m, 1H); 7.40 (m, 3H); 7.27 (m, 3H); 7.10 (m, 3H); 4.70 (d, 1H); 4.66 (d, 1H); 3.81 (s, 3H). | A/ (see below) |
| 34 | 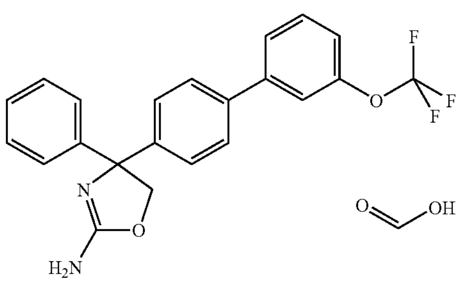 | (RS)-4-(3-trifluoromethoxy-phenyl-4-yl-phenyl)-4-phenyl-4,5-dihydro-oxazol-2-ylamine | 399 | 100 | $^1$H-NMR (DMSO-d$_6$) δ (ppm): 8.17 (s, 1H); 7.68 (m, 1H); 7.63 (m, 2H); 7.57 (m, 2H); 7.52 (m, 2H); 7.46 (m, 2H); 7.32 (m, 3H); 7.19 (m, 1H); 4.78 (d, 1H); 4.73 (d, 1H) | F/3 |
| 35 | 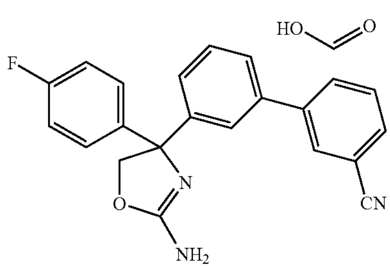 | (RS)-3'-(2-Amino-4-(4-fluoro-phenyl)-4,5-dihydro-oxazol-4-yl)-biphenyl-3-carbonitrile formate | 358 | 100 | 1H-NMR (DMSO-d$_6$) δ (ppm): 8.13 (s, 1H); 8.11 (m, 1H); 7.94 (m, 1H); 7.81 (m, 1H); 7.76 (m, 1H); 7.65 (m, 1H); 7.54 (m, 1H); 7.48 (m, 3H); 7.39 (m, 1H); 7.08 (m, 2H); 6.35 (bs, 3H); 4.79 (d, 1H); 4.69 (d, 1H). | G/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | ¹H-NMR | Build. Block/ Synthetic Method |
|---|---|---|---|---|---|---|
| 36 | 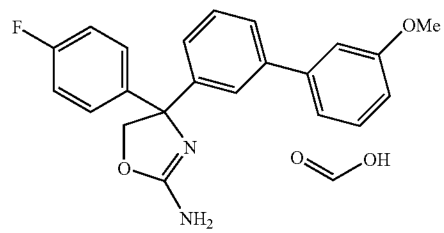 | (RS)-4-(4-Fluoro-phenyl)-4-(3'-methoxy-biphenyl-3-yl)-4,5-dihydro-oxazol-2-yl-amine formate | 363 | 100 | 1H-NMR (DMSO-$d_6$) δ (ppm): 8.13 (m, 1H); 7.65 (m, 1H); 7.47 (m, 3H); 7.36 (m, 3H); 7.10 (m, 4H); 6.92 (m, 1H); 4.73 (m, 2H); 3.79 (s, 3H). | G/3 |
| 37 | 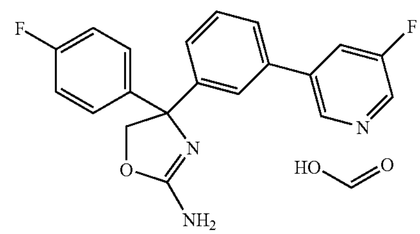 | (RS)-4-(4-Fluoro-phenyl)-4-(3-(5-fluoro-pyridin-3-yl)-phenyl)-4,5-dihydro-oxazol-2-yl-amine formate | 352 | 100 | 1H-NMR (DMSO-$d_6$) δ (ppm): 8.73 (m, 1H); 8.56 (d, 1H); 8.13 (s, 1H); 8.01 (m, 1H); 7.78 (m, 1H); 7.58 (m, 1H); 7.48 (m, 3H); 7.41 (m, 1H); 7.08 (m, 2H); 6.28 (bs, 3H); 4.79 (d, 1H); 4.67 (d, 1H). | G/5 |
| 38 | 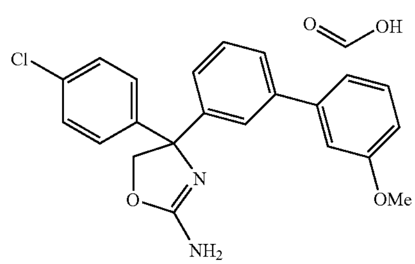 | (RS)-4-(4-Chloro-phenyl)-4-(3'-methoxy-biphenyl-3-yl)-4,5-dihydro-oxazol-2-yl-amine formate | 379 | 100 | ¹H-NMR (DMSO-$d_6$) δ (ppm): 8.13 (s, 1H); 7.65 (m, 1H); 7.46 (m, 3H); 7.34 (m, 5H); 7.13 (m, 1H); 7.08 (m, 1H); 6.91 (m, 1H); 6.33 (bs, 3H); 4.74 (d, 1H); 4.69 (d, 1H); 3.79 (s, 3H) | H/5 |
| 39 | 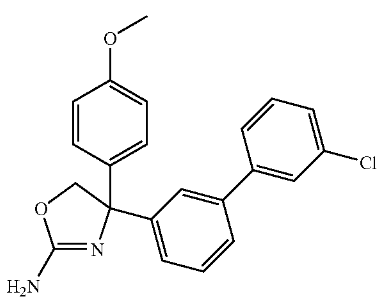 | (RS)-4-(3'-Chloro-biphenyl-3-yl)-4-(4-methoxy-phenyl)-4,5-dihydro-oxazol-2-ylamine formate | 379 | 100 | | C/4 |
| 39A | Chiral | (R)-4-(3'-Chloro-biphenyl-3-yl)-4-(4-methoxy-phenyl)-4,5-dihydro-oxazol-2-ylamine | 379 | 89% ee | | Chiral See below |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | 1H-NMR | Build. Block/ Synthetic Method |
|---|---|---|---|---|---|---|
| 40 | 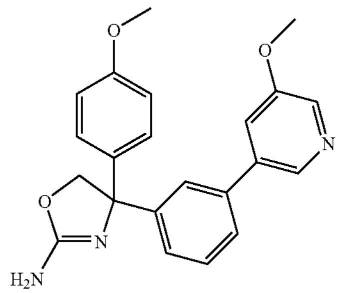 | (RS)-4-(4-Methoxy-phenyl)-4-[3-(5-methoxy-pyridin-3-yl)-phenyl]-4,5-dihydro-oxazol-2-ylamine formate | 376 | 98 | | C/5 |
| 41 | 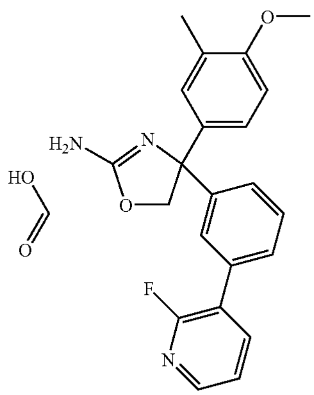 | (RS)-4-[3-(2-Fluoro-pyridin-3-yl)-phenyl]-4-(4-methoxy-3-methyl-phenyl)-4,5-dihydro-oxazol-2-ylamine formate | 378 | 95 | 1H-NMR (CD3OD) δ (ppm): 8.44 (s, 1H); 8.19 (m, 1H); 8.03 (m, 1H); 7.57 (m, 3H); 7.40 (m, 2H); 7.12 (m, 2H); 6.92 (m, 2H); 5.18 (m, 2H); 3.83 (s, 3H); 2.18 (s, 3H) | I/5 |
| 42 | 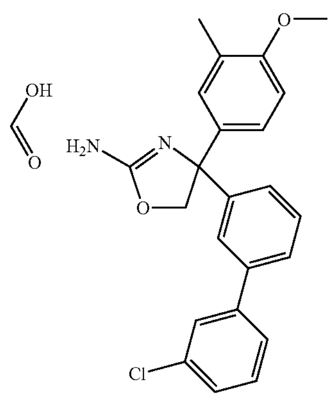 | (RS)-4-(3'-Chloro-biphenyl-3-yl)-4-(4-methoxy-3-methyl-phenyl)-4,5-dihydro-oxazol-2-ylamine formate | 393 | 100 | 1H-NMR (CD3OD) δ (ppm): 8.46 (s, 1H); 7.60 (m, 3H); 8.03 (m, 1H); 7.51 (m, 2H); 7.42 (m, 1H); 7.35 (m, 2H); 7.12 (m, 2H); 6.92 (m, 1H); 5.21 (dd, 2H); 3.82 (s, 3H); 2.18 (s, 3H) | I/4 |
| 43 | 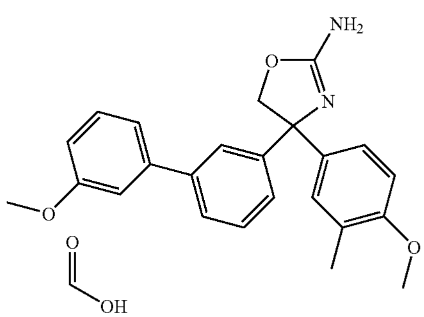 | (RS)-4-(3'-Methoxy-biphenyl-3-yl)-4-(4-methoxy-3-methyl-phenyl)-4,5-dihydro-oxazol-2-ylamine format | 389 | 95 | 1H-NMR (CD3OD) δ (ppm): 8.46 (s, 1H); 7.60 (m, 1H); 7.55 (m, 1H); 7.49 (m, 1H); 7.32 (m, 2H); 7.13 (m, 3H); 7.09 (m, 1H); 6.92 (m, 2H); 5.23 (dd, 2H); 3.82 (s, 6H); 2.18 (s, 3H) | I/3 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 44 | 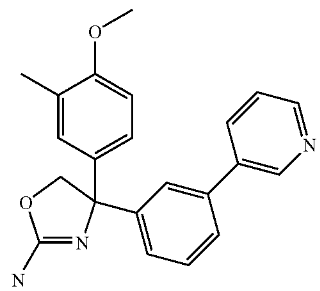 | (RS)-4-(4-Methoxy-3-methyl-phenyl)-4-(3-pyridin-3-yl-phenyl)-4,5-dihydro-oxazol-2-ylamine formate | 360 | 100 | | I/3 |
| 45 | 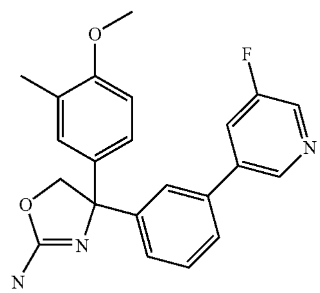 | (RS)-4-[3-(5-Fluoro-pyridin-3-yl)-phenyl]-4-(4-methoxy-3-methyl-phenyl)-4,5-dihydro-oxazol-2-ylamine formate | 378 | 96 | | I/5 |
| 46 | 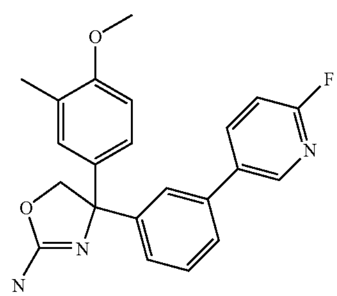 | (RS)-4-[3-(6-Fluoro-pyridin-3-yl)-phenyl]-4-(4-methoxy-3-methyl-phenyl)-4,5-dihydro-oxazol-2-ylamine formate | 378 | 99 | | I/5 |
| 47 | 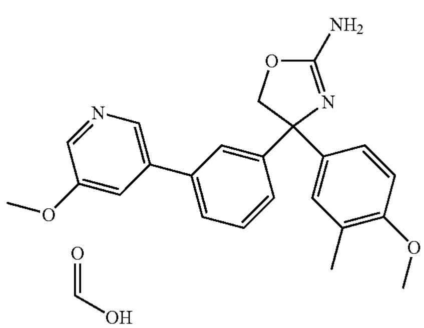 | (RS)-4-(4-Methoxy-3-methyl-phenyl)-4-[3-(5-methoxy-pyridin-3-yl)-phenyl]-4,5-dihydro-oxazol-2-ylamine formate | 390 | 100 | $^1$H-NMR (CD$_3$OD) δ (ppm): 8.43 (m, 1H); 8.34 (d, 1H); 8.23 (d, 1H); 7.67 (m, 1H); 7.60 (m, 2H); 7.55 (m, 1H); 7.39 (m, 1H); 7.12 (m, 2H); 6.91 (m, 1H); 5.19 (dd, 2H); 3.94 (s, 3H); 3.82 (s, 3H), 2.17 (s, 3H) | I/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 48 | 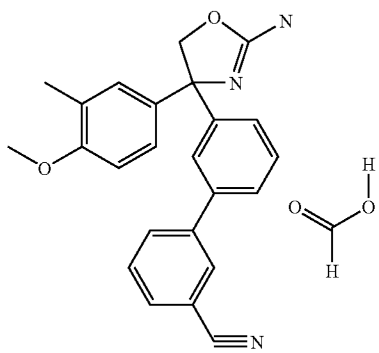 | (RS)-3'-[2-Amino-4-(4-methoxy-3-methyl-phenyl)-4,5-dihydro-oxazol-4-yl]-biphenyl-3-carbonitrile formate | 384 | 100 | | I/5 |
| 49 | 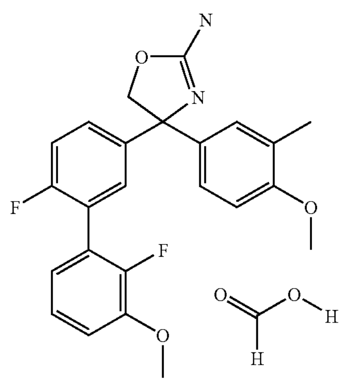 | (RS)-4-(6,2'-Difluoro-3'-methoxy-biphenyl-3-yl)-4-(4-methoxy-3-methyl-phenyl)-4,5-dihydro-oxazol-2-ylamine formate | 425 | 98 | | E/5 |
| 50 | 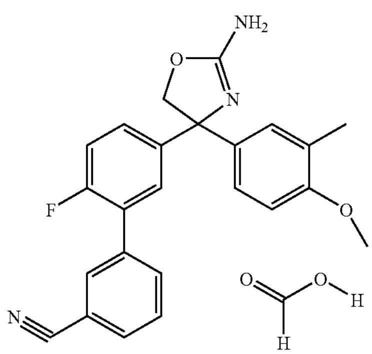 | (RS)-5'-[2-Amino-4-(4-methoxy-3-methyl-phenyl)-4,5-dihydro-oxazol-4-yl]-2'-fluoro-biphenyl-3-carbonitrile formate | 402 | 99 | | E/5 |
| 51 | 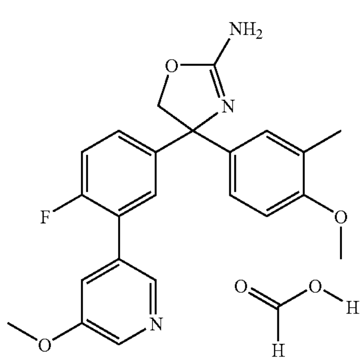 | (RS)-4-[4-Fluoro-3-(5-methoxy-pyridin-3-yl)-phenyl]-4-(4-methoxy-3-methyl-phenyl)-4,5-dihydro-oxazol-2-ylamine formate | 408 | 99 | | E/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 52 | 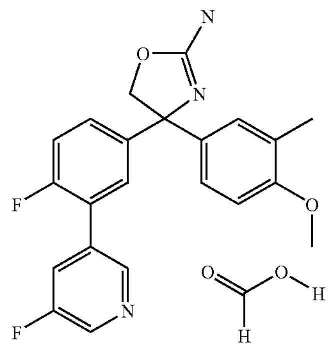 | (RS)-4-[4-Fluoro-3-(5-fluoro-pyridin-3-yl)-phenyl]-4-(4-methoxy-3-methyl-phenyl)-4,5-dihydro-oxazol-2-ylamine formate | 396 | 99 | | E/5 |
| 53 | 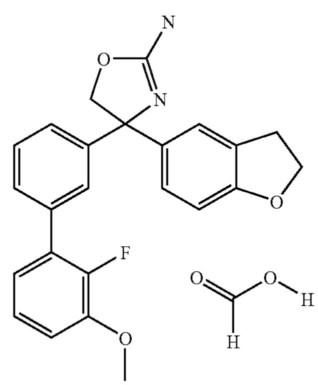 | (RS)-4-(2,3-Dihydro-benzofuran-5-yl)-4-(2'-fluoro-3'-methoxy-biphenyl-3-yl)-4,5-dihydro-oxazol-2-ylamine formate | 405 | 99 | | K/5 |
| 54 | 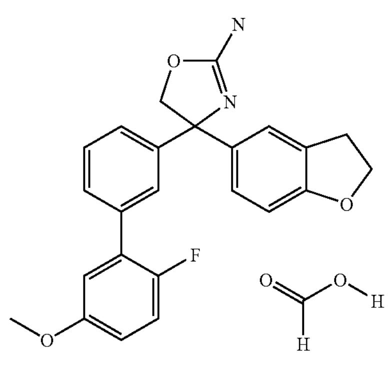 | (RS)-4-(2,3-Dihydro-benzofuran-5-yl)-4-(2'-fluoro-5'-methoxy-biphenyl-3-yl)-4,5-dihydro-oxazol-2-ylamine formate | 405 | 99 | | K/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 55 | 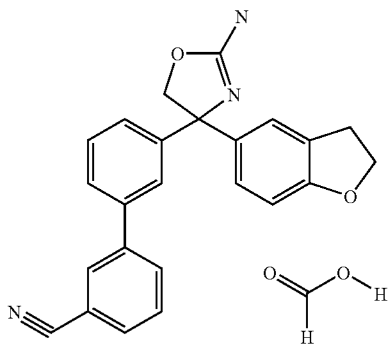 | (RS)-3'-[2-Amino-4-(2,3-dihydro-benzofuran-5-yl)-4,5-dihydro-oxazol-4-yl]-biphenyl-3-carbonitrile formate | 382 | 99 | | K/5 |
| 56 | 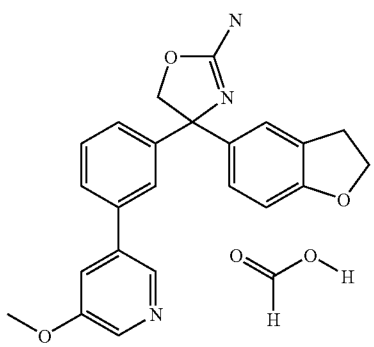 | (RS)-4-(2,3-Dihydro-benzofuran-5-yl)-4-[3-(5-methoxy-pyridin-3-yl)-phenyl]-4,5-dihydro-oxazol-2-ylamine formate | 388 | 98 | | K/5 |
| 57 | 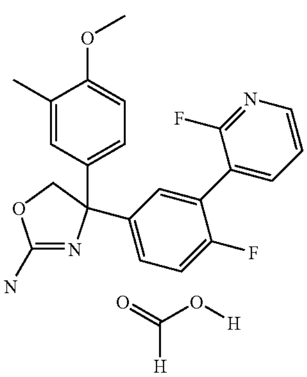 | (RS)-4-[4-Fluoro-3-(2-fluoro-pyridin-3-yl)-phenyl]-4-(4-methoxy-3-methyl-phenyl)-4,5-dihydro-oxazol-2-ylamine formate | 396 | 100 | | E/5 |
| 58 | 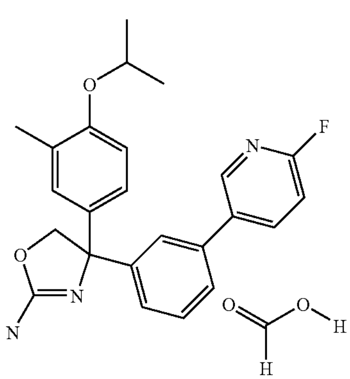 | (RS)-4-[3-(6-Fluoro-pyridin-3-yl)-phenyl]-4-(4-isopropoxy-3-methyl-phenyl)-4,5-dihydro-oxazol-2-ylamine formate | 406 | 93 | | L/5 |

TABLE 2-continued

*Experimental procedures with the synthesis of Examples 1-207.*
*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | $^1$H-NMR | Build. Block/ Synthetic Method |
|---|---|---|---|---|---|---|
| 59 | 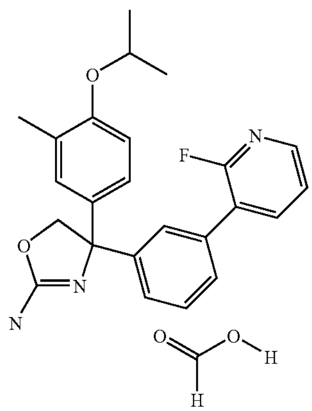 | (RS)-4-[3-(2-Fluoro-pyridin-3-yl)-phenyl]-4-(4-isopropoxy-3-methyl-phenyl)-4,5-dihydro-oxazol-2-ylamine formate | 406 | 100 | | L/5 |
| 60 | 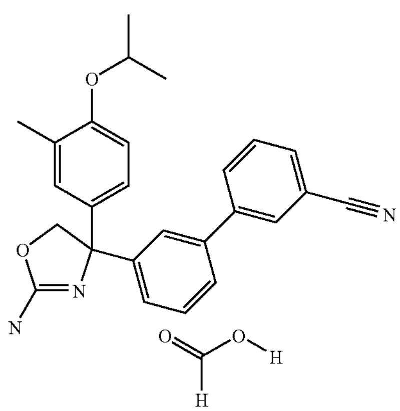 | (RS)-3'-[2-Amino-4-(4-isopropoxy-3-methyl-phenyl)-4,5-dihydro-oxazol-4-yl]-biphenyl-3-carbonitrile formate | 412 | 100 | | L/5 |
| 61 | 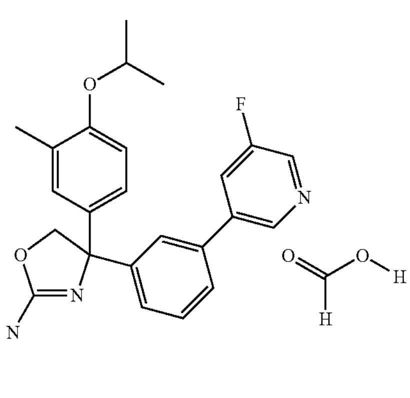 | (RS)-4-[3-(5-Fluoro-pyridin-3-yl)-phenyl]-4-(4-isopropoxy-3-methyl-phenyl)-4,5-dihydro-oxazol-2-ylamine formate | 406 | 96 | | L/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 62 | 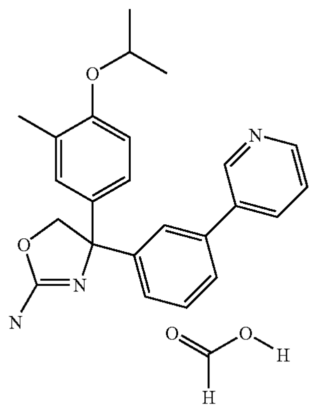 | (RS)-4-(4-Isopropoxy-3-methyl-phenyl)-4-(3-pyridin-3-yl-phenyl)-4,5-dihydro-oxazol-2-ylamine formate | 388 | 96 | | L/5 |
| 63 | 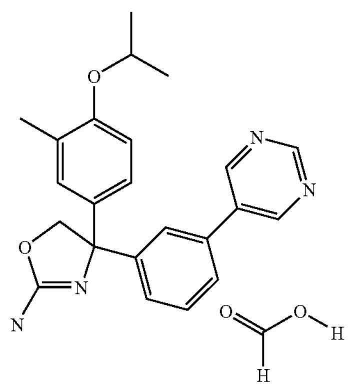 | (RS)-4-(4-Isopropoxy-3-methyl-phenyl)-4-(3-pyrimidin-5-yl-phenyl)-4,5-dihydro-oxazol-2-ylamine formate | 389 | 98 | | L/5 |
| 64 | 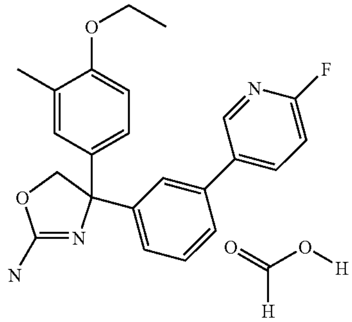 | (RS)-4-(4-Ethoxy-3-methyl-phenyl)-4-[3-(6-fluoro-pyridin-3-yl)-phenyl]-4,5-dihydro-oxazol-2-ylamine formate | 392 | 100 | | M/5 |
| 65 | 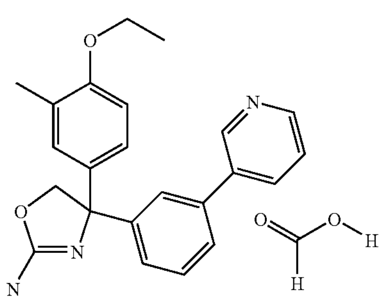 | (RS)-4-(4-Ethoxy-3-methyl-phenyl)-4-(3-pyridin-3-yl-phenyl)-4,5-dihydro-oxazol-2-ylamine formate | 374 | 100 | | M/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 66 | 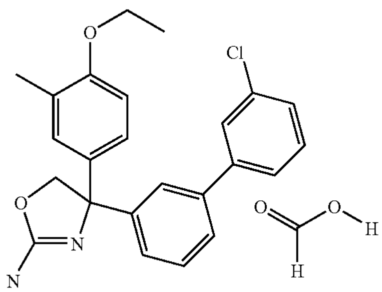 | (RS)-4-(3'-Chloro-biphenyl-3-yl)-4-(4-ethoxy-3-methyl-phenyl)-4,5-dihydro-oxazol-2-ylamine formate | 407 | 95 | | M/5 |
| 67 | 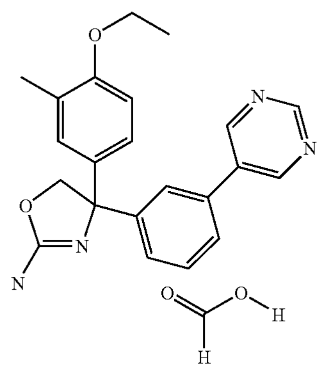 | (RS)-4-(4-Ethoxy-3-methyl-phenyl)-4-(3-pyrimidin-5-yl-phenyl)-4,5-dihydro-oxazol-2-ylamine formate | 375 | 100 | | M/5 |
| 68 | 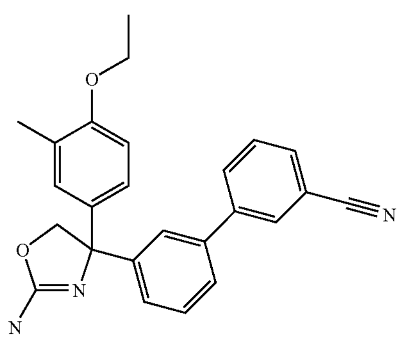 | (RS)-3'-[2-Amino-4-(4-ethoxy-3-methyl-phenyl)-4,5-dihydro-oxazol-4-yl]-biphenyl-3-carbonitrile formate | 398 | 100 | | M/5 |
| 69 | 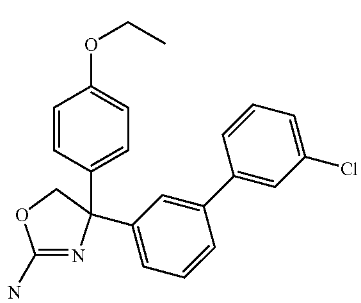 | (RS)-4-(3'-Chloro-biphenyl-3-yl)-4-(4-ethoxy-phenyl)-4,5-dihydro-oxazol-2-ylamine formate | 393 | 98 | | AF/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 70 | 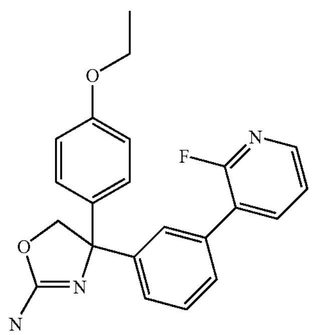 | (RS)-4-(4-Ethoxy-phenyl)-4-[3-(2-fluoro-pyridin-3-yl)-phenyl]-4,5-dihydro-oxazol-2-ylamine formate | 378 | 100 | | AF/5 |
| 71 | 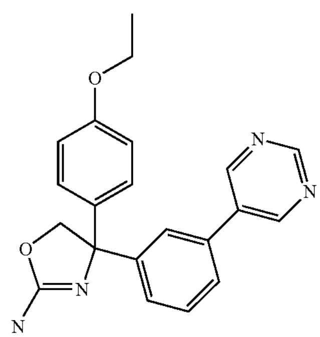 | (RS)-4-(4-Ethoxy-phenyl)-4-(3-pyrimidin-5-yl-phenyl)-4,5-dihydro-oxazol-2-ylamine formate | 361 | 96 | | AF/5 |
| 72 | 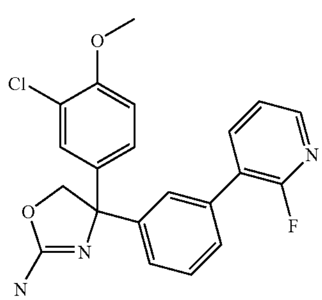 | (RS)-4-(3-Chloro-4-methoxy-phenyl)-4-[3-(2-fluoro-pyridin-3-yl)-phenyl]-4,5-dihydro-oxazol-2-ylamine | 398 | 95 | | O/5 |
| 73 | 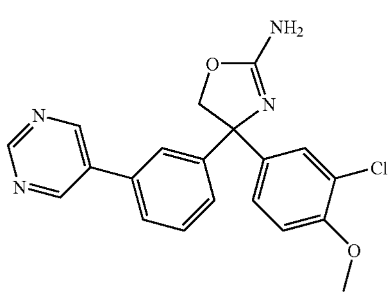 | (RS)-4-(3-Chloro-4-methoxy-phenyl)-4-(3-pyrimidin-5-yl-phenyl)-4,5-dihydro-oxazol-2-ylamine | 381 | 99 | $^1$H-NMR (DMSO-d$_6$) δ (ppm): 9.18 (s, 1H); 9.09 (s, 2H); 7.82 (m, 1H); 7.61 (m, 1H); 7.52 (m, 2H); 7.44 (t, 1H); 7.37 (dd, 1H); 7.04 (d, 1H); 6.29 (brs, 2H); 4.73 (dd, 2H); 3.78 (s, 3H) | O/5 |

TABLE 2-continued

*Experimental procedures with the synthesis of Examples 1-207.*

*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | $^1$H-NMR | Build. Block/ Synthetic Method |
|---|---|---|---|---|---|---|
| 74 | 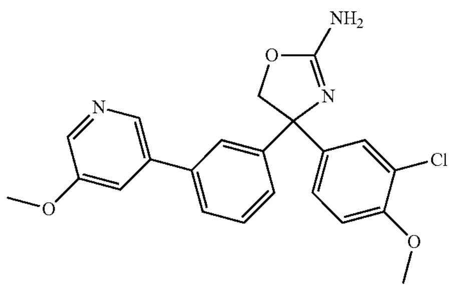 | (RS)-4-(3-Chloro-4-methoxy-phenyl)-4-[3-(5-methoxy-pyridin-3-yl)-phenyl]-4,5-dihydro-oxazol-2-ylamine | 410 | 99 | $^1$H-NMR (DMSO-d$_6$) δ (ppm): 8.41 (d, 1H); 8.28 (d, 1H); 7.73 (m, 1H); 7.54 (m, 2H); 7.48 (m, 1H); 7.46 (m, 1H); 7.38 (m, 2H); 7.03 (d, 1H); 6.28 (brs, 2H), 4.72 (dd, 2H); 3.89 (s, 3H); 3.78 (s, 3H) | O/5 |
| 75 | 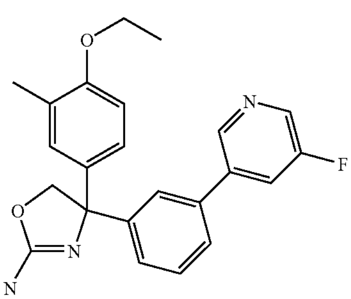 | (RS)-4-(4-Ethoxy-3-methyl-phenyl)-4-[3-(5-fluoro-pyridin-3-yl)-phenyl]-4,5-dihydro-oxazol-2-ylamine formate | 392 | 100 | | M/5 |
| 76 | 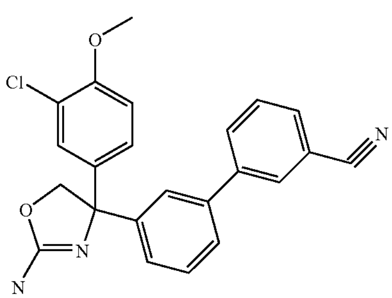 | (RS)-3'-[2-Amino-4-(3-chloro-4-methoxy-phenyl)-4,5-dihydro-oxazol-4-yl]-biphenyl-3-carbonitrile | 404 | 100 | | O/5 |
| 77 | 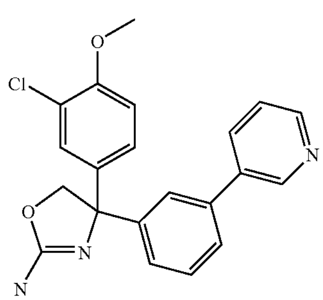 | (RS)-4-(3-Chloro-4-methoxy-phenyl)-4-(3-pyridin-3-yl-phenyl)-4,5-dihydro-oxazol-2-ylamine | 380 | 100 | | O/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | ¹H-NMR | Build. Block/ Synthetic Method |
|---|---|---|---|---|---|---|
| 78 | 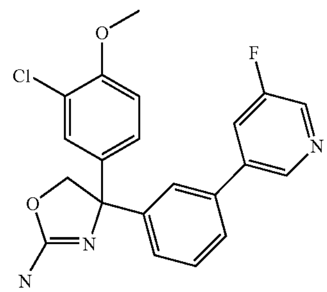 | (RS)-4-(3-Chloro-4-methoxy-phenyl)-4-[3-(5-fluoro-pyridin-3-yl)-phenyl]-4,5-dihydro-oxazol-2-ylamine | 398 | 99 | | O/5 |
| 79 | 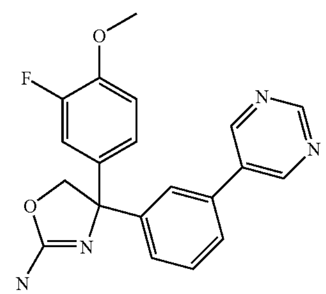 | (RS)-4-(3-Fluoro-4-methoxy-phenyl)-4-(3-pyrimidin-5-yl-phenyl)-4,5-dihydro-oxazol-2-ylamine formate | 365 | 98 | | P/5 |
| 80 | 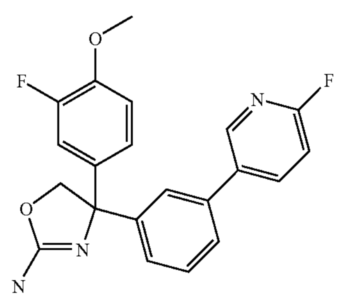 | (RS)-4-(3-Fluoro-4-methoxy-phenyl)-4-[3-(6-fluoro-pyridin-3-yl)-phenyl]-4,5-dihydro-oxazol-2-ylamine formate | 382 | 99 | | P/5 |
| 81 | | (RS)-4-(3-Fluoro-4-methoxy-phenyl)-4-[3-(2-fluoro-pyridin-3-yl)-phenyl]-4,5-dihydro-oxazol-2-ylamine formate | 382 | 99 | | P/5 | ns
TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 82 | 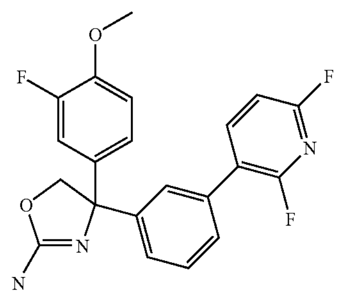 | (RS)-4-[3-(2,6-Difluoro-pyridin-3-yl)-phenyl]-4-(3-fluoro-4-methoxy-phenyl)-4,5-dihydro-oxazol-2-ylamine formate | 400 | 100 | | P/5 |
| 83 | 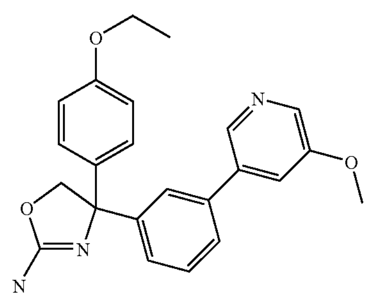 | (RS)-4-(4-Ethoxy-phenyl)-4-[3-(5-methoxy-pyridin-3-yl)-phenyl]-4,5-dihydro-oxazol-2-ylamine formate | 390 | 95 | | AF/5 |
| 84 | 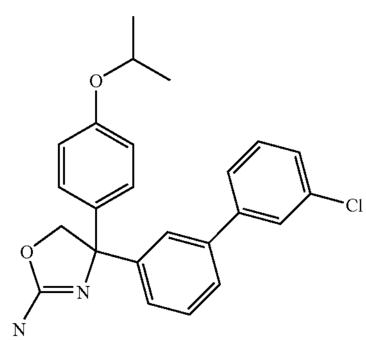 | (RS)-4-(3'-Chloro-biphenyl-3-yl)-4-(4-isopropoxy-phenyl)-4,5-dihydro-oxazol-2-ylamine formate | 407 | 100 | | Q/5 |
| 85 | 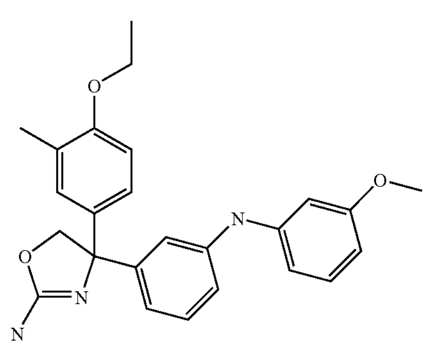 | (RS)-4-(4-Ethoxy-3-methyl-phenyl)-4-[3-(3-methoxy-phenylamino)-phenyl]-4,5-dihydro-oxazol-2-ylamine formate | 418 | 97 | | M/see below |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 86 | 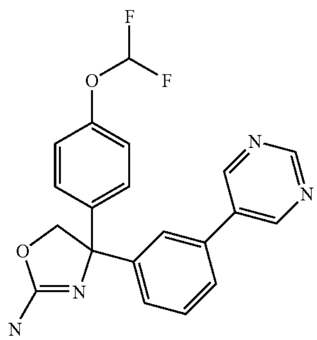 | (RS)-4-(4-Difluoromethoxy-phenyl)-4-(3-pyrimidin-5-yl-phenyl)-4,5-dihydro-oxazol-2-ylamine | 383 | 100 | | R/5 |
| 87 | 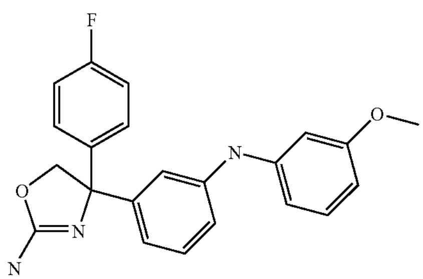 | (RS)-4-(4-Fluoro-phenyl)-4-[3-(3-methoxy-phenylamino)-phenyl]-4,5-dihydro-oxazol-2-ylamine formate | 378 | 100 | | G/see below |
| 88 | 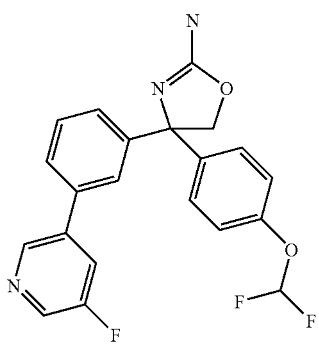 | (RS)-4-(4-Difluoromethoxy-phenyl)-4-[3-(5-fluoro-pyridin-3-yl)-phenyl]-4,5-dihydro-oxazol-2-ylamine formate | 400 | 100 | | R/5 |
| 89 | 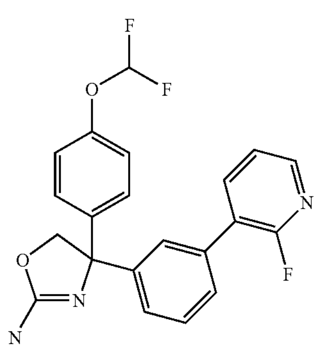 | (RS)-4-(4-Difluoromethoxy-phenyl)-4-[3-(2-fluoro-pyridin-3-yl)-phenyl]-4,5-dihydro-oxazol-2-ylamine formate | 400 | 100 | | R/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 90 | 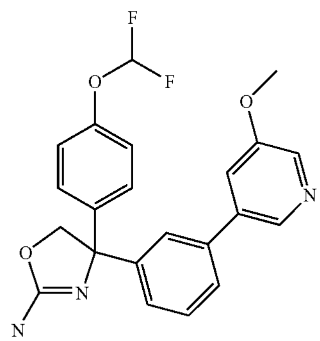 | (RS)-4-(4-Difluoromethoxy-phenyl)-4-[3-(5-methoxy-pyridin-3-yl)-phenyl]-4,5-dihydro-oxazol-2-ylamine formate | 412 | 100 | | R/5 |
| 91 | 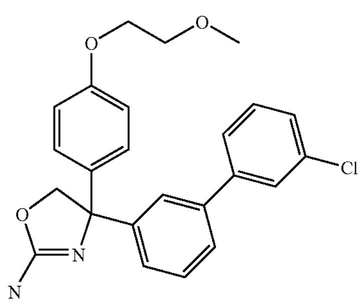 | (RS)-4-(3'-Chloro-biphenyl-3-yl)-4-[4-(2-methoxy-ethoxy)-phenyl]-4,5-dihydro-oxazol-2-ylamine formate | 423 | 100 | | N/5 |
| 92 | 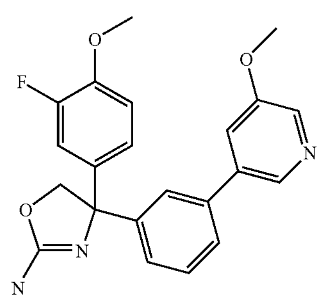 | (RS)-4-(3-Fluoro-4-methoxy-phenyl)-4-[3-(5-methoxy-pyridin-3-yl)-phenyl]-4,5-dihydro-oxazol-2-ylamine formate | 394 | 100 | | P/5 |
| 93 | 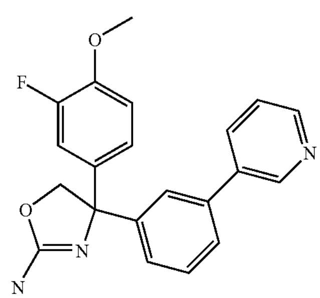 | (RS)-4-(3-Fluoro-4-methoxy-phenyl)-4-(3-pyridin-3-yl-phenyl)-4,5-dihydro-oxazol-2-ylamine formate | 364 | 100 | | P/5 |

TABLE 2-continued

*Experimental procedures with the synthesis of Examples 1-207.*
*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | $^1$H-NMR | Build. Block/ Synthetic Method |
|---|---|---|---|---|---|---|
| 94 | 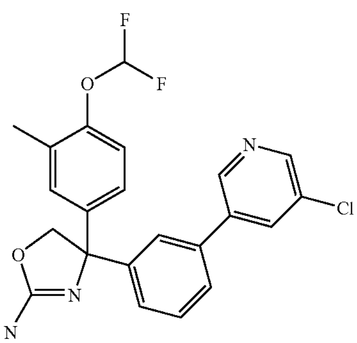 | (RS)-4-[3-(5-Chloro-pyridin-3-yl)-phenyl]-4-(4-difluoromethoxy-3-methyl-phenyl)-4,5-dihydro-oxazol-2-ylamine formate | 430 | 96 | | S/5 |
| 94A | Chiral | (R)-4-[3-(5-Chloro-pyridin-3-yl)-phenyl]-4-(4-difluoromethoxy-3-methyl-phenyl)-4,5-dihydro-oxazol-2-ylamine | | | | AO/ see below |
| 95 | 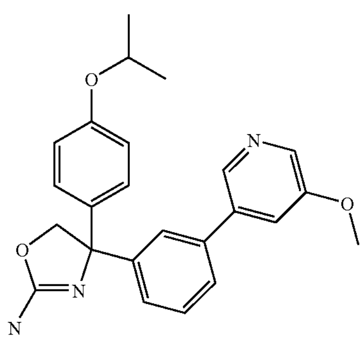 | (RS)-4-(4-Isopropoxy-phenyl)-4-[3-(5-methoxy-pyridin-3-yl)-phenyl]-4,5-dihydro-oxazol-2-ylamine | 404 | 95 | | Q/5 |
| 96 | 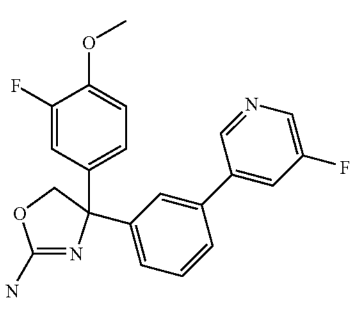 | (RS)-4-(3-Fluoro-4-methoxy-phenyl)-4-[3-(5-fluoro-pyridin-3-yl)-phenyl]-4,5-dihydro-oxazol-2-ylamine | 382 | 96 | | P/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 97 | 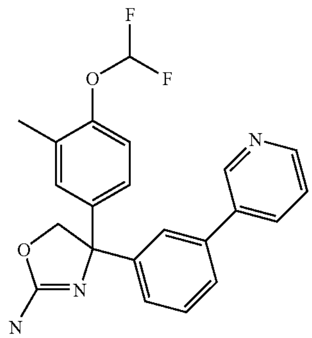 | (RS)-4-(4-Difluoromethoxy-3-methyl-phenyl)-4-(3-pyridin-3-yl-phenyl)-4,5-dihydro-oxazol-2-ylamine formate | 396 | 100 | | S/5 |
| 98 | 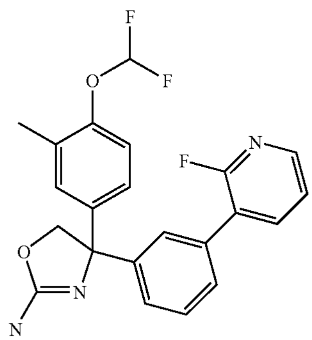 | (RS)-4-(4-Difluoromethoxy-3-methyl-phenyl)-4-[3-(2-fluoro-pyridin-3-yl)-phenyl]-4,5-dihydro-oxazol-2-ylamine formate | 414 | 100 | | S/5 |
| 99 | 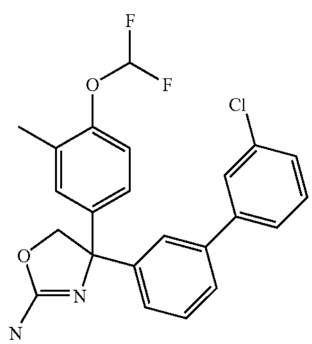 | (RS)-4-(3'-Chloro-biphenyl-3-yl)-4-(4-difluoromethoxy-3-methyl-phenyl)-4,5-dihydro-oxazol-2-ylamine formate | 429 | 100 | | S/5 |
| 100 | 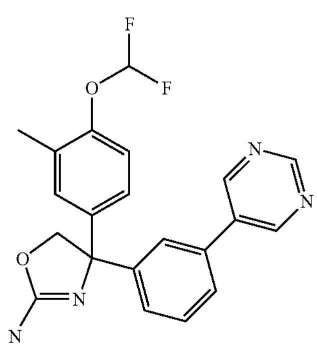 | (RS)-4-(4-Difluoromethoxy-3-methyl-phenyl)-4-(3-pyrimidin-5-yl-phenyl)-4,5-dihydro-oxazol-2-ylamine formate | 397 | 100 | | S/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 101 | 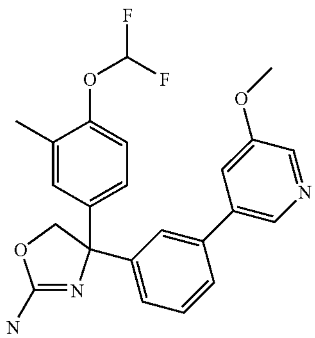 | (RS)-4-(4-Difluoromethoxy-3-methyl-phenyl)-4-[3-(5-methoxy-pyridin-3-yl)-phenyl]-4,5-dihydro-oxazol-2-ylamine formate | 426 | 96 | | S/5 |
| 102 | 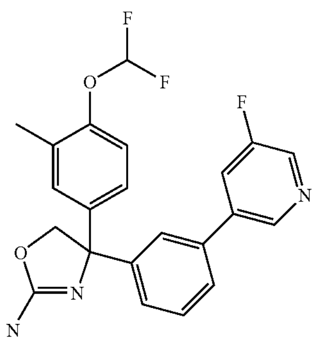 | (RS)-4-(4-Difluoromethoxy-3-methyl-phenyl)-4-[3-(5-fluoro-pyridin-3-yl)-phenyl]-4,5-dihydro-oxazol-2-ylamine formate | 414 | 95 | | S/5 |
| 103 | 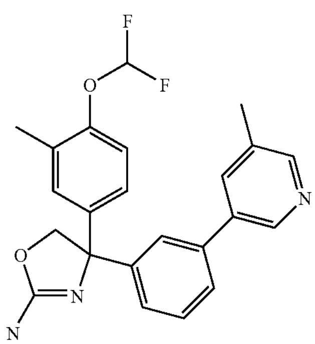 | (RS)-4-(4-Difluoromethoxy-3-methyl-phenyl)-4-[3-(5-methyl-pyridin-3-yl)-phenyl]-4,5-dihydro-oxazol-2-ylamine formate | 410 | 100 | | S/5 |
| 104 | 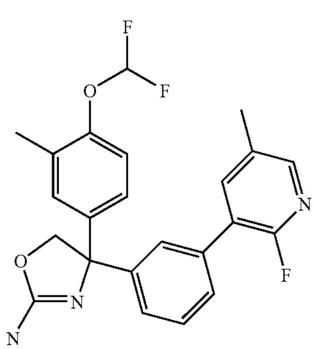 | (RS)-4-(4-Difluoromethoxy-3-methyl-phenyl)-4-[3-(2-fluoro-5-methyl-pyridin-3-yl)-phenyl]-4,5-dihydro-oxazol-2-ylamine formate | 428 | 100 | | S/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 105 | 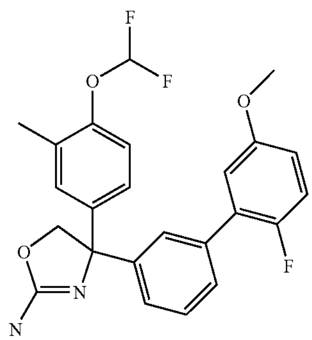 | (RS)-4-(4-Difluoromethoxy-3-methyl-phenyl)-4-(2'-fluoro-5'-methoxy-biphenyl-3-yl)-4,5-dihydro-oxazol-2-ylamine formate | 443 | 100 | | S/5 |
| 106 | 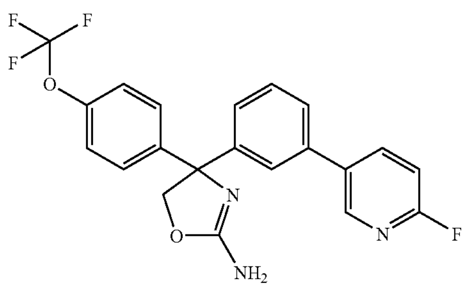 | (RS)-4-[3-(6-Fluoro-pyridin-3-yl)-phenyl]-4-(4-trifluoromethoxy-phenyl)-4,5-dihydro-oxazol-2-ylamine | 418 | 100 | $^1$H-NMR (DMSO-d$_6$) δ (ppm): 8.74 (s, 1H); 8.56 (d, 1H); 8.02 (m, 1H); 7.81 (m, 1H); 7.59 (m, 3H); 7.53 (m, 1H); 7.41 (t, 1H); 7.26 (m, 2H), 6.32 (brs, 2H); 4.76 (dd, 2H) | T/5 |
| 107 | 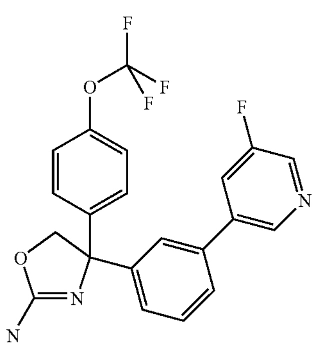 | (RS)-4-[3-(5-Fluoro-pyridin-3-yl)-phenyl]-4-(4-trifluoromethoxy-phenyl)-4,5-dihydro-oxazol-2-ylamine | 418 | 100 | | T/5 |
| 108 | 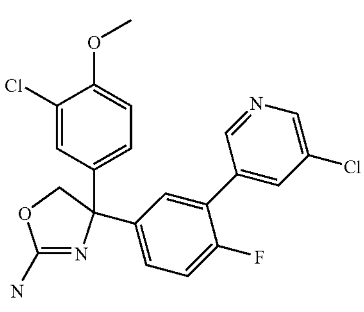 | (RS)-4-(3-Chloro-4-methoxy-phenyl)-4-[3-(5-chloro-pyridin-3-yl)-4-fluoro-phenyl]-4,5-dihydro-oxazol-2-ylamine formate | 432 | 100 | | U/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 109 | 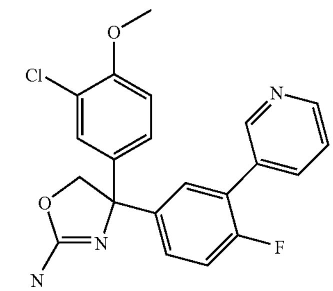 | (RS)-4-(3-Chloro-4-methoxy-phenyl)-4-(4-fluoro-3-pyridin-3-yl-phenyl)-4,5-dihydro-oxazol-2-ylamine formate | 398 | 97 | | U/5 |
| 110 | 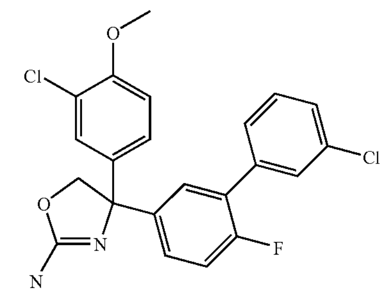 | (RS)-4-(3'-Chloro-6-fluoro-biphenyl-3-yl)-4-(3-chloro-4-methoxy-phenyl)-4,5-dihydro-oxazol-2-ylamine formate | 431 | 100 | | U/5 |
| 111 | 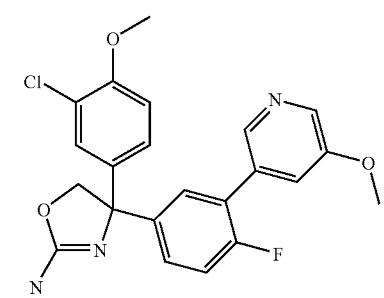 | (RS)-4-(3-Chloro-4-methoxy-phenyl)-4-[4-fluoro-3-(5-methoxy-pyridin-3-yl)-phenyl]-4,5-dihydro-oxazol-2-ylamine formate | 427 | 90 | | U/5 |
| 112 | 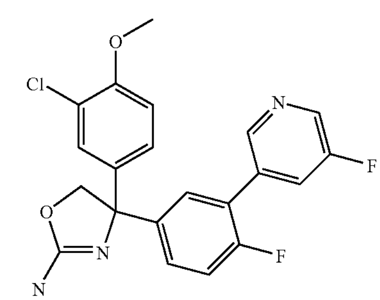 | (RS)-4-(3-Chloro-4-methoxy-phenyl)-4-[4-fluoro-3-(5-fluoro-pyridin-3-yl)-phenyl]-4,5-dihydro-oxazol-2-ylamine | 416 | 100 | | U/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 113 | 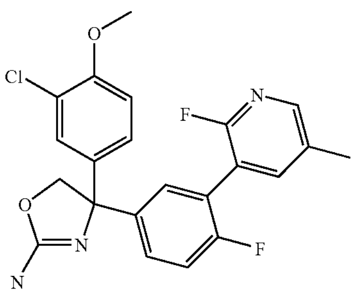 | (RS)-4-(3-Chloro-4-methoxy-phenyl)-4-[4-fluoro-3-(2-fluoro-5-methyl-pyridin-3-yl)-phenyl]-4,5-dihydro-oxazol-2-ylamine | 430 | 100 | | U/5 |
| 114 | 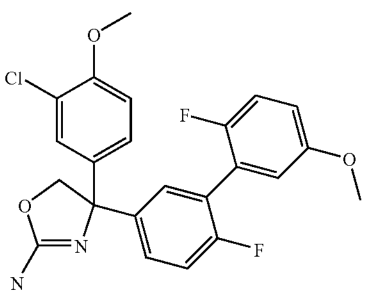 | (RS)-4-(3-Chloro-4-methoxy-phenyl)-4-(6,2'-difluoro-5'-methoxy-biphenyl-3-yl)-4,5-dihydro-oxazol-2-ylamine formate | 445 | 96 | | U/5 |
| 115 | 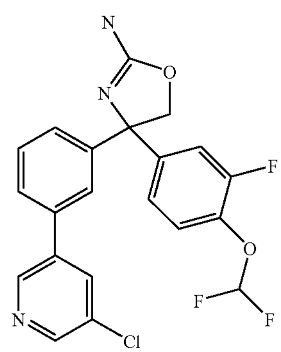 | (RS)-4-[3-(5-Chloro-pyridin-3-yl)-phenyl]-4-(4-difluoromethoxy-3-fluoro-phenyl)-4,5-dihydro-oxazol-2-ylamine formate | 434 | 100 | | V/5 |
| 116 | 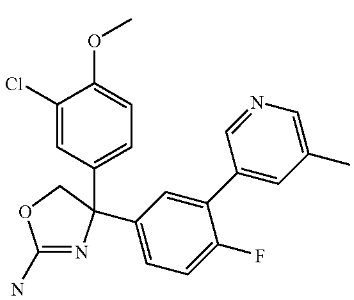 | (RS)-4-(3-Chloro-4-methoxy-phenyl)-4-[4-fluoro-3-(5-methyl-pyridin-3-yl)-phenyl]-4,5-dihydro-oxazol-2-ylamine formate | 412 | 100 | | U/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 117 | 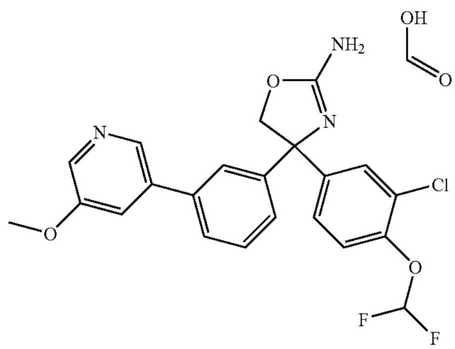 | (RS)-4-(3-Chloro-4-difluoromethoxy-phenyl)-4-[3-(5-methoxy-pyridin-3-yl)-phenyl]-4,5-dihydro-oxazol-2-ylamine formate | 446 | 95 | $^1$H-NMR (DMSO-d$_6$) δ (ppm): 8.42 (d, 1H); 8.27 (d, 1H); 8.13 (s, 1H); 7.76 (m, 1H); 7.68 (d, 1H); 7.54 (m, 2H); 7.49 (m, 2H); 7.41 (m, 1H); 7.27 (d, 1H) 7.19 (t, 1H); 4.77 (dd, 2H); 3.88 (s, 3H) | W/5 |
| 118 | 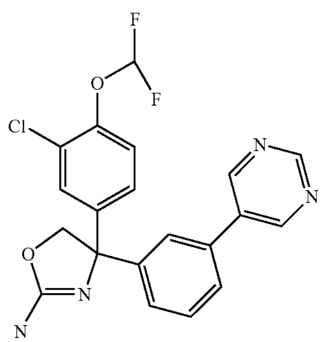 | (RS)-4-(3-Chloro-4-difluoromethoxy-phenyl)-4-(3-pyrimidin-5-yl-phenyl)-4,5-dihydro-oxazol-2-ylamine formate | 417 | 99 | | W/5 |
| 119 | 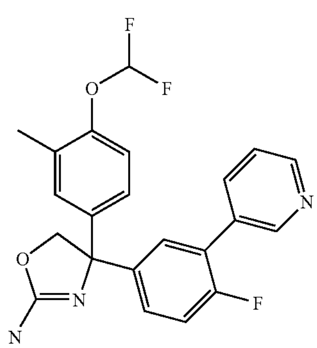 | (RS)-4-(4-Difluoromethoxy-3-methyl-phenyl)-4-(4-fluoro-3-pyridin-3-yl-phenyl)-4,5-dihydro-oxazol-2-ylamine formate | 414 | 100 | | X/5 |
| 120 | 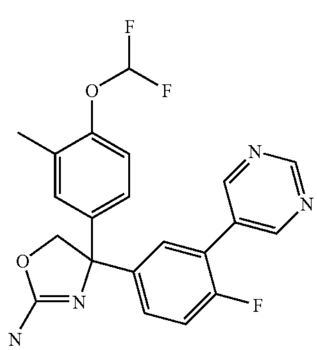 | (RS)-4-(4-Difluoromethoxy-3-methyl-phenyl)-4-(4-fluoro-3-pyrimidin-5-yl-phenyl)-4,5-dihydro-oxazol-2-ylamine formate | 415 | 100 | | X/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 121 | 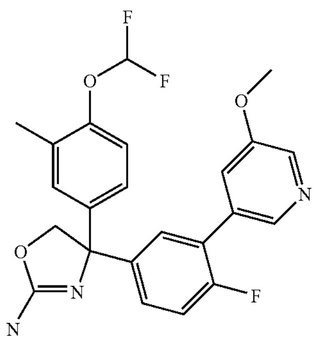 | (RS)-4-(4-Difluoromethoxy-3-methyl-phenyl)-4-[4-fluoro-3-(5-methoxy-pyridin-3-yl)-phenyl]-4,5-dihydro-oxazol-2-ylamine formate | 444 | 100 | | X/5 |
| 122 | 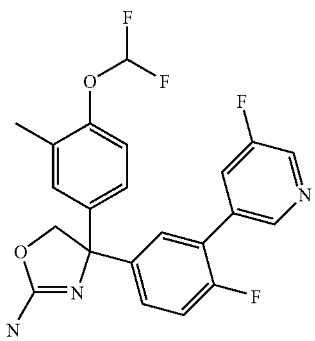 | (RS)-4-(4-Difluoromethoxy-3-methyl-phenyl)-4-[4-fluoro-3-(5-fluoro-pyridin-3-yl)-phenyl]-4,5-dihydro-oxazol-2-ylamine formate | 432 | 100 | | X/5 |
| 123 | 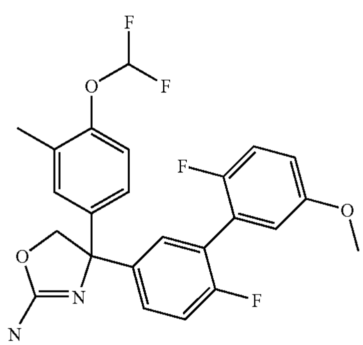 | (RS)-4-(6,2'-Difluoro-5'-methoxy-biphenyl-3-yl)-4-(4-difluoromethoxy-3-methyl-phenyl)-4,5-dihydro-oxazol-2-ylamine formate | 461 | 100 | | X/5 |
| 124 | 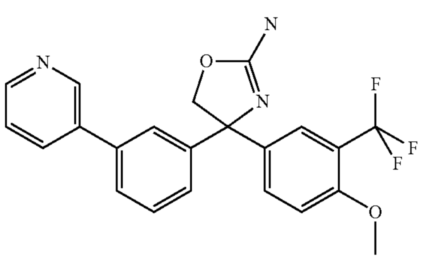 | (RS)-4-(4-Methoxy-3-trifluoromethyl-phenyl)-4-(3-pyridin-3-yl-phenyl)-4,5-dihydro-oxazol-2-ylamine formate | 414 | 97 | | Y/5 |

TABLE 2-continued

*Experimental procedures with the synthesis of Examples 1-207.*

*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | $^1$H-NMR | Build. Block/ Synthetic Method |
|---|---|---|---|---|---|---|
| 125 | 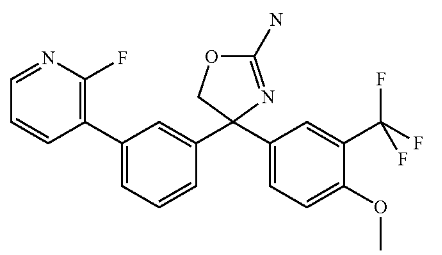 | (RS)-4-[3-(2-Fluoro-pyridin-3-yl)-phenyl]-4-(4-methoxy-3-trifluoromethyl-phenyl)-4,5-dihydro-oxazol-2-ylamine formate | 432 | 100 | | Y/5 |
| 126 | 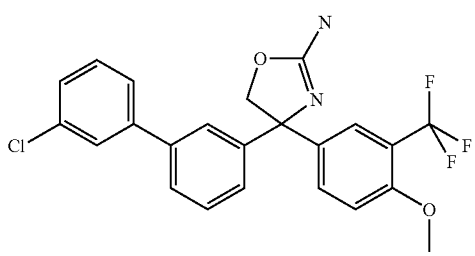 | (RS)-4-(3'-Chloro-biphenyl-3-yl)-4-(4-methoxy-3-trifluoromethyl-phenyl)-4,5-dihydro-oxazol-2-ylamine formate | 447 | 100 | | Y/5 |
| 127 | 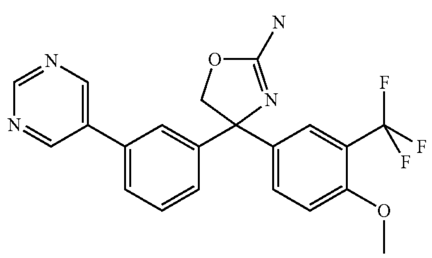 | (RS)-4-(4-Methoxy-3-trifluoromethyl-phenyl)-4-(3-pyrimidin-5-yl-phenyl)-4,5-dihydro-oxazol-2-ylamine formate | 415 | 93 | | Y/5 |
| 128 | 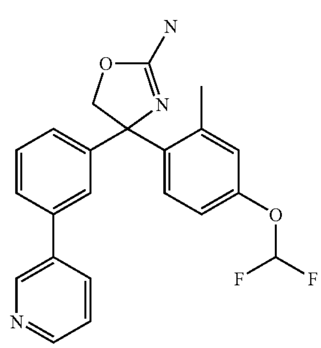 | (RS)-4-(4-Difluoromethoxy-2-methyl-phenyl)-4-(3-pyridin-3-yl-phenyl)-4,5-dihydro-oxazol-2-ylamine formate | 396 | 100 | | Z/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 129 | 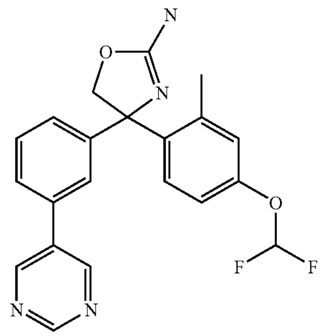 | (RS)-4-(4-Difluoromethoxy-2-methyl-phenyl)-4-(3-pyrimidin-5-yl-phenyl)-4,5-dihydro-oxazol-2-ylamine formate | 397 | 99 | | Z/5 |
| 130 | 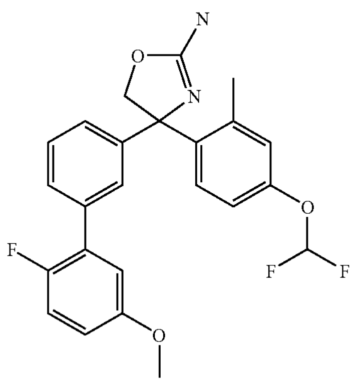 | (RS)-4-(4-Difluoromethoxy-2-methyl-phenyl)-4-(2'-fluoro-5'-methoxy-biphenyl-3-yl)-4,5-dihydro-oxazol-2-ylamine formate | 443 | 98 | | Z/5 |
| 131 | 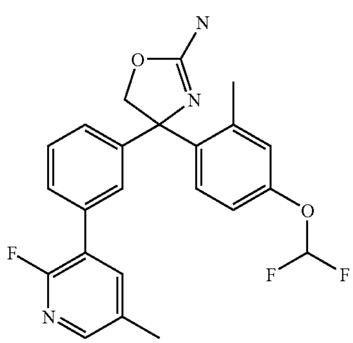 | (RS)-4-(4-Difluoromethoxy-2-methyl-phenyl)-4-[3-(2-fluoro-5-methyl-pyridin-3-yl)-phenyl]-4,5-dihydro-oxazol-2-ylamine formate | 428 | 98 | | Z/5 |
| 132 | 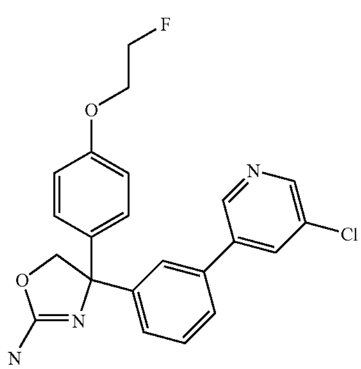 | (RS)-4-[3-(5-Chloro-pyridin-3-yl)-phenyl]-4-[4-(2-fluoro-ethoxy)-phenyl]-4,5-dihydro-oxazol-2-ylamine formate | 412 | 98 | | AA/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|------|-----------|------|------------|-------------|-----------|-------------------------------|
| 133 | 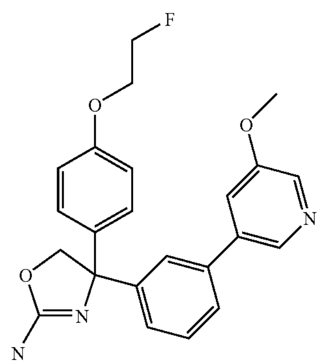 | (RS)-4-[4-(2-Fluoro-ethoxy)-phenyl]-4-[3-(5-methoxy-pyridin-3-yl)-phenyl]-4,5-dihydro-oxazol-2-ylamine formate | 408 | 100 | | AA/5 |
| 134 | 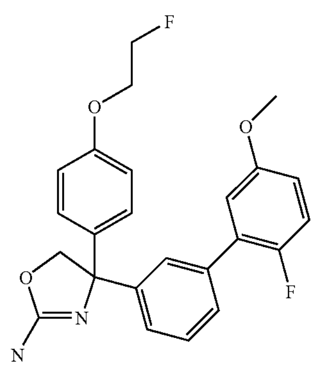 | (RS)-4-[4-(2-Fluoro-ethoxy)-phenyl]-4-(2'-fluoro-5'-methoxy-biphenyl-3-yl)-4,5-dihydro-oxazol-2-ylamine formate | 425 | 98 | | AA/5 |
| 135 | 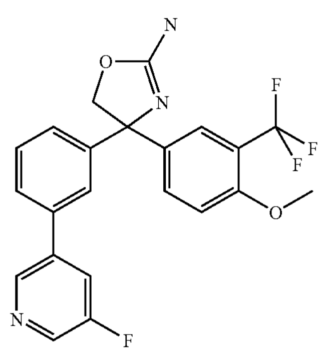 | (RS)-4-[3-(5-Fluoro-pyridin-3-yl)-phenyl]-4-(4-methoxy-3-trifluoromethyl-phenyl)-4,5-dihydro-oxazol-2-ylamine formate | 432 | 100 | | Y/5 |
| 136 | 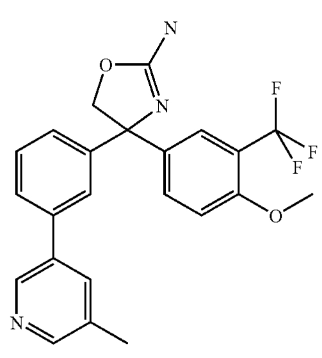 | (RS)-4-(4-Methoxy-3-trifluoromethyl-phenyl)-4-[3-(5-methyl-pyridin-3-yl)-phenyl]-4,5-dihydro-oxazol-2-ylamine formate | 428 | 97 | | Y/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | ¹H-NMR | Build. Block/ Synthetic Method |
|---|---|---|---|---|---|---|
| 137 | 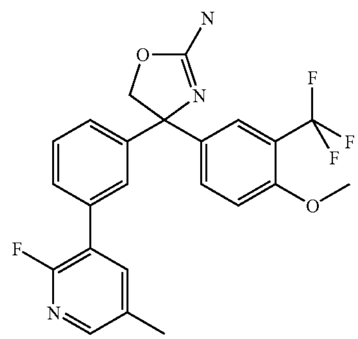 | (RS)-4-[3-(2-Fluoro-5-methyl-pyridin-3-yl)-phenyl]-4-(4-methoxy-3-trifluoromethyl-phenyl)-4,5-dihydro-oxazol-2-ylamine formate | 446 | 100 | | Y/5 |
| 138 | 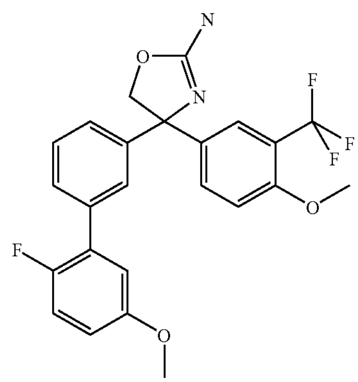 | (RS)-4-(2'-Fluoro-5'-methoxy-biphenyl-3-yl)-4-(4-methoxy-3-trifluoromethyl-phenyl)-4,5-dihydro-oxazol-2-ylamine formate | 461 | 96 | | Y/5 |
| 139 | 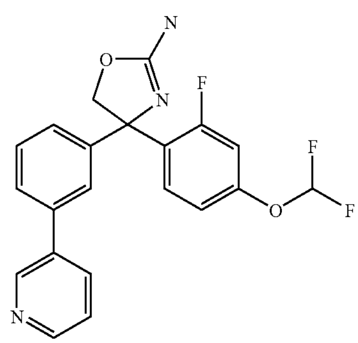 | (RS)-4-(4-Difluoromethoxy-2-fluoro-phenyl)-4-(3-pyridin-3-yl-phenyl)-4,5-dihydro-oxazol-2-ylamine formate | 400 | 98 | | AB/5 |
| 140 | 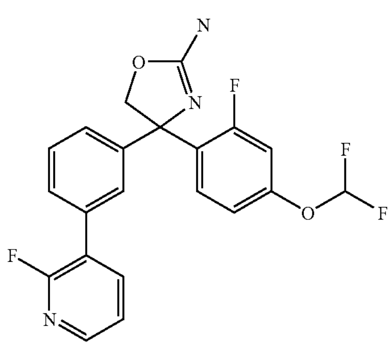 | (RS)-4-(4-Difluoromethoxy-2-fluoro-phenyl)-4-[3-(2-fluoro-pyridin-3-yl)-phenyl]-4,5-dihydro-oxazol-2-ylamine formate | 418 | 100 | | AB/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 141 | 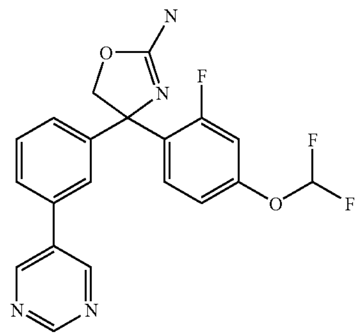 | (RS)-4-(4-Difluoromethoxy-2-fluoro-phenyl)-4-(3-pyrimidin-5-yl-phenyl)-4,5-dihydro-oxazol-2-ylamine formate | 401 | 100 | | AB/5 |
| 142 | 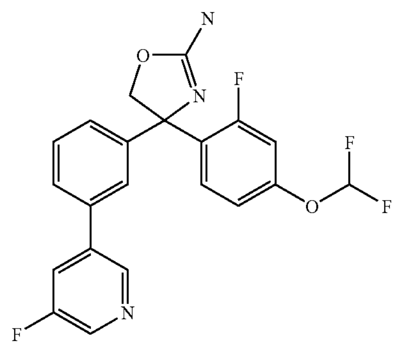 | (RS)-4-(4-Difluoromethoxy-2-fluoro-phenyl)-4-[3-(5-fluoro-pyridin-3-yl)-phenyl]-4,5-dihydro-oxazol-2-ylamine formate | 418 | 100 | | AB/5 |
| 143 | 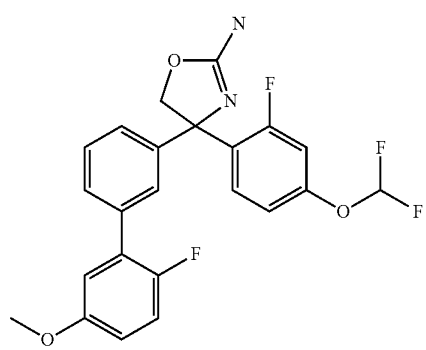 | (RS)-4-(4-Difluoromethoxy-2-fluoro-phenyl)-4-(2'-fluoro-5'-methoxy-biphenyl-3-yl)-4,5-dihydro-oxazol-2-ylamine formate | 447 | 99 | | AB/5 |
| 144 | 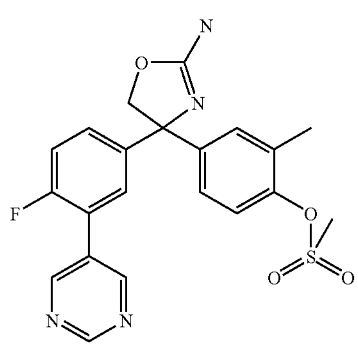 | Methanesulfonic acid 4-[(RS)-2-amino-4-(4-fluoro-3-pyrimidin-5-yl-phenyl)-4,5-dihydro-oxazol-4-yl]-2-methyl-phenyl ester | 443 | 100 | | AC/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 145 | 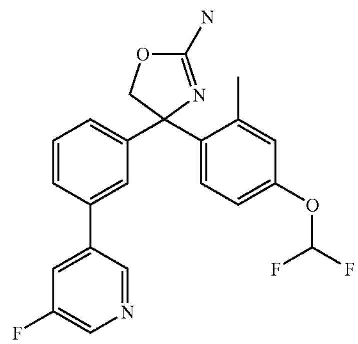 | (RS)-4-(4-Difluoromethoxy-2-methyl-phenyl)-4-[3-(5-fluoro-pyridin-3-yl)-phenyl]-4,5-dihydro-oxazol-2-ylamine formate | 414 | 98 | | Z/5 |
| 146 | 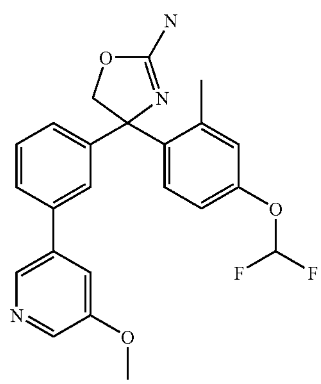 | (RS)-4-(4-Difluoromethoxy-2-methyl-phenyl)-4-[3-(5-methoxy-pyridin-3-yl)-phenyl]-4,5-dihydro-oxazol-2-ylamine formate | 426 | 97 | | Z/5 |
| 147 | 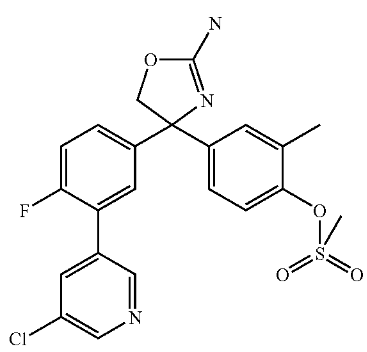 | Methanesulfonic acid 4-{(RS)-2-amino-4-[3-(5-chloro-pyridin-3-yl)-4-fluoro-phenyl]-4,5-dihydro-oxazol-4-yl}-2-methyl-phenyl ester formate | 476 | 99 | | AC/5 |
| 148 | 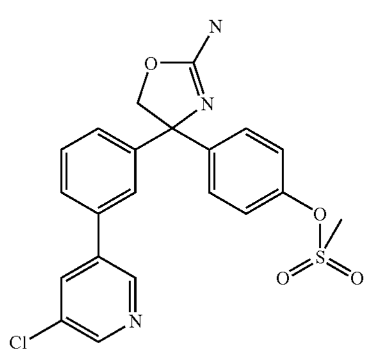 | Methanesulfonic acid 4-{(RS)-2-amino-4-[3-(5-chloro-pyridin-3-yl)-phenyl]-4,5-dihydro-oxazol-4-yl}-phenyl ester formate | 444 | 100 | | AD/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 149 | 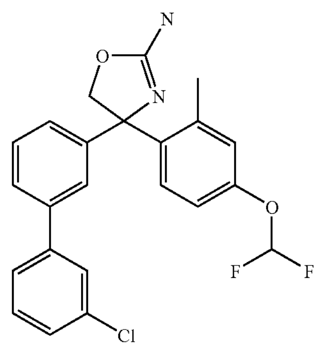 | (RS)-4-(3'-Chloro-biphenyl-3-yl)-4-(4-difluoromethoxy-2-methyl-phenyl)-4,5-dihydro-oxazol-2-ylamine formate | 429 | 98 | | Z/5 |
| 150 | 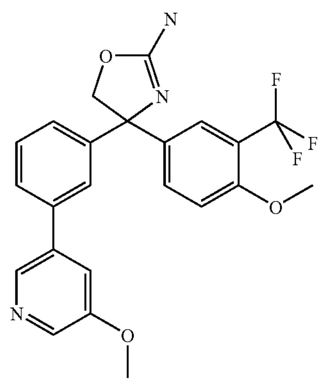 | (RS)-4-[3-(5-Chloro-pyridin-3-yl)-phenyl]-4-[4-(2-fluoro-ethoxy)-phenyl]-4,5-dihydro-oxazol-2-ylamine formate | 444 | 94 | | Y/5 |
| 151 | 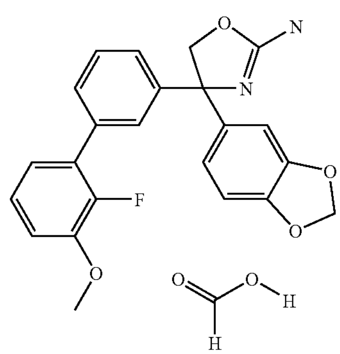 | (RS)-4-Benzo[1,3]dioxol-5-yl-4-(2'-fluoro-3'-methoxy-biphenyl-3-yl)-4,5-dihydro-oxazol-2-ylamine formate | 407 | 100 | | J/5 |
| 152 | 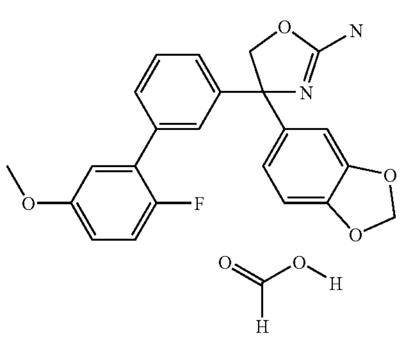 | (RS)-4-Benzo[1,3]dioxol-5-yl-4-(2'-fluoro-5'-methoxy-biphenyl-3-yl)-4,5-dihydro-oxazol-2-ylamine formate | 407 | 100 | | J/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | ¹H-NMR | Build. Block/ Synthetic Method |
|---|---|---|---|---|---|---|
| 153 | 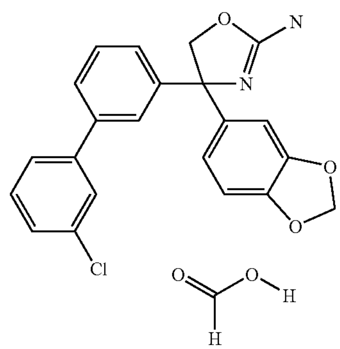 | (RS)-4-Benzo[1,3]dioxol-5-yl-4-(3'-chloro-biphenyl-3-yl)-4,5-dihydro-oxazol-2-ylamine formate | 393 | 100 | | J/5 |
| 154 | 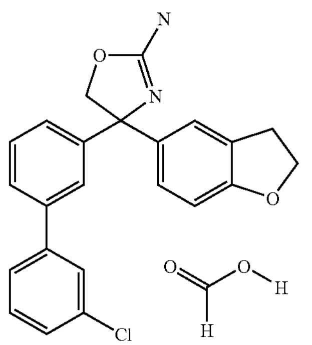 | (RS)-4-(3'-Chloro-biphenyl-3-yl)-4-(2,3-dihydro-benzofuran-5-yl)-4,5-dihydro-oxazol-2-ylamine formate | 391 | 98 | | K/5 |
| 155 | 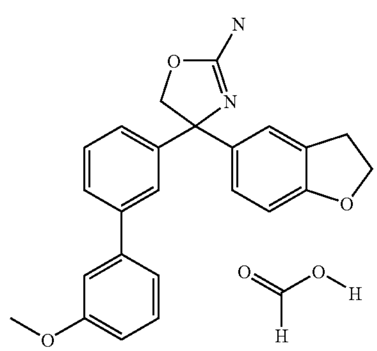 | (RS)-4-(2,3-Dihydro-benzofuran-5-yl)-4-(3'-methoxy-biphenyl-3-yl)-4,5-dihydro-oxazol-2-ylamine formate | 387 | 99 | | K/5 |
| 156 | 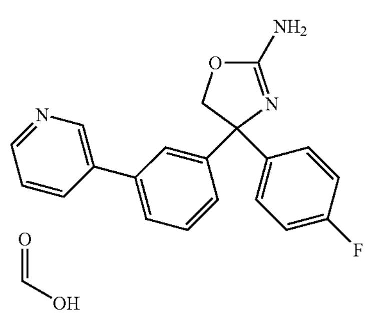 | (RS)-4-(4-Fluoro-phenyl)-4-(3-pyridin-3-yl-phenyl)-4,5-dihydro-oxazol-2-ylamine formate | 334 | 95 | ¹H-NMR (DMSO-d₆) δ (ppm): 8.15 (d, 1H); 8.55 (m, 1H); 8.13 (s, 1H); 7.98 (m, 1H); 7.72 (m, 1H); 7.47 (m, 5H); 7.39 (m, 1H); 7.08 (m, 2H); 6.38 (brs, 2H); 4.73 (dd, 2H) | G/5 |

TABLE 2-continued

Experimental procedures with the synthesis of Examples 1-207.

Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | ¹H-NMR | Build. Block/ Synthetic Method |
|---|---|---|---|---|---|---|
| 157 | 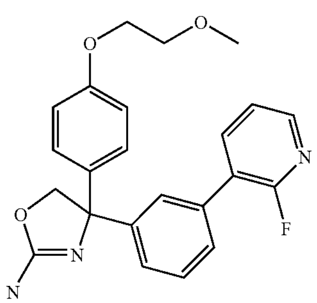 | (RS)-4-[3-(2-Fluoro-pyridin-3-yl)-phenyl]-4-[4-(2-methoxy-ethoxy)-phenyl]-4,5-dihydro-oxazol-2-ylamine formate | 408 | 100 | | N/5 |
| 158 | 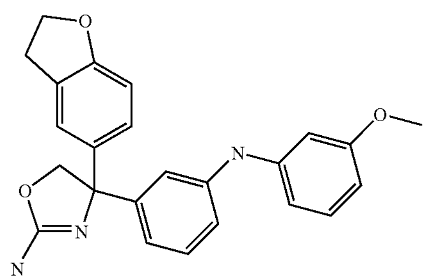 | (RS)-4-(2,3-Dihydro-benzofuran-5-yl)-4-[3-(3-methoxy-phenylamino)-phenyl]-4,5-dihydro-oxazol-2-ylamine formate | 402 | 100 | | K/see below |
| 159 | 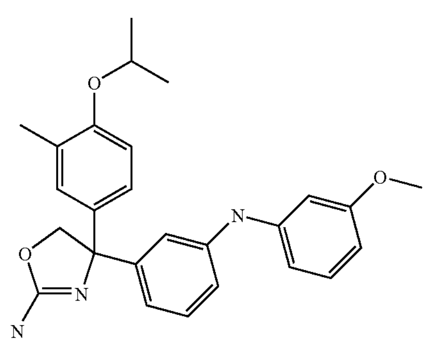 | (RS)-4-(4-Isopropoxy-3-methyl-phenyl)-4-[3-(3-methoxy-phenylamino)-phenyl]-4,5-dihydro-oxazol-2-ylamine formate | 432 | 100 | | L/see below |
| 160 | 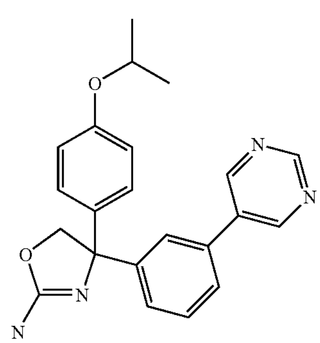 | (RS)-4-(4-Isopropoxy-phenyl)-4-(3-pyrimidin-5-yl-phenyl)-4,5-dihydro-oxazol-2-ylamine formate | 375 | 95 | | Q/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 161 | 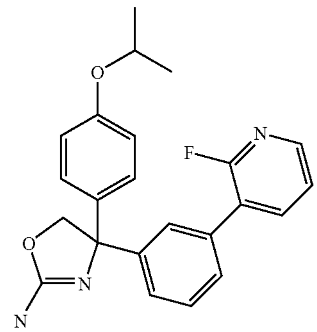 | (RS)-4-[3-(2-Fluoro-pyridin-3-yl)-phenyl]-4-(4-isopropoxy-phenyl)-4,5-dihydro-oxazol-2-ylamine | 392 | 98 | | Q/5 |
| 162 | 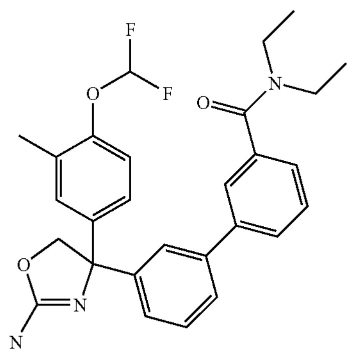 | (RS)-3'-[2-Amino-4-(4-difluoromethoxy-3-methyl-phenyl)-4,5-dihydro-oxazol-4-yl]-biphenyl-3-carboxylic acid diethylamide formate | 494 | 100 | | S/5 |
| 163 | 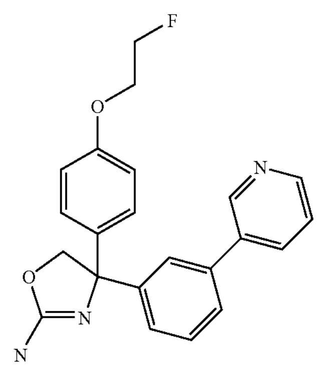 | (RS)-4-[4-(2-Fluoro-ethoxy)-phenyl]-4-(3-pyridin-3-yl-phenyl)-4,5-dihydro-oxazol-2-ylamine formate | 378 | 98 | | AA/5 |
| 164 | 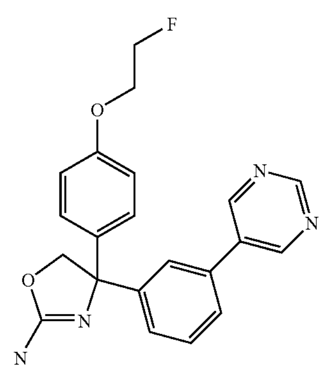 | (RS)-4-[4-(2-Fluoro-ethoxy)-phenyl]-4-(3-pyrimidin-5-yl-phenyl)-4,5-dihydro-oxazol-2-ylamine formate | 379 | 100 | | AA/5 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 165 | 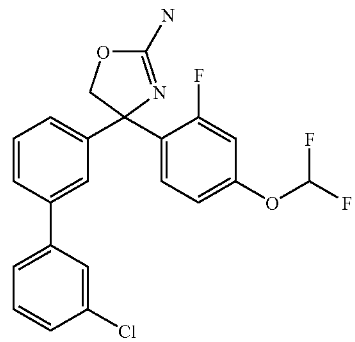 | (RS)-4-(3'-Chloro-biphenyl-3-yl)-4-(4-difluoromethoxy-2-fluoro-phenyl)-4,5-dihydro-oxazol-2-ylamine formate | 433 | 100 | | AB/5 |
| 166 | 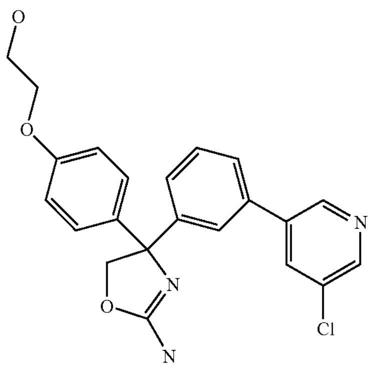 | (RS)-2-(4-{2-Amino-4-[3-(5-chloro-pyridin-3-yl)-phenyl]-4,5-dihydro-oxazol-4-yl}-phenoxy)-ethanol | 410 | 98 | | AE/5 |
| 167 | 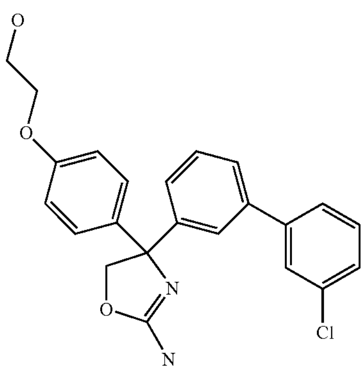 | (RS)-2-{4-[2-Amino-4-(3'-chloro-biphenyl-3-yl)-4,5-dihydro-oxazol-4-yl]-phenoxy}-ethanol | 409 | 99 | | AE/5 |
| 168 | 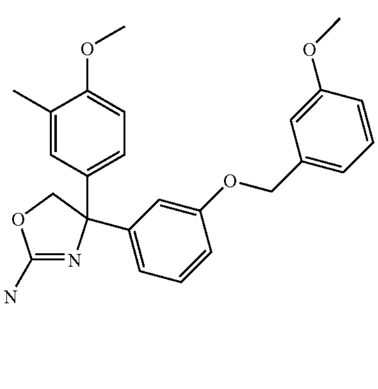 | (RS)-4-[3-(3-Methoxy-benzyloxy)-phenyl]-4-(4-methoxy-3-methyl-phenyl)-4,5-dihydro-oxazol-2-ylamine formate | 419 | 100 | | Example 168-See below |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 169 And 170 | 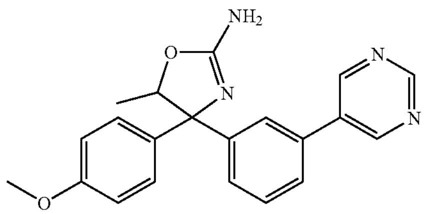 | (4RS,5RS)-4-(4-Methoxy-phenyl)-5-methyl-4-(3-pyrimidin-5-yl-phenyl)-4,5-dihydro-oxazol-2-ylamine | 361 | | | Examples 169-170 (see below) |
| 171 | 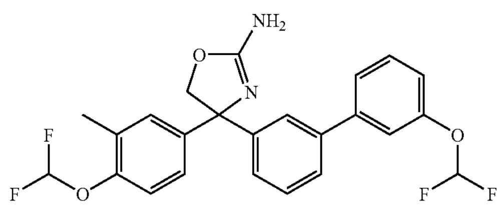 | (RS)-4-(3'-Difluoromethoxy-biphenyl-3-yl)-4-(4-difluoromethoxy-3-methyl-phenyl)-4,5-dihydro-oxazol-2-ylamine | 461 | | | (see below) |
| 172 | 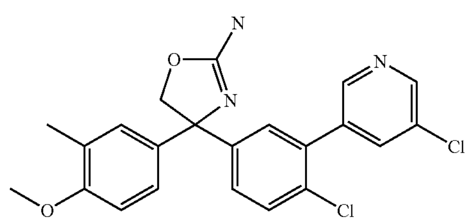 | 4-[4-Chloro-3-(5-chloro-pyridin-3-yl)-phenyl]-4-(4-methoxy-3-methyl-phenyl)-4,5-dihydro-oxazol-2-ylamine | 428.2 | | | AM/5 |
| 173 | 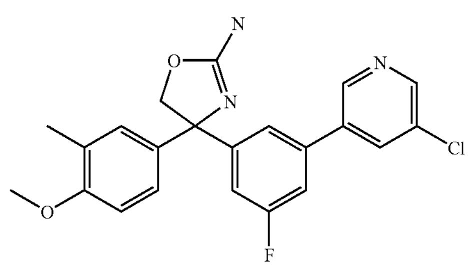 | 4-[3-(5-Chloro-pyridin-3-yl)-5-fluoro-phenyl]-4-(4-methoxy-3-methyl-phenyl)-4,5-dihydro-oxazol-2-ylamine | 408.3. | | | AH/5 |
| 174 | 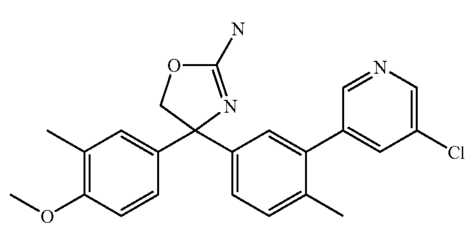 | 4-[3-(5-Chloro-pyridin-3-yl)-4-methyl-phenyl]-4-(4-methoxy-3-methyl-phenyl)-4,5-dihydro-oxazol-2-ylamine | 412.2 | | | AN/5 |
| 175 | 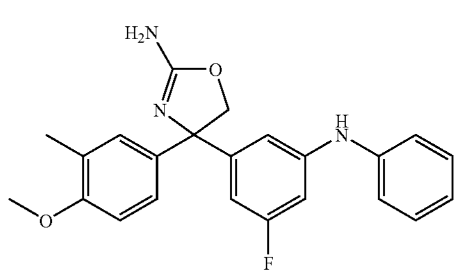 | (RS)-4-(3-Fluoro-5-phenylamino-phenyl)-4-(4-methoxy-3-methyl-phenyl)-4,5-dihydro-oxazol-2-ylamine | 392 | | | (see below) |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 176 | 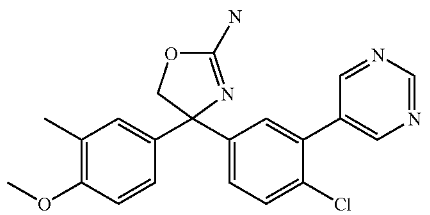 | (RS)-4-(4-Chloro-3-pyrimidin-5-yl-phenyl)-4-(4-methoxy-3-methyl-phenyl)-4,5-dihydro-oxazol-2-ylamine | 395.2 | | | AM/5 |
| 177 | 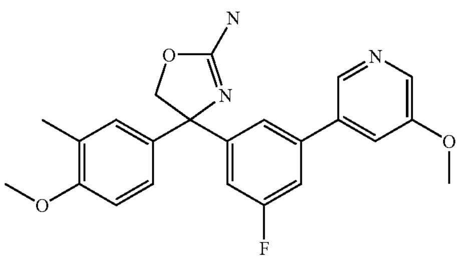 | (RS)-4-[3-Fluoro-5-(5-methoxy-pyridin-3-yl)-phenyl]-4-(4-methoxy-3-methyl-phenyl)-4,5-dihydro-oxazol-2-ylamine | 408.4 | | | AH/5 |
| 178 | 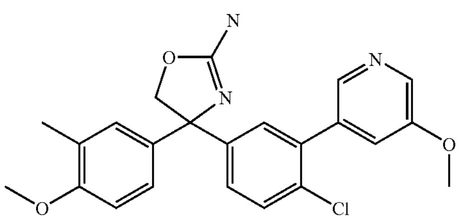 | (RS)-4-[4-Chloro-3-(5-methoxy-pyridin-3-yl)-phenyl]-4-(4-methoxy-3-methyl-phenyl)-4,5-dihydro-oxazol-2-ylamine | 424.2 | | | AM/5 |
| 179 | 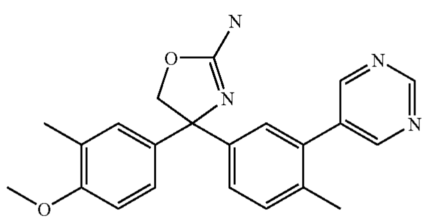 | (RS)-4-(4-Methoxy-3-methyl-phenyl)-4-(4-methyl-3-pyrimidin-5-yl-phenyl)-4,5-dihydro-oxazol-2-ylamine | 375.3 | | | AN/5 |
| 180 | 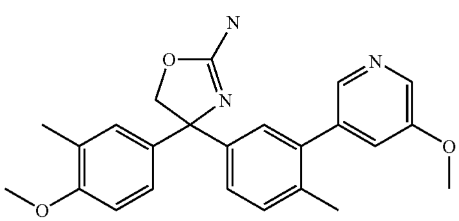 | (RS)-4-(4-Methoxy-3-methyl-phenyl)-4-[3-(5-methoxy-pyridin-3-yl)-4-methyl-phenyl]-4,5-dihydro-oxazol-2-ylamine | 404.4 | | | AN/5 |
| 181 | 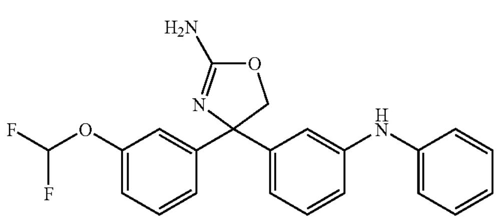 | (RS)-4-(3-Difluoromethoxy-phenyl)-4-(3-phenylamino-phenyl)-4,5-dihydro-oxazol-2-ylamine | 396 | | | AQ/as for 175 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 182 | 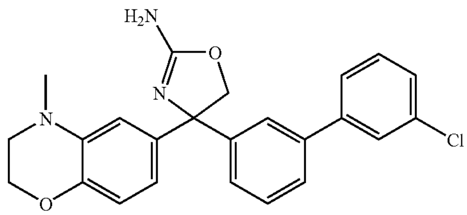 | (RS)-4-(3'-Chloro-biphenyl-3-yl)-4-(4-methyl-3,4-dihydro-2H-benzo[1,4]oxazin-6-yl)-4,5-dihydro-oxazol-2-ylamine | 420 | | | AR/4 |
| 183 | 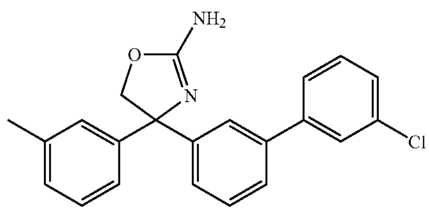 | (RS)-4-(3'-Chloro-biphenyl-3-yl)-4-m-tolyl-4,5-dihydro-oxazol-2-ylamine | 363 | | | AS/As for 175 |
| 184 | 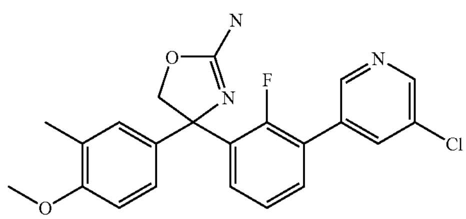 | (RS)-4-[3-(5-Chloro-pyridin-3-yl)-2-fluoro-phenyl]-4-(4-methoxy-3-methyl-phenyl)-4,5-dihydro-oxazol-2-ylamine | 412.2 | | | AG/5 |
| 185 | 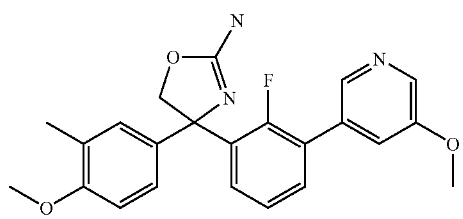 | (RS)-4-[2-Fluoro-3-(5-methoxy-pyridin-3-yl)-phenyl]-4-(4-methoxy-3-methyl-phenyl)-4,5-dihydro-oxazol-2-ylamine | 408.4 | | | AG/5 |
| 186 | 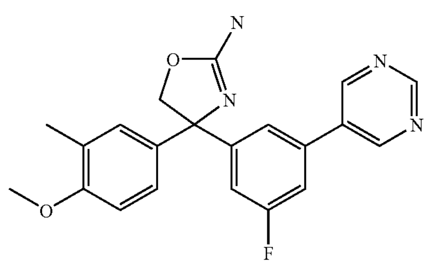 | (RS)-4-(3-Fluoro-5-pyrimidin-5-yl-phenyl)-4-(4-methoxy-3-methyl-phenyl)-4,5-dihydro-oxazol-2-ylamine | 404.4 | | | AH/5 |
| 187 | 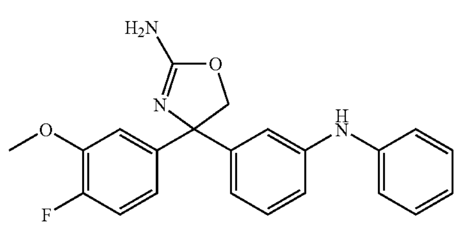 | (RS)-4-(4-Fluoro-3-methoxy-phenyl)-4-(3-phenylamino-phenyl)-4,5-dihydro-oxazol-2-ylamine | 432 | | | AT/As for 175 |

TABLE 2-continued

*Experimental procedures with the synthesis of Examples 1-207.*
*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | $^1$H-NMR | Build. Block/ Synthetic Method |
|---|---|---|---|---|---|---|
| 188 | 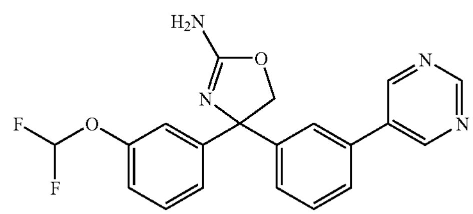 | (RS)-4-(3-Difluoromethoxy-phenyl)-4-(3-pyrimidin-5-yl-phenyl)-4,5-dihydro-oxazol-2-ylamine | 383 | | | AQ/as for 171 |
| 189 | 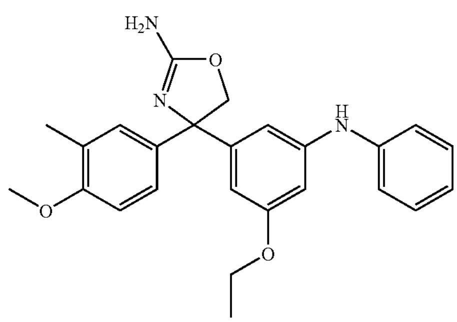 | (RS)-4-(3-Ethoxy-5-phenylamino-phenyl)-4-(4-methoxy-3-methyl-phenyl)-4,5-dihydro-oxazol-2-ylamine | 418 | | | AU/as for 175 |
| 190 | 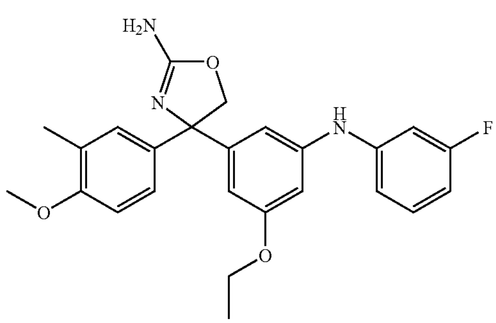 | (RS)-4-[3-Ethoxy-5-(3-fluoro-phenylamino)-phenyl]-4-(4-methoxy-3-methyl-phenyl)-4,5-dihydro-oxazol-2-ylamine | 436 | | | AU/as for 175 |
| 191 | 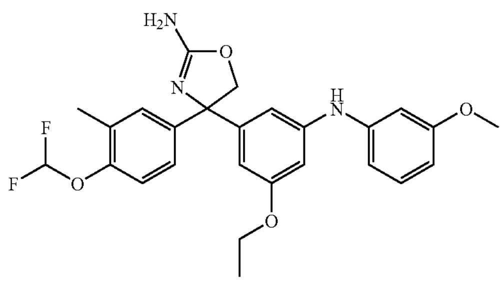 | (RS)-4-(4-Difluoromethoxy-3-methyl-phenyl)-4-[3-ethoxy-5-(3-methoxy-phenylamino)-phenyl]-4,5-dihydro-oxazol-2-ylamine | 484 | | | AV/as for 175 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 192 | 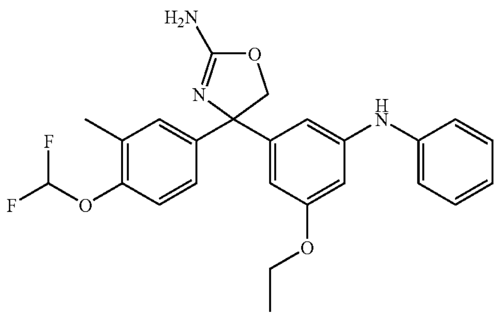 | (RS)-4-(4-Difluoromethoxy-3-methyl-phenyl)-4-[3-ethoxy-5-(3-methoxy-phenylamino)-phenyl]-4,5-dihydro-oxazol-2-ylamine | 454 | | | AV/as for 175 |
| 193 | 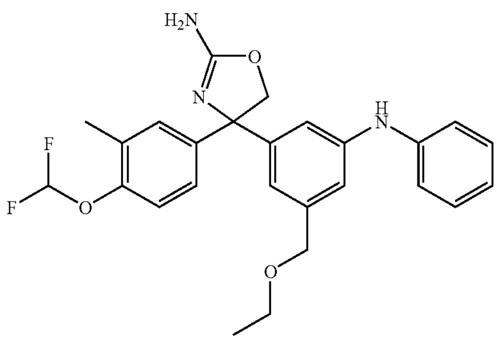 | (RS)-4-(4-Difluoromethoxy-3-methyl-phenyl)-4-(3-ethoxymethyl-5-phenylamino-phenyl)-4,5-dihydro-oxazol-2-ylamine | 468 | | | AW/as for 175 |
| 194 | 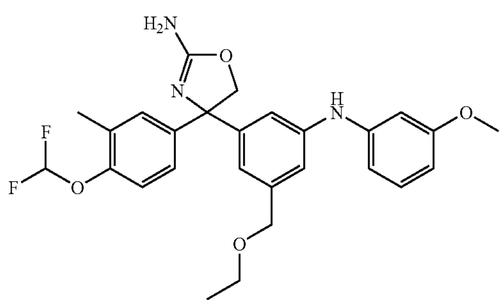 | (RS)-4-(4-Difluoromethoxy-3-methyl-phenyl)-4-[3-ethoxymethyl-5-(3-methoxy-phenylamino)-phenyl]-4,5-dihydro-oxazol-2-ylamine | 498 | | | AW/as for 175 |
| 195 | 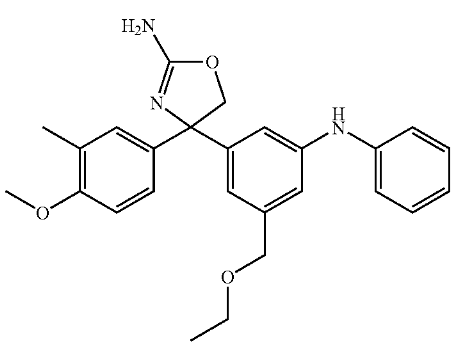 | (RS)-4-(3-Ethoxymethyl-5-phenylamino-phenyl)-4-(4-methoxy-3-methyl-phenyl)-4,5-dihydro-oxazol-2-ylamine | 432 | | | AW/as for 175 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 196 | 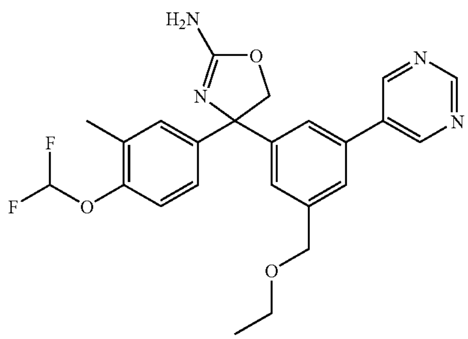 | (RS)-4-(4-Difluoromethoxy-3-methyl-phenyl)-4-(3-ethoxymethyl-5-pyrimidin-5-yl-phenyl)-4,5-dihydro-oxazol-2-ylamine | 455 | | | AW/as for example 171 |
| 197 | 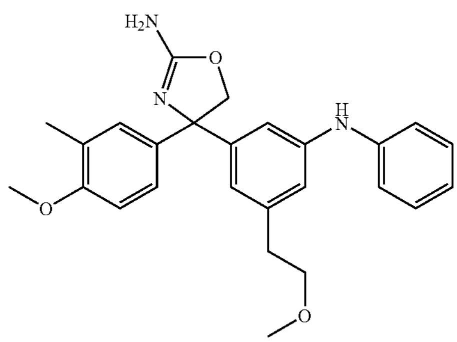 | (RS)-4-[3-(2-Methoxy-ethyl)-5-phenylamino-phenyl]-4-(4-methoxy-3-methyl-phenyl)-4,5-dihydro-oxazol-2-ylamine | 432 | | | AY/as for 175 |
| 198 | 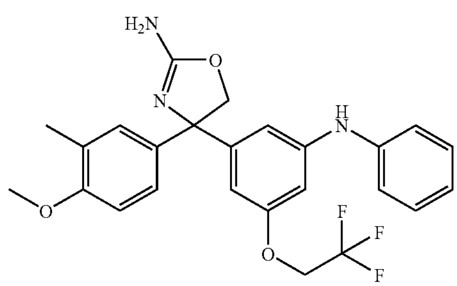 | (RS)-4-(4-Methoxy-3-methyl-phenyl)-4-[3-phenylamino-5-(2,2,2-trifluoro-ethoxy)-phenyl]-4,5-dihydro-oxazol-2-ylamine | 472 | | | AZ/as for 175 |
| 199 | 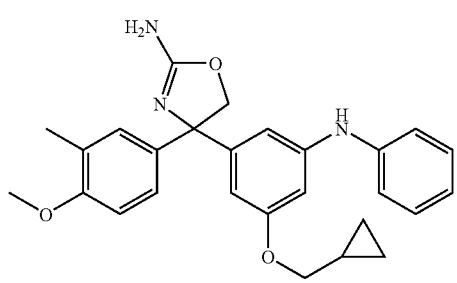 | (RS)-4-(3-Cyclopropylmethoxy-5-phenylamino-phenyl)-4-(4-methoxy-3-methyl-phenyl)-4,5-dihydro-oxazol-2-ylamine | 444 | | | BA/as for 175 |

TABLE 2-continued

Experimental procedures with the synthesis of Examples 1-207.
Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.

| Expl | Structure | name | Mass found | LC purity % | $^1$H-NMR | Build. Block/ Synthetic Method |
|---|---|---|---|---|---|---|
| 200 | 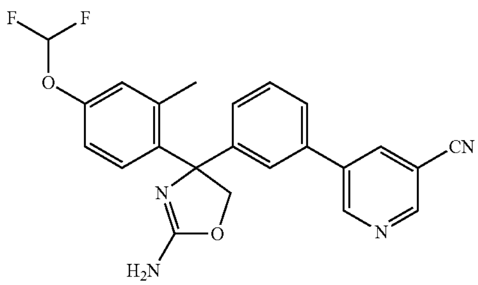 | (RS)-5-{3-[2-Amino-4-(4-difluoromethoxy-2-methyl-phenyl)-4,5-dihydro-oxazol-4-yl]-phenyl}-nicotinonitrile formate | 421 | 95 | | Z/5 |
| 201 | 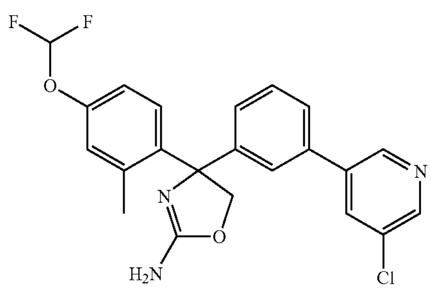 | (RS)-4-[3-(5-Chloro-pyridin-3-yl)-phenyl]-4-(4-difluoromethoxy-2-methyl-phenyl)-4,5-dihydro-oxazol-2-ylamine formate | 430 | 95 | | Z/5 |
| 202 | 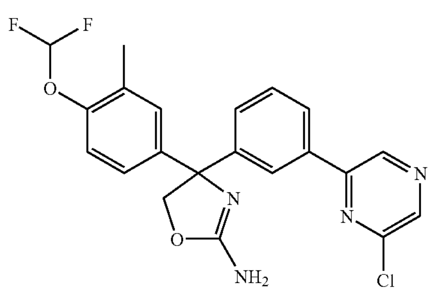 | (RS)-4-[3-(6-Chloro-pyrazin-2-yl)-phenyl]-4-(4-difluoromethoxy-3-methyl-phenyl)-4,5-dihydro-oxazol-2-ylamine formate | 431 | 96 | | BE/5 |
| 203 | 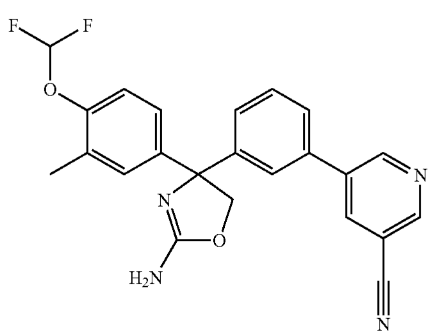 | (RS)-5-{3-[2-Amino-4-(4-difluoromethoxy-3-methyl-phenyl)-4,5-dihydro-oxazol-4-yl]-phenyl}-nicotinonitrile formate | 421 | 100 | | S/5 |

TABLE 2-continued

*Experimental procedures with the synthesis of Examples 1-207.*
*Table 2 shows synthesized compounds, which were prepared according to the method indicated in the last column of the table and discussed in detail in the description above. Apart from examples 31, 32, 33, 39A, 85, 87, 94A, 158, 159, 168, 169, 170, 171 and 175 all other examples were prepared following the general procedures 1 to 5. Synthesis of examples 31, 32, 33, 39A, 85, 87, 94A, 158, 159, 168, 169, 170, 171 and 175 is described below Table 2.*

| Expl | Structure | name | Mass found | LC purity % | 1H-NMR | Build. Block/ Synthetic Method |
|---|---|---|---|---|---|---|
| 204 | 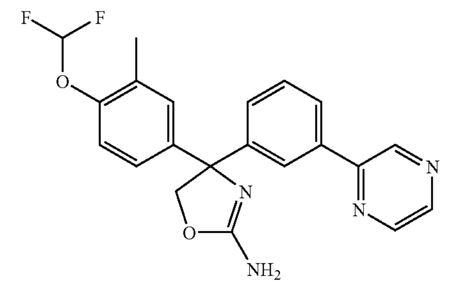 | (RS)-4-(4-Difluoromethoxy-3-methyl-phenyl)-4-(3-pyrazin-2-yl-phenyl)-4,5-dihydro-oxazol-2-ylamine formate | 397 | 98 | | BE/5 |
| 205 | 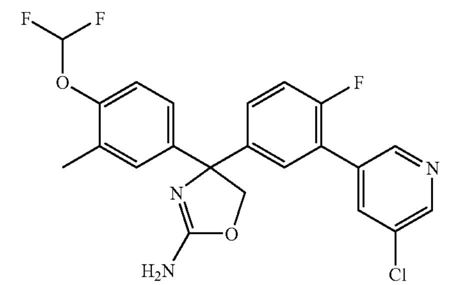 | (RS)-4-[3-(5-Chloro-pyridin-3-yl)-4-fluoro-phenyl]-4-(4-difluoromethoxy-3-methyl-phenyl)-4,5-dihydro-oxazol-2-ylamine formate | 448 | 98 | | S/5 |
| 206 | 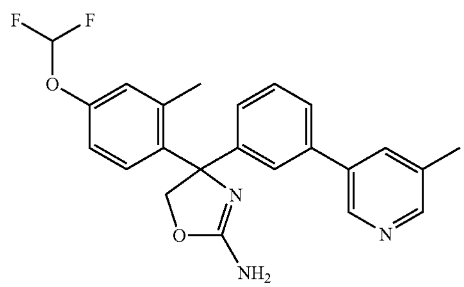 | (RS)-4-(4-Difluoromethoxy-2-methyl-phenyl)-4-[3-(5-methyl-pyridin-3-yl)-phenyl]-4,5-dihydro-oxazol-2-ylamine formate | 410 | 100 | | Z/5 |
| 207 | 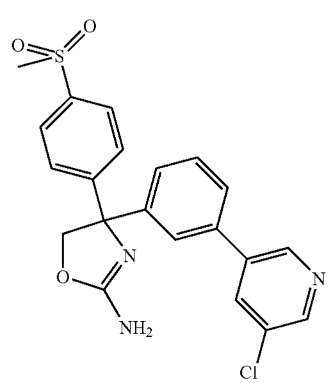 | (RS)-4-[3-(5-Chloro-pyridin-3-yl)-phenyl]-4-(4-methanesulfonyl-phenyl)-4,5-dihydro-oxazol-2-ylamine formate | 428 | 97 | | BD/3 |

Example 31

(RS)-4-(4-Methoxy-phenyl)-4-[3(3-methoxy-phenylamino)-phenyl]-4,5-dihydro-oxazol-2-ylamine

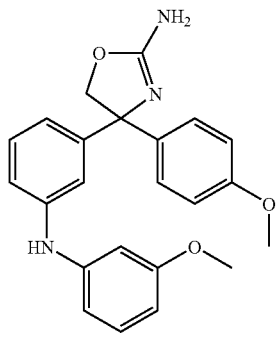

A microwave tube was charged with (RS)-4-(3-bromophenyl)-4-(4-methoxy-phenyl)-4,5-dihydro-oxazol-2-ylamine (Building Block C, 100 mg, 0.288 mmol), sodium tert-butoxide (55 mg, 0.58 mmol), 2-di-t-butylphosphino-2',4',6'-tri-1-propyl-1,1'biphenyl (11 mg, 0.028 mmol), tris(dibenzylideneacetone)dipalladium (7 mg, 0.008 mmol) and 3-methoxyaniline (71 mg, 0.576 mmol). After three vacuum-nitrogen cycles, toluene was introduced (0.7 mL), the tube was sealed and stirred at 100° C. for 16 hours. After cooling to room temperature, water (1 mL) and ethyl acetate (1 mL) were added. The organic fraction of the reaction mixture was placed on an SCX column. This was then washed with dichloromethane/methanol. The desired product was obtained by eluting with 2 M ammonia in methanol. Fractions containing the compound were combined and the product purified further using preparative HPLC to yield 35 mg (31% yield) of the title compound as a white solid.

$C_{22}H_{21}N_3O_2$ Mass (calculated) [389]]; (found) [M+H$^+$]= 390

LC Rt=2.28, 95% (10 min method)

$^1$H-NMR (DMSO-d$_6$) δ (ppm). 8.16 (s, 1H); 8.15 (bs, 1H); 7.28 (m, 2H); 7.10 (m, 3H); 6.84 (m, 4H); 6.54 (m, 2H); 6.34 (m, 1H); 4.69 (d, 1H); 4.60 (d, 1H); 3.70 (s, 3H): 3.68 (s, 3H).

Example 32

(RS)-4-[3-(1,3-Benzodioxol-5-ylamino)-phenyl]-4-phenyl-4,5-dihydro-oxazol-2-ylamine

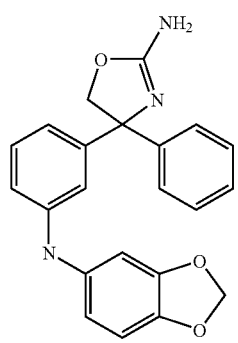

An oven dried pressure tube was charged with (RS)-4-(3-bromo-phenyl)-4-phenyl-4,5-dihydro-oxazol-2-ylamine (Building Block A, 100 mg, 0.315 mmol), sodium tert-butoxide (61 mg, 0.63 mmol), 2-di-t-butylphosphino-2',4',6'-tri-1-propyl-1,1'biphenyl (12 mg, 0.028 mmol), tris(dibenzylideneacetone)dipalladium (7 mg, 0.008 mmol) and 3,4-(methylendioxy)-aniline (86 mg, 0.631 mmol). After three vacuum-nitrogen cycles, toluene was introduced (0.7 mL), the tube was sealed and stirred at 100° C. for 16 hours. After cooling to room temperature, water (1 mL) and ethyl acetate (1 mL) were added. The organic fraction of the reaction mixture was placed on an SCX column. This was then washed with dichloromethane/methanol. The desired product was obtained by eluting with 2M ammonia in methanol. Fractions containing the compound were combined and the product purified further using preparative HPLC to yield 32 mg (26% yield) of the title compound as a white solid.

$C_{22}H_{19}N_3O_3$ Mass (calculated) [373]; (found) [M+H$^+$]= 374

LC Rt=2.27, 95% (10 min method)

$^1$H-NMR (DMSO-d$_6$) δ (ppm): 8.14 (s, 1H); 7.89 (bs, 1H); 7.37 (m, 2H); 7.26 (m, 2H); 7.16 (m, 1H); 7.06 (m, 1H); 7.01 (m, 1H); 6.73 (m, 3H); 6.58 (m, 1H); 6.45 (m, 1H); 5.92 (s, 2H); 4.68 (d, 1H); 4.59 (d, 1H).

Example 33

(RS)-N-[3-(2-Amino-4-phenyl-4,5-dihydro-oxazol-4-yl)-phenyl]-3-methoxy-benzamide

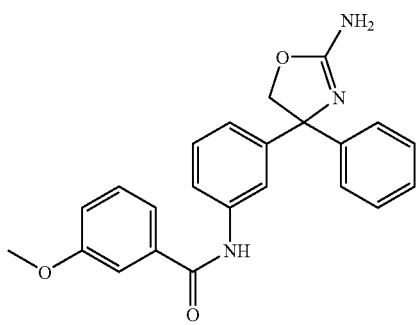

A oven dried pressure tube was charged with (RS)-1-bromo-3-(1-phenyl-vinyl)-benzene (Building Block C, 300 mg, 1.16 mmol), cesium carbonate (567 mg, 1.74 mmol), 4,5-bis(diphenyl-phosphino)-9,9-dimethylxanthene (40 mg, 0.07 mmol), tris(dibenzylideneacetone)dipalladium (17 mg, 0.023 mmol) and 3-(methoxy)-benzamide (95 mg, 0.631 mmol). After three vacuum-nitrogen cycles, dioxane was introduced (2.3 mL), the tube was sealed and stirred at 100° C. for 16 hours. After cooling to room temperature, water (1 mL) and ethyl acetate (1 mL) were added. The organic fraction of the reaction mixture was filtered on a silica plug, concentrated and purified on a silica column (cyclohexane/ethyl acetate 100:0 to 90:10, TLC Rf=0.6 eluted with cyclohexane/ethyl acetate 90:10) giving 3-methoxy-N-[3-(1-phenyl-vinyl)-phenyl]-benzamide as a white powder (250 mg, 65%, LC Rt=1.53, 100% 5 min method, $C_{22}H_{19}NO_2$ Mass (calculated) [329]; (found) [M+H$^+$]=330). This was dissolved in 2:1 acetonitrile/ethyl acetate mixture (4.5 mL) and silver cyanate (173 mg, 1.16 mmol) was added. The resulting suspension was cooled to 0° C. and a solution of I$_2$ (295 mg, 1.66 mmol, 1.1 eq) in ethyl acetate (5 mL) was added dropwise (5 min). At the end of dropping reaction was examined by LC-MS which showed consumption of double bond. The mixture was filtered and the solution was concentrated under reduced pressure. The crude was suspended in 10 mL of ammonium hydroxide solution and stirred for 4 h at room temperature and at 70° C. overnight. The precipitated was filtered, washed with water and purified further using preparative HPLC to yield 56 mg (12% yield over 2 steps) of the title compound as a white solid. $C_{23}H_{21}N_3O_3$ Mass (calculated) [387]; (found) $[M+H^+]=388$ LC Rt=1.97, 100% (10 min method)

$^1$H-NMR (DMSO-$d_6$) δ (ppm): 10.18 (s, 1H); 8.14 (s, 1H); 7.81 (m, 1H); 7.61 (m, 1H); 7.47 (m, 1H): 7.45 (m, 1H); 7.40 (m, 3H); 7.27 (m, 3H); 7.10 (m, 3H); 4.70 (d, 1H); 4.66 (d, 1H); 3.81 (s, 3H).

Example 39A (R)-4-(3'-Chloro-biphenyl-3-yl)-4-(4-methoxy-phenyl)-4,5-dihydro-oxazol-2-ylamine

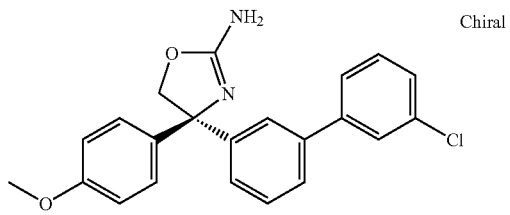

The separation of the racemic mixture of (RS)-4-(3'-chloro-biphenyl-3-yl)-4-(4-methoxy-phenyl)-4,5-dihydro-oxazol-2-ylamine (Example 39) by chiral LC on chiralpak AD with EtOH-heptane 15:85 yielded the title compound with an ee=82.9%.

Example 85

4-(4-Ethoxy-3-methyl-phenyl)-4-[3-(3-methoxy-phenylamino)-phenyl]-4,5-dihydro-oxazol-2-ylamine

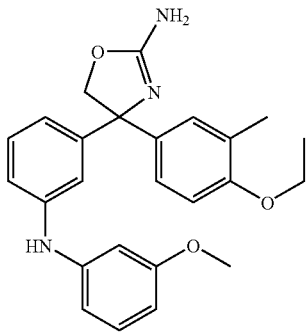

A microwave tube was charged with 4-(3-bromo-phenyl)-4-(4-ethoxy-3-methyl-phenyl)-4,5-dihydro-oxazol-2-ylamine (Building Block M, 175 mg, 0.467 mmol, 1.0 eq), sodium tert-butoxide (89 mg, 0.933 mmol, 2.0 eq.), 2-di-t-butylphosphino-2',4',6'-tri-1-propyl-1,1'biphenyl (18 mg, 0.042 mmol, 0.042 eq.), tris(dibenzylideneacetone)dipalladium (10 mg, 0.012 mmol, 0.025 eq.) and 3-methoxyaniline (115 mg, 0.933 mmol, 2.0 eq.). After three vacuum-nitrogen cycles, toluene was introduced (1 mL), the tube was sealed and stirred at 100° C. for 16 hours. After cooling to room temperature, water (1 mL) and ethylacetate (1 mL) were added. The organic fraction of the reaction mixture was placed on an SCX column. This was then washed with dichloromethane/methanol. The desired product was obtained by eluting with 2 M ammonia in methanol. Fractions containing the compound were combined and the product purified further using preparative HPLC to yield 95 mg (30% yield) of the title compound as a white solid.

Example 87

4-(4-Fluoro-phenyl)-4-[3-(3-methoxy-phenylamino)-phenyl]-4,5-dihydro-oxazol-2-ylamine

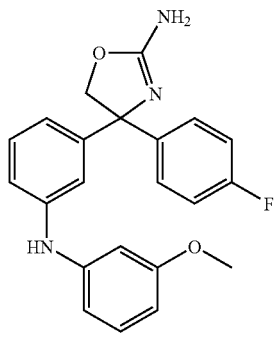

A microwave tube was charged with 4-(3-bromo-phenyl)-4-(4-fluoro-phenyl)-4,5-dihydro-oxazol-2-ylamine (Building Block G 156 mg, 0.467 mmol, 1.0 eq), sodium tert-butoxide (89 mg, 0.933 mmol, 2.0 eq.), 2-di-t-butylphosphino-2',4',6'-tri-1-propyl-1,1biphenyl (18 mg, 0.042 mmol, 0.042 eq.), tris(dibenzylideneacetone)dipalladium (10 mg, 0.012 mmol, 0.025 eq.) and 3-methoxyaniline (115 mg, 0.933 mmol, 2.0 eq.). After three vacuum-nitrogen cycles, toluene was introduced (1 mL), the tube was sealed and stirred at 100° C. for 16 hours. After cooling to room temperature, water (1 mL) and ethylacetate (1 mL) were added. The organic fraction of the reaction mixture was placed on an SCX column. This was then washed with dichloromethane/methanol. The desired product was obtained by eluting with 2 M ammonia in methanol. Fractions containing the compound were combined and the product purified further using preparative HPLC to yield 68 mg (40% yield) of the title compound as a white solid.

Example 94A (R)-4-[3-(5-Chloro-pyridin-3-yl)-phenyl]-4-(4-difluoromethoxy-3-methyl-phenyl)-4,5-dihydro-oxazol-2-ylamine

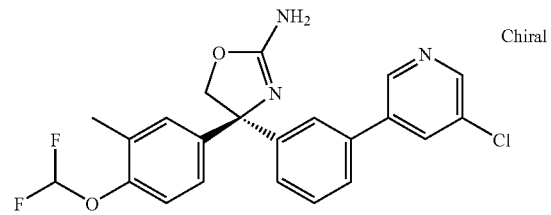

A dried pressure tube was charged with (R)-(−)-4-(3-bromo-phenyl)-4-(4-difluoromethoxy-3-methyl-phenyl)-4, 5-dihydro-oxazol-2-ylamine (Building Block AO, 520 mg, 1.3 mmol), 3-chlorophenylboronic acid (309 mg, 2.0 mmol), triphenylphosphine (71 mg, 0.3 mmol), 2 N sodium carbonate solution (2 mL), and 1,2-dimethoxyethane (10 mL). The mixture was purged with nitrogen before palladium(II) acetate (29 mg, 0.1 mmol) was added. The sealed pressure tube was heated at 100° C. for 15 hours. For the working-up, the reaction mixture was cooled and evaporated under reduced pressure. The residue was directly chromatographed on silica gel using a gradient of dichloromethane/methanol=100/0 to 95/5 as the eluent. There were obtained 220 mg (39% of theory) of (R)-4-[3-(5-chloro-pyridin-3-yl)-phenyl]-4-(4-difluoromethoxy-3-methyl-phenyl)-4,5-dihydro-oxazol-2-ylamine as an off-white solid; Mass (calculated) $C_{22}H_{18}ClF_2N_3O_2$ [429]; (found) $[M+H]^+$=430.

Example 158

4-(2,3-Dihydro-benzofuran-5-yl)-4-[3-(3-methoxy-phenylamino)-phenyl]-4,5-dihydro-oxazol-2-ylamine

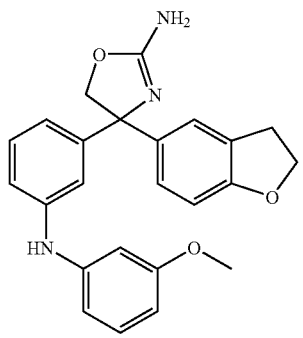

A microwave tube was charged with 4-(3-bromo-phenyl)-4-(2,3-dihydro-benzofuran-5-yl)-4,5-dihydro-oxazol-2-ylamine (Building Block K, 167 mg, 0.467 mmol, 1.0 eq), sodium tert-butoxide (89 mg, 0.933 mmol, 2.0 eq.), 2-di-t-butylphosphino-2',4',6'-tri-1-propyl-1,1'biphenyl (18 mg, 0.042 mmol, 0.042 eq.), tris(dibenzylideneacetone)dipalladium (10 mg, 0.012 mmol, 0.025 eq.) and 3-methoxyaniline (115 mg, 0.933 mmol, 2.0 eq.). After three vacuum-nitrogen cycles, toluene was introduced (1 mL), the tube was sealed and stirred at 100° C. for 16 hours. After cooling to room temperature, water (1 mL) and ethyl acetate (1 mL) were added. The organic fraction of the reaction mixture was placed on an SCX column. This was then washed with dichloromethane/methanol. The desired product was obtained by eluting with 2 M ammonia in methanol. Fractions containing the compound were combined and the product purified further using preparative HPLC to yield 53 mg (30% yield) of the title compound as a white solid.

Example 159

4-(4-Isopropoxy-3-methyl-phenyl)-4-[3-(3-methoxy-phenylamino)-phenyl]-4,5-dihydro-oxazol-2-ylamine

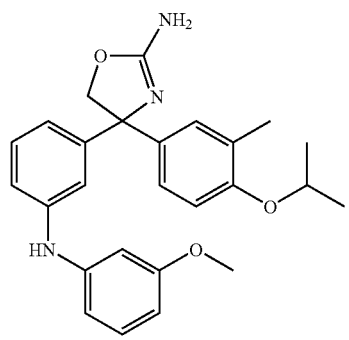

A microwave tube was charged with 4-(3-bromo-phenyl)-4-(4-isopropoxy-3-methyl-phenyl)-4,5-dihydro-oxazol-2-ylamine (Building Block L, 181 mg, 0.467 mmol, 1.0 eq), sodium tert-butoxide (89 mg, 0.933 mmol, 2.0 eq.), 2-di-t-butylphosphino-2',4',6'-tri-1-propyl-1,1'biphenyl (18 mg, 0.042 mmol, 0.042 eq.), tris(dibenzylideneacetone)dipalladium (10 mg, 0.012 mmol, 0.025 eq.) and 3-methoxyaniline (115 mg, 0.933 mmol, 2.0 eq.). After three vacuum-nitrogen cycles, toluene was introduced (1 mL), the tube was sealed and stirred at 100° C. for 16 hours. After cooling to room temperature, water (1 mL) and ethylacetate (1 mL) were added. The organic fraction of the reaction mixture was placed on an SCX column. This was then washed with dichloromethane/methanol. The desired product was obtained by eluting with 2 M ammonia in methanol. Fractions containing the compound were combined and the product purified further using preparative HPLC to yield 99 mg (31% yield) of the title compound as a white solid.

Example 168

(RS)-4-[3-(3-Methoxy-benzyloxy)-phenyl]-4-(4-methoxy-3-methyl-phenyl)-4,5-dihydro-oxazol-2-ylamine tert-Butyl-{3-[1-(4-methoxy-3-methyl-phenyl)-vinyl]-phenoxy}-dimethyl-silane

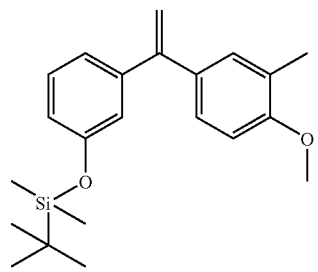

To a suspension of magnesium turnings (828 mg, 34.8 mmol, 1.2 eq) in 5 mL of dry tetrahydrofuran, 0.1 mL of 1,2-dibromoethane were added followed by 5 mL of a tetrahydrofuran solution of 4-bromo-2-methylanisole (5.7 g, 28.4 mmol, 1.0 eq in 25 mL tetrahydrofuran). The resulting mixture was gently heated to initiate the reaction. The remaining solution of bromide was added dropwise at such a rate that the reaction could reflux without external heating. After the addition the reaction mixture was heated at reflux for further 2 hours. The mixture was cooled to 0° C. and a solution of 1-[3-(tert-butyl-dimethyl-silanyloxy)-phenyl]-ethanone (7.1 g, 28.4 mmol, 1.0 eq) in tetrahydrofuran (30 mL) was added dropwise. After 2 hours LC-MS showed complete conversion to the desired product. 50 mL of water were added followed by 35 mL of 1 M aqueous HCl. The organic fraction was washed with brine, dried over sodium sulfate and concentrated to give a yellow oil. The oil was dissolved in 10 mL of acetic acid and 0.3 mL of 98% sulfuric acid were added and the dark solution was stirred at room temperature. After 30 min LCMS which showed complete conversion to the desired product. Crushed ice was poured in the reaction mixture which was then extracted with DCM. The organic fraction was collected, washed with water, aq. NaHCO$_3$ and dried with over sodium sulfate The crude product was purified by flash chromatography eluting with cyclohexane/ethylacetate (100:0 to 98:2). 7.2 g of clean product was obtained as colorless liquid (yield: 70%)

Mass (calculated) C$_{22}$H$_{30}$O$_2$Si [354]; (found) [M+H$^+$]=355

Rf=0.85 (cyclohexane/ethyl acetate 80:20).

3-[1-(4-Methoxy-3-methyl-phenyl)-vinyl]-phenol

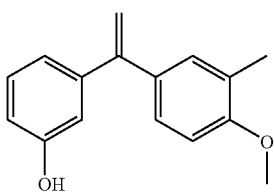

tert-Butyl-{3-[1-(4-methoxy-3-methyl-phenyl)-vinyl]-phenoxy}-dimethyl-silane (7.1 g, 19.8 mmol, 1.0 eq) was dissolved in 50 mL of dry tetrahydrofuran, the solution was cooled to 0° C. 21.8 mL of a tetrabutylammonium fluoride solution (1 M tetrahydrofuran, 21.8 mmol, 1.1 eq) was added and the mixture was allowed to warm up to room temperature. After 1 hour LCMS which showed complete conversion to the desired product. Water was added to the reaction mixture which was then extracted with ethyl acetate. The organic fraction was collected and dried with over sodium sulfate The crude product was purified by flash chromatography eluting with cyclohexane/ethylacetate (100:0 to 90:10). 5.3 g of clean product was obtained as colorless liquid (yield: 95%)

Mass (calculated) C$_{16}$H$_{16}$O$_2$ [240]; (found) [M−H$^-$]=239

Rf=0.75 (cyclohexane/ethyl acetate 90:10)

$^1$H-NMR (CDCl$_3$): 2.19 (s, 3H); 3.83 (s, 3H); 5.33 (d, 2H), 6.79 (m, 1H), 6.91 (m, 1H), 7.10 (m, 3H), 7.16 (m, 2H).

1-Methoxy-4-{1-[3-(3-methoxy-benzyloxy)-phenyl]-vinyl}-2-methyl-benzene

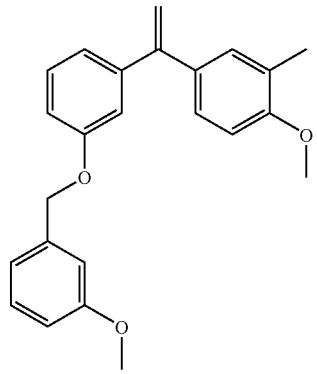

To a solution of 3-[1-(4-methoxy-3-methyl-phenyl)-vinyl]-phenol (400 mg, 1.67 mmol, 1.0 eq) in 3 mL of dry N,N-dimethylformamide, anhydrous cesium carbonate was added (1.08 g, 3.33 mmol, 2.0 eq.) and the mixture was stirred for 20 min at room temperature. After this time, 3-methoxy-benzylbromide (167 mg, 0.832 mmol, 1.2 eq.) was added and the resulting mixture was further stirred for 16 hours at 50° C. The reaction mixture was examined LC-MS which showed>90% conversion to the desired product. The reaction mixture was cooled to room temperature, 10 mL of water was added and the mixture was extracted with DCM. The organic fraction was dried over sodium sulfate and the crude product was purified by flash chromatography eluting with cyclohexane/ethylacetate (100:0 to 90:10). 408 mg of clean product was obtained as colorless liquid (yield: 95%)

Mass (calculated) C$_{24}$H$_{24}$O$_3$ [360]; (found) [M+H$^+$]=361

$^1$H-NMR (CDCl$_3$): 2.20 (s, 3H); 3.81 (s, 3H); 3.85 (s, 3H); 5.10 (s, 2H), 5.35 (d, 2H), 6.79 (d, 1H), 6.85 (dd, 1H), 6.90 (m, 5H), 7.10 (m, 1H), 7.12 (m, 2H), 7.31 (m, 2H).

4-[3-(3-Methoxy-benzyloxy)-phenyl]-4-(4-methoxy-3-methyl-phenyl)-4,5-dihydro-oxazol-2-ylamine (example 168)

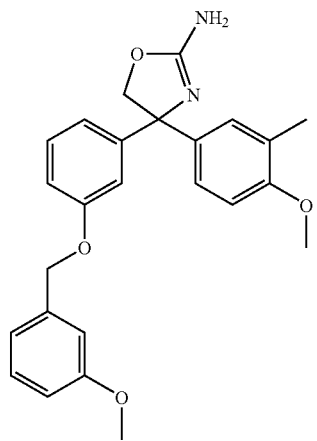

According to general method 2, a solution of iodine in ethyl acetate was added to a mixture of 1-methoxy-4-{1-[3-(3-methoxy-benzyloxy)-phenyl]-vinyl}-2-methyl-benzene (400 mg, 1.11 mmol) and silver cyanate in ethyl acetate/acetonitrile. The crude product of this reaction was subsequently reacted with aqueous ammonia (30% by vol). Purification by preparative HPLC yield 181 mg of product (39%).

Examples 169 and 170

(4RS,5RS)-4-(4-Methoxy-phenyl)-5-methyl-4-(3-pyrimidin-5-yl-phenyl)-4,5-dihydro-oxazol-2-ylamine

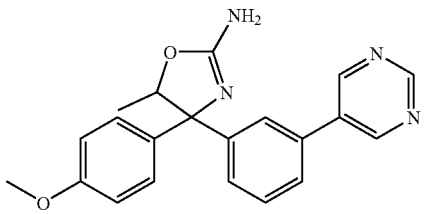

A dried pressure tube was charged with (4RS,5RS)-4-(3-bromo-phenyl)-4-(4-methoxy-phenyl)-5-methyl-4,5-dihydro-oxazol-2-ylamine (Building Block AP, (64 mg, 0.2 mmol), pyrimidine-5-boronic acid (25 mg, 0.2 mmol), triphenylphosphine (10 mg, 0.04 mmol), 2 N sodium carbonate solution (0.4 mL), and 1,2-dimethoxyethane (2 mL). The mixture was purged with argon before palladium(II)acetate (4 mg, 0.018 mmol) was added. The sealed pressure tube was heated at 100° C. for 60 hours. The incomplete reaction was stopped, the reaction mixture was cooled and evaporated under reduced pressure. The residue was directly chromatographed on silica gel using a gradient of dichloromethane/methanol=100/0 to 85/15 as the eluent. The mixture of the diastereomeric racemates was chromatographed on a preparative silica gel LC-plate using a 9:1-mixture of dichloromethane/methanol as the eluent. There were obtained 2 fractions of the desired product: 5 mg of a 9:1-mixture of diastereomeric racemates (example 169) [Mass (calculated) $C_{21}H_{20}N_4O_2$ [360]; (found) [M+H]$^+$=361 and 3 mg of a 6:4-mixture of diastereomeric racemates (example 170) [Mass (calculated) $C_{21}H_{20}N_4O_2$ [360]; (found) [M+H]$^+$=361

Example 171

(RS)-4-(3'-Difluoromethoxy-biphenyl-3-yl)-4-(4-difluoromethoxy-3-methyl-phenyl)-4,5-dihydro-oxazol-2-ylamine

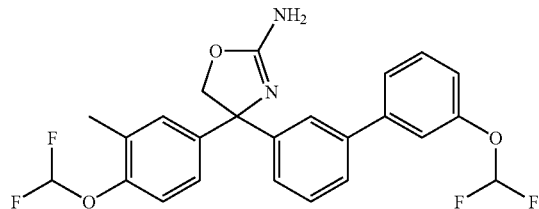

A dried pressure tube was charged with (RS)-4-(3-bromo-phenyl)-4-(4-difluoromethoxy-3-methyl-phenyl)-4,5-dihydro-oxazol-2-ylamine (Building Block S) (131 mg, 0.3 mmol), 3-(difluoromethoxy)-benzeneboronic acid (93 mg, 0.5 mmol), triphenylphosphine (18 mg, 0.1 mmol), 2 N sodium carbonate solution (0.5 mL), and 1,2-dimethoxyethane (3 mL). The mixture was purged with nitrogen before palladium(II) acetate (7 mg, 0.03 mmol) was added. The sealed pressure tube was heated at 100° C. for 15 hours. For the working-up, the reaction mixture was cooled and evaporated under reduced pressure. The residue was directly chromatographed on silica gel using a gradient of dichloromethane/methanol=100/0 to 95/5 as the eluent. There were obtained 43 mg (28% of theory) of (RS)-4-(3'-difluoromethoxy-biphenyl-3-yl)-4-(4-difluoromethoxy-3-methyl-phenyl)-4,5-dihydro-oxazol-2-ylamine as light yellow solid. Mass (calculated) $C_{24}H_{20}F_4N_2O_3$ [460]; (found) [M+H]$^+$= 461.

Example 175

(RS)-4-(3-Fluoro-5-phenylamino-phenyl)-4-(4-methoxy-3-methyl-phenyl)-4,5-dihydro-oxazol-2-ylamine

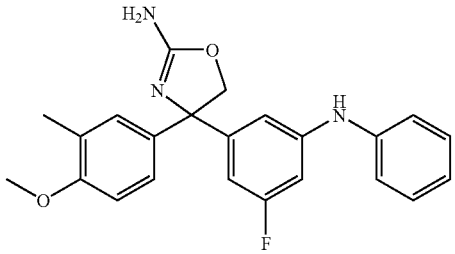

A dried pressure tube was charged consecutively with (RS)-4-(3-bromo-5-fluoro-phenyl)-4-(4-methoxy-3-methyl-phenyl)-4,5-dihydro-oxazol-2-ylamine (Building Block AH, 100 mg, 0.3 mmol), toluene (1.5 mL), sodium tert-butylate (52 mg, 0.5 mmol), and tert-butyl x-phos [di-tert-butyl(2',4',6'-triisopropylbiphenyl-2-yl)phosphine] (12 mg, 0.03 mmol). The mixture was purged with argon before [tris(dibenzylidenacetone)dipalladium chloroform complex] (8 mg, 0.008 mmol) and aniline (49 mg, 0.5 mmol) were added. The sealed tube was heated at 105° C. for 15 hours. For the working-up, the reaction mixture was cooled and evaporated under reduced pressure. The residue was directly chromatographed on an Isolute Flash NH$_2$ column using a gradient of heptane/ethyl acetate=100/0 to 100/0 as the eluent. There were obtained 49 mg (47% of theory) of (RS)-4-(3-fluoro-5-phenylamino-phenyl)-4-(4-methoxy-3-methyl-phenyl)-4,5-dihydro-oxazol-2-ylamine as a white foam; Mass (calculated) $C_{23}H_{22}FN_3O_2$ [391]; (found) [M+H]$^+$=392.

Solutions and Materials

Assay plate: 384 well microtiter plate, Corning clear, flat bottom, non binding surface
Assaybuffer: 100 mM Na-acetate pH 4.0, 20 mM EDTA, 0.05% BSA
BACE-1: 6his-tagged full length BACE 1 from SF9 cells
Substrate peptide: WSEVNLDAEFRC-MR121
BACE1 MR121 protease assay
39 µl of a 38 nM 6his-BACE-1 solution in assay buffer (final conc. in the assay: 30 nM) were pipetted into the assay plate. 1 µl of a concentration of a potential inhibitor in dimethylsulfoxide was added to the enzyme and incubated for 10 min. Finally, 10 μl of a 1.5 μM solution of the substrate in assay buffer (final conc. in the assay: 300 nM) was added to start the enzymatic reaction. After strong mixing for 2 min the enzymatic reaction was followed by measuring the fluorescence intensity every two minutes for 15 min on a suitable fluorescence reader. Cleavage of the substrate peptide resulted in an increase of fluorescence intensity. The slope was calculated from the linear part of the kinetic as a measure of the activity of BACE-1. A range of concentrations of the potential inhibitor was used to generate data for calculating the concentration of inhibitor resulting in 50% of the effect (e.g. $IC_{50}$, the concentration of the compound inhibiting the BACE-1 activity by 50%).

SPR Based Direct Binding Assay for β-Secretase Inhibitors

Direct binding experiments were performed on a Biacore S5I or Biacore A100 instrument. Wilde type β-secretase was immobilized (~12000 RU) by standard amine coupling chemistry on different channels of a CM-5 sensor chip. Binding experiments were performed using acetate buffer 1 (50 mM pH 4.6, 150 mM NaCl, 3 mM EDTA, 0.01% P20, 4% dimethylsulfoxide) as the running buffer and acetate buffer 2 (10 mM, pH 4.6) as the coupling buffer. The same immobilization conditions were used to immobilize D93A mutated β-secretase as a reference protein in a parallel channel.

Test compounds were first dissolved in dimethylsulfoxide (10 mM) and afterwards diluted into acetate buffer in a ratio that leads to the final concentration of the test compound and to the targeted dimethylsulfoxide content (4%). Concentration series were generated by diluting this aqueous stock solution with running buffer.

Acetate buffer 1 was used as the running buffer in binding experiments with test compounds. In a typical binding experiment the immobilized proteins were contacted for 1 min with the test solutions. Responses from the channel with the wild type and the mutant protein are determined at the end of the injection phase. Regeneration of the surface was achieved by washing the surface with running buffer.

The set up was used to characterize compounds in a single experiment with respect to affinity and site specificity of binding. The response measured in the channel with the wt-protein was taken as a positive indication for binding when it exceeds 3 times the standard deviation of the negative control (approx. 5 RU). KD's were determined via concentration dependent measurements by fitting the measured responses to a sigmoid dose response curve (response versus log C). Site specificity was indicative from the ratio of the responses measured in the channels with the wt- and the channel with the mutant protein (Rwt/Rmu>1.2).

SPR Based Competition Assay

Site specificity of binding was further checked by a competition assay. In this assay a known active site binder of high affinity (KD<100 nM) was used as the competitor compound. The wt β-secretase was immobilized using the same procedure as described above. In a typical series, the protein was first contacted with the test compound (C=50 μM) followed by the injection of the competitor compound (C>50*KD) and finally followed by the injection of a mixture containing the two compounds (test and competitor) at the same concentration as in the preceding solutions. The responses measured for the three solutions are clearly indicative for competitive or non competitive behavior. Clear competition (binding to the same site) is indicated when the signal observed for the mixture ($R_{mix}$) corresponds to the signal observed for the competitor compound alone ($R_{comp}$). No competition is indicated when the response of the mixture ($R_{mix}$) corresponds to the sum of the individual responses ($R_{test}+R_{comp}$). If the mixture has a signal that is intermediate between $R_{comp}$ and ($R_{comp}+R_{test}$) only partial inhibition occurs. Binding is in this case only partially site specific.

The preferred compounds show an $IC_{50}$ value<1 μM. Values for some compounds of the invention are shown in the table below.

| Example | $IC_{50}$ (μM) |
|---|---|
| 14 | 0.81 |
| 15 | 0.82 |
| 17 | 0.91 |
| 19 | 0.531 |
| 21 | 0.794 |
| 22 | 0.831 |
| 24 | 0.290 |
| 25 | 0.945 |
| 39 | 0.81 |
| 39A | 0.44 |
| 41 | 0.80 |
| 42 | 0.80 |
| 43 | 0.68 |
| 47 | 0.40 |
| 51 | 0.12 |
| 52 | 0.19 |
| 57 | 0.41 |
| 66 | 0.74 |
| 67 | 0.89 |
| 72 | 0.74 |
| 73 | 0.84 |
| 74 | 0.13 |
| 75 | 0.44 |
| 78 | 0.64 |
| 83 | 0.97 |
| 86 | 0.41 |
| 88 | 0.37 |
| 89 | 0.35 |
| 90 | 0.15 |
| 92 | 0.75 |
| 94 | 0.06 |
| 94A | 0.04 |
| 97 | 0.12 |
| 98 | 0.15 |
| 99 | 0.17 |
| 100 | 0.12 |
| 101 | 0.06 |
| 102 | 0.21 |
| 103 | 0.32 |
| 104 | 0.13 |
| 105 | 0.13 |
| 108 | 0.29 |
| 109 | 0.77 |
| 111 | 0.16 |
| 112 | 0.64 |
| 113 | 0.73 |
| 114 | 0.66 |
| 115 | 0.24 |
| 117 | 0.08 |
| 118 | 0.20 |
| 119 | 0.13 |
| 120 | 0.09 |
| 121 | 0.05 |
| 122 | 0.15 |
| 123 | 0.20 |
| 129 | 0.50 |
| 130 | 0.49 |
| 131 | 0.46 |
| 142 | 0.84 |
| 145 | 0.72 |
| 146 | 0.20 |
| 149 | 0.96 |
| 150 | 0.33 |
| 192 | 0.66 |
| 193 | 0.08 |
| 194 | 0.14 |
| 195 | 0.96 |
| 197 | 0.53 |
| 200 | 0.38 |

-continued

| Example | IC$_{50}$ (μM) |
|---------|----------------|
| 201 | 0.16 |
| 202 | 0.44 |
| 203 | 0.11 |
| 204 | 0.16 |
| 205 | 0.09 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

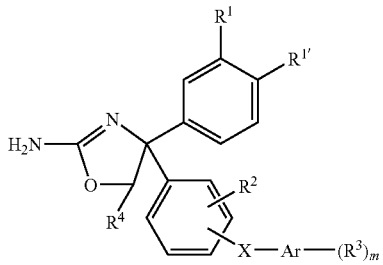

wherein
R¹ and R¹' are each independently hydrogen, halogen, lower alkoxy, lower alkyl, lower alkyl substituted by halogen, lower alkoxy substituted by halogen, lower alkoxy substituted by hydroxy, —O—(CH$_2$)$_o$—O-lower alkyl, —(CH$_2$)$_p$—O-lower alkyl, —O—S(O)$_2$-lower alkyl, —S(O)$_2$-lower alkyl or cyano;
or R¹ and R¹' together are —(CH$_2$)$_2$O—, —O—CH$_2$—O— or —N(R)—(CH$_2$)$_2$—O— which forms a 5- or 6-membered ring with the carbon atoms to which they are attached; R is hydrogen or lower alkyl;
R² is hydrogen, halogen, lower alkyl, cyano, lower alkoxy, lower alkoxy substituted by halogen, —O—(CH$_2$)$_p$— C$_{3-6}$-cycloalkyl or (CH$_2$)$_o$—O-lower alkyl;
each R³ is independently hydrogen, cyano, lower alkoxy, lower alkyl, lower alkyl substituted by halogen, lower alkoxy substituted by halogen, —CH$_2$—O-lower alkyl, —C(O)N-di-lower alkyl or halogen;
R⁴ is hydrogen or lower alkyl;
X is a bond, —NH—C(O)—, —NH— or —O—CH$_2$;
Ar is aryl or heteroaryl;
and wherein —X—Ar—(R³)$_m$ is in the 3 or 4 position of the phenyl ring; or X—Ar—(R³)$_m$ represents benzo[1,3]dioxole;
m is 0, 1 or 2;
o is 2 or 3; and
p is 1, 2 or 3;
or a pharmaceutically active acid addition salt thereof.
2. The compound of claim 1, wherein —X—Ar—(R³)$_m$ is in the 3-position, X is a bond and Ar is phenyl.
3. The compound of claim 2, selected from the group consisting of
(RS)-4-(3'-chloro-biphenyl-3-yl)-4-(4-methoxy-phenyl)-4,5-dihydro-oxazol-2-ylamine;
(RS)-4-(3'-methoxy-biphenyl-3-yl)-4-(4-methoxy-phenyl)-4,5-dihydro-oxazol-2-ylamine;
(RS)-4-(6-fluoro-3'-methoxy-biphenyl-3-yl)-4-(4-methoxy-3-methyl-phenyl)-4,5-dihydro-oxazol-2-ylamine;
(RS)-4-(5'-chloro-2'-fluoro-biphenyl-3-yl)-4-(4-methoxy-phenyl)-4,5-dihydro-oxazol-2-ylamine;
(RS)-4-(3'-chloro-biphenyl-3-yl)-4-(4-methoxy-phenyl)-4,5-dihydro-oxazol-2-ylamine;
(R)-4-(3'-chloro-biphenyl-3-yl)-4-(4-methoxy-phenyl)-4,5-dihydro-oxazol-2-ylamine;
(RS)-4-(3'-chloro-biphenyl-3-yl)-4-(4-methoxy-3-methyl-phenyl)-4,5-dihydro-oxazol-2-ylamine; and
(RS)-4-(3'-methoxy-biphenyl-3-yl)-4-(4-methoxy-3-methyl-phenyl)-4,5-dihydro-oxazol-2-ylamine.

4. The compound of claim 2, selected from the group consisting of
(RS)-4-(3'-chloro-biphenyl-3-yl)-4-(4-ethoxy-3-methyl-phenyl)-4,5-dihydro-oxazol-2-ylamine;
(RS)-4-(3'-chloro-biphenyl-3-yl)-4-(4-difluoromethoxy-3-methyl-phenyl)-4,5-dihydro-oxazol-2-ylamine;
(RS)-4-(4-difluoromethoxy-3-methyl-phenyl)-4-(2'-fluoro-5'-methoxy-biphenyl-3-yl)-4,5-dihydro-oxazol-2-ylamine;
(RS)-4-(3-chloro-4-methoxy-phenyl)-4-(6,2'-difluoro-5'-methoxy-biphenyl-3-yl)-4,5-dihydro-oxazol-2-ylamine;
(RS)-4-(6,2'-difluoro-5'-methoxy-biphenyl-3-yl)-4-(4-difluoromethoxy-3-methyl-phenyl)-4,5-dihydro-oxazol-2-ylamine;
(RS)-4-(4-difluoromethoxy-2-methyl-phenyl)-4-(2'-fluoro-5'-methoxy-biphenyl-3-yl)-4,5-dihydro-oxazol-2-ylamine; and
(RS)-4-(3'-chloro-biphenyl-3-yl)-4-(4-difluoromethoxy-2-methyl-phenyl)-4,5-dihydro-oxazol-2-ylamine.
5. The compound of claim 1, wherein —X—Ar—(R³)$_m$ is in the 3-position, X is a bond and Ar is heteroaryl.
6. The compound of claim 5, selected from the group consisting of
4-[3-(2-Fluoro-pyridin-3-yl)-phenyl]-4-(4-methoxy-phenyl)-4,5-dihydro-oxazol-2-yl-amine;
4-(4-fluoro-3-pyrimidin-5-yl-phenyl)-4-(4-methoxy-3-methyl-phenyl)-4,5-dihydro-oxazol-2-ylamine;
4-(4-fluoro-3-pyridin-3-yl-phenyl)-4-(4-methoxy-3-methyl-phenyl)-4,5-dihydro-oxazol-2-ylamine;
4-[4-fluoro-3-(6-fluoro-pyridin-3-yl)-phenyl]-4-(4-methoxy-3-methyl-phenyl)-4,5-dihydro-oxazol-2-ylamine;
(RS)-4-[3-(2-fluoro-pyridin-3-yl)-phenyl]-4-(4-methoxy-3-methyl-phenyl)-4,5-dihydro-oxazol-2-ylamine;
(RS)-4-(4-methoxy-3-methyl-phenyl)-4-[3-(5-methoxy-pyridin-3-yl)-phenyl]-4,5-dihydro-oxazol-2-ylamine;
(RS)-4-[4-fluoro-3-(5-methoxy-pyridin-3-yl)-phenyl]-4-(4-methoxy-3-methyl-phenyl)-4,5-dihydro-oxazol-2-ylamine;
(RS)-4-[4-fluoro-3-(5-fluoro-pyridin-3-yl)-phenyl]-4-(4-methoxy-3-methyl-phenyl)-4,5-dihydro-oxazol-2-ylamine;
(RS)-4-[4-fluoro-3-(2-fluoro-pyridin-3-yl)-phenyl]-4-(4-methoxy-3-methyl-phenyl)-4,5-dihydro-oxazol-2-ylamine;
(RS)-4-(4-ethoxy-3-methyl-phenyl)-4-(3-pyrimidin-5-yl-phenyl)-4,5-dihydro-oxazol-2-ylamine; and
(RS)-4-(3-chloro-4-methoxy-phenyl)-4-[3-(2-fluoro-pyridin-3-yl)-phenyl]-4,5-dihydro-oxazol-2-ylamine.
7. The compound of claim 5, selected from the group consisting of
(RS)-4-(3-chloro-4-methoxy-phenyl)-4-(3-pyrimidin-5-yl-phenyl)-4,5-dihydro-oxazol-2-ylamine;
(RS)-4-(3-chloro-4-methoxy-phenyl)-4-[3-(5-methoxy-pyridin-3-yl)-phenyl]-4,5-dihydro-oxazol-2-ylamine;
(RS)-4-(4-ethoxy-3-methyl-phenyl)-4-[3-(5-fluoro-pyridin-3-yl)-phenyl]-4,5-dihydro-oxazol-2-ylamine;
(RS)-4-(3-chloro-4-methoxy-phenyl)-4-[3-(5-fluoro-pyridin-3-yl)-phenyl]-4,5-dihydro-oxazol-2-ylamine;
(RS)-4-(4-ethoxy-phenyl)-4-[3-(5-methoxy-pyridin-3-yl)-phenyl]-4,5-dihydro-oxazol-2-ylamine;
(RS)-4-(4-difluoromethoxy-phenyl)-4-(3-pyrimidin-5-yl-phenyl)-4,5-dihydro-oxazol-2-ylamine;
(RS)-4-(4-difluoromethoxy-phenyl)-4-[3-(5-fluoro-pyridin-3-yl)-phenyl]-4,5-dihydro-oxazol-2-ylamine;
(RS)-4-(4-difluoromethoxy-phenyl)-4-[3-(2-fluoro-pyridin-3-yl)-phenyl]-4,5-dihydro-oxazol-2-ylamine;

(RS)-4-(4-difluoromethoxy-phenyl)-4-[3-(5-methoxy-pyridin-3-yl)-phenyl]-4,5-dihydro-oxazol-2-ylamine;

(RS)-4-(3-fluoro-4-methoxy-phenyl)-4-[3-(5-methoxy-pyridin-3-yl)-phenyl]-4,5-dihydro-oxazol-2-ylamine; and (RS)-4-[3-(5-chloro-pyridin-3-yl)-phenyl]-4-(4-difluoromethoxy-3-methyl-phenyl)-4,5-dihydro-oxazol-2-ylamine.

8. The compound of claim 5, selected from the group consisting of (R)-4-[3-(5-chloro-pyridin-3-yl)-phenyl]-4-(4-difluoromethoxy-3-methyl-phenyl)-4,5-dihydro-oxazol-2-ylamine;

(RS)-4-(4-difluoromethoxy-3-methyl-phenyl)-4-(3-pyridin-3-yl-phenyl)-4,5-dihydro-oxazol-2-ylamine;

(RS)-4-(4-difluoromethoxy-3-methyl-phenyl)-4-[3-(2-fluoro-pyridin-3-yl)-phenyl]-4,5-dihydro-oxazol-2-ylamine;

(RS)-4-(4-difluoromethoxy-3-methyl-phenyl)-4-(3-pyrimidin-5-yl-phenyl)-4,5-dihydro-oxazol-2-ylamine;

(RS)-4-(4-difluoromethoxy-3-methyl-phenyl)-4-[3-(5-methoxy-pyridin-3-yl)-phenyl]-4,5-dihydro-oxazol-2-ylamine;

(RS)-4-(4-difluoromethoxy-3-methyl-phenyl)-4-[3-(5-fluoro-pyridin-3-yl)-phenyl]-4,5-dihydro-oxazol-2-ylamine;

(RS)-4-(4-difluoromethoxy-3-methyl-phenyl)-4-[3-(5-methyl-pyridin-3-yl)-phenyl]-4,5-dihydro-oxazol-2-ylamine;

(RS)-4-(4-difluoromethoxy-3-methyl-phenyl)-4-[3-(2-fluoro-5-methyl-pyridin-3-yl)-phenyl]-4,5-dihydro-oxazol-2-ylamine;

(RS)-4-(3-chloro-4-methoxy-phenyl)-4-[3-(5-chloro-pyridin-3-yl)-4-fluoro-phenyl]-4,5-dihydro-oxazol-2-ylamine;

(RS)-4-(3-chloro-4-methoxy-phenyl)-4-(4-fluoro-3-pyridin-3-yl-phenyl)-4,5-dihydro-oxazol-2-ylamine; and (RS)-4-(3-chloro-4-methoxy-phenyl)-4-[4-fluoro-3-(5-methoxy-pyridin-3-yl)-phenyl]-4,5-dihydro-oxazol-2-ylamine.

9. The compound of claim 5, selected from the group consisting of (RS)-4-(3-chloro-4-methoxy-phenyl)-4-[4-fluoro-3-(5-fluoro-pyridin-3-yl)-phenyl]-4,5-dihydro-oxazol-2-ylamine;

(RS)-4-(3-chloro-4-methoxy-phenyl)-4-[4-fluoro-3-(2-fluoro-5-methyl-pyridin-3-yl)-phenyl]-4,5-dihydro-oxazol-2-ylamine;

(RS)-4-[3-(5-chloro-pyridin-3-yl)-phenyl]-4-(4-difluoromethoxy-3-fluoro-phenyl)-4,5-dihydro-oxazol-2-ylamine;

(RS)-4-(3-chloro-4-difluoromethoxy-phenyl)-4-[3-(5-methoxy-pyridin-3-yl)-phenyl]-4,5-dihydro-oxazol-2-ylamine;

(RS)-4-(3-chloro-4-difluoromethoxy-phenyl)-4-(3-pyrimidin-5-yl-phenyl)-4,5-dihydro-oxazol-2-ylamine;

(RS)-4-(4-difluoromethoxy-3-methyl-phenyl)-4-(4-fluoro-3-pyridin-3-yl-phenyl)-4,5-dihydro-oxazol-2-ylamine;

(RS)-4-(4-difluoromethoxy-3-methyl-phenyl)-4-(4-fluoro-3-pyrimidin-5-yl-phenyl)-4,5-dihydro-oxazol-2-ylamine;

(RS)-4-(4-difluoromethoxy-3-methyl-phenyl)-4-[4-fluoro-3-(5-methoxy-pyridin-3-yl)-phenyl]-4,5-dihydro-oxazol-2-ylamine;

(RS)-4-(4-difluoromethoxy-3-methyl-phenyl)-4-[4-fluoro-3-(5-fluoro-pyridin-3-yl)-phenyl]-4,5-dihydro-oxazol-2-ylamine;

(RS)-4-(4-difluoromethoxy-2-methyl-phenyl)-4-(3-pyrimidin-5-yl-phenyl)-4,5-dihydro-oxazol-2-ylamine; and (RS)-4-(4-difluoromethoxy-2-methyl-phenyl)-4-[3-(2-fluoro-5-methyl-pyridin-3-yl)-phenyl]-4,5-dihydro-oxazol-2-ylamine.

10. The compound of claim 5, selected from the group consisting of (RS)-4-(4-difluoromethoxy-2-fluoro-phenyl)-4-[3-(5-fluoro-pyridin-3-yl)-phenyl]-4,5-dihydro-oxazol-2-ylamine;

(RS)-4-(4-difluoromethoxy-2-methyl-phenyl)-4-[3-(5-fluoro-pyridin-3-yl)-phenyl]-4,5-dihydro-oxazol-2-ylamine;

(RS)-4-(4-difluoromethoxy-2-methyl-phenyl)-4-[3-(5-methoxy-pyridin-3-yl)-phenyl]-4,5-dihydro-oxazol-2-ylamine;

(RS)-4-[3-(5-chloro-pyridin-3-yl)-phenyl]-4-[4-(2-fluoro-ethoxy)-phenyl]-4,5-dihydro-oxazol-2-ylamine;

(RS)-5-{3-[2-amino-4-(4-difluoromethoxy-2-methyl-phenyl)-4,5-dihydro-oxazol-4-yl]-phenyl}-nicotinonitrile;

(RS)-4-[3-(5-chloro-pyridin-3-yl)-phenyl]-4-(4-difluoromethoxy-2-methyl-phenyl)-4,5-dihydro-oxazol-2-ylamine;

(RS)-4-[3-(6-chloro-pyrazin-2-yl)-phenyl]-4-(4-difluoromethoxy-3-methyl-phenyl)-4,5-dihydro-oxazol-2-ylamine;

(RS)-5-{3-[2-amino-4-(4-difluoromethoxy-3-methyl-phenyl)-4,5-dihydro-oxazol-4-yl]-phenyl}-nicotinonitrile;

(RS)-4-(4-difluoromethoxy-3-methyl-phenyl)-4-(3-pyrazin-2-yl-phenyl)-4,5-dihydro-oxazol-2-ylamine; and (RS)-4-[3-(5-chloro-pyridin-3-yl)-4-fluoro-phenyl]-4-(4-difluoromethoxy-3-methyl-phenyl)-4,5-dihydro-oxazol-2-ylamine.

11. The compound of claim 1, wherein —X—Ar—$(R^3)_m$ is in the 3-position, X is —NH— and Ar is phenyl.

12. The compound of claim 11, selected from the group consisting of (RS)-4-(4-difluoromethoxy-3-methyl-phenyl)-4-[3-ethoxy-5-(3-methoxy-phenylamino)-phenyl]-4,5-dihydro-oxazol-2-ylamine;

(RS)-4-(4-difluoromethoxy-3-methyl-phenyl)-4-(3-ethoxymethyl-5-phenylamino-phenyl)-4,5-dihydro-oxazol-2-ylamine;

(RS)-4-(4-difluoromethoxy-3-methyl-phenyl)-4-[3-ethoxymethyl-5-(3-methoxy-phenylamino)-phenyl]-4,5-dihydro-oxazol-2-ylamine;

(RS)-4-(3-ethoxymethyl-5-phenylamino-phenyl)-4-(4-methoxy-3-methyl-phenyl)-4,5-dihydro-oxazol-2-ylamine; and (RS)-4-[3-(2-methoxy-ethyl)-5-phenylamino-phenyl]-4-(4-methoxy-3-methyl-phenyl)-4,5-dihydro-oxazol-2-ylamine.

13. A compound of formula I according to claim 1, wherein —X—Ar—$(R^3)_m$ is in the 3-position, X is —NH— and Ar is heteroaryl.

14. A compound of formula I according to claim 1, wherein —X—Ar—$(R^3)_m$ is in the 3-position, X is —NHC(O)— and Ar is phenyl.

15. A compound of formula I according to claim 1, wherein —X—Ar—$(R^3)_m$ is in the 4-position, X is a bond and Ar is phenyl.

16. A compound of formula I according to claim 1, wherein —X—Ar—(R³)ₘ is in the 3-position, X is —O—CH₂— and Ar is phenyl.

17. The compound of claim 1, having formula I-A

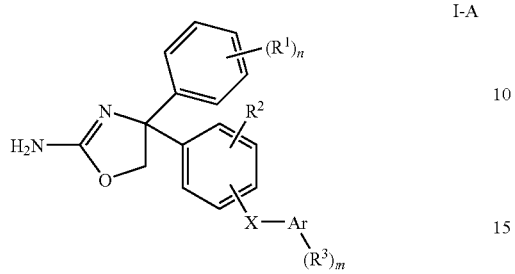

I-A wherein
each R¹ is independently hydrogen, halogen, lower alkoxy, lower alkyl, lower alkyl substituted by halogen or lower alkoxy substituted by halogen;
R² is H or halogen;
each R³ is independently hydrogen, cyano, lower alkoxy, lower alkyl, lower alkyl substituted by halogen, lower alkoxy substituted by halogen, —CH₂—O-lower alkyl or halogen;
X is a bond, —NHC(O)—, —NH—, NHCH₂—, —CH=CH— or —O—;
Ar is aryl or heteroaryl;
and wherein —X—Ar—(R³)ₘ is in the 3 or 4 position of the phenyl ring;
n is 1 or 2; and
m is 1 or 2;
or a pharmaceutically acceptable acid addition salt thereof.

18. A pharmaceutical composition comprising a compound of formula I wherein
R¹ and R¹' are each independently hydrogen, halogen, lower alkoxy, lower alkyl, lower alkyl substituted by halogen, lower alkoxy substituted by halogen, lower alkoxy substituted by hydroxy, —O—(CH₂)ₒ—O-lower alkyl, —(CH₂)ₚ—O-lower alkyl, —O—S(O)₂-lower alkyl, —S(O)₂-lower alkyl or cyano;

or R¹ and R¹' together are —(CH₂)₂O—, —O—CH₂—O— or —N(R)—(CH₂)₂—O— which together form a 5- or 6-membered ring with the carbon atoms to which they are attached; R is hydrogen or lower alkyl;

R² is hydrogen, halogen, lower alkyl, cyano, lower alkoxy, lower alkoxy substituted by halogen, —O—(CH₂)ₚ—C₃₋₆-cycloalkyl or (CH₂)ₒ—O-lower alkyl;
each R³ is independently hydrogen, cyano, lower alkoxy, lower alkyl, lower alkyl substituted by halogen, lower alkoxy substituted by halogen, —CH₂—O-lower alkyl, —C(O)N-di-lower alkyl or halogen;

R⁴ is hydrogen or lower alkyl;
X is a bond, —NH—C(O)—, —NH— or —O—CH₂;
Ar is aryl or heteroaryl;
and wherein —X—Ar—(R³)ₘ is in the 3 or 4 position of the phenyl ring; or X—Ar—(R³)ₘ represents benzo[1,3]dioxole;

m is 0, 1 or 2;
o is 2 or 3; and
p is 1, 2 or 3;

or a pharmaceutically active acid addition salt thereof and a pharmaceutically acceptable carrier.

* * * * *

UNITED STATES PATENT AND TRADEMARK OFFICE
CERTIFICATE OF CORRECTION

PATENT NO. : 7,989,449 B2
APPLICATION NO. : 12/369782
DATED : August 2, 2011
INVENTOR(S) : Andreini et al.

It is certified that error appears in the above-identified patent and that said Letters Patent is hereby corrected as shown below:

TITLE PAGE ITEM (73),
•The Assignees information reads "Hoffman-La Roche Inc., Nutley, NJ (US); Siena Biotech S.p.A. Siena (IT)". The Assignees information should read -- Hoffmann-La Roche Inc., Nutley, NJ (US); Siena Biotech S.p.A. Siena (IT) --.

Signed and Sealed this
Twentieth Day of September, 2011

David J. Kappos
*Director of the United States Patent and Trademark Office*